United States Patent
Correa, Jr. et al.

(10) Patent No.: US 12,173,368 B2
(45) Date of Patent: Dec. 24, 2024

(54) COMPOSITIONS AND ANALYSIS OF DEPHOSPHORYLATED OLIGORIBONUCLEOTIDES

(71) Applicant: New England Biolabs, Inc., Ipswich, MA (US)

(72) Inventors: Ivan R. Correa, Jr., Hamilton, MA (US); Eric Wolf, Manchester, MA (US); Nan Dai, Ipswich, MA (US); Erbay Yigit, Boxford, MA (US); Sebastian Grünberg, Salem, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 18/298,291

(22) Filed: Apr. 10, 2023

(65) Prior Publication Data

US 2023/0287489 A1    Sep. 14, 2023

Related U.S. Application Data

(63) Continuation-in-part of application No. 18/182,122, filed on Mar. 10, 2023.

(60) Provisional application No. 63/329,262, filed on Apr. 8, 2022, provisional application No. 63/319,157, filed on Mar. 11, 2022.

(51) Int. Cl.
*C12Q 1/6806* (2018.01)
*C12Q 1/6872* (2018.01)

(52) U.S. Cl.
CPC .... *C12Q 1/6872* (2013.01); *C12Y 301/13005* (2013.01); *C12Q 1/6806* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 11,702,698 B2 * | 7/2023 | Stoeckius | C12Q 1/6841 435/6.11 |
| 2018/0237849 A1 * | 8/2018 | Thompson | C12Q 1/6872 |
| 2021/0108252 A1 | 4/2021 | Beverly | |

FOREIGN PATENT DOCUMENTS

WO    2018081462 A1    5/2018

OTHER PUBLICATIONS

Verbeure et al. Nucleic Acids Research, vol. 29, No. 24, pp. 4941-4947. (Year: 2001).*
Schwer et al. (PNAS 101 (9), p. 2788-2793, 2004).*
O'Brien and Herschlag, Biochemistry 2001, 40, 5691-5699, 2001.*
Yoluc, et al., Critical reviews in Biochemistry and Molecular Biology, 56, 2, 178-204, 2021.
Damase, et al., Front Bioeng Biotechnol, 9:628137, 2021.
Jiang, et al., Anal Chem, 91(13):8500-8506, 2019.
Das, et al., Nucleic Acids Research, 41(1): 355-65, 2013.
Wein, et al., Nat Commun. 11(1): 926, 2020.
Terzyan, et al., J Mol Biol., 285(1):205-14, 1999.
Thakur, et al., Analyst, 145(3):816-827, 2020.
Zhou, Eur J Biochem., 217(1):401-10, 1993.
Lechner, et al., Anal Chem, 92(10):7363-7370, 2020.
Krivos, et al., Rapid Commun Mass Spectrom. 25(23):3609-16, 2011.
Kariko, et al., Mol Ther. 20(5):948-53, 2012.
Thess,et al., Mol Ther. 23(9): 1456-64, 2015.
Henderson, et al., Curr Protoc. 1(2):e39, 2021.
Vaidyanathan, et al., Mol Ther Nucleic Acids, 12:530-542, 2018.
Addepalli, et al., RNA, 21(10):1746-56, 2015.
Addepalli, et al., Anal Bioanal Chem, ;409(24):5645-5654, 2017.
Grunberg, et al., Protein Expr Purif, 190:105987, 2021.
Shapiro, et al., Biochemistry, 25(23):7255-64, 1986.
Houser, et al., Anal Biochem, 478:52-8, 2015.
Vogel, et al., Nature, 592(7853):283-289, 2021.
Wolf, et al., Nucleic Acids Research, 50, 18, e106, 2022.
Chan, et al., RNA, 28, 8, 1144-1155, 2022.
Nwokeoji, et al., ACS Synth. Biol., 12, 1, 329-339, 2022.
Hermanson, Bioconjugate Techniques, 2nd Ed; Academic Press: London, Bioconjugate Reagents, pp. 276-335, 2008.
Thermo Scientific, Product Information, RNase T1, Pub. No. MAN0012004, Jan. 9, 2017.

* cited by examiner

*Primary Examiner* — Richard G Hutson
(74) *Attorney, Agent, or Firm* — New England Biolabs, Inc

(57) ABSTRACT

The present disclosure relates, according to some embodiments, to compositions and analysis of RNA (e.g., dephosphorylated oligoribonucleotides) including, for example, natural and/or synthetic RNAs. A composition may comprise, for example, an endoribonuclease having an amino acid sequence that (i) corresponds to an amino acid sequence of a first species (e.g., *Homo sapiens*, *Escherichia coli*, *Aspergillus oryzae*, *Momordica charantia*, *Pyrococcus furiosus*, *Cucumis sativus*, and *Sus scrofa*) or (ii) is a non-naturally occurring sequence; and/or an RNA end repair enzyme having an amino acid sequence that (i) corresponds to an amino acid sequence of a species other than the first species (e.g., a bacterial species or a bacteriophage species) or (ii) is a non-naturally occurring sequence.

6 Claims, 43 Drawing Sheets

Specification includes a Sequence Listing.

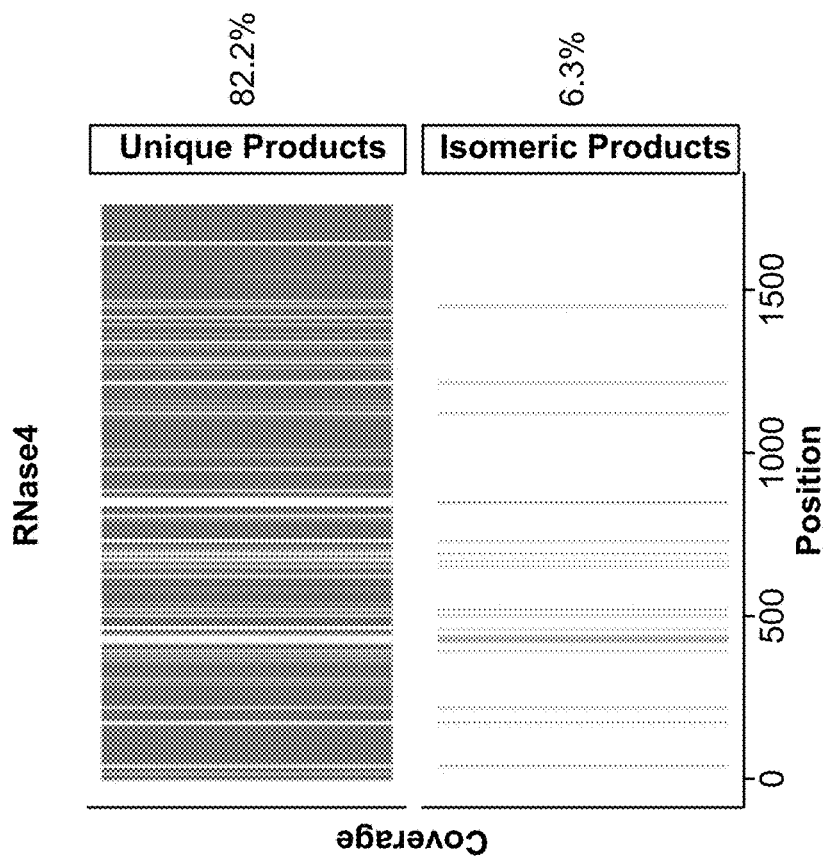
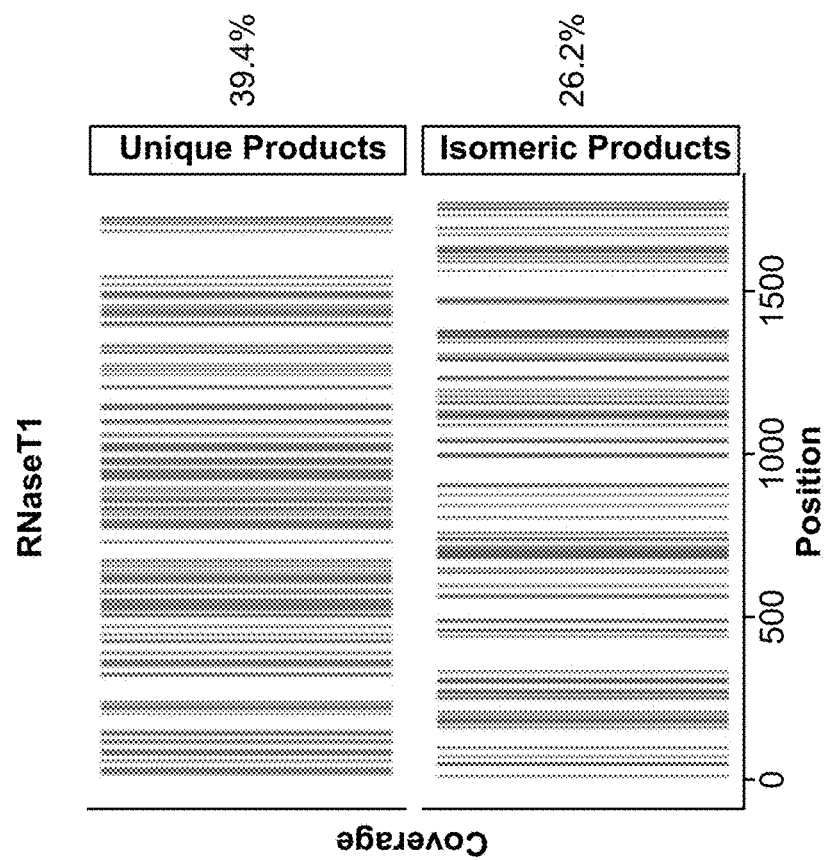
FIG. 9

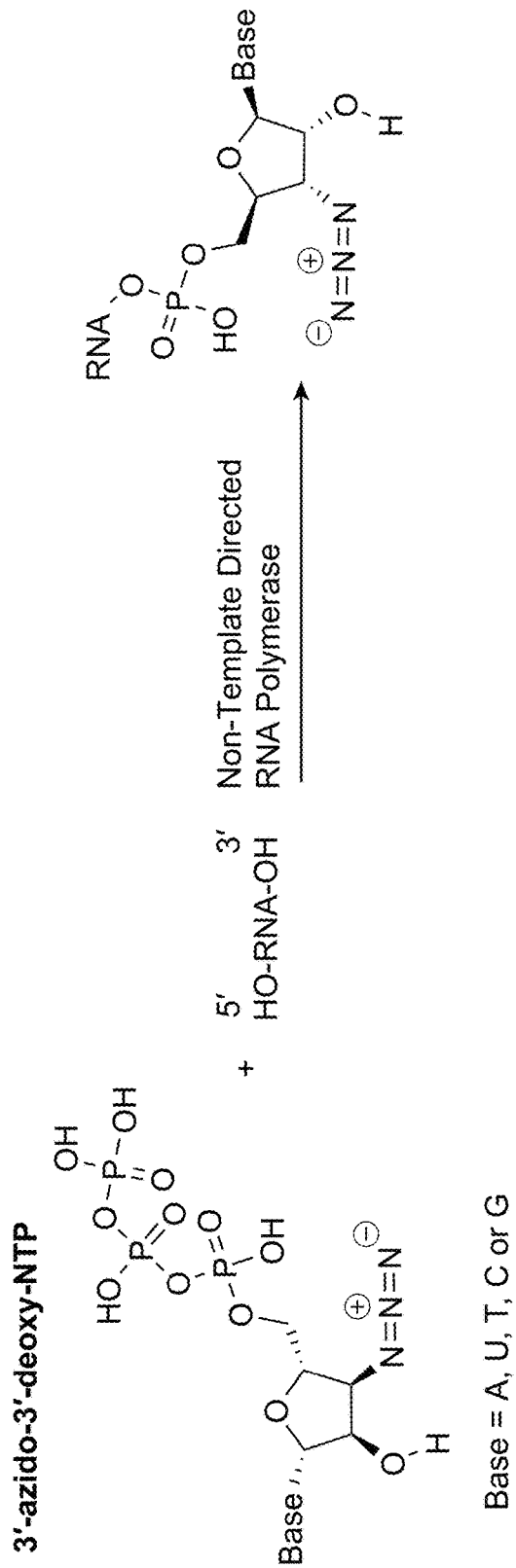
FIG. 24A
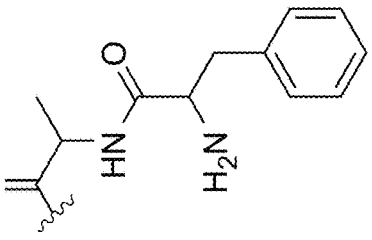
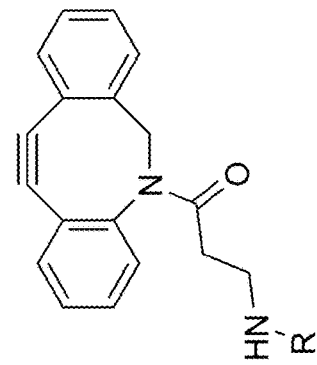
FIG. 24B

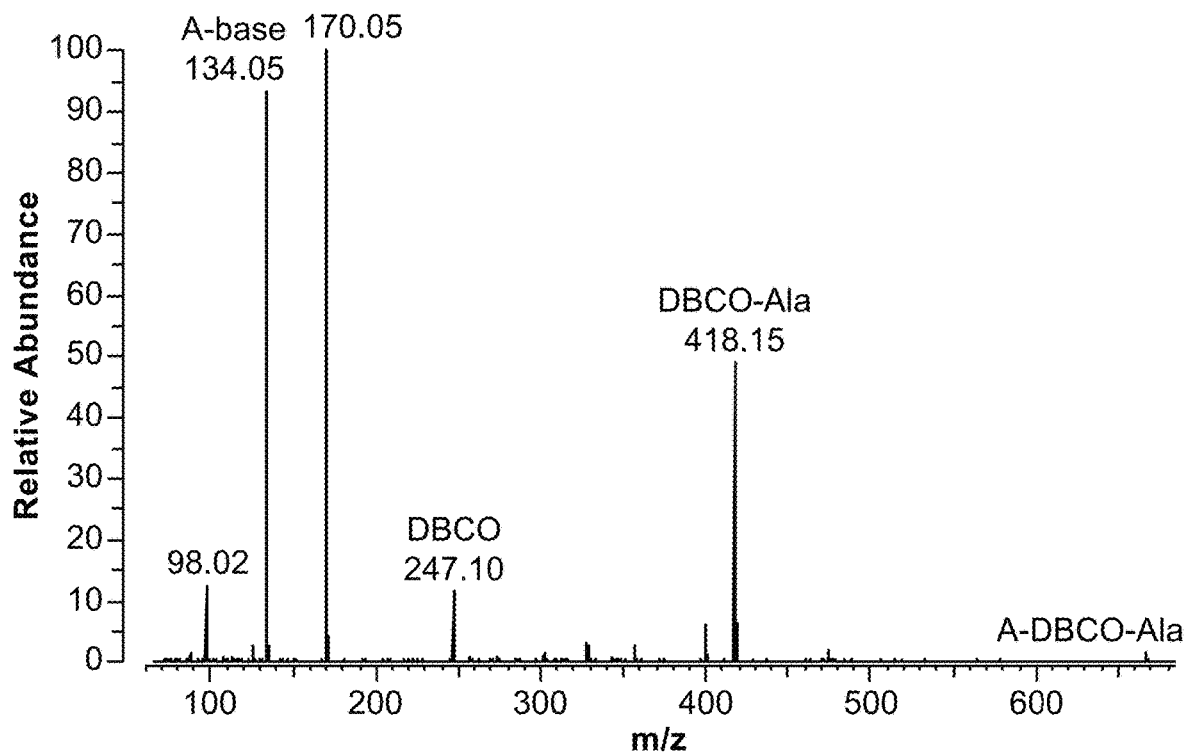
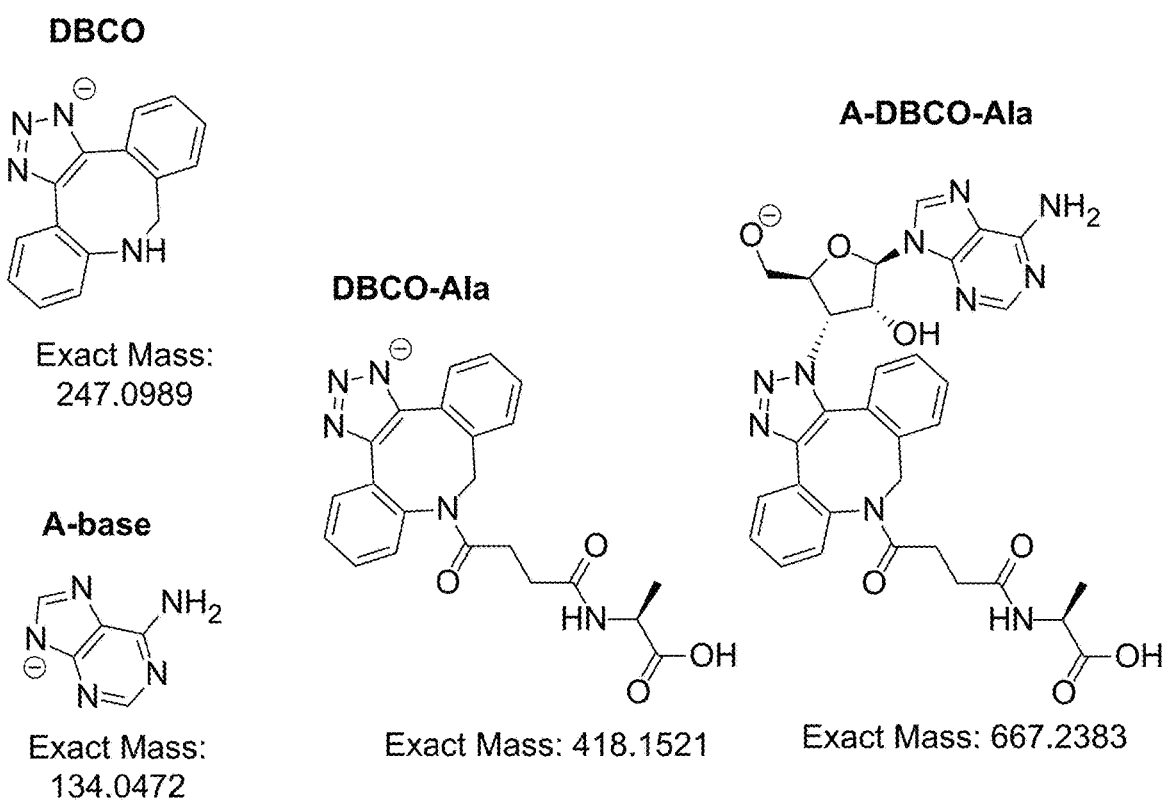
FIG. 24D

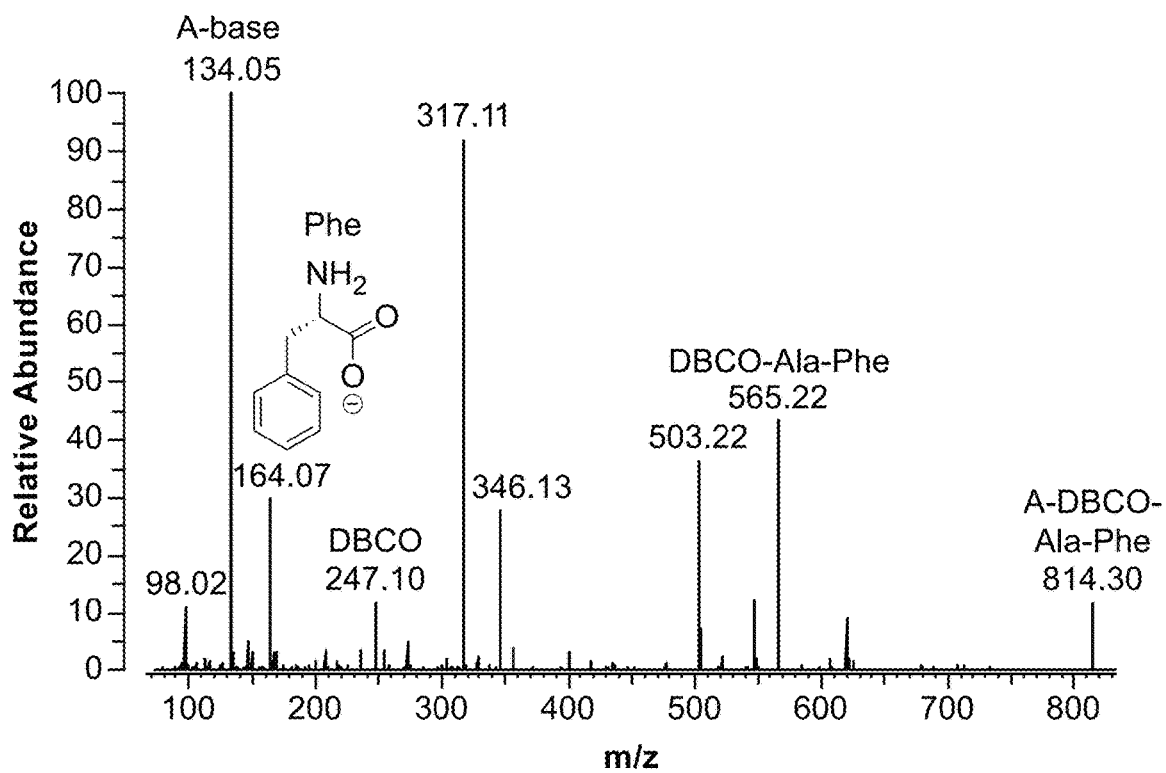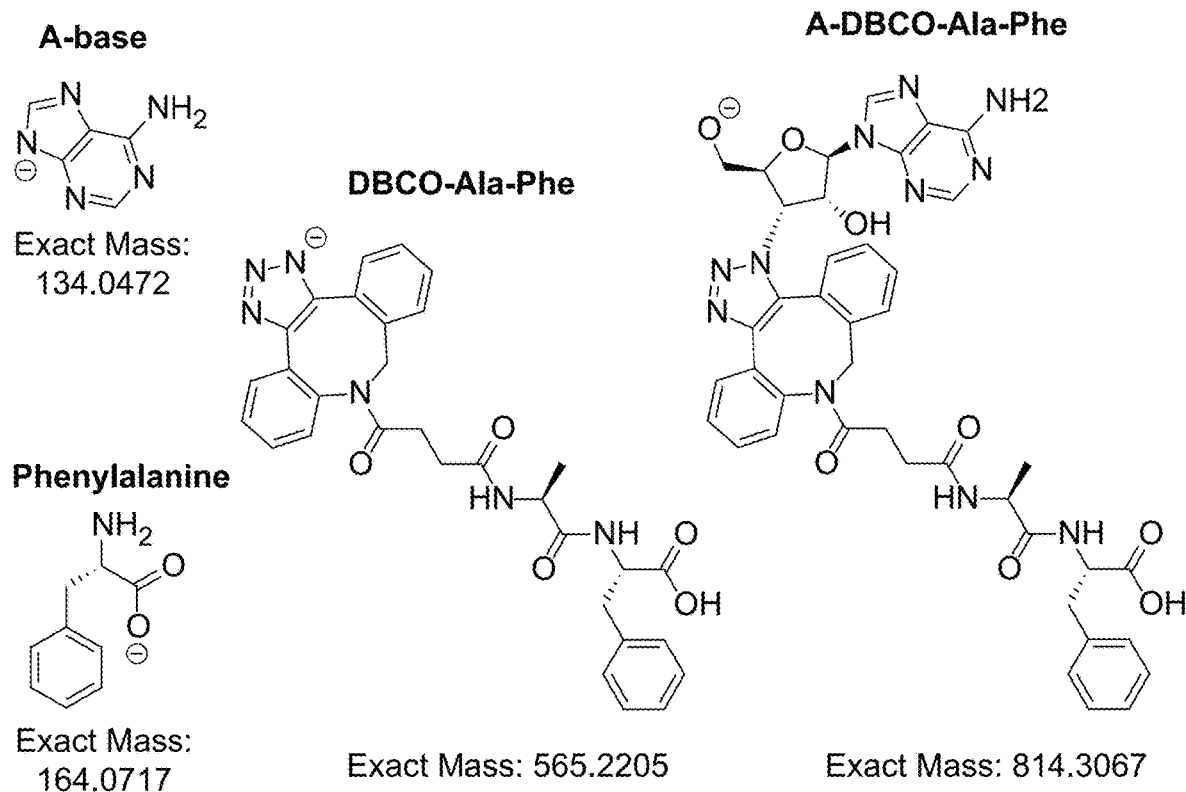
FIG. 24E

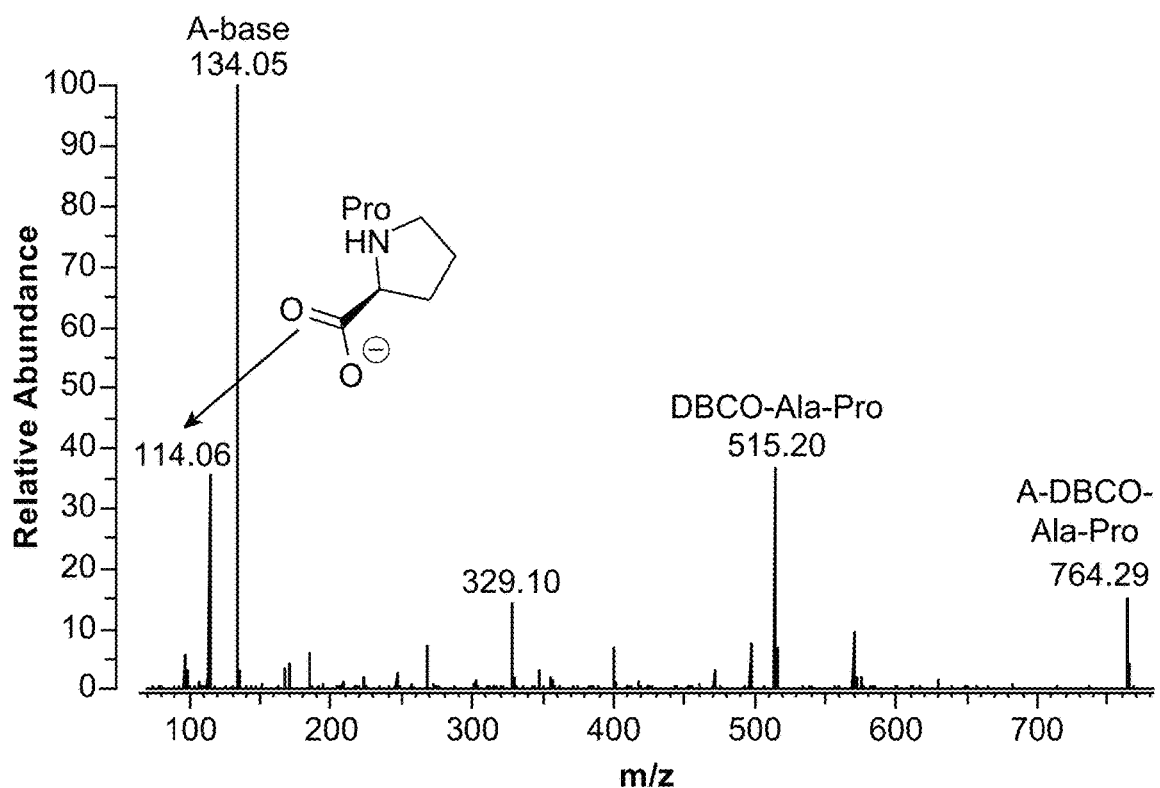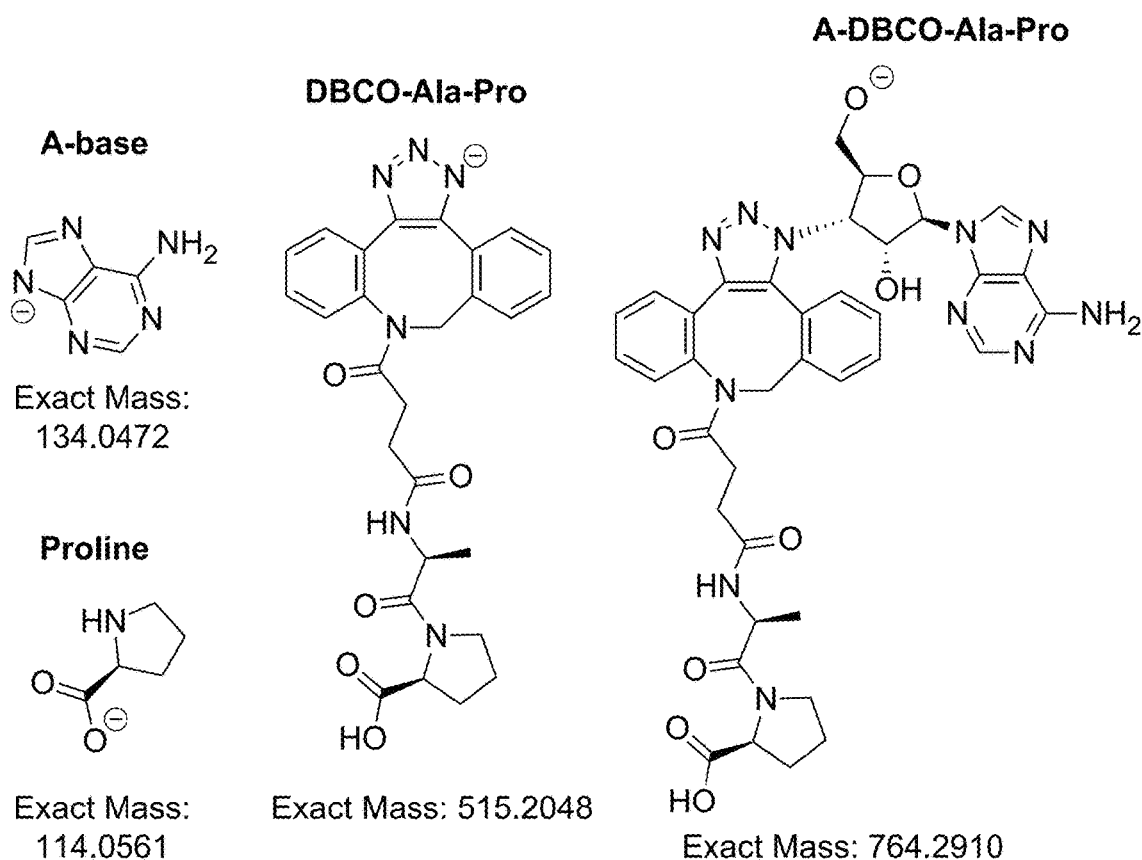
FIG. 24F

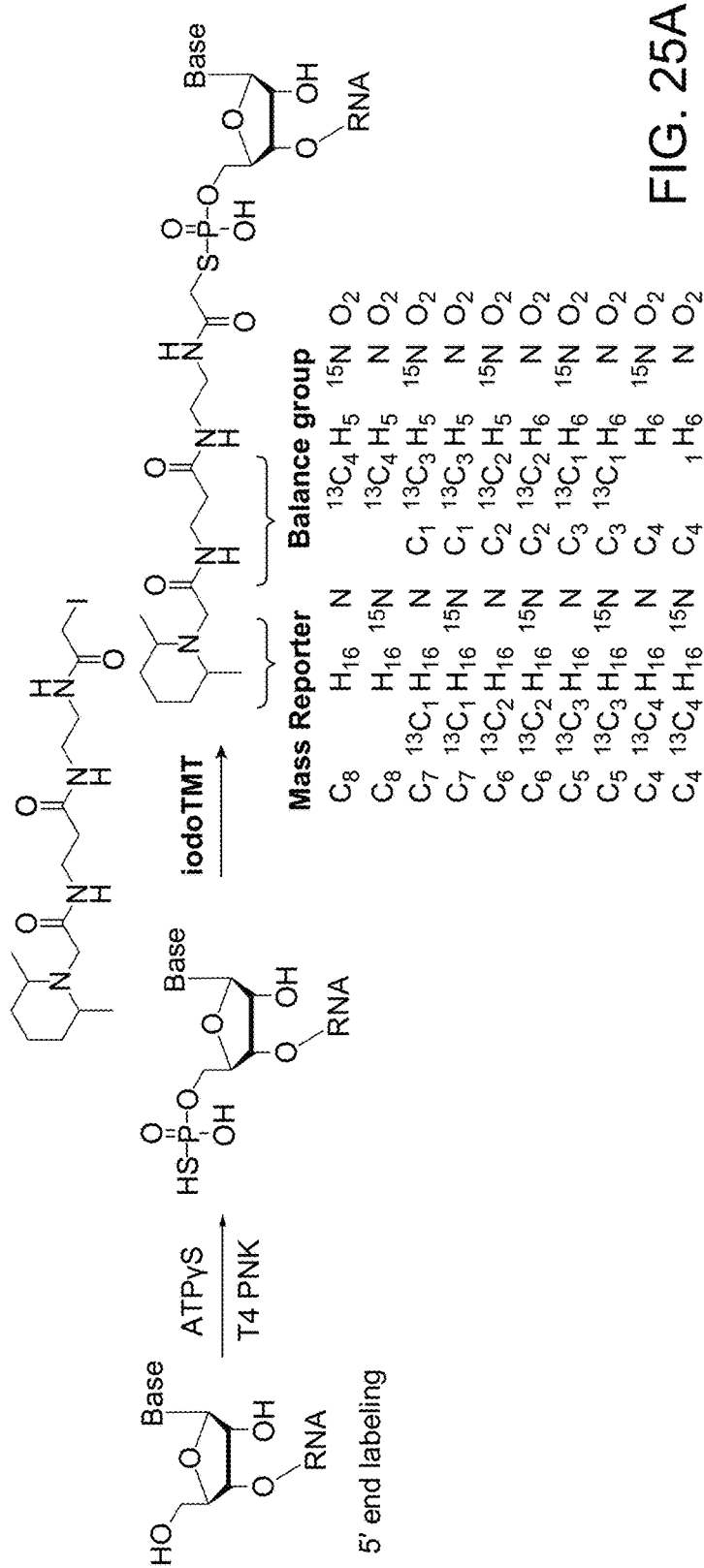
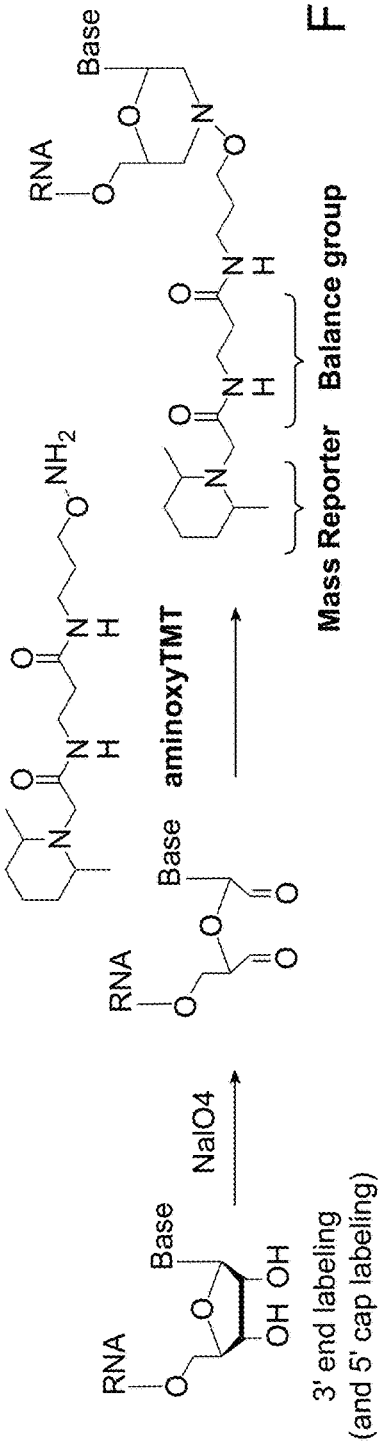
FIG. 25A
FIG. 25B

RNase 4 (U|R)

GGGACUCUAACUAUGUCAAUCGCCGUGAUGUAAUUAUCGC
GGGACUCUAACUAUGUCAAUCGCCGU 1-26

MC1 (K|U)

GGGACUCUAACUAUGUCAAUCGCCGUGAUGUAAUUAUCGC
GGGACUCUAACUAUGUCAAUCGCCGUGAUGUAAUUAUCGC
GGGACUCUAACUAUGUCAA 1-19
GGGACUCUAACUAUGUCAAUCGCCGUGA 1-28

RNase T1 (G|N)

GGGACUCUAACUAUGUCAAUCGCCGUGAUGUAAUUAUCGC
GGGACUCUAACUAUGUCAAUCG 1-22
GGACUCUAACUAUGUCAAUCG 2-22
GACUCUAACUAUGUCAAUCG 3-22
ACUCUAACUAUGUCAAUCG 4-22

RNase A (Y|N)

GGGACUCUAACUAUGUCAAUCGCCGUGAUGUAAUUAUCGC
GGGACUCUAACUAUGUC 1-17
GGGACUCUAACUAUGUCAAU 1-20

RNase 1f

GGGACUCUAACUAUGUCAAUCGCCGUGAUGUAAUUAUCGC
GGGACUCUAACUAUGUCAAU 1-20
GGGACUCUAACUAUGUCAAUC 1-21
GGGACUCUAACUAUGUCAAUCG 1-22
GGGACUCUAACUAUGUCAAUCGC 1-23

FIG. 29B

```
                         26  29 31
GGGACUCUAACUAUGUCAAUCGCCGUGAUGUAAUUAUCGC hRNase 4
                      19         28   33
GGGACUCUAACUAUGUCAAUCGCCGUGAUGUAAUUAUCGC MC1
                         22   25 27  30
GGGACUCUAACUAUGUCAAUCGCCGUGAUGUAAUUAUCGC RNaseT1
```

FIG. 30C fLuc mRNA 5'-end hRNase 4

25mer Biotinylated DNA Probe

XGGGUCUAGAAAUAAUUUUGUUUAACUUU|AAGAAGGA-
                                  28 | 29
                          hRNase 4 Cut Site

RNaseH

25mer Biotinylated DNA/RNA Probe

XGGGUCUAGAAAUAAUUUUGUUUAA|CUUUAAGAAGGA-
                          24 | 25
                    RNase Cut Site

FIG. 31A

COMPOSITIONS AND ANALYSIS OF DEPHOSPHORYLATED OLIGORIBONUCLEOTIDES

CROSS-REFERENCE TO RELATED APPLICATIONS

This application is a continuation-in-part of U.S. patent application Ser. No. 18/182,122 filed Mar. 10, 2023. This application also claims priority to U.S. Provisional Application No. 63/329,262 filed Apr. 8, 2022. The contents of all of the above are hereby incorporated in their entirety by reference.

SEQUENCE LISTING STATEMENT

This disclosure includes a Sequence Listing submitted electronically in .xml format under the file name "NEB-450.xml" created on Mar. 30, 2023, and having a size of 64.8 KB. This Sequence Listing is incorporated herein in its entirety by this reference.

BACKGROUND

Increasing the breadth of analytical approaches to assess the purity, quantity, sequence, and identity of synthetic RNAs (e.g., RNA produced by in vitro transcription (IVT)), including synthetic RNAs for use in therapeutics and/or vaccines, is an important area of technical development. Liquid chromatography-tandem mass spectrometry (LC-MS/MS) may be used to directly sequence and to verify the position and identity of RNA modifications (e.g., 5' cap structures, nucleobase and ribose modifications) within native and synthetic RNAs. To characterize full-length RNA substrates by LC-MS/MS, RNA samples may be digested with one or more endoribonuclease(s) of selected specificity. Coupling endoribonuclease digestion to LC-MS/MS analysis presents several key challenges. First, RNA structure may interfere with the activity of an endoribonuclease. Second, incubation of RNA with one or more endoribonucleases often produces a mixture that may contain 2',3'-cyclic-phosphorylated, 3'-phosphorylated, and 2',3'-hydroxylated oligoribonucleotide products, convoluting the analysis of the resultant oligonucleotide mixture and reducing the intensity of the signal for individual oligonucleotides in LC-MS/MS experiments. Third, the limited availability to endoribonucleases with discrete recognition and cleavage specificities that have been fully characterized, are robust, and are presented with enough purity to generate reliable and reproducible digestion products for downstream mass spectrometry analysis.

SUMMARY

Accordingly, needs have arisen for improved analytical methods to assess the purity, quantity, sequence, and identity of synthetic RNAs (e.g., RNA-based therapeutics and vaccines). The present disclosure relates to methods and compositions for analyzing polyribonucleotides including natural and/or synthetic RNAs. A composition may comprise, for example, an endoribonuclease having an amino acid sequence that (i) corresponds to an amino acid sequence of a first species (e.g., a vertebrate species (for example, *Homo sapiens, Sus scrofa*), a bacterial species (for example, *Escherichia coli*), a fungus species (for example, *Aspergillus oryzae*), a plant species (for example, *Momordica charantia, Cucumis sativus*), and an archaea species (for example, *Pyrococcus furiosus*)) or (ii) is a non-naturally occurring sequence; and/or an RNA end repair enzyme having an amino acid sequence that (i) corresponds to an amino acid sequence of a species other than the first species (e.g., a bacterial species or a bacteriophage species) or (ii) is a non-naturally occurring sequence. In some embodiments, an endoribonuclease may have an amino acid sequence that corresponds to an amino acid sequence of a vertebrate (e.g., mammalian) species. An endoribonuclease may have specificity selected from (1) cleavage after a specific nucleotide followed by a purine, (2) cleavage after a specific nucleotide followed by a pyrimidine, (3) cleavage after a purine followed by a specific nucleotide, and (4) cleavage after a pyrimidine followed by a specific nucleotide, according to some embodiments. An endoribonuclease may have an average cleavage rate of once every 6-12 nucleotides. Example endoribonucleases include hRNase 4, RNase T1, RNase U2, RNase A, Colicin E5, MC1, Cusativin, Csx1, MazF, ChpB, MqsR, and YafO. An end repair enzyme may comprise phosphodiesterase and phosphomonoesterase activities. An end repair enzyme may comprise a polynucleotide kinase-phosphatase. Example end repair enzymes include T4 polynucleotide kinase-phosphatases and Cth polynucleotide kinase-phosphatases. In some embodiments, a composition may further comprise one or more of a denaturing agent, a buffering agent, and an RNA substrate. Optionally, a composition may comprise one or more oligoribonucleotides, which may be, for example, substrates and/or products of an endoribonuclease and/or an end repair enzyme.

The present disclosure relates to methods for analyzing polyribonucleotides. For example, methods may comprise (a) contacting an RNA substrate and an endoribonuclease to produce oligoribonucleotides comprising one or more unrepaired ends that are 2',3'-cyclic-phosphorylated, 3'-phosphorylated and/or 2'-phosphorylated; (b) contacting an RNA end repair enzyme and the oligoribonucleotides comprising the unrepaired ends to produce oligoribonucleotides comprising one or more repaired ends that are 2',3'-hydroxylated, and (c) optionally, characterizing the oligoribonucleotides comprising one or more repaired ends that are 2',3'-hydroxylated. Endoribonucleases used in methods of the disclosure may have specificity selected from (1) cleavage after a specific nucleotide followed by a purine, (2) cleavage after a specific nucleotide followed by a pyrimidine, (3) cleavage after a purine followed by a specific nucleotide, and (4) cleavage after a pyrimidine followed by a specific nucleotide and/or an average cleavage rate of the RNA substrate of once every 6-12 nucleotides (e.g., once every 8 nucleotides). Example endoribonucleases used in methods of the disclosure may include hRNase 4, RNase T1, RNase U2, RNase A, Colicin E5, MC1, Cusativin, Csx1, MazF, ChpB, MqsR, and YafO. End repair enzymes used in methods of the disclosure may comprise phosphodiesterase and phosphomonoesterase activities. An end repair enzyme may comprise a polynucleotide kinase-phosphatase. Example end repair enzymes include T4 polynucleotide kinase-phosphatases and Cth polynucleotide kinase-phosphatases. According to some embodiments, a methods may be performed as a coupled reaction. For example, (a) contacting and the (b) contacting occur in a single location or occur in separate locations that are in fluid communication with one another. In some embodiments, an RNA substrate may be a denatured RNA substrate. For example, contacting an RNA substrate and an endoribonuclease may further comprise denaturing the RNA substrate to form a denatured RNA substrate and contacting the denatured RNA substrate and the endoribonuclease.

Denaturing an RNA substrate may include, for example, contacting the RNA substrate with a denaturing agent (e.g., urea, formamide, dimethylformamide, guanidinium thiocyanate, sodium salicylate, dimethyl sulfoxide, propylene glycol, poly(ethylene glycol), and cetyltrimethylammonium bromide) at a salt concentration of up to 50 mM or incubating the RNA substrate at a temperature of 65° C. or higher at a salt concentration of up to 50 mM. In some embodiments, contacting an RNA substrate and an endoribonuclease may further comprise denaturing the RNA substrate to form a denatured RNA substrate, diluting the denatured RNA substrate for form a diluted denatured RNA substrate, and contacting the diluted denatured RNA substrate and the endoribonuclease. According to some embodiments, (a) contacting and/or (b) contacting may further comprise contacting a buffering agent. In some embodiments, contacting an RNA end repair enzyme and the oligoribonucleotides may further comprise separating the oligoribonucleotides comprising one or more unrepaired ends from the endoribonuclease to form separated oligoribonucleotides comprising one or more unrepaired ends. In some embodiments, the (c) characterizing may comprise characterizing the oligoribonucleotides comprising one or more repaired ends by one or more of gel electrophoresis, capillary electrophoresis, liquid chromatography, and mass spectrometry. In some embodiments, the (c) characterizing may comprise separating the oligoribonucleotides from one or more of the RNA substrate, the endoribonuclease, the RNA end repair enzyme to form separated oligoribonucleotides and characterizing the separated oligoribonucleotides. For example, characterizing may include fractionating the oligoribonucleotides comprising one or more repaired ends that are 2',3'-hydroxylated by liquid chromatography to form fractionated oligoribonucleotides and ionizing the fractionated oligoribonucleotides for mass spectrometry.

According to some embodiments, an RNA substrate (e.g., an RNA substrate included in a method of the disclosure) may comprise in vitro transcribed RNA, chemically synthesized RNA, viral RNA, prokaryotic RNA, eukaryotic RNA, archaeal RNA, or combinations thereof. An RNA substrate (e.g., an RNA substrate included in a method of the disclosure), in some embodiments, may comprise tissue culture RNA, biopsy RNA, feces RNA, urine RNA, lymph RNA, blood RNA, mucous RNA, sputum RNA, skin RNA, saliva RNA, wound RNA, sweat RNA, semen RNA, shoot RNA, root RNA, seed RNA, sewage RNA, sludge RNA, soil RNA, or any combination thereof. RNA substrates that may be analyzed by methods of the disclosure may comprise any RNA substrate including, for example, messenger RNA (mRNA), ribosomal RNA (rRNA), transfer RNA (tRNA), small RNA (sRNA), microRNA (miRNA), long non-coding RNA (lncRNA), circular RNA (circRNA), aptamer RNA, antisense RNA, silencing RNA (siRNA), guide RNA (gRNA), or any combination thereof.

In some embodiments, the present disclosure relates to kits for analysis of polyribonucleotides including natural and/or synthetic RNA. For example, a kit may include (a) an endoribonuclease having an amino acid sequence that (i) corresponds to an amino acid sequence of a first species (e.g., a vertebrate species (for example, *Homo sapiens*, *Sus scrofa*), a bacterial species (for example, *Escherichia coli*), a fungus species (for example, *Aspergillus oryzae*), a plant species (for example, *Momordica charantia*, *Cucumis sativus*), and an archaea species (for example, *Pyrococcus furiosus*)) or (ii) is a non-naturally occurring sequence; (b) an RNA end repair enzyme having an amino acid sequence that (i) corresponds to an amino acid sequence of a species other than the first species (e.g., a bacterial species or a bacteriophage species) or (ii) is a non-naturally occurring sequence; (c) optionally, a denaturing agent (e.g., urea, formamide, dimethylformamide, guanidinium thiocyanate, sodium salicylate, dimethyl sulfoxide, propylene glycol, poly(ethylene glycol), and cetyltrimethylammonium bromide); (d) optionally, a buffering agent; and (e) optionally, an affinity-labeled DNA probe. In some embodiments, an endoribonuclease included in a kit may have an amino acid sequence that corresponds to an amino acid sequence of a vertebrate (e.g., mammalian) species.

An endoribonuclease included in a kit may have specificity selected from (1) cleavage after a specific nucleotide followed by a purine, (2) cleavage after a specific nucleotide followed by a pyrimidine, (3) cleavage after a purine followed by a specific nucleotide, and (4) cleavage after a pyrimidine followed by a specific nucleotide, according to some embodiments. An endoribonuclease included in a kit may have an average cleavage rate of once every 6-12 nucleotides. Example endoribonucleases that may be included in a kit include hRNase 4, RNase T1, RNase U2, RNase A, Colicin E5, MC1, Cusativin, Csx1, MazF, ChpB, MqsR, and YafO. An end repair enzyme included in a kit may comprise phosphodiesterase and phosphomonoesterase activities. An end repair enzyme included in a kit may comprise a polynucleotide kinase-phosphatase. Example end repair enzymes that may be included in a kit include T4 polynucleotide kinase-phosphatases and Cth polynucleotide kinase-phosphatases. A kit, in some embodiments, may further include a divalent metal, wherein the divalent metal is optionally selected from magnesium(II), manganese(II), cobalt(II), and nickel(II). In some embodiments, a kit may further include one or more additional enzymes, wherein the one or more additional enzymes are optionally selected from RNA polymerases and RNA ligases.

The present disclosure relates, according to some embodiments, to methods of targeting specific portions of an RNA substrate for analysis. For example, a method may include (a) contacting an RNA substrate and one or more DNA probes, each DNA probe shorter than the RNA substrate and each comprising an affinity domain, wherein at least a portion of the RNA substrate and at least a portion of the DNA probe(s) are complementary, to form a DNA-RNA hybrid duplex comprising a double-stranded portion and at least one single-stranded overhang; (b) contacting the DNA-RNA hybrid duplex with an enzyme composition, the enzyme composition comprising a single-strand-specific nucleotide-specific endoribonuclease (e.g., hRNase 4, RNase T1, RNase U2, RNase A, Colicin E5, MC1, Cusativin, Csx1, MazF, ChpB, MqsR, and YafO) and, optionally, an RNA end-repair enzyme, to form a cleaved DNA-RNA hybrid duplex and a released RNA fragment of the RNA substrate by cleavage of the RNA substrate at a site within the single-stranded overhang by the single-strand-specific nucleotide-specific endoribonuclease; (c) contacting the cleaved DNA-RNA hybrid duplex and a solid support comprising an affinity capture domain to form an affinity capture complex comprising the affinity domain bound to the affinity capture domain; (d) optionally, washing the affinity capture complex to remove unbound materials, if any; and (e) optionally, dissociating the cleaved DNA-RNA hybrid duplex to release the remaining portion of the RNA substrate from the one or more DNA probes. In some embodiments, a DNA-RNA hybrid duplex may comprise the double-stranded portion and two single-stranded overhangs. For example, a DNA-RNA hybrid duplex may comprise the double-stranded portion and a 5' single-stranded RNA overhang and a 3' single-stranded RNA overhang. End repair enzymes used in methods of the disclosure may comprise phosphodiesterase and phosphomonoesterase activities. An end repair enzyme may comprise a polynucleotide kinase-phosphatase. Example end repair enzymes include T4 polynucleotide kinase-phosphatases and Cth polynucleotide kinase-phosphatases.

The present disclosure relates, in some embodiments to methods for quantitatively analyzing an RNA. Methods may include, for example, (a) contacting an RNA substrate, an enzyme, and an isotopically labeled nucleoside triphosphate to form a labeled RNA substrate, wherein the enzyme is optionally selected from an RNA polymerase and an RNA ligase; (b) contacting the labeled RNA substrate and an endoribonuclease to produce oligoribonucleotides comprising one or more unrepaired ends that are 2',3'-cyclic-phosphorylated, 3'-phosphorylated and/or 2'-phosphorylated; and (c) contacting an RNA end repair enzyme and the oligoribonucleotides comprising the unrepaired ends to produce oligoribonucleotides comprising one or more repaired ends that are 2',3'-hydroxylated. In some embodiments, a method may comprise contacting an RNA substrate, an enzyme, and a nucleoside triphosphate comprising a chemically reactive group to form a chemically reactive RNA substrate, wherein the enzyme is optionally selected from an RNA polymerase and an RNA ligase; (b) contacting the chemically reactive RNA substrate and a molecule reactive with the chemically reactive RNA substrate to form a labeled RNA substrate, wherein the molecule comprises one or more stable isotopics; (c) contacting the labeled RNA substrate and an endoribonuclease to produce oligoribonucleotides comprising one or more unrepaired ends that are 2',3'-cyclic-phosphorylated, 3'-phosphorylated and/or 2'-phosphorylated; and (d) contacting an RNA end repair enzyme and the oligoribonucleotides comprising the unrepaired ends to produce oligoribonucleotides comprising one or more repaired ends that are 2',3'-hydroxylated.

The present disclosure further provides methods for analyzing an RNA substrate. A method may comprise, in some embodiments, contacting an RNA substrate and one or more RNA substrate binding molecules (e.g., a "DNA probe, an RNA probe, a synthetic nucleic acid probe, an RNA binding protein, an antibody, an RNA ligand) to form RNA substrate-RNA binding molecule complexes, each complex comprising a bound portion and at least one single-stranded portion, wherein each bound portion comprises at least a portion of the RNA substrate and an RNA binding molecule. For example, a method may comprise contacting an RNA substrate with two species of DNA probe, a first species complementary to a more 5' portion of the RNA substrate and a second species complementary to a more 3' portion of the RNA substrate to form RNA substrate-RNA binding molecule complexes, each complex comprising (e.g., in a 5' to 3' direction) a first bound portion a single-stranded portion and a second bound portion. A first bound portion may comprise the first DNA probe and the more 5' portion of the RNA substrate. A second bound portion may comprise the second DNA probe and the more 3' portion of the RNA substrate. A single-stranded portion may comprise a portion of the RNA substrate linking the more 5' portion and the more 3' portion. According to some embodiments, a method may further comprise contacting the RNA substrate-RNA binding molecule complexes with an enzyme composition (e.g., an enzyme composition comprising a single-strand-specific nucleotide-specific endoribonuclease and, optionally, an RNA end-repair enzyme) to form by cleavage of the RNA substrate at one or more sites within the single-stranded portion by the single-strand-specific nucleotide-specific endoribonuclease cleaved bound portions and one or more fragments of the single-stranded portion. A method may comprise, in some embodiments, separating the cleaved bound portions from the one or more fragments of the at least one single-stranded portion.

According to some embodiments, a method may comprise analyzing one or more properties of the cleaved bound portions and/or analyzing one or more properties of the fragments. Analyzing one or more properties of the cleaved bound portions may include, in some embodiments, characterizing at least the RNA substrate fragment of the cleaved bound portions (e.g., the more 5' portion and/or the more 3' portion of the RNA substrate) by one or more of gel electrophoresis, capillary electrophoresis, liquid chromatography, and mass spectrometry, wherein the characterizing optionally comprises at least one of assessing the molecular mass of the RNA substrate, assessing the sequence of the RNA substrate (or a portion thereof), and assessing the modification status (e.g., modified bases appearing in the RNA substrate including 1-methylpseudouridine and 5-methoxycytidine; 5' ends having a pp, ppp, Cap0, Cap1, or Cap2; 3' ends having a polyA tail or inverted thymidine) of the RNA substrate fragment of the cleaved bound portions. Analyzing one or more properties of the fragments of the at least one single-stranded portion may include, in some embodiments, characterizing the fragments by one or more of gel electrophoresis, capillary electrophoresis, liquid chromatography, and mass spectrometry, wherein the characterizing optionally comprises at least one of assessing the molecular mass of the fragments, assessing the sequence of the fragments (or a portion thereof), and assessing the modification status (e.g., modified bases appearing in the RNA substrate including 1-methylpseudouridine and 5-methoxycytidine; 5' ends having a pp, ppp, Cap0, Cap1, or Cap2; 3' ends having a polyA tail or inverted thymidine) of the fragments.

Examples of a single-strand-specific nucleotide-specific endoribonuclease include hRNase 4, RNase T1, RNase U2, RNase A, Colicin E5, MC1, Cusativin, Csx1, MazF, ChpB, MqsR, and YafO. An RNA end repair enzyme may comprise phosphodiesterase and phosphomonoesterase activities (e.g., a polynucleotide kinase-phosphatase). Examples of an RNA end repair enzyme include a T4 polynucleotide kinase-phosphatase or a Cth polynucleotide kinase-phosphatase. In some embodiments, an RNA substrate may comprise in vitro transcribed RNA, chemically synthesized RNA, viral RNA, prokaryotic RNA, eukaryotic RNA, archaeal RNA, or any combination thereof. An RNA substrate may comprise tissue culture RNA, biopsy RNA, feces RNA, urine RNA, lymph RNA, blood RNA, mucous RNA, sputum RNA, skin RNA, saliva RNA, wound RNA, sweat RNA, semen RNA, shoot RNA, root RNA, seed RNA, sewage RNA, sludge RNA, soil RNA, or any combination thereof. An RNA substrate may comprise messenger RNA (mRNA), ribosomal RNA (rRNA), transfer RNA (tRNA), small RNA (sRNA), microRNA (miRNA), long non-coding RNA (lncRNA), circular RNA (circRNA), aptamer RNA, antisense RNA, silencing RNA (siRNA), guide RNA (gRNA), or any combination thereof.

BRIEF DESCRIPTION OF THE FIGURES

FIG. 5 shows an example comparison of predicted (theoretical) coverage of mRNA transcripts cleaved with hRNase 4 and various endoribonucleases. Cleavage products with lengths greater than 4 and less than 40 nucleotides were considered for sequence coverage calculations.

FIG. 6 shows an example comparison of predicted (theoretical) coverage of mRNA transcripts cleaved with endoribonucleases having hRNase 4-like cleavage specificities, namely those directed to a single nucleotide followed by either a purine or a pyrimidine (N(Y/R)) or to a purine or a pyrimidine followed by a single nucleotide ((Y/R)N) and with endoribonucleases having a single dinucleotide sequence (NN) or a single nucleotide (N) specificity. Cleavage products with lengths greater than 4 and less than 40 nucleotides were considered for sequence coverage calculations.

FIG. 8A shows an example generic workflow. FIG. 8B shows an example workflow in which the subject RNA is digested with RNase T1. FIG. 8C shows an example workflow in which the subject RNA is digested with a composition comprising hRNase 4 and T4 PNK.

FIG. 9 shows an example theoretical sequence coverage map obtained from digestion of FLuc IVT mRNA with either hRNase 4 or RNaseT1. hRNase 4 is predicted to generate a much larger number of unique cleavage products than RNase T1. RNase T1 is predicted to generate a high percentage of isomeric cleavage products (i.e., products with the same nucleotide composition but with distinct sequences of nucleotides).

FIG. 10 shows the scoring distribution (violin plots) of an example search of the deconvoluted masses of cleavage products, resulting from digestion of FLuc IVT mRNA against a human transcriptome database spiked with FLuc mRNA.

FIG. 24A, FIG. 24B, and FIG. 24C each show a schematic for isotopically labeling RNA oligonucleotides for quantification analysis. As illustrated in FIG. 24A, a non-isotopically labeled nucleotide comprising a chemically reactive group (3'-azido-3' deoxy-nucleotide) may be incorporated at the 3' end of an RNA oligonucleotide by incubation of the non-isotopically labeled nucleotide (e.g., a 3'-azido-3' deoxy-nucleoside triphosphate) and an RNA polymerase. While isotopically labeled molecules may be functionalized with a number of chemically reactive groups, the example scheme of FIG. 24B shows isotopically labeled molecules, wherein the chemically reactive group is DBCO and the "light" and "heavy" isotopically labeled molecules are derived from the amino acid alanine. An example of a tandem mass tag dipeptide conjugate is also shown. This tandem mass tag comprises a reporter and a balancing amino acid (for simplicity heavy isotopes are omitted from illustration; the site of HCD fragmentation is represented by a dashed line). FIG. 24C shows an example of a chemoselective reaction involving a 3'-terminal 3'-azido-modified RNA oligonucleotide and a DBCO conjugate.

FIG. 24D, FIG. 24E and FIG. 24F each illustrate an example HCD fragmentation pattern of an RNA nucleoside that has been chemoselectively labeled with a reporter group. In this example, the reporter group is attached to the RNA nucleotide 3' end by the reaction of a 3'-azido-3'-deoxyadenosine with a DBCO peptide conjugate. The DBCO peptide conjugate may comprise one or more isotopically labeled atoms (e.g., 2H, 13C and 15N) and may be used for quantitative analysis of multiple oligonucleotides in a single experiment (e.g., for quantification of capped versus uncapped 5' end oligonucleotides in a capping assay). FIG. 24D illustrates an example HCD fragmentation mass spectrum of an alanine derived peptide-deoxyadenosine conjugate. FIG. 24E illustrates an example HCD fragmentation mass spectrum of an alanine-phenylalanine derived dipeptide-deoxyadenosine conjugate. FIG. 24F illustrates an example HCD fragmentation mass spectrum of an alanine-proline derived dipeptide-deoxyadenosine conjugate. The data demonstrate the identification of characteristic phenylalanine or proline amino acid reporter anions in the HCD spectra from each dipeptide conjugate, respectively. These reporter anions may further comprise isotopically labeled atoms and be used for quantification of the corresponding oligonucleotide conjugates.

FIG. 25A and FIG. 25B each show an example schematic for isotopically labeling RNA oligonucleotides by incorporating a chemically reactive group. FIG. 25A shows labeling the 5' end of an oligonucleotide by first incubating the oligonucleotide with ATPγS and T4 PNK to form a 5' terminal thiophosphate oligonucleotide, and then reacting it with an iodoacetyl tandem mass tag (iodoTMT) reagent set comprising an isobaric mixture of isotopes as shown. FIG. 25B shows labeling the 3' end of an oligonucleotide by first incubating the oligonucleotide with sodium periodate to form a 3' terminal dialdehyde oligonucleotide, and then reacting it with an aminoxy tandem mass tag (aminoxyTMT) reagent set comprising an isobaric mixture of isotopes analogous to the one shown in FIG. 25A.

FIG. 29B illustrates sequences of the most abundant protected products for each enzyme. Specifically, the 20mer DNA probe is represented as a bar aligned above the substrate 40-mer (SEQ ID NO: 31) with the respective protected products appearing below. Fragments of the substrate 40-mer are shown with numeric ranges to the right indicating the corresponding positions of SEQ ID NO:31.

FIG. 30C illustrates predominant cleavage site positions within the 40mer substrate (SEQ ID NO: 31) for hRNase 4, MC1, and RNase T1. hRNase 4 displayed less cleavage product heterogenicity regardless of the DNA probe chosen.

FIG. 31A illustrates a ribonuclease protection assay of FLuc mRNA (SEQ ID NO: 26) using hRNase 4 or RNase H. The 25mer probe is represented as a bar (light shade represents deoxyribonucleotides; dark shade represents ribonucleotides). Black circles indicate position of biotin group. X represents a capped or uncapped 5' modification. RNase cut sites are marked.

BRIEF DESCRIPTION OF THE SEQUENCES

Figure 2:
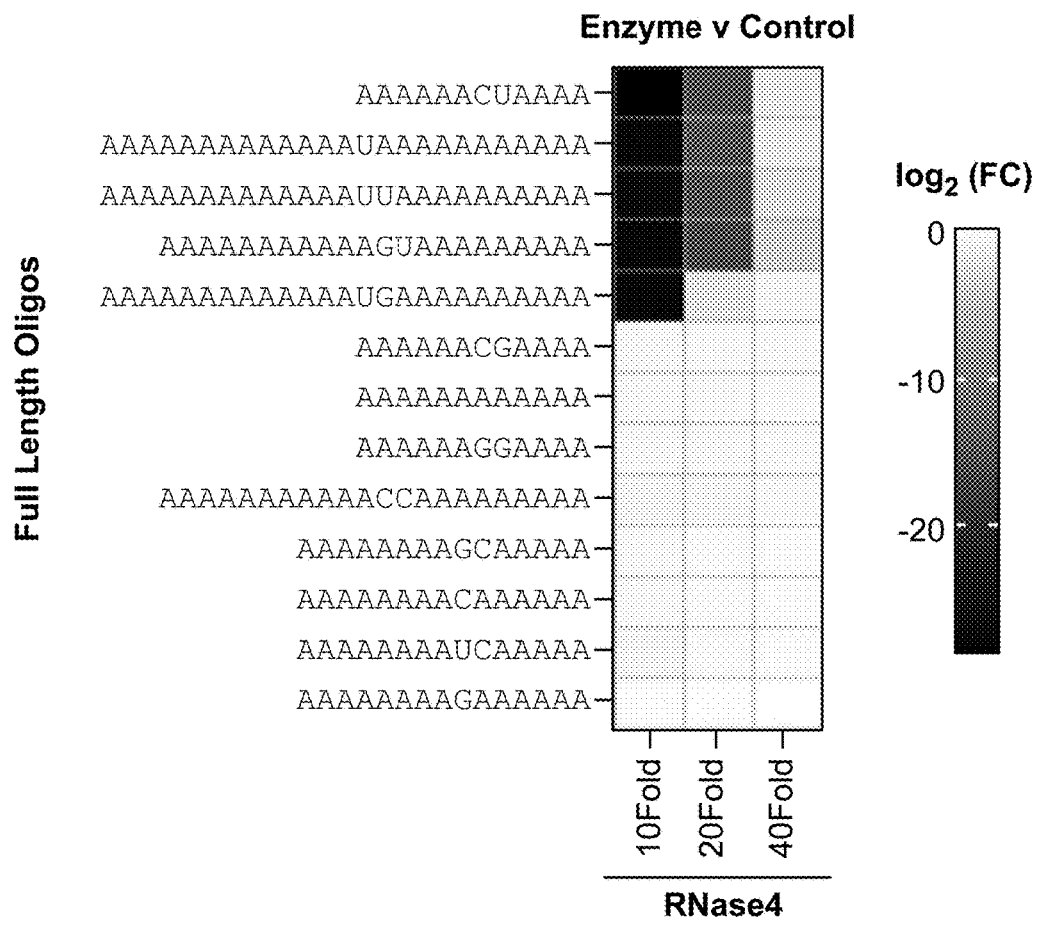
FIG. 2 shows an example cleavage efficiency heatmap for pooled synthetic oligonucleotides (top to bottom, SEQ ID NOS: 1-13, respectively) using hRNase 4 at the indicated dilutions of enzyme. Darker boxes indicate more efficient cleavage by hRNase 4.

SEQ ID NOS: 1-13, which are also illustrated in FIG. 2 and Table 1, are example oligoribonucleotides for assessing cleavage capabilities of an RNase.

Figure 7:
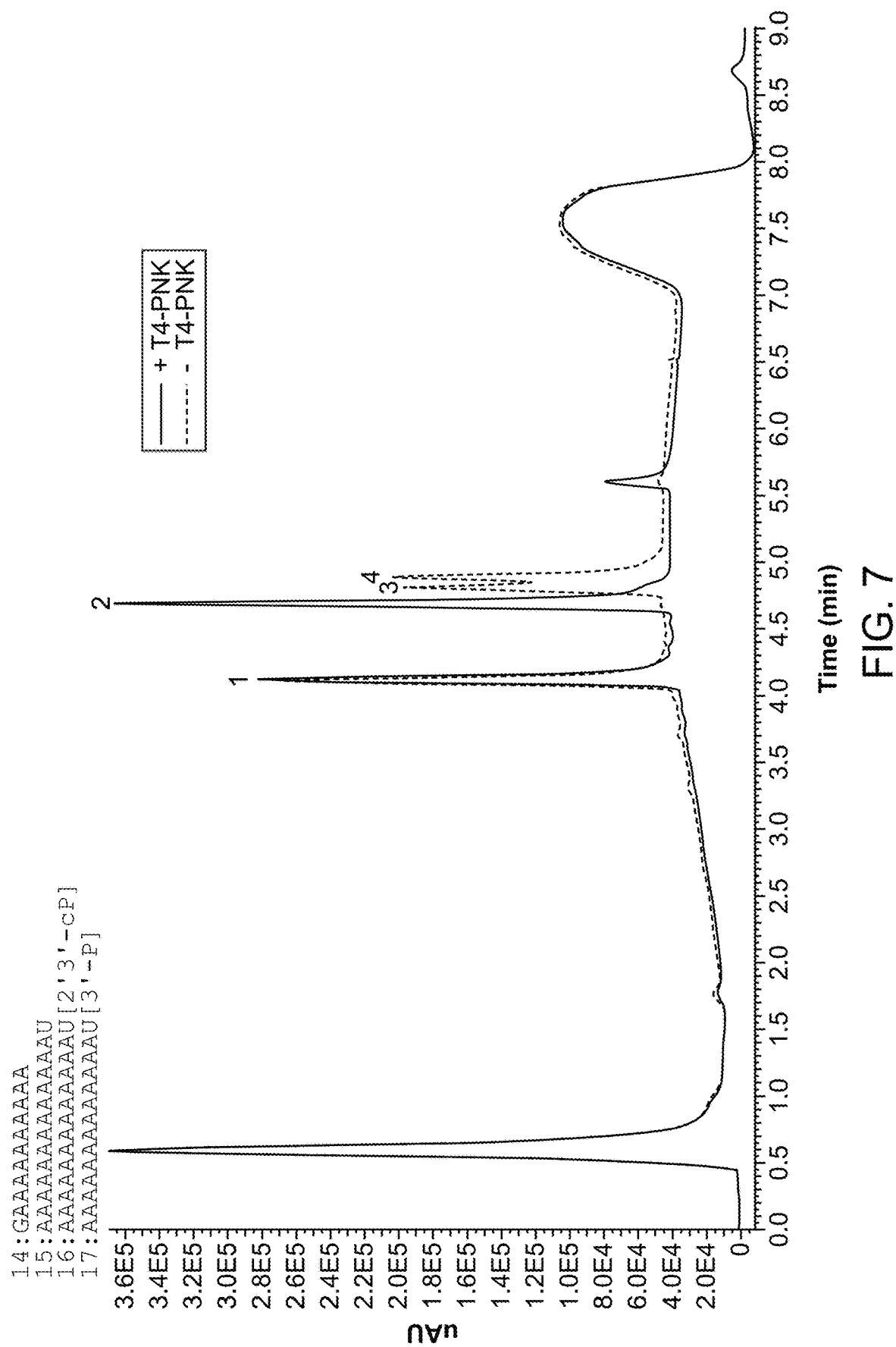
FIG. 7 shows example overlaid UV chromatograms of the digestion of a synthetic oligoribonucleotide (SEQ ID NOS: 14-17) with hRNase 4 in the presence or absence of T4 PNK (lighter and darker traces, respectively). Cleavage products detected in this assay are represented by the sequences 1 to 4. Co-incubation of hRNase 4 with T4 PNK resulted in the conversion of a mixture of 5-prime cleavage products comprising 2',3'-cyclic phosphorylated (peak marked as #3) and 3'-phosphorylated (peak marked as #4) termini into a single 2',3'-hydroxylated product (peak marked as #2), thereby simplifying the sequence identity analysis of 5-prime cleavage products. The 3-prime cleavage product (peak marked as #1) is the same in either treatment.

SEQ ID NOS: 14-17, which are also illustrated in FIG. 7, are example oligoribonucleotides for assessing cleavage capabilities of an RNase.

Figure 19:
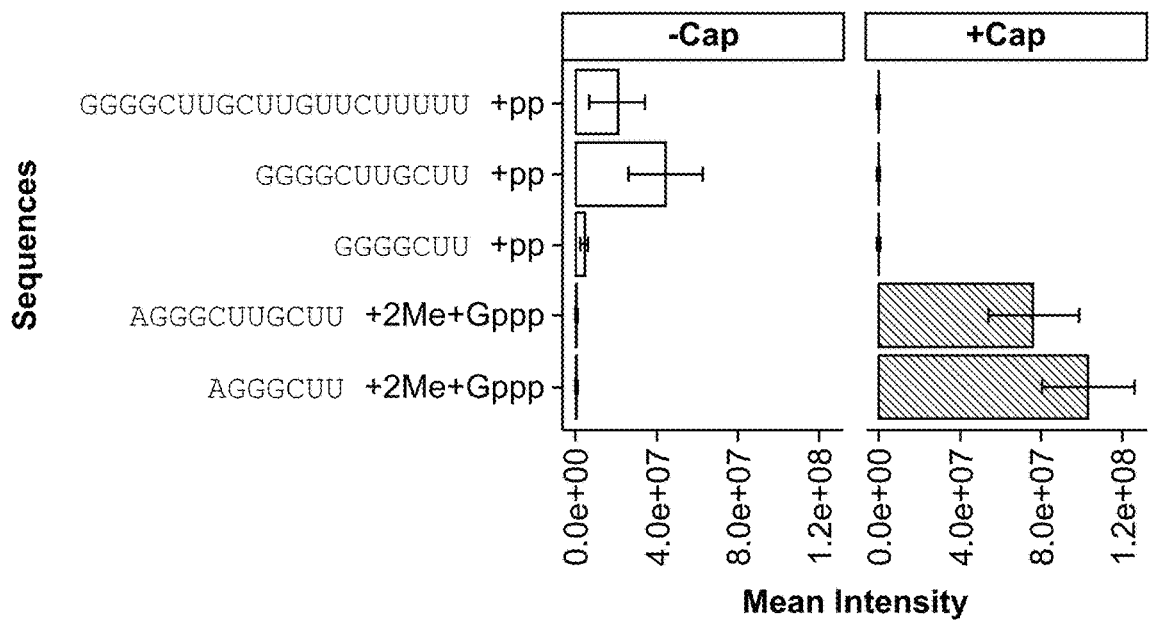
FIG. 19 shows an example in which capped versus uncapped Epo mRNA (including cap modifications, such as cap methylation) (SEQ ID NOS:18-22) are differentiated by cleavage with hRNase 4/T4 PNK. Error bars represent standard deviation from two replicate digests.

SEQ ID NOS: 18-22, which are also illustrated in FIG. 19, are hRNase 4/T4 PNK cleavage products of Epo mRNA (SEQ ID NO:27).

SEQ ID NO: 23 is an example RNase substrate for assessing cleavage capabilities of an RNase.

SEQ ID NO: 24 is an example biotinylated DNA probe sequence for hybridization with an RNase substrate.

SEQ ID NO: 25 is a portion of an EPO mRNA (SEQ ID NO: 27) example RNase substrate for assessing cleavage capabilities of an RNase.

SEQ ID NO: 26, which is also illustrated in Table 1 and, in part, in FIG. 31A, is a FLuc mRNA example RNase substrate for assessing cleavage capabilities of an RNase.

Figure 33:
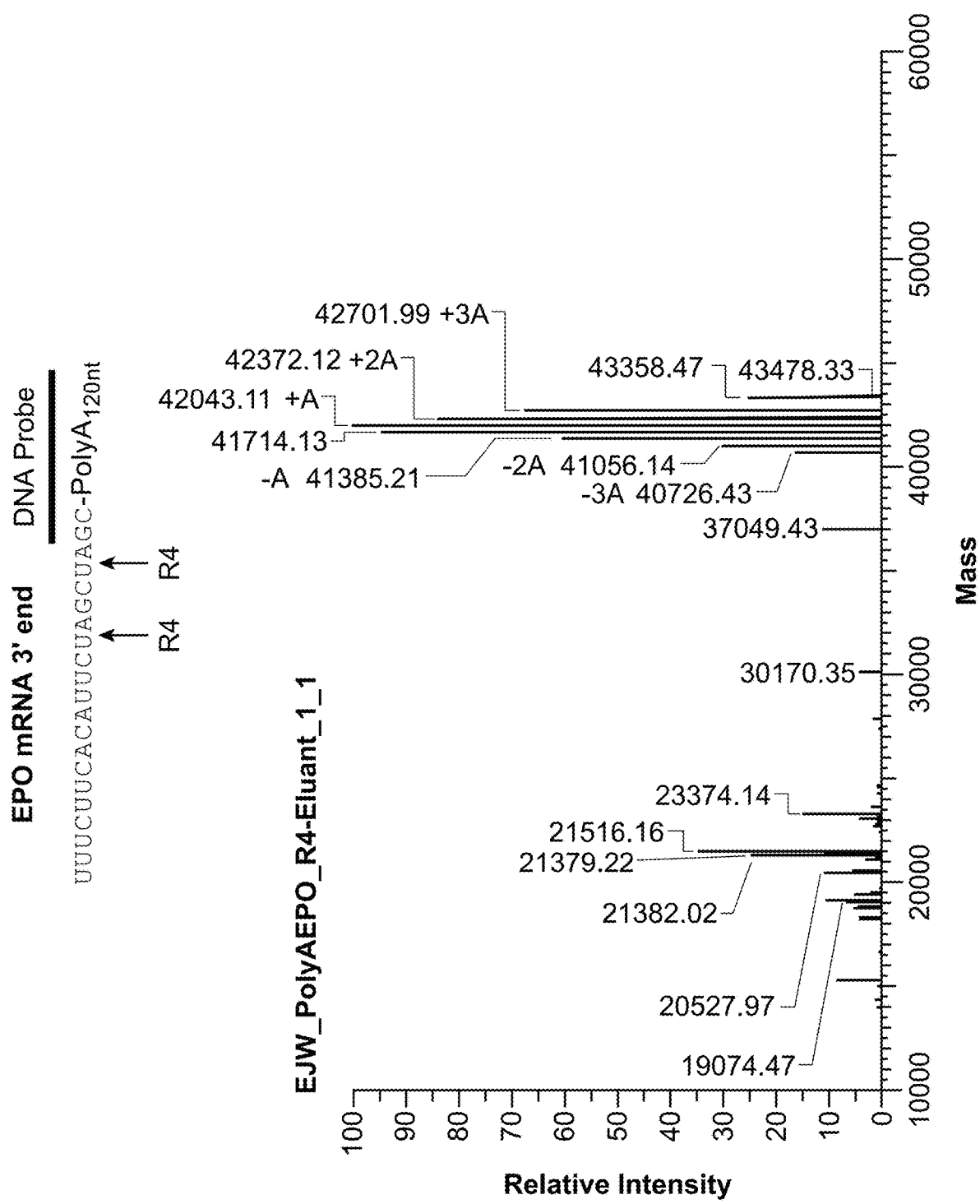
FIG. 33 illustrates an example ribonuclease protection assay applied to the analysis of 3' end of EPO mRNA (SEQ ID NO:27) using hRNase 4. A DNA probe was designed to direct RNA cleavage a few nucleotides upstream of the mRNA poly(A) tail (cleavage sites for hRNase 4 are designated with R4). The deconvoluted mass spectra of the product of the 3' end cleavage shows a distribution of peaks between 40,000 and 45,000 u that differ from each other by an adenosine (A) nucleotide and indicative of the presence of a poly(A) tail.

SEQ ID NO: 27, which is also illustrated in Table 1 and, in part, in FIG. 33, is an EPO mRNA example RNase substrate for assessing cleavage capabilities of an RNase.

SEQ ID NO: 28, which is also illustrated in Table 1, is a ClucU1 mRNA example RNase substrate for assessing cleavage capabilities of an RNase.

SEQ ID NO: 29, which is also illustrated in Table 1, is a ClucU2 mRNA example RNase substrate for assessing cleavage capabilities of an RNase.

SEQ ID NO: 30, which is also illustrated in Table 1, is a ClucU3 mRNA example RNase substrate for assessing cleavage capabilities of an RNase.

Figure 29A:
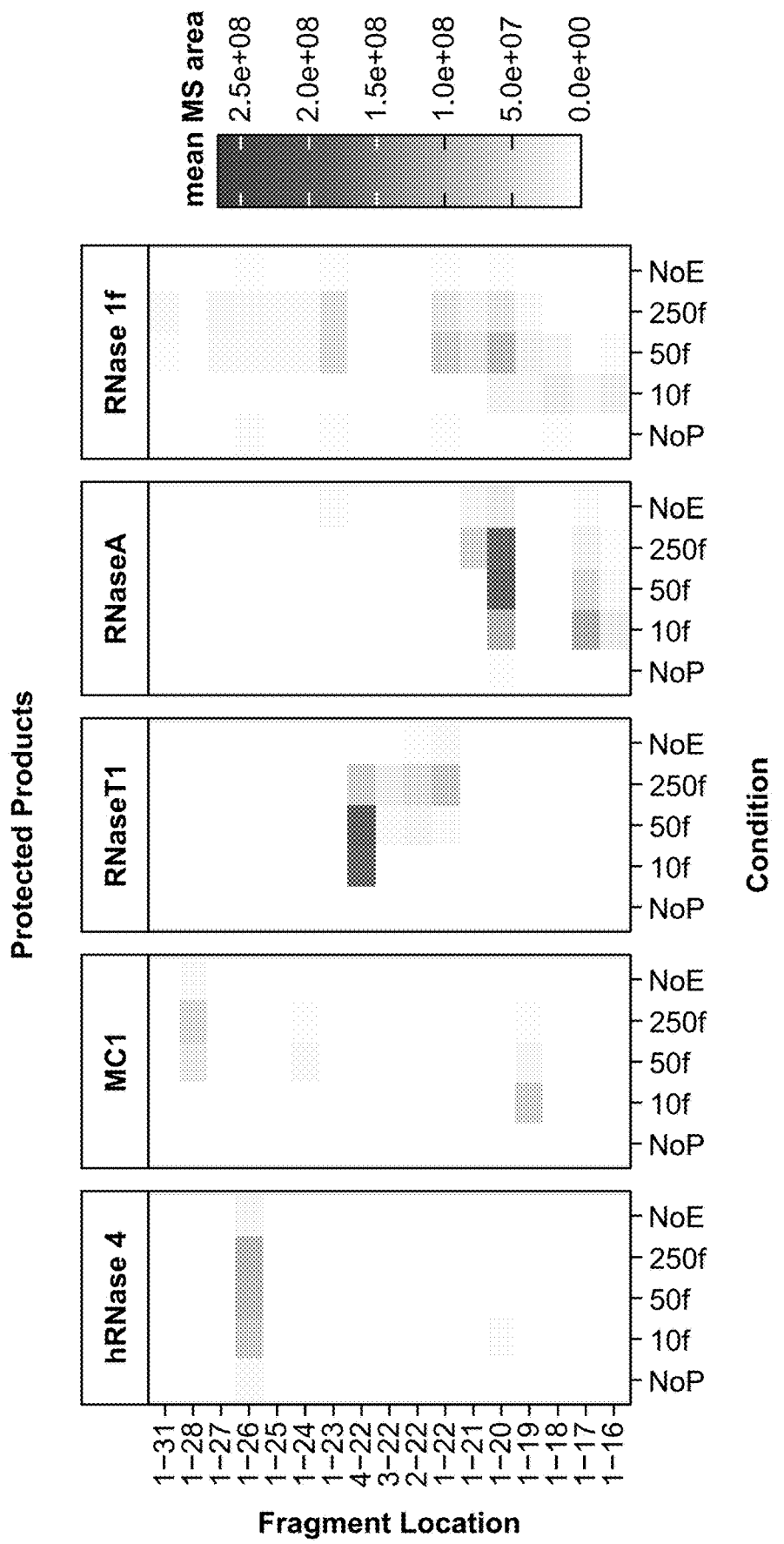
FIG. 29A illustrates a heatmap depicting oligonucleotide products from a DNA probe-directed, RNA cleavage protection assay using example nucleotide specific and dinucleotide specific single-stranded ribonucleases. 'Protected Products' refers to those oligonucleotide cleavage products spanning the DNA hybridized region. Numbers designating the start and end position of each identified cleaved oligonucleotide within the 40mer RNA sequence are shown in the y-axis. NoP: no probe; NoE: no enzyme; 10f, 50f and 250f are fold dilutions of each ribonuclease. Data shown demonstrate that the cleavage product heterogenicity is dependent on the identity and concentration of the ribonuclease utilized in the protection assay.

SEQ ID NO: 31, which is also illustrated in FIGS. 29 and 30C, is an example oligoribonucleotide for assessing cleavage capabilities of an RNase. When hybridized with an oligodeoxyribonucleotide, cleavage products may include a first fragment (e.g., consisting of positions 1-17, 1-19, 1-20, 1-21, 1-22, 1-23, 1-25, 1-26, 1-27, 1-28, 1-29, 1-30, 1-31, 1-33, 2-22, 3-22, or 4-22 of SEQ ID NO:31), one or more additional oligoribonucleotides (e.g., 4-23 nucleotides in length), and optionally one or more mono-di- and tri-ribonucleotides.

SEQ ID NO: 32 is an example DNA probe sequence for hybridization with an RNase substrate.

SEQ ID NOS: 33-42, which are also illustrated in Table 5, are example DNA probe sequences for hybridization with an RNase substrate.

SEQ ID NOS: 43-45 are example RNase 4 sequences.

SEQ ID NO: 46 is an example polynucleotide kinase sequence.

SEQ ID NOS: 47-50, which are also illustrated in Table 6, are example mRNA 5'-UTR coding sequences.

SEQ ID NOS: 52-58, which are also illustrated in Table 7, are example probe sequences used to assess probe-directed RNA cleavage of mRNAs comprising distinct 5'-UTRs.

SEQ ID NO: 59 is an example biotinylated DNA probe sequence for hybridization with an RNase substrate.

DETAILED DESCRIPTION

Precise analytical approaches may be desirable and/or necessary to directly confirm the nucleotide sequence, and the identity and position of nucleotide modifications in a subject RNA. Mass spectrometry (MS) is a technique that allows direct and comprehensive characterization of nucleic acids and their chemical modifications without any prior knowledge or assumptions (Yoluç et al., 2021). Mass spectrometry analysis of RNA may be conducted with non-hydrolyzed RNA species (top-down analysis), partially hydrolyzed RNA species (bottom-up analysis) or fully hydrolyzed RNA species (nucleoside analysis). Typically, prior to bottom-up MS analysis, RNA is partially hydrolyzed by enzymatic digestion to oligonucleotides using site-specific ribonucleases (RNases), such as RNase T1 (guanosine-specific), RNase A (pyrimidine-specific) and RNase U2 (purine-specific). The efficacy and reproducibility of RNA analysis approaches may be highly dependent on the quality and purity of RNases. However, to date just a few RNases have been fully characterized and validated for RNA analysis. Because RNases are often toxic to the expression host, the production of RNases in high yields and high purities is challenging. In many cases, the resulting RNase preparations are of low quality and sometimes may be contaminated with other undesired RNase activities, making it difficult to precisely define the RNase specific activity. In other cases, the RNase itself does not exhibit clear-cut specificity and thus produces secondary cleavage of RNA (i.e., cleavage at sites that are different from the main cleavage motif), which often increases with the RNase concentration. Furthermore, depending on the nature and concentration of the RNase(s), digestion buffer(s), and incubation time(s), a complex mixture of RNA cleavage products comprising diverse phosphorylation states at the 5' (5-prime) and 3' (3-prime) ends may be obtained (e.g., 5'-phosphate, 5-hydroxy, 3'-phosphate, 3'-hydroxy, 2'-phosphate, 2'-hydroxy, and/or 2',3'-cyclic-phosphate), thereby complicating comprehensive RNA analysis. The presence of RNA digestion products of the same or different sequence with multiple possible phosphorylation status at their ends, including non-phosphorylated ends, increases the spectral complexity and the likelihood of peak overlaps, and reduces the overall abundance of each ion.

Ribonuclease mapping may be used to determine RNA sequence and modification status by mass spectrometry. In some instances, as part of ribonuclease mapping, the protocol for RNA digestion comprises an additional step of treating the digested RNA, often (but optionally) after purification of the digested RNA, with a phosphodiesterase (e.g., a cyclic phosphodiesterase) to reduce the sample complexity. Phosphodiesterases (PDEs) are enzymes that are characterized by their ability to cleave a phosphodiester bond. Cyclic PDEs (2',3'-cyclic nucleotide phosphodiesterase, also referred as to CNPase or CNP) cleave a phosphodiester bond in 2',3'-cyclic nucleotide to form a nucleoside 2'-phosphate. Cyclic PDEs, such as human CNP, do not hydrolyze phosphate monoesters (i.e., they do not exhibit phosphomonoesterase activity).

Development of methods that not only simplify and shorten RNA processing steps prior to downstream mass spectrometry analysis, but also increase the depth of RNA analysis are desired, for example, (i) to improve the accuracy of the resulting sequence data, (ii) to enable accurate sequencing of smaller amounts of input RNA, and/or (iii) to better differentiate sequencing errors from true sequence variations. Such methods may benefit from endoribonucleases showing one or more of the following properties: (a) robust and reproducible specific activity; (b) easy to express and purify as soluble protein; (c) long shelf-life stability; (d) tolerates the presence of salts and/or denaturing agents; (e) conditionally inhibited and/or deactivated (e.g., to limit activity when desired); (f) at least moderately thermostable; (g) cleavage frequencies of, on average, every 6-12 nucleotides; (h) nominal or no spurious cleavage activity; and (i) capable of cleaving RNA modifications. Endonucleases having some or all of these properties may reduce or minimize the extent of the formation of isomeric digestion products and/or increase the sequence coverage of long, complex RNAs.

The present disclosure relates, in some embodiments, to methods and compositions for RNA characterization, which may include, for example, chromatographic and/or spectroscopic characterization. For example, methods and compositions may include RNA analysis or characterization (e.g., sequencing) by LC-MS/MS. Methods and compositions, according to some embodiments, may include and/or use human endoribonuclease 4. In some embodiments, compositions and methods may include one or more endoribonucleases and one or more RNA end repair enzymes that work (e.g., work concurrently) to recognize, cleave, and heal specific RNA sequences and may produce from a RNA substrate oligoribonucleotides having fully hydroxylated ends (i.e., RNA oligonucleotides comprising 5'-OH, 3'-OH, and 2'-OH termini).

In some embodiments, the present disclosure relates to methods and compositions for analyzing RNA substrates using, for example, tandem liquid chromatography-mass spectrometry (e.g., LC-MS/MS). Methods may include, for example, preparing oligoribonucleotides from RNA substrates and analyzing the oligoribonucleotides. Compositions and kits to produce oligoribonucleotides may comprise one or more components according to some embodiments. For example, compositions and kits to produce oligoribonucleotides may comprise one or more enzymes or catalysts active on RNA substrates including, for example, an endoribonuclease (e.g., human endoribonuclease 4) and an RNA end repair enzyme (e.g., bacteriophage T4 polynucleotide kinase (T4 PNK)). Compositions and kits to produce oligoribonucleotides may comprise one or more buffering agents and/or one or more RNA denaturing agents. Compositions and methods, in some embodiments, have application to analysis of RNA-based cancer immunotherapies, protein-replacement therapies, and prophylactic and therapeutic vaccines.

General Considerations

Aspects of the present disclosure can be further understood in light of the embodiments, section headings, figures, descriptions and examples, none of which should be construed as limiting the entire scope of the present disclosure in any way. Accordingly, the innovations set forth herein should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible. Unless otherwise expressly stated to be required herein, each component, feature, and method step disclosed herein is optional and the disclosure contemplates embodiments in which each optional element may be expressly excluded. As such, this statement is intended to serve as antecedent basis for use of such exclusive terminology as "solely," "only" and the like in connection with the recitation of claim elements or use of a "negative" limitation.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

In the context of the present disclosure, the singular forms "a" and "an" include plural referents unless the context clearly dictates otherwise. For example, the term "a protein" refers to one or more proteins, i.e., a single protein and multiple proteins.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified. Concentration percentages are disclosed as (w/v) unless expressly stated otherwise.

Definitions

In the context of the present disclosure, an "affinity capture domain" refers to a domain capable of binding a corresponding affinity domain. Example materials having such properties include avidin, streptavidin, neutravidin, maltose-binding protein, GST, antibodies (e.g., anti-HA, anti-Myc, anti-FLAG), S-protein, calmodulin, lectins, nickel, cobalt, zinc, and poly-histidine. Further examples include groups that form an irreversible bond with a protein tag, including benzylguanine or benzylchoropyrimidine (SNAP-tag); benzoylcytosine (CLIP-tag); haloalkane (HaloTag); CoA analogues (MCP-tag and ACP-tag); trimethoprim or methotrexate (TMP-tag); FlAsH or ReAsH (Tetracysteine tag); a substrate of biotin ligase; a substrate of phosphopantetheine transferase; and a substrate of lipoic acid ligase. An affinity capture method may be used for selectively enriching samples by means of affinity purification methods, wherein the affinity binding partner is immobilized in a column, bead, microtiter plate, membrane or other solid support.

In the context of the present disclosure, an "affinity domain" refers to a domain capable of binding a corresponding affinity capture domain with high affinity (e.g., at least $10^{-8}$ M) and specificity. Example materials having such properties include biotin, DBT, desthiobiotin, oxybiotin, iminobiotin, diaminobiotin, biotin sulfoxide, biocytin, digoxigenin, glutathione, heparin, maltose, coenzyme A, protein A, Brilliant Blue FCF, azaribine, phytoestrogen, nickel, cobalt, zinc, poly-histidine, HA-tag, c-myc tag, FLAG-tag, S-tag, CBP-tag, dihydrofolate reductase, a hapten to an antibody, a mono- or oligosaccharide ligand to a lectin, hormones, cytokines, toxins, dyes, and vitamins. Such molecules may be fused with a molecule to be marked as desired. For example, an affinity domain may be fused to the 5' end, the 3' end, or anywhere along the length of a polyribonucleotide.

In the context of the present disclosure, "buffer" or "buffering agent" refers to an agent that, when in solution or in contact with a solution, contributes to or causes such solution to resist changes in pH upon addition of acid(s) or alkali(s) to the solution. Examples of suitable non-naturally occurring buffering agents that may be used include, for example, any of Tris, HEPES, TAPS, MOPS, tricine, and MES.

In the context of the present disclosure, "coupled reaction" refers to a reaction in which two or more reaction steps occur in a single reaction mixture and in a single reaction location (e.g., a tube, a container, a vessel, a well, a capillary, a flow cell, a surface or other space) or separate locations that are in fluid communication with one another (e.g., where enzymes are deposited in separate locations on a surface and the locations are immersed in a common fluid comprising, for example, one or more substrates, buffers, reaction intermediates, and/or reaction products). A reaction location may be defined by one or more walls (e.g., of a tube), a liquid (e.g., a liquid immiscible with a reaction fluid), a fluid (e.g., a gas including, for example gaseous nitrogen or air), a vacuum, or combinations thereof. Sequential reaction steps in a coupled reaction may begin and/or continue without changes to reaction conditions (e.g., without addition or removal of reagents, changes in temperature, pH, volume, or washing) beyond those that arise or follow from the reactions themselves.

In the context of the present disclosure, "denaturing agent" or "RNA denaturing agent" refers to an agent that, in contact with RNA, disrupts intramolecular hydrogen bonding in the RNA by melting existing hydrogen bonds, if present, and/or interfering with formation of new hydrogen bonds. An RNA denaturing agent may lack any ribonuclease activity. Examples of RNA denaturing agents include formamide, dimethylformamide (DMF), guanidinium thiocyanate, sodium salicylate, dimethyl sulfoxide (DMSO), propylene glycol, poly(ethylene glycol) (PEG), cetyltrimethylammonium bromide (CTAB), and urea.

In the context of the present disclosure, "DNA probe" refers to a oligodeoxyribonucleotide having a length of 10-20 nucleotides, 10-30 nucleotides, 10-40 nucleotides, 10-50 nucleotides, or 10-200 nucleotides. A DNA probe may comprise a sequence complementary to an RNA substrate or complementary to any portion along the length of an RNA substrate. A DNA probe sequence may be selected to bind to an RNA substrate or bind to a specific portion of an RNA substrate. For example, a DNA probe may have a sequence complementary to an RNA sequence at or near (e.g., within 1-5, 1-10, 1-15, or 1-20 nucleotides of) the 5' end of the RNA, at or near (e.g., within 1-5, 1-10, 1-15, or 1-20 nucleotides of) the 3' end of the RNA, or positioned between the 5' and 3' ends. A DNA probe may comprise a sequence complementary to an RNA sequence comprising and/or adjacent (e.g., within 3-15, 4-14, 5-13, or 6-12 nucleotides of and on the 5' or 3' side) to one or more endoribonuclease cut sites. When hybridized to a complementary RNA sequence, a DNA probe may limit or block access to one or more endoribonuclease cut sites (e.g., within the duplex) without limiting or blocking access to one or more other endoribonuclease cut sites (e.g., outside the duplex). A DNA probe sequence may be selected or configured to produce one or more endoribonuclease digestion products having one or more desired properties (e.g., length, 5' fragment, 3' fragment). A DNA probe and an RNA substrate may form a duplex flush with the 5' end of the RNA, offset from the 5' end by 1-5, 1-10, 1-15, or 1-20 nucleotides, flush with the 3' end of the RNA, or offset from the 3' end by 1-5, 1-10, 1-15, or 1-20 nucleotides.

A DNA probe may comprise solely deoxyribonucleosides or may comprise mostly deoxyribonucleosides with one or more ribonucleosides (e.g., a chimeric probe for use with RNase H). A DNA probe may comprise solely phosphate linkages or may include one or more alternate linkages (e.g., phosphorothioate). A DNA probe may comprise solely canonical nucleotides or may comprise one or more modified nucleotides. For example, a DNA probe may comprise one or more affinity tags (e.g., biotin).

In the context of the present disclosure, "fusion" refers to two or more polypeptides, subunits, or proteins covalently joined to one another (e.g., by a peptide bond). For example, a protein fusion may refer to a non-naturally occurring polypeptide comprising a protein of interest covalently joined to a second polypeptide. A second polypeptide may confer upon the fusion one or more desirable properties over the protein of interest alone. For example, a second polypeptide may provide an additional binding property (e.g., an affinity and/or purification tag), a selection and/or detection tag (e.g., a reporter protein) Examples of a second polypeptide include a reporter protein, a purification tag (e.g., maltose binding protein, a histidine tag), and expression tag, a polynucleotide binding protein, an enzyme, a conjugation tag (e.g., a SNAP® tag), and a peptide linker. Unless otherwise disclosed, the protein of interest may be nearer to the N-terminal end or nearer to the C-terminal end than the second polypeptide to which it is joined. A fusion may comprise a non-naturally occurring combined polypeptide chain comprising two proteins or two protein domains joined directly to each other by a peptide bond or joined through a peptide linker. An example fusion may include an MBP and an hRNA4.

In the context of the present disclosure, "human endoribonuclease 4" refers to a human protein encoded by the RNASE4 gene, having endoribonuclease activity, and cutting RNA at UR. It is an example of a strand-specific, sequence specific endoribonuclease and an example of an RNase 4. Human endoribonuclease 4 may also be referred to as "hRNase 4", "*Homo sapiens* RNase4", "hRNase IV", "hRNase4", or "Hs RNase4". hRNase 4 is one of the eight members of the human RNase A superfamily of endoribonucleases (Lu et al., Immune Modulation by Human Secreted RNases at the Extracellular Space, Front Immunol. 2018, 9:1012). hRNase 4 retains a high interspecies homology within mammals, and shares conserved structural features with non-mammalian vertebrate RNases. Example hRNase 4 amino acid sequences include SEQ ID NOS:

43-45. hRNase 4 shows strong selectivity for RNA recognition with preference for uridine at the main binding site. hRNase 4 preference for uridine over cytidine in comparison to other family members can be correlated with some structural features at the binding pocket, such as the presence of an asparagine residue at position 80. Substitution of Asp80 to alanine reduces preference for uridine over cytidine.

In the context of the present disclosure, "immobilized" refers to covalent attachment to a solid support with or without a linker. Examples of solid supports include beads (e.g., magnetic, agarose, polystyrene, polyacrylamide, chitin). Beads may include one or more surface modifications (e.g., $O^6$-benzylguanine, polyethylene glycol) that facilitate covalent attachment and/or activity of an enzyme of interest. For example, a support may comprise a ligand and an enzyme may have a receptor for such ligand or an enzyme may comprise a ligand and a support may comprise a receptor for such ligand. Receptor-ligand binding may be covalent or non-covalent. Non-covalent attachment (e.g., avidin:biotin, chitin:CBP) may be useful in some embodiments, for example, where the level of dissociation of the binding partner is deemed tolerable. A linker may be disposed, for example, between a support and an enzyme or between a support and a DNA probe. For example, a linker disposed between a support and an enzyme may have a first covalent bond to the support and a second covalent bond to the enzyme. An immobilized enzyme comprising a ligand-receptor attachment may have a linker disposed between the support and the ligand-receptor attachment, a linker disposed between the enzyme and the ligand-receptor attachment, or both. An immobilized enzyme comprising a linker may also comprise an optional covalent bond directly between the enzyme and the support. A linker may be of any desired length and have any desired range of motion. A peptide linker may comprise one or more repeats (e.g., 1-10 repeats) of glycine-serine.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) lacking one or more components otherwise found in naturally occurring compositions (e.g., a cell-free composition, a chromosome-free composition, a histone-free composition, a polymerase-free composition, a cell membrane-free composition, a lyophilized composition), (d) having a form not found in nature, e.g., dried, freeze dried, crystalline, aqueous, and (e) having one or more additional components beyond those found in nature (e.g., buffering agents, a detergent, a dye, a solvent or a preservative).

In the context of the present disclosure, "nucleotide" refers to a molecule comprising a base, a sugar and one or more phosphate groups. A base (also referred to as a "nitrogenous base" or a "nucleobase") may be a purine or pyrimidine. A sugar may be a five-carbon ribose (as in ribonucleotides) or a 2-deoxyribose (as in deoxyribonucleotides), which is bound via a glycosidic linkage to the base. Nucleotides may have one, two or three phosphate groups (mono-, di- or triphosphates). Phosphate groups may form a chemical bond at the 5-carbon position of the sugar, although they may also bond at the 2 or 3-carbon positions of the sugar group. Cyclic nucleotides form when a phosphate group is bound to two hydroxyl groups on the sugar. A "nucleoside" comprises a nucleobase and sugar. A nucleotide may also be called a nucleoside mono-, di- or triphosphate.

In the context of the present disclosure, "oligoribonucleotide" refers to a polymer of ribonucleotides that are less than 500 nucleotides long, less than 200 nucleotides long or less than 100 nucleotides long. For example, oligoribonucleotides may be 4-80 nucleotides long, 4-60 nucleotides long, or 4-40 nucleotides long. An oligoribonucleotide may be an RNA substrate.

In the context of the present disclosure, "ribonuclease" or "RNase" refers to a nuclease that catalyzes the cleavage of RNA into smaller components. Ribonucleases include endoribonucleases and exoribonucleases. Ribonucleases may cleave single-stranded RNA, double-stranded RNA, or single-stranded RNA and double-stranded RNA. Examples of ribonucleases may include hRNase 4, RNase T1, RNase U2, RNase A, Colicin E5, MC1, Cusativin, Csx1, MazF, ChpB, MqsR, and YafO. Different specificities, cleavage frequencies, activities, salt tolerance, temperature sensitivities, and other factors may favor using one or more endoribonucleases. Thus, according to some embodiments, methods and compositions may exclude one or more of the foregoing example ribonucleases.

An endoribonuclease may have mononucleotide specificity, dinucleotide specificity, trinucleotide specificity, or higher nucleotide specificity. In this context, an endoribonuclease with a single dinucleotide specificity might be expected to cleave RNA substrates (having a random distribution of all 4 bases within their sequences) on average once every 16 nucleotides. An endoribonuclease having specificity for one or more dinucleotide or trinucleotide combinations may cleave an RNA substrate more frequently, for example, on average once every 6 to 12 nucleotides, for example on average once every 8 nucleotides (e.g., calculated with reference to an RNA substrate having a random distribution of all 4 bases within its sequence). Examples of endoribonucleases with specificity for one or more dinucleotide combinations are those whose specificity comprise a main nucleotide anchoring site (referred as B1 site) and a secondary nucleotide binding site (referred as B2 site). In some embodiments, a selected endoribonuclease is capable of cleaving a 3',5' phosphodiester bond between B1 and B2 sites with selectivity for one of: uridine at the main anchoring site B1 and pyrimidines at the secondary site B2; or cytidine at the main anchoring site B1 and pyrimidines at the secondary site B2; or adenosine at the main anchoring site B1 and pyrimidines at the secondary site B2; or guanosine at the main anchoring site B1 and pyrimidines at the secondary site B2; or uridine at the main anchoring site B1 and purines at the secondary site B2; or cytidine at the main anchoring site B1 and purines at the secondary site B2; or adenosine at the main anchoring site B1 and purines at the secondary site B2; or guanosine at the main anchoring site B1 and purines at the secondary site B2. Example endoribonucleases include those whose specificity comprise a secondary nucleotide binding at the B1 site and a main nucleotide anchoring binding at the B2 site. Such examples include endoribonucleases that are capable of cleaving a 3',5' phosphodiester bond between B1 and B2 sites with selectivity for one of: purines at the secondary site B1 and uridine at the main anchoring site B2; or purines at the secondary site B1 and cytidine at the main anchoring site B2; or purines at the secondary site B1 and adenosine at the main anchoring site B2; or purines at the secondary site B1 and guanosine at the main anchoring site B2; or pyrimidines at the secondary site B1 and uridine at the main anchoring site B2; or pyrimidines at the secondary site B1 and cytidine at the main anchoring site B2; or pyrimidines at the secondary site B1 and adenosine at the main anchoring site B2; or pyrimidines at the secondary site B1 and guanosine at the main anchoring site B2. Representative examples of such endoribonucleases are *Homo sapiens* (Hs) RNase4 (preferentially cleaves uridine at B1 position and either adenosine or guanosine at B2 position); Hs RNases 2, 3, 6, and 7 (cleave either uridine or cytidine at B1 position with strong preference for adenosine at B2 position); and *Rana pipiens* (Rp) RNase, *Chelonia mydas* (Cm) RNase1, and *Gallus gallus* (Gg) RNase1 (cleave either uridine or cytidine at B1 position with preference for guanosine at B2 position). In some examples, the endoribonuclease may present a mild preference for a given nucleotide at B1 or B2 positions, and this preference may be tuned in such a way (for example, by dilution of enzyme concentration, by buffer change, by pH change, or by temperature change) that the endonuclease may effectively cleave at frequencies that are on average once every 6 to 12 nucleotides. Those examples include endoribonucleases such as Hs RNase5 (cleaves either uridine or cytidine at B1 position with mild preference for adenosine over guanosine at B2 position). An endoribonuclease may have any desired form, for example, a fluid form (e.g., with or without glycerol), a lyophilized form, a dried form, and/or an immobilized form.

In the context of the present disclosure, "ribonuclease inhibitor" or "RNase inhibitor" refers to a material that reduce (e.g., partially or completely) the RNA cleavage activity of a ribonuclease. Examples of endoribonuclease inhibitors include human placental RNase inhibitor, murine RNase inhibitor, ribonucleoside-vanadyl complex, guanidine thiocyanate, IRE1 RNase inhibitor, diethyl pyrocarbonate (DEPC), egtazic acid (EGTA), ethylenediaminetetraacetic acid (EDTA), and any combination thereof. A ribonuclease inhibitor may have any desired form, for example, a fluid form (e.g., with or without glycerol), a lyophilized form, a dried form, and/or an immobilized form. A ribonuclease inhibitor may bind to a ribonuclease (e.g., a susceptible ribonuclease) with high affinity, for example, an affinity similar to the affinity of avidin and biotin.

In the context of the present disclosure, "RNA end repair" refers to a process of converting RNA phosphorylated ends (e.g., cyclic and/or linear phosphorylated ends) into RNA hydroxylated ends (e.g., 5'-OH, 2'-OH and/or 3'-OH ends). RNA end repair, in the context of the present disclosure, excludes ligation of 5' and 3' ends to one another.

In the context of the present disclosure, "RNA end repair enzyme" refers to an enzyme that performs RNA end repair and comprises both phosphodiesterase (PDE) and phosphomonoesterase (PME) activities. An RNA end repair enzyme may maintain or manipulate RNA structure in response to RNA breakage events. RNA end repair enzymes are present in diverse taxa in all phylogenetic domains of life and repair RNA breaks inflicted by sequence-specific or structure-specific endoribonucleases during physiological RNA processing (e.g., tRNA splicing; kinetoplast mRNA editing) and under conditions of cellular stress (e.g., virus infection; unfolded protein response). A repair enzyme may resolve 2',3'-cyclic-phosphorylated oligoribonucleotide ends, 3'-phosphorylated oligoribonucleotide ends and/or 2'-phosphorylated oligoribonucleotide ends. A repair enzyme may have any desired form, for example, a fluid form (e.g., with or without glycerol), a lyophilized form, a dried form, and/or an immobilized form.

Examples of RNA end repair enzymes include polynucleotide kinases including polynucleotide kinase-phosphatase (Pnkp) enzymes with 5'-hydroxyl kinase, 3'-phosphatase and/or 2',3'-cyclic phosphodiesterase activities that function in nucleic acid repair. Similar proteins are found in many species, including Enterobacterial phage (such as phages RB55 and RB59), *Desulfovibrio* sp, *Shigella* phage, *Escherichia* phage, *Yersinia* phage, *Bacillus cereus*, *Salmonella* phage, *Citrobacter* phage, *Serratia* phage, *Vibrio* phage, *Aeromonas* phage, *Acinetobacter* phage, *Klebsiella* phage, *Stenotrophomonas* phage, and *Staphylococcus aureus* (AAA family ATPase). The PNKP gene (named pseT) is conserved in many species, including *H. sapiens*, chimpanzee, Rhesus monkey, dog, cow, mouse, rat, zebrafish, fruit fly, *C. elegans*, *S. pombe*, *M. oryzae*, *N. crassa*, and frog. Example PNKs in this family of enzymes include bacteriophage T4 polynucleotide kinase (T4 PNK; also referred as to T4 polynucleotide kinase-phosphatase or T4 Pnkp) (Das and Shuman, 2013) and *Clostridium thermocellum* (Cth) polynucleotide kinase-phosphatase. An example RNA end repair enzyme amino acid sequence is SEQ ID NO:46.

T4 PNK heals 2',3'-cyclic-phosphorylated oligoribonucleotide ends, 3'-phosphorylated oligoribonucleotide ends, and 2'-phosphorylated oligoribonucleotide ends, in each case, resulting in products that comprise a 2',3'-hydroxylated (2'-OH, 3'-OH) end. In vivo, T4 PNK heals broken tRNA ends through (i) hydrolysis of a 2',3'-cyclic phosphate to a 3'-hydroxy end and (ii) phosphorylation of a 5'-hydroxy (via its polynucleotide kinase activity) to form a 5'-phosphate end (these tRNA healed ends are eventually sealed by another enzyme, RNA ligase 1, Rnl1). Phosphorylation of the 5'-OH (kinase activity) may be NTP-dependent (e.g., ATP-dependent). For example, phosphorylation of the 5'-OH may not occur without an NTP, which produces healed ends comprising 5'-OH, 2'-OH and/or 3'-OH. In vitro, T4 PNK is capable of phosphorylating the 5' end of double- and single-stranded RNA or DNA.

Cth PNK is a multifunctional enzyme that belongs to a family of RNA end-healing enzymes found in diverse bacteria. Cth PNK has three catalytic modules: (i) an N-terminal polynucleotide 5'-kinase; (ii) a central 2',3'-phosphatase; and (iii) a C-terminal ligase (Das and Shuman, 2013). As with T4 PNK, Cth PNK converts an RNA 2'-phosphate, 3'-phosphate, or a 2',3'-cyclic phosphate end to an RNA product comprising a 2'-OH, 3'-OH end by means of its phosphodiesterase and phosphomonoesterase activities. Cth PNK may use either Mn(II) or Ni(II) as a metal cofactor.

In the context of the present disclosure, "RNA substrate" refers to any composition including one or more ribonucleotide (RNA) species of one or more lengths from one or more sources. An RNA substrate may be obtained from one or more sources, including viruses, prokaryotic cells, eukaryotic cells, or archaea cells. An RNA substrate may arise from or include any biological material (e.g., solid, fluid, aerosol) including organs, tissues, tissue cultures, biopsies, blood, lymph, mucous, sputum, skin, saliva, lesions, swabs, sweat, semen, urine, feces, and secretions. Biological materials may be fresh or processed (e.g., embedded with a paraffin or other support). An RNA substrate may arise from or include an environmental sample (e.g., air, water, soil, and/or biota or other substrate), food materials, agricultural materials, medical materials, and/or waste products. An RNA substrate may arise from or include RNA from in-vitro transcription (e.g., by the use of RNA polymerases) and/or from chemical synthesis (e.g., by the use of phosphoramidite chemistry or related processes).

An RNA substrate may comprise solely ribonucleosides or may comprise mostly ribonucleosides with one or more deoxyribonucleosides. An RNA substrate may comprise solely phosphate linkages or may include one or more alternate linkages (e.g., phosphorothioate). An RNA substrate may comprise solely canonical nucleotides or may comprise one or more modified nucleotides. For example, an RNA substrate may comprise one or more adenosines, cytidines, guanosines, uridines, 1-methyladenosines, 2-methyladenosines, $N^5$-methyladenosines, 5-methylcytidines, 5-hydromethylcytidines, wyosines, 1-methylguanosines, 7-methylguanosines, pseudouridines, 1-methypseudouridines, 5-methyluridines, and/or 5-hydroxyuridines. An RNA substrate may have any desired length. For example, an RNA substrate may have over 50 nucleotides, over 100 nucleotides, or over 200 nucleotides. An RNA substrate may have 50-500 nucleotides, 100-1000 nucleotides, or 200-2000 nucleotides. An RNA substrate may have 1000-5000 nucleotides, 5000-9000 nucleotides, or 9000-22000 nucleotides. An RNA substrate may be linear, folded, or circular. An RNA substrate may comprise one or more endoribonuclease cut sites.

An RNA substrate may comprise, according to some embodiments, a plurality of RNA species, including one or more of in vitro transcribed RNA, artificially synthesized RNA by chemical methods, or RNA obtained from native sources. An RNA substrate may include RNA pol I transcripts, RNA pol II transcripts, RNA pol III transcripts, nascent RNA, primase, prokaryotic RNA polymerase, or any combination thereof. In some embodiments, an RNA substrate may comprise a plurality of RNA species including one or more of single-stranded or double-stranded RNAs. An RNA substrate may arise from or include messenger RNA (mRNA), ribosomal RNA (rRNA), transfer RNAs (tRNAs), small RNA (sRNA), microRNA (miRNA), long non-coding RNA (lncRNA), circular RNA (circRNA), or any combination thereof.

An RNA substrate may include mature and/or nascent RNA species. An RNA substrate may comprise RNAs that are capped or uncapped (eukaryotic mRNAs, except for nascent transcripts and mature uncapped RNA, exhibit a 5'-Gppp cap; archaeal and bacterial mRNAs are typically uncapped and exhibit a terminal 5' triphosphate). The RNA may be naturally or artificially capped (for example with a 5'-m7Gppp cap).

All publications, patents, and patent applications mentioned in this specification are herein incorporated by reference to the same extent as if each individual publication, patent, or patent application was specifically and individually indicated to be incorporated by reference. Reagents referenced in this disclosure may be made using available materials and techniques, obtained from the indicated source, and/or obtained from New England Biolabs, Inc. (Ipswich, MA).

Compositions

The present disclosure provides, in some embodiments, compositions for analyzing and characterizing RNA. Compositions may include, according to some embodiments, one or more RNA substrates, one or more endoribonucleases (naturally-occurring or non-naturally occurring variants; having specificity for one or more dinucleotide or trinucleotide combinations, for example, cleaving an RNA substrate on average once every 6 to 12 nucleotides), one or more RNA end repair enzymes (naturally-occurring or non-naturally occurring variants), or combinations thereof. In some embodiments, compositions may comprise one or more of an RNA substrate, an endoribonuclease, and an RNA end repair enzyme, wherein the RNA end repair enzyme is capable of healing RNA ends. For example, a composition may comprise an RNA substrate and an endoribonuclease, an RNA substrate, an endoribonuclease, and an RNA end repair enzyme, or an endoribonuclease and an RNA end repair enzyme.

Compositions may include, according to some embodiments, one or more buffering agents. Compositions with a buffer may have, for example, a pH of 5-9, 6-8, 6.7-7.4, 6.8-7.3, 6.8-8.0, 7.0-8.2, 7.0, 7.5, or 8.0. In some embodiments, a composition may include a metal ion, examples of which include magnesium(II), manganese(II), cobalt(II), or nickel(II).

In some embodiments, compositions may include one or more RNA denaturing agents including, for example, 0.5 M-4 M urea (e.g., 1 M urea). A composition may comprise, for example, less than 0.5 M urea, less than 0.75 M urea, less than 1.0 M urea, less than 2.0 M urea, less than 3.0 M urea, less than 4.0 M urea, less than 5.0 M urea, less than 6.0 M urea, less than 7.0 M urea, less than 8.0 M urea, 8.0 M urea, more than 7.0 M urea, more than 8.0 M urea. A composition may comprise, for example, less than 10% formamide, less than 15% formamide, less than 20% formamide, less than 25% formamide, less than 30% formamide, less than 35% formamide, less than 40% formamide, less than 45% formamide, less than 50% formamide, less than 55% formamide, more than 50% formamide, or more than 55% formamide. For example, a composition may include an endoribonuclease (e.g., an endoribonuclease having specificity for one or more dinucleotide or trinucleotide combinations, for example, cleaving an RNA substrate on average once every 6 to 12 nucleotides) and one or more RNA denaturing agents.

In some embodiments, a composition may comprise an RNA substrate in any amount and/or at any concentration. For example, a composition may comprise less than 1 ng, less than 1 μg, less than 2 μg, less than 3 μg, less than 4 μg, less than 5 μg, less than 6 μg, less than 7 μg, less than 8 μg, less than 9 μg, less than 10 μs, less than 11 μg, less than 12 μg, less than 13 μg, less than 14 μg, less than 15 μg, less than 16 μg, less than 17 μg, less than 18 μg, less than 19 μg, less than 20 μg, 20 μg, more than 19 μg, or more than 20 μg. A fluid composition may comprise, for example, less than 1 ng/μL, less than 1 μg/μL, less than 2 μg/μL, less than 3 μg/μL, less than 4 μg/μL, less than 5 μg/μL, less than 6 μg/μL, less than 7 μg/μL, less than 8 μg/μL, less than 9 μg/μL, less than 10 μg/μL, less than 11 μg/μL, less than 12 μg/μL, less than 13 μg/μL, less than 14 μg/μL, less than 15

µg/µL, less than 16 µg/µL, less than 17 µg/µL, less than 18 µg/µL, less than 19 µg/µL, less than 20 µg/µL, 20 µg/µL, more than 19 µg/µL, or more than 20 µg/µL.

An RNA substrate, in some embodiments, may comprise a subject RNA and one or more additional materials (e.g., impurities and/or supports). For example, an RNA substrate comprising a synthetic RNA may also comprise impurities resulting from the process of in vitro synthesizing the RNA, either via an enzymatic process or a chemical process or a combination of both processes. An RNA substrate comprising a native RNA may also comprise impurities from or associated with the isolation or enrichment method including, for example, partially degraded or fragmented RNA species, undesired RNA species (e.g., contaminant ribosomal RNA in a mRNA preparation), DNA, and/or proteins. An RNA substrate may comprise RNA and a solid support (e.g., magnetic or non-magnetic polymeric beads), for example, where the RNA is attached to the solid support through its 5' end, through its 3' end or through an internal nucleotide, in each case, with or without an optional linker (e.g., a linear or branched linker). An optional linker may serve as steric spacer and does not necessarily have to be of defined length. Examples of suitable linkers may be selected from any of the hetero-bifunctional cross-linking molecules described by Hermanson, Bioconjugate Techniques, 2nd Ed; Academic Press: London, Bioconjugate Reagents, pp 276-335 (2008), incorporated by reference. An optional linker may be a flexible linker connecting the solid support to one or a plurality of same or different RNAs.

An endoribonuclease may be expressed in *E. coli*, such as the periplasm of *E. coli*, or *Pichia pastoris* and purified utilizing an affinity tag. In some embodiments, an endoribonuclease may have a discrete substrate specificity. For example, an endoribonuclease may have the capacity to cleave an RNA 3',5' phosphodiester bond with specific activity towards a nucleotide or a combination of one or more nucleotide sequences comprising 2-7 nucleotides each; or towards a structural element such as a stem, an internal loop, a multibranch loop, or a pseudoknot. In some respects, the substrate specificity of an endoribonuclease may include recognition and cleavage of one or more modified nucleotides (e.g., pseudouridine, 1-methylpseudouridine, 5-methoxyuridine, 5-methylcytidine, 6-methyladenosine, and inosine). RNA end repair enzymes, in some embodiments, may have both phosphodiesterase and phosphomonoesterase activities.

In some embodiments, a composition comprising an RNA end repair enzyme and an endoribonuclease, optionally in a denaturing buffering solution, may be used to prepare oligoribonucleotide mixtures from an RNA substrate. In some embodiments, a composition of T4 PNK and an endoribonuclease, optionally in a denaturing buffering solution, is used to prepare oligoribonucleotide mixtures from an RNA substrate. Optionally, pre-heating the RNA substrate and/or including an RNA denaturing agent in the reaction mixture may reduce the impact of RNA structure (e.g., Watson-Crick base pairing and/or other intra- and/or intermolecular hydrogen bonding) on the production of endoribonuclease digestion products.

Compositions, according to some embodiments, may include one or more endoribonucleases that are capable of cleaving 3',5' phosphodiester bonds with specific activity towards a nucleotide or a sequence of one or more nucleotides, towards one or more nucleotide modifications, or towards a structural element such as a stem, an internal loop, a multibranch loop, a pseudoknot, a duplex segment, a triplex segment, or a quadruplex segment. Examples include endoribonucleases of the RNase A superfamily that cleave a 3',5' phosphodiester bond with specificity for pyrimidines at the main anchoring site (often called B1 site) and preference for purines at the secondary site (often called B2 site). Illustrative examples are hRNase5 (cuts both uridine and cytidine at B1 position and shows only a mild preference for adenosine over guanosine at B2 position), hRNase 4 (shows a significant preference for cutting uridine at B1 position and a minor preference for adenosine over guanosine at B2 position), and hRNases 2, 3, 6, and 7 (cut both uridine and cytidine at B1 position and do not have any detectable activity for guanosine at B2 position). Other examples include mutant endoribonucleases, such as porcine RNase4 D80A, wherein the substitution of Asp80 by alanine decreased the preference for cutting uridine at B1 position and increased the preference for cutting cytidine at B1 position. Further examples of endoribonucleases with specificity for pyrimidines at the main anchoring site B1 are some enzymes of the RNase T2 family, such as RNase MC1, which has been isolated from seeds of *Momordica charantia* (specificity for uridine at B1 position), and RNase Cusativin, which has been isolated from *Cucumis sativus* (specificity for uridine at B1 position).

Examples of endoribonucleases include endoribonucleases that are capable of cleaving a 3',5' phosphodiester bond with specificity for purines at the main anchoring site B1. Examples are endoribonucleases of the RNase T1 superfamily (specificity for guanosine at B1 position), RNase U2 (purine-specific at B1 position), and Csx1 (specificity for adenosine at B1 position).

Examples of endoribonucleases also include endoribonucleases that are part of toxin-antitoxin systems in bacteria or archaea. Endoribonucleases that are part of toxin-antitoxin systems may have a wider recognition cleavage site. Examples of endoribonucleases that are part of toxin-antitoxin systems include *E. coli* MazF (preferentially cuts before ACA trinucleotide motif), ChpB (preferentially cuts after uridine in UAC trinucleotide motiftrinucleotide), MqsR (preferentially cuts after guanosine in GC dinucleotide motif), and YafO (preferentially cuts after uridine). In some embodiments, endoribonucleases include thermostable endoribonucleases, for example, endoribonucleases that are active at temperatures above 50° C., above 55° C., above 60° C., above 65° C., above 70° C., above 80° C., or above 90° C. Endoribonucleases that are capable of cleaving a subject RNA at such high temperatures may support cleavage of an RNA in absence of a denaturing reagent and/or eliminate the prior step of heating the RNA sample in a low salt solution (e.g., up to 50 mM salt) to reduce RNA structure biases during the digestion reaction. A low salt solution may comprise, for example, sodium chloride, magnesium sulfate, potassium nitrate, and/or sodium bicarbonate.

In some embodiments an endoribonuclease utilized for digestion of an mRNA may originate from a vertebrate species (for example, *Homo sapiens, Sus scrofa*), a bacterial species (for example, *Escherichia coli*), a fungus species (for example, *Aspergillus oryzae*), a plant species (for example, *Momordica charantia, Cucumis sativus*), and an archaea species (for example, *Pyrococcus furiosus*). In some embodiments a recombinant endoribonuclease is expressed in the periplasm of *E. coli* or *Pichia pastoris* and purified utilizing an affinity tag.

An enzyme comprising phosphodiesterase and phosphomonoesterase activities may be included in a composition with oligonucleotides having one or more ends that are 2',3'-cyclic-phosphorylated, 3'-phosphorylated and/or 2'-phosphorylated. Contacting such an enzyme with an oligoribonucleotide may dephosphorylate one or more ends.

In some embodiments, a composition may comprise 0.1 to 10 µL (e.g., 1 to 3 µL) of an endoribonuclease, wherein 1 µL of a given endoribonuclease is capable of cleaving RNA with catalytic activity comparable to that of 1 µL of commercially available RNase T1 (1000 U/µL; ThermoFisher Scientific #EN0541, wherein one unit of RNase T1 causes an increase in absorbance of 1.0 at 260 nm in 15 minutes when yeast RNA is hydrolyzed at 37° C. and pH 7.5 in a reaction comprising 50 mM Tris-HCl, 2 mM EDTA, and 3 mg/mL of the yeast RNA). In some embodiments, a composition may comprise 50 to 500 U/µL (e.g., 100 to 200 U/µL) of an RNA end repair enzyme. In some embodiments, the ratio of RNA substrate to endoribonuclease may be from 0.1 to 10 µg of RNA substrate per 1 µL of the endoribonuclease, preferably 1 to 10 µg of RNA substrate per 1 µL of the endoribonuclease. It may be desirable to decrease the ratio of RNA substrate to endoribonuclease where the RNA substrate comprises modified nucleotides. For example, the ratio of RNA substrate to endoribonuclease may be decreased as a function of the proportion of modified nucleotides present. For example, a ratio of RNA substrate to hRNase 4 of 10 µg (of substrate)/1 µL (of enzyme), of 5 µg/1 µL, of 2 µg/1 µL, 1 µg/1 µL, or of 0.1 µg/1 µL may be used to digest a fully-modified (e.g., all uridines replaced with 1-methylpseudouridine) mRNA comprising about 800 nucleotides (e.g., EPO mRNA). In some embodiments, the ratio of RNA end repair enzymes to endoribonuclease may be from 0.1:1 to 0.2:1 to 0.5:1 to 1:1 to 1:2 to 1:5 to 1:10 . . . . It may be desirable to increase the ratio of RNA end repair enzymes to endoribonuclease where the RNA substrate comprises longer RNA substrates (for example, greater than 1000 nucleotides, greater than 2000 nucleotides, greater than 3000 nucleotides, greater than 5000 nucleotides). For example, the ratio of RNA end repair enzymes to endoribonuclease may be increased as a function of the length of the RNA substrate present. For example, a ratio of T4 PNK to hRNase 4 of 40 U/1 µL, of 80 U/1 µL, of 160 U/1 µL, 320 U/1 µL, or of 500 U/1 µL may be used to digest a mRNA comprising about 800 nucleotides (e.g., EPO mRNA).

According to some embodiments, an enzyme (e.g., an endoribonuclease and/or an end repair enzyme), a ribonuclease inhibitor, and/or a DNA probe may be immobilized. For example, an enzyme may be immobilized to a solid support, including covalent bonding to the support surface and non-covalent interaction (binding by adsorption, e. g. cationic, anionic, lipophilic, or hydrophilic surfaces) of the enzyme with the surface. Covalent immobilization may include reaction of an active functional group on the enzyme with an activated functional group on the solid support. Examples of reactive functional groups include amines, hydroxylamines, hydrazines, hydrazides, thiols, phosphines, isothiocyanates, isocyanates, N-hydroxysuccinimide (NHS) esters, carbodiimides, thioesters, haloacetyl derivatives, sulfonyl chlorides, nitro- and dinitrophenyl esters, tosylates, mesylates, triflates, maleimides, disulfides, carboxyl groups, hydroxyl groups, carbonyldiimidazoles, epoxides, aldehydes, acyl-aldehydes, ketones, azides, alkynes, alkenes, nitrones, tetrazines, isonitriles, tetrazoles, and boronates. Examples of such reactions include the reaction between an amine and an activated carboxy group forming an amide, between a thiol and a maleimide forming a thioether bond, between an azide and an alkyne derivative undergoing a 1,3-dipolar cycloaddition reaction, between an amine and an epoxy group, between an amine and another amine functional group reacting with an added bifunctional linker reagent of the type of activated bis-dicarboxylic acid derivative giving rise to two amide bonds, or other combinations known in the art. Other reactions, such as UV-mediated cross-linking or chemical-mediated crosslinking (e.g., using formaldehyde or glutaraldehyde) can be used for covalent attachment of enzymes to solid supports. Disclosed methods may be used/adapted to prepare an immobilized ribonuclease inhibitor and/or an immobilized DNA probe.

A functional group may be inherently present in the material used for the solid support synthesis or a functional group may be provided by treating or coating the support with a suitable material. A functional group may also be introduced by contacting the solid support surface with an appropriate chemical agent. Activation in this context includes a modification of a functional group on the solid support surface to enable coupling of a binding agent to the surface. Solid support in this context includes any solid (flexible or rigid) material onto which it is desired to capture and immobilize the enzyme. Solid support may be biological, non-biological, organic, inorganic or a combination thereof, and may be in the form of particles, strands, precipitates, gels, sheets, tubings, spheres, containers, capillaries, cartridges, pads, slices, films, plates, slides, and have any convenient shape, including flat, disc, sphere, circle, etc. The surface of the solid support may be composed of a variety of materials, for example, polymers, plastics, resins, polysaccharides, silica or silica-based materials, carbon, metals, inorganic glasses, membranes, among others, provided that the surface may support functional groups. Examples of a convenient solid support include glass surfaces such as glass slides, microtiter plates, and suitable sensor elements, for example, functionalized polymers (e.g. in the form of beads), chemically modified oxidic surfaces, (e.g. silicon dioxide, tantalum pentoxide or titanium dioxide), or also chemically modified metal surfaces, e.g. noble metal surfaces such as gold or silver, copper or aluminium surfaces, magnetic surfaces, e.g. Fe, Mn, Ni, Co, and their oxides, quantum dots, e.g., III-V (GaN, GaP, GaAs, InP, or InAs) or II-VI (ZnO, ZnS, CdS, CdSe, or CdTe) semiconductors, or Ln-doped fluoride nanocrystals, rare earth-doped oxidic nanomaterials.

A solid support surface may be provided with a layer of a polymer, for example, a polymer comprising functional groups to be activated. A polymer may be selected from any suitable class of compounds, for example, polyethylene glycols, polyethylene imides, polysaccharides, polypeptides, or polynucleotides, just to name a few. Attachment of the polymers to the support surface may be achieved by a variety of methods which are readily apparent to a person skilled in the art. For example, polymers bearing trichlorosilyl or trialkoxy groups may be reacted with hydroxyl groups on the substrate surface to form siloxane bonds. Attachment to a gold or silver surface may take place via thiol groups on the polymer. Alternatively, the polymer may be attached via an intermediate species, such as a self-assembled monolayer of alkanethiols. The type of polymers selected, and the method selected for attaching the polymers to the surface, will thus depend on the polymer having suitable reactivity for being attached to the substrate surface, and on the properties of the polymers regarding non-specific adsorption to, especially, DNA and RNA. The functional groups may be present on the polymer or may be added to the polymer by the addition of single or multiple functional groups. Optionally, a spacer arm can be used to provide flexibility to the binding enzyme allowing it to interact with its environment in a way which minimizes steric hindrance with the solid support. In some instances, the solid support surface may comprise additional coating molecules, for example, polyethylene glycols, polyethylene imides, polysaccharides, polypeptides, or polynucleotides, that do not carry a reactive functional group. Additional coating molecules that do not carry a reactive functional group may increase the specific activity and/or stability of the immobilized enzyme, for example, by providing a local hydrophilic environment that favors the enzyme folding.

To immobilize an endoribonuclease and/or a RNA repair enzyme on a solid support, activated functional groups on a solid support may be present on the predefined regions only, or alternatively on the entire surface, are reacted selectively with the functional groups present in the enzyme molecules. Suitable reaction conditions, including time, temperature, pH, solvent(s), and additives, will depend on inter alia the particular species and may be selected in accordance with conditions for similar reactions. Functional group may be inherent to the enzyme amino acid sequence. Enzymes may be synthesized to incorporate a desired functional group either through a chemical reaction or through genetic engineering. Amino acids can be modified either chemically or enzymatically with any type of functional group in order to provide the desired reactivity.

Endoribonucleases and/or RNA repair enzymes may be included in a fusion protein and immobilized on a solid support by means of such fusion protein. For example, a fusion protein construct of an endoribonuclease and/or a RNA repair enzyme may generated with, for example, a maltose-binding protein (MBP), a chitin or chitin-binding domain (CBD), a poly-histidine 6×His or poly-His-tag), a HA-tag, a c-myc tag, a FLAG-tag, a SNAP-tag (U.S. Pat. Nos. 7,939,284; 8,367,361; 7,799,524; 7,888,090; and 8,163,479), a CLIP-tag (U.S. Pat. No. 8,227,602), a Halotag (Los, et al. Methods Mol Biol. 2007, 356:195-208), an ACP-tag (U.S. Pat. No. 7,666,612), a S-tag, a glutathione-S-transferase (GST), and others known to those skilled in the art. A solid support surface may be coated with an affinity group that is capable of specifically binding to the corresponding protein fusion partner, for example, a maltose moiety for MBP fusions, a benzylguanine (BG) moiety for SNAP-tag fusions, a benzoylcytosine (BC) moiety for CLIP-tag fusions, a chloroalkane moiety for Halotag fusions, a peptide sequence (Lys-Glu-Thr-Ala-Ala-Ala-Lys-Phe-Glu-Arg-Gln-His-Met-Asp-Ser) for S-tag fusions, a nickel-nitrilotriacetic acid (Ni-NTA) chelate for His-tag fusions, and so on. In some embodiments, immobilization is achieved using an affinity binding pair, such as in streptavidin-functionalized on the beads and biotinylated enzymes. In some other cases, the protein fusion of the endoribonuclease and/or the RNA repair enzyme (e.g., with MBP) may be used to enhance their solubility and facilitate their proper folding.

Endoribonucleases and/or RNA repair enzymes may be immobilized on a solid support by means of physical adsorption, for example, where binding is mainly by hydrogen bonds, multiple salt linkages, and/or Van der Waal's forces. In some embodiments, magnetic or paramagnetic solid supports (e.g., silica beads) are coated with negatively charged molecules (e.g., carboxyl-containing molecules) or positively charged (e.g., amino-containing molecules) which reversibly bind the enzymes of interest. In some instances, a crowding agent (e.g., polyethylene glycol, such as 10-50% PEG) and/or salt (e.g., NaCl, such as 0.1-4 M NaCl) may be used. In some embodiments, immobilization may be based on the entrapment of the enzyme within the lattice of a polymer matrix (e.g., synthetic polymers such as polyarylamide and polyvinylalcohol) or of a membrane (e.g., polymeric microcapsule).

One or a plurality of endoribonucleases and/or RNA repair enzymes may be immobilized on the same or different solid supports. They may be immobilized randomly on a given solid surface; or they may be immobilized at a specific arrangement, for example, on specific compartments of a given solid surface, so that the enzymes are arranged in series or in parallel to each other, or a combination of both arrangements. Such arrangement may serve different purposes, such as the sequential treatment of an RNA sample with an endoribonuclease followed by an RNA repair enzyme. Or a parallel treatment of an RNA sample with two or more endoribonucleases, wherein the sample is spatially confined to separate compartments (in the same of different reaction vessels) so that there is no cross-reaction of the sample with different enzymes. One or a plurality of endoribonucleases and/or the RNA repair enzymes may be immobilized on cartridges and these cartridges may be integrated in LC-MS/MS systems, wherein the cartridges may be individually selected by column selectors according to the requirements of a given experiment and allowing subsequential incubations with any of these enzymes.

Use of immobilized endoribonucleases and/or RNA repair enzymes may enable automation of one or more RNA sample processing steps (e.g., digestion) prior to downstream analysis (e.g., LC-MS/MS). Use of immobilized endoribonucleases and/or RNA repair enzymes may reduce the amount of sample and/or time required for processing the RNA prior to downstream analysis. Use of immobilized endoribonucleases and/or RNA repair enzymes may enable miniaturization and/or high-throughput analysis of RNA samples. Use of immobilized enzymes may provide the ability to multiplex reactions, streamline reaction processes and workflows, reduce level of degradation byproducts (e.g., unwanted RNA hydrolysis, oxidation, deamination, etc.), reduce manual steps and the risk of manual (human) errors, and importantly, in some cases increase hydrolytic and/or thermal stability of the enzymes (relative to their non-immobilized forms). The endoribonuclease(s) and/or the RNA repair enzyme(s) may be irreversibly adsorbed or covalently linked to the solid surface using any one of the methods described in this invention. The endoribonuclease(s) and/or the RNA repair enzyme(s) may be stably and efficiently immobilized on a microchip or any column reactor or fluid channel network, in such a way that buffers and reagents are flowed through (e.g., manually or using a peristaltic pump) the reaction vessel.

Methods

The present disclosure provides, in some embodiments, methods for analyzing and characterizing RNA. Methods may include, for example, preparing oligoribonucleotides from RNA substrates (e.g., total RNA, genomic RNA, messenger RNA, transfer RNA, ribosomal RNA, coding RNA, non-coding RNA, micro RNA, small interfering RNA, nuclear RNA, nucleolar RNA). Methods may include, in some embodiments, contacting an RNA substrate with an RNA denaturing agent to form a denatured RNA substrate. For example, a method may include heating an RNA sample (e.g., at 90° C. for 10 min) in a low salt solution (e.g., containing 0-50 mM NaCl) or in a denaturing solution (e.g., containing 3 M urea) to form the denatured RNA substrate. In some embodiments, a denaturing agent, if used, may be separated from the denatured RNA substrate (e.g., by dialysis, affinity or size-exclusion chromatography or other methods). Compositions including RNA substrates and RNA denaturing agents, according to some embodiments, may be diluted (e.g., more than 10-fold, more than 100-fold, more than 500-fold, more than 1000-fold). For example, compositions including RNA substrates and RNA denaturing agents may be diluted to reduce the impact of included RNA denaturing agent(s) on enzymes in one or more subsequent steps. Dilution may reduce the RNA denaturing agent to a concentration that permits an enzyme in a subsequent (e.g., an endoribonuclease and/or an RNA end repair enzyme) step to have at least 1% of its activity in the absence of such RNA denaturing agent(s) (e.g., under otherwise the same conditions of temperature, pH, enzyme concentration, substrate concentration, kind and concentration of buffer, and/or other components).

Digestion of RNA with some endoribonucleases may produce a mixture of cleavage products comprising 2',3'-cyclic-phosphate (sometimes also referred as to 2',3'-phosphodiester) and 3'-phosphate (sometimes also referred as to 3'-linear phosphate or 3'-phosphomonoester) termini, whereas some other endoribonucleases may produce a mixture of cleavage products comprising 2',3'-cyclic-phosphate and 2'-phosphate (sometimes also referred as to 2'-linear phosphate or 2'-phosphomonoester) termini. The extent of formation of 2',3'-cyclic-phosphate and 2'- or 3'-linear phosphate may depend on the enzyme concentration, the digestion buffer and/or incubation time. A mixture of cleavage products may also comprise 2',3'-hydroxylated species. Enzyme-independent hydrolytic opening of 2',3'-cyclic-phosphate may generate a mixture comprising 2',3'-cyclic-phosphate, 3'-phosphate, 2'-phosphate, and/or 2',3'-hydroxy termini in any combination. Enzyme-independent hydrolytic cleavage of RNA may further produce a mixture of 5'-phosphate and 5'-hydroxy termini. The potential presence of any of these products, in any combination, can convolute analysis by mass spectrometry techniques.

Methods may include contacting an RNA substrate (or a denatured RNA substrate) with a composition comprising an endoribonuclease and/or an optional RNA end repair enzyme under conditions (e.g., temperature, pH, enzyme and substrate concentrations, and buffers or other components) permitting the RNA substrate (or the denatured RNA substrate) to be cleaved and oligoribonucleotides to be formed. In some embodiments, the optional RNA end repair enzyme may be omitted. In such embodiments, it may be desirable to use an endoribonuclease with specificity for cleavage of RNA substrates that results in cleavage on average once every 6 to 12 nucleotides, for example on average once every 8 nucleotides.

Methods, according to some embodiments, may further comprise analyzing oligoribonucleotides (e.g., oligoribonucleotides formed by digestion of an RNA substrate with an endoribonuclease) by LC-MS/MS. For example, oligoribonucleotides may be analyzed by capillary electrophoresis-mass spectrometry (CE-MS). In some embodiments, oligoribonucleotides may be analyzed by gel electrophoresis. In some embodiments, LC-MS/MS and/or CE-MS are used to determine the masses and/or fragmentation profiles of species in compositions of oligoribonucleotides (e.g., oligoribonucleotides formed by digestion of an RNA substrate with an endoribonuclease).

Methods, according to some embodiments, may include contacting an RNA substrate with an RNA substrate binding molecule to form a complex, the complex comprising a binding molecule-RNA substrate interface and single-stranded RNA substrate portion. Examples of an RNA substrate binding molecule may include a DNA probe (e.g., at least partially complementary to the RNA substrate), an RNA probe (e.g., at least partially complementary to the RNA substrate), a synthetic nucleic acid probe (e.g., a locked nucleic acid that is at least partially complementary to the RNA substrate), an RNA binding protein, an antibody, an RNA ligand (e.g., adenosylcobalamin, lysine, glycine, flavin mononucleotide, fluorescent dyes, and drugs including, for example, branaplam and risdiplam), divalent ions (e.g., salts of magnesium, calcium, zinc, manganese, etc.), ribosomes, and lipid-based membranes. A binding molecule-RNA substrate interface may comprise one or more endoribonuclease cut sites for which access by the corresponding endoribonuclease is limited. A single-stranded RNA substrate portion may comprise one or more endoribonuclease cut sites that are accessible to the corresponding endoribonuclease. A method may comprise, in some embodiments, contacting a complex with an endoribonuclease to form cleavage products. Cleavage products may include (two or more) fragments of the single-stranded RNA substrate portion and a cleaved binding molecule-RNA substrate interface, the RNA component of which remains uncut by the endoribonuclease and wherein the site(s) of cleavage of the cleaved binding molecule-RNA substrate interface are adjacent to the interface (e.g., not within the interface). For example, methods may include hybridizing an RNA substrate to at least one DNA probe to form an RNA/DNA duplex comprising a double-stranded portion and at least one single-stranded portion. A double-stranded portion of a duplex may comprise one or more endoribonuclease cut sites. A single-stranded portion of a duplex may comprise one or more endoribonuclease cut sites. A method may include contacting a duplex and an endoribonuclease to form cleavage products, the cleavage products comprising two or more fragments of the single-stranded portion and a cleaved double-stranded portion, the RNA component of which remains uncut by the endoribonuclease.

In some embodiments, a method may include assessing the integrity, identity, presence and/or purity of a target RNA in a sample (e.g., through "fingerprinting", "signature profiling", and/or "ID testing") and/or confirming the identity of an RNA produced by synthesis or isolated from native sources. According to some embodiments, ID testing may be performed by HPLC retention time analysis, intact mass analysis, failure sequence analysis, MS/MS sequencing, MS-fragmentation pattern analysis, NMR, melting temperature analysis, or any combination thereof. Methods may include, according to some embodiments, de novo sequencing a subject RNA (e.g., RNA in an RNA substrate) using mass spectrometry including sequencing oligoribonucleotides and assembling resulting sequences to form an assembled sequence corresponding to the subject RNA. In some embodiments, these oligoribonucleotide mixtures are used for determining the identity and location of a modified nucleotide in an RNA substrate ("modification mapping").

In some embodiments, oligoribonucleotides from RNA substrates may be used for characterizing impurities in an RNA sample. Impurities may include, for example, truncated RNA species, protracted RNA species, for example, obtained from read-through synthesis, degraded RNA species, RNA species containing nucleotide misincorporations, deletions, or additions, RNA species containing impurities derived from phosphoramidite-based synthesis, such as RNA containing residual protective groups (e.g., DMT, CEP, TBDMS, Bz, iBu, and others), RNA containing depurinated bases, and RNA containing by-products of RNA synthesis and deprotection, such as cyanoethyl adducts; carried-over reagents (e.g., plasmids), exogenous nucleic acid contaminants, and any combination of the foregoing.

Methods, according to some embodiments, may further comprise analyzing activity and/or specificity of an enzyme (e.g., a ligase, a polymerase, a transferase, a methyltransferase, a carbamoyltransferase, a glycosyltransferase, an acyltransferase, an aminotransferase, a peptidyltransferase, a pseudouridine synthase, a transglycosylase, a transaminase, a glycosidase, a capping enzyme, a decapping enzyme, a kinase, a phosphatase, a nuclease (endo or exo), a lyase, an oxidoreductase, and/or a deaminase) by analyzing RNA products of such enzyme.

In some embodiments, methods include digestion of an RNA substrate using a composition of at least one endoribonuclease and at least one an RNA end repair enzyme, wherein the RNA end repair enzyme comprises both phosphodiesterase (PDE) and phosphomonoesterase (PME) activities, in a buffering solution optionally containing an RNA denaturing agent. An example of an RNA end repair enzyme comprising both phosphodiesterase and phosphomonoesterase activities is the bacteriophage T4 polynucleotide kinase (T4 PNK; also referred as to T4 polynucleotide kinase-phosphatase or T4 Pnkp) (Das and Shuman, 2013). T4 PNK heals each of 2',3'-cyclic-phosphorylated, 3'-phosphorylated and 2'-phosphorylated oligoribonucleotide ends resulting in products that comprise a 2',3'-hydroxylated (2'-OH, 3'-OH) end. Hence, co-incubation of T4 PNK with an endoribonuclease resolves 2',3'-cyclic-phosphorylated, 3'-phosphorylated and/or 2'-phosphorylated oligoribonucleotides that may be produced upon endoribonuclease cleavage. By converting 2',3'-cyclic-phosphorylated, 3'-phosphorylated and/or 2'-phosphorylated oligoribonucleotide ends into 2',3'-hydroxylated ends, T4 PNK reduces spectral complexity and enhances the mass signal of endoribonuclease digestion products.

Methods may comprise contacting a polyribonucleotide substrate with an endoribonuclease to form a cleaved polyribonucleotide product and contacting the cleaved product with an RNA end repair enzyme to form a polyribonucleotide cleavage product with healed ends (e.g., 5' ends comprising a 5'-OH and/or 3' ends comprising a 3'-OH and/or 2'-OH). Contacting, in some embodiments, may be performed in sequential steps (e.g., contact with endoribonuclease followed by repair enzyme, often with an intervening cleanup step) or concurrently as a coupled reaction (e.g., in a single compartment, tube, container, vessel or other space). In this context, reactions may be concurrent if they overlap in time with one another, even if their start times and/or completions times are not synchronized. For example, a method may comprise simultaneously adding an endoribonuclease and an RNA end repair enzyme to a composition comprising an RNA substrate (and, optionally, a buffering agent and/or an RNA denaturing agent). Even if the starting composition is free of 2',3'-cyclic-phosphorylated, 3'-phosphorylated and/or 2'-phosphorylated ends until the endoribonuclease begins cleaving the RNA substrate, the cleavage and repair processes would be concurrent as long as repair begins before RNA substrate is exhausted by the cleavage reaction. An RNA product with healed ends may be subjected to characterization by tandem liquid chromatography-mass spectrometry (LC-MS) or by tandem capillary electrophoresis-mass spectrometry (CE-MS).

An enzyme comprising a phosphodiesterase and phosphomonoesterase may be contacted with (e.g., added to) a composition comprising oligoribonucleotides having one or more 2',3'-cyclic-phosphorylated, 3'-phosphorylated and/or 2'-phosphorylated ends to produce one or more dephosphorylated ends. Oligoribonucleotides having one or more 2',3'-cyclic-phosphorylated, 3'-phosphorylated and/or 2'-phosphorylated ends may be provided as such or, in some embodiments, an RNA substrate may be contacted with an endoribonuclease in the same composition or space to form the oligonucleotides.

In some embodiments, a method may comprise contacting an RNA substrate with an endoribonuclease to form oligoribonucleotides having one or more 2',3'-cyclic-phosphorylated, 3'-phosphorylated and/or 2'-phosphorylated ends and, following exhaustion of RNA substrate, contacting the oligoribonucleotides with an enzyme comprising a phosphodiesterase and a phosphomonoesterase to form one or more dephosphorylated ends. In some embodiments, a method may further comprise purifying the oligoribonucleotides prior to contact with the enzyme comprising a phosphodiesterase and a phosphomonoesterase.

A method may include, according to some embodiments, incubating (e.g., heating) an RNA substrate (e.g., prior to or upon contacting with an endoribonuclease) to form a denatured or melted RNA substrate. Incubating an RNA substrate may comprise maintaining the RNA substrate at a temperature of 65° C. or higher, for example, 65° C.-75° C., 70° C.-80° C., 75° C.-85° C., 80° C.-90° C., 85° C.-95° C., 90° C.-100° C., more than 95° C., or more than 100° C. Heating may comprise maintaining the RNA substrate at a selected temperature for up to a minute, 1-10 minutes, at least a minute, at least 5 minutes, at least 6 minutes, at least 7 minutes, at least 8 minutes, at least 9 minutes, at least 10 minutes, or up to 20 minutes.

In some embodiments, a method may comprise contacting an RNA substrate (e.g., a melted RNA substrate) with an endoribonuclease at a temperature of less than 30° C., 25° C.-35° C., 30° C.-40° C., 35° C.-45° C., 37° C., 40° C.-50° C., 45° C.-55° C., 50° C.-60° C., more than 50° C., or more than 55° C. A method may include, according to some embodiments, contacting an RNA substrate (e.g., a melted RNA substrate) with an endoribonuclease for 30-120 minutes, up to 30 minutes, at least 30 minutes, up to 45 minutes, up to 60 minutes, up to 75 minutes, up to 90 minutes, up to 105 minutes, up to 120 minutes, or at least 105 minutes.

In some embodiments, a method may comprise fingerprinting 2',3'-hydroxylated oligonucleotides (e.g., arising from a subject RNA following contact with an endoribonuclease and an RNA end repair enzyme) by LC-MS analysis. Fingerprinting by LC-MS analysis may comprise, for example, deconvoluting the charge state distribution of raw mass spectra and comparing the observed masses to masses from a theoretical digestion of a subject RNA. The resulting mass "fingerprint" may be utilized to assess the identity of a subject RNA. In some embodiments, fingerprinting by LC-MS comprises comparing deconvoluted mass spectrum to a database of RNA transcripts using a computer and assessing the "identity" of the characterized transcript by a mathematical metric.

In some embodiments, a method may comprise sequencing 2',3'-hydroxylated oligonucleotides (e.g., arising from a subject RNA following contact with an endoribonuclease and an RNA end repair enzyme) by LC-MS/MS analysis. For example, a sequencing method may comprise acquiring mass spectra (e.g., MS and/or MS/MS spectra) from an oligoribonucleotide comprising healed ends and comparing the acquired mass spectra with theoretical mass spectra from a theoretical digestion of a subject RNA with an endoribonuclease of selected specificity. Sequencing an RNA by LC-MS/MS is utilized to verify the sequence of a subject RNA and identify the position of mass altering RNA modifications.

Methods, according to some embodiments, may comprise preparing oligoribonucleotides from RNA substrates using one or more endoribonucleases in absence of an RNA end repair enzyme. An endoribonuclease (e.g., an endoribonuclease for methods including analysis of RNA by LC-MS/MS) may cleave RNA substrates on average once every 4 to 64 nucleotides, once every 6-12 nucleotides, or once every 8 nucleotides. Endoribonucleases with average cleavage frequencies of every 6-12 nucleotides may provide better mapping coverage relative to endoribonucleases with average cleavage frequencies of every 4 nucleotides or less and/or relative to relative to endoribonucleases with average cleavage frequencies of once every 16 nucleotides or more. Example 3 and FIG. 5 and FIG. 6 show the theoretical mapping coverage of 1000 randomly selected human transcripts comparing oligonucleotides generated by endoribonucleases with cleavage frequencies of 1 out 2 nucleotides (RNase A), 1 out 4 nucleotides (RNase T1, MC1-2015) and Cusativin-2021), 3 out of 16 nucleotides (Cusativin-2017 and MC1-2021), 1 out 8 nucleotides (hRNase 4), and 1 out 16 nucleotides (Colicin E5). Endoribonucleases with specificity that result in RNA cleavage on average once every 8 nucleotides (e.g., cleavage after a specific nucleotide followed by a purine; cleavage after a specific nucleotide followed by a pyrimidine; cleavage after a purine followed by a specific nucleotide; cleavage after a pyrimidine followed by a specific nucleotide; among others) are capable of producing a higher theoretical sequence coverage of the human transcriptome, whether based on the total content of their cleavage products or on the content of their cleavage products comprising unique sequences (see FIG. 6).

A method, according to some embodiments, may include separation or removal of a ribonuclease from reactants and/or products. For example, a method may comprise contacting an RNA substrate with an endoribonuclease (e.g., RNase 4) to form one or more reaction products comprising at least one RNA substrate cleavage product and the endoribonuclease. A method may further include separating the at least one RNA substrate cleavage product from the endoribonuclease. An endoribonuclease (and, optionally, an end repair enzyme, if included) may be immobilized on a magnetic bead and separating may comprise magnetically gathering the immobilized endoribonuclease (e.g., into a pellet), thereby allowing the at least one RNA substrate cleavage product to be removed. In some embodiments, an endoribonuclease may be susceptible to a ribonuclease inhibitor and separating may comprise contacting the reaction products with an immobilized ribonuclease inhibitor to form immobilized complexes comprising the immobilized ribonuclease inhibitor, thereby allowing the at least one RNA substrate cleavage product to be removed. Optionally, an endoribonuclease or a ribonuclease inhibitor may be immobilized on a surface (e.g., a column) or in a filter and reaction materials (e.g., reactions and/or reaction products) may be passed over the surface or through the filter. Additional information about separating an immobilized material from reaction products may be found in U.S. patent application Ser. No. 18/182,122 filed Mar. 10, 2023, incorporated herein by reference.

According to some embodiments, a ribonuclease inhibitor provided in an immobilized form may be utilized to capture and remove an endoribonuclease (e.g., a soluble endoribonuclease) from a reaction mixture or vessel. Removal of a soluble endoribonuclease from a reaction mixture or vessel may be used to stop the digestion reaction of the RNA substrate at desired time points. In some embodiments, removal of soluble endoribonuclease at designed time points may be used as a strategy to produce incomplete or partial cleavage of the RNA substrate thus resulting in oligonucleotides cleavage products with one or more uncut cleavage sites. Such partially uncut oligonucleotides are longer in size than those that have been cut all at possible cleavage sites, and thus may increase mapping coverage at certain RNA substrate regions. In some embodiments, removal of a soluble endoribonuclease from a reaction mixture or vessel may be used to prevent contamination of downstream analytical instrumentation (e.g., chromatographic columns) with active endoribonucleases. In some embodiments, the removal of a soluble endoribonuclease from a reaction mixture or vessel may be used in automation protocols to facilitate and streamline methods of analysis.

Quantification Methods

In some embodiments, methods may include identifying and/or quantifying one or more components in an RNA sample or RNA substrate. For example, it may be desirable to accurately identify and/or quantify certain features of an RNA substrate, such as the presence of a 5'-cap structure, a 3'-poly(A) tail, or an RNA modification within an RNA. In the context of an RNA obtained by chemical synthesis or by enzymatic in vitro transcription (IVT) (e.g., intended for use as a vaccine or another therapeutic application), the presence and/or quantity of certain features (e.g., cap structures, polyA tails) may be desirable for the functional stability and/or high translational efficiency of the RNA.

In some embodiments, oligoribonucleotide products generated by cleavage of RNA substrates, using either an endoribonuclease or a composition comprising an endoribonuclease and an RNA end-repair enzyme, may be quantified by mass spectrometric methods. In some embodiments, oligoribonucleotides may be quantified using calibration curves constructed with authentic standards. Oligoribonucleotides may be labeled, according to some embodiments, at their 5' or 3' end with stable isotopes for relative or absolute quantification. Differential incorporation of stable isotopes (also referred as to Tandem Mass Tag) may be used for multiplex quantitative analysis of oligonucleotides in which multiple oligonucleotide features (e.g., presence of a cap structure, one or more RNA modifications, presence of a polyA tail) may be analyzed simultaneously by means of isobaric tags.

In some embodiments, methods may include isotope labeling for quantitative analysis of oligonucleotides. Isotope labeling, according to some embodiments, may be performed in one step, wherein an isotopically labeled nucleotide is incorporated at the 3' end of an oligonucleotide by the action of an RNA polymerase. In some embodiments, the isotopically labeled nucleotide is blocked at its 3' position to prevent further extension of oligonucleotides beyond a single labeled nucleotide. Examples of such nucleotides are 3'-deoxynucleotides and 2',3'-dideoxynucleotides, including but not limited to 3'-deoxyadenosine (Cordycepin), 3'-deoxyinosine, 3'-deoxyguanosine, 3'-deoxyuridine, 3'-deoxycytidine, 2',3'-dideoxyadenosine, 2',3'-dideoxyinosine, 2',3'-dideoxyguanosine, 2',3'-dideoxyuridine, 2',3'-dideoxycytidine, 3'-azido-3'-deoxyadenosine, 3'-azido-3'-deoxyinosine, 3'-azido-3'-deoxyguanosine, 3'-azido-3'-deoxyuridine, 3'-azido-3'-deoxycytidine, 3'-azidomethyl-3'-deoxyadenosine, 3'-azidomethyl-3'-deoxyinosine, 3'-azidomethyl-3'-deoxyguanosine, 3'-azidomethyl-3'-deoxyuridine, 3'-azidomethyl-3'-deoxycytidine, 3'-fluoro-3'-deoxyadenosine, 3'-fluoro-3'-deoxyinosine, 3'-fluoro-3'-deoxyguanosine, 3'-fluoro-3'-deoxyuridine, 3'-fluoro-3'-deoxycytidine, 3'-amino-3'-deoxyadenosine, 3'-amino-3'-deoxyinosine, 3'-amino-3'-deoxyguanosine, 3'-amino-3'- deoxyuridine, 3'-amino-3'-deoxycytidine, 3'-O-methyl-3'-deoxyadenosine, 3'-O-methyl-3'-deoxyinosine, 3'-O-methyl-3'-deoxyguanosine, 3'-O-methyl-3'-deoxyuridine, 3'-O-methyl-3'-deoxycytidine. Examples also include nucleotide analogues, including Carbovir, Ganciclovir, Lamivudine, and Clofarabine, among others. The stable isotope may be selected from one or more of Deuterium (d), Carbon-13 (13C), and Nitrogen-15 (15N), in any combination (for instance, Cordycepin-13C5, Carbovir-13C,d2; Ganciclovir-d5; Lamivudine-15N2,13C; and Clofarabine-13C,15N3). An isotopically labeled nucleotide may be incorporated at the 3' end of an oligonucleotide by reaction of the corresponding nucleoside triphosphate with a polymerase. Examples of polymerases that may catalyze template independent addition of a desired nucleotide monophosphate (NMP) from the nucleoside triphosphate (NTP) to the 3' end of RNA are (including recombinant and mutants thereof): *E. coli* Poly(A) Polymerase, Yeast Poly(A) Polymerase, Poly(U) Polymerase, and DNA Polymerase θ (Polθ).

In some embodiments, isotope labeling for quantitative analysis of oligonucleotides may be performed by incorporation of an isotopically labeled nucleotide at the 5' or 3' end of an oligonucleotide by the action of an RNA ligase. The 3' end labeling may be performed in one step using a T4 RNA ligase and a pre-adenylated nucleotide. Examples of a pre-adenylated nucleotide include A(5')pp(5')Cp, wherein the cytidine comprises a 3'-phosphate and one or more isotope labels; A(5')pp(5')Gp, wherein the guanosine comprises a 3'-phosphate and one or more isotope labels; A(5')pp(5')Up, wherein the uridine comprises a 3'-phosphate and one or more isotope labels; A(5')pp(5')Ip, wherein the inosine comprises a 3'-phosphate and one or more isotope labels; and A(5')pp(5')Ap, wherein the 3' terminal adenosine comprises a 3'-phosphate and one or more isotope labels. The 3' end labeling may comprise (i) adenylating an isotopically labeled pCp, pGp, pIp, pUp, or pAp using a *Methanobacterium* thermoautotrophicum (Mth) RNA ligase in the presence of ATP, (ii) inactivating the Mth RNA ligase, and (iii) ligating the adenylated isotopically labeled nucleotide using a T4 RNA ligase.

In some embodiments, methods may include converting oligonucleotides to their 5'-phosphorylated form (for instance, by using T4 PNK in the presence of ATP) prior to ligation. 5' end labeling may be performed by ligation of a 5' adapter (e.g., 5-50 nucleotides in length) to an oligonucleotide, the adapter comprising one or more isotopically labeled nucleotides (e.g., adenosine, guanosine, uridine or cytidine labeled with one or more of Deuterium, Carbon-13, and Nitrogen-15). Ligation of a 5' adapter to a target oligonucleotide may be performed by an RNA ligase such as T4 RNA ligase 2 and may be carried out in the presence of additives (e.g., PEG) and/or splint adapters (e.g., 5-50 nucleotides in length whose sequence is randomized or partially annealing to the 5' adapter). 3' end labeling may be performed by ligation of a 3' adapter (e.g., 5-50 nucleotides in length) to an oligonucleotide, the adapter comprising one or more isotopically labeled nucleotides (e.g., adenosine, guanosine, uridine or cytidine labeled with one or more of Deuterium, Carbon-13, and Nitrogen-15) using, for example, a T4 RNA ligase or variant thereof.

In some embodiments, a method for labeling an oligonucleotide for quantitative analysis may comprise incorporating a non-isotopically labeled nucleotide at the 5' or 3' end of the oligonucleotide, wherein the non-isotopically labeled nucleotide comprises a chemically reactive group that is capable of reacting with an isotopically labeled molecule (also referred as to a mass label). A non-isotopically labeled nucleotide may comprise, in some embodiments, a 3'-deoxynucleotide or a 2',3'-dideoxynucleotide, in each case, having a chemically reactive group at the 2' or 3' position. In some embodiments, a chemically reactive group may be or comprise any of a carbonyl; a carboxyl; an active ester, e.g., a succinimidyl ester; a maleimide; an amine; a thiol; an alkyne, an azide; an alkyl halide; an isocyanate; an isothiocyanate; an iodoacetamide; a 2-thiopyridine; a 3-arylpropionitrile; a diazonium salt; an alkoxyamine; a hydrazine; a hydrazide; a phosphine; an alkene; a semicarbazone; an epoxy; a phosphonate; and a tetrazine. An isotopically labeled molecule may be selected from an amino acid (e.g., L-alanine-15N; L-alanine-13C3,15N; L-alanine-d4,15N; L-phenylalanine-15N; L-phenylalanine-13C9,15N; L-phenylalanine-d8,15N; L-proline-15N; L-proline-13C5,15N; L-proline-d7,15N); an α-keto acid (e.g., α-ketobutyric acid-13C4; α-ketoisocaproic acid-13C; α-ketoisovaleric acid-13C5); a nucleotide (e.g., adenosine-15N5; 2'-deoxyadenosine-15N5; uridine-15N2; thymidine-15N2; thymidine-13C10,15N2); a bile acid (e.g., chenodeoxycholic acid-13C; cholic acid-13C; deoxycholic acid-d4; etc); a carbohydrate (e.g., N-acetylglucosamine-15N; D-arabinose-13C; D-fructose-13C; D-galactose-13C; D-galactose-d; D-glucosamine-15N; D-glucose-13C); a drug (e.g., Phenacetin ethoxy-13C; Erythromycin N-methyl-13C; 5,5-Diphenylhydantoin diphenyl-d10; Dopamine·HCl-d3); a fatty acid (e.g., arachidic acid-d39; butyric acid-d7, L-carnitine·HCl-methyl-d3; decanoic acid-d19; linoleic acid-13C, palmitic acid-13C), a steroid (cholesterol-3-octanoate-13C; diethylstilbestrol-d8); or any derivative or combination thereof (e.g., putrescine-13C4; L-azidohomoalanine-13C4,15N2; ornithine-d2; pipecolic acid-13C6,15N; 3-bromo-L-tryosine-13C6; uric acid-15N2; choline chloride-13C2; D-mannitol-13C; glycerol-d5; propionic acid-d2; L-alanine-15N-L-phenylalanine-13C9,15N; L-alanine-13C3,15N-L-phenylalanine-d8,15N; L-alanine-d4,15N-L-proline-13C5, 15N), including the use of differentially isotopically labeled isobaric tags (e.g., Tandem Mass Tags TMT, iodoTMT, and aminoxyTMT). The isotopically labeled molecule may comprise a chemically reactive group that is capable of chemoselectively reacting with the non-isotopically labeled nucleotide, once the latter is incorporated into the target oligonucleotide (for instance, a L-azidohomoalanine-13C4, 15N2 reacts with a 3'-alkyne-3'-deoxyadenosine by means of a Cu(I)-catalyzed azide-alkyne cycloaddition). Examples of chemoselective reactions include a reaction between an amine reactive group and an electrophile (e.g., an alkyl halide or an N-hydroxysuccinimide ester (NHS ester)); a reaction between a thiol reactive group and an iodoacetamide or a maleimide; a reaction between an azide and an alkyne (azide-alkyne cycloaddition or "Click Chemistry"). An azide-alkyne cycloaddition may be catalyzed by Cu(I) or strain-promoted to yield a 1,4-substituted triazole. Another type of useful cycloaddition is the reaction between a trans-cyclooctene (TCO) and a tetrazine (Tz) to form a dihydropyridazine bond. Examples and uses of chemoselective reactions in biological systems are reviewed in a variety of publications, such as in Sletten, E. M. and Bertozzi C. R. "Bioorthogonal Chemistry: Fishing for Selectivity in a Sea of Functionality" Angewandte Chemie International Edition English 2009, 48(38): 6974-98.

In some embodiments, an appropriate chemically reactive group is installed in the isotopically labeled molecule prior to its reaction with an oligonucleotide comprising non-isotopically labeled nucleotide. For example, a chemically reactive group (e.g., dibenzocyclooctyne (DBCO)) may be installed on a L-alanine-d4 or on a dipeptide L-alanine-d4-L-phenylalanine-13C9,15N, and then reacted with an oligonucleotide comprising a 3'-azido-3'-deoxyadenosine through a strain-promoted 1,3-dipolar cycloaddition to form a 1,4-substituted triazole linkage (FIG. 24). In some embodiments, non-isotopically labeled nucleotides may be selected from one of 3'-azido-3'-deoxyadenosine, 3'-azido-3'-deoxyinosine, 3'-azido-3'-deoxyguanosine, 3'-azido-3'-deoxyuridine, 3'-azido-3'-deoxycytidine, 3'-azido-2',3'-dideoxy-adenosine, 3'-azido-2',3'-dideoxyinosine, 3'-azido-2',3'-dideoxyguanosine, 3'-azido-2',3'-dideoxyuridine, 3'-azido-2',3'-dideoxycytidine, 2'-azido-2',3'-dideoxy-adenosine, 2'-azido-2',3'-dideoxyinosine, 2'-azido-2',3'-dideoxyguanosine, 2'-azido-2',3'-dideoxyuridine, and 2'-azido-2',3'-dideoxycytidine. Examples of non-isotopically labeled nucleotides further include 3'-alkyne-3'-deoxyadenosine, 3'-alkyne-3'-deoxyinosine, 3'-alkyne-3'-deoxyguanosine, 3'-alkyne-3'-deoxyuridine, 3'-alkyne-3'-deoxycytidine, 3'-alkyne-2',3'-dideoxy-adenosine, 3'-alkyne-2',3'-dideoxyinosine, 3'-alkyne-2',3'-dideoxyguanosine, 3'-alkyne-2',3'-dideoxyuridine, 3'-alkyne-2',3'-dideoxycytidine, 2'-alkyne-2',3'-dideoxy-adenosine, 2'-alkyne-2',3'-dideoxyinosine, 2'-alkyne-2',3'-dideoxyguanosine, 2'-alkyne-2',3'-dideoxyuridine, 2'-alkyne-2',3'-dideoxycytidine, 3'-propargyl-3'-deoxyadenosine, 3'-propargyl-3'-deoxyinosine, 3'-propargyl-3'-deoxyguanosine, 3'-propargyl-3'-deoxyuridine, 3'-propargyl-3'-deoxycytidine, 3'-propargyl-2',3'-dideoxy-adenosine, 3'-propargyl-2',3'-dideoxyinosine, 3'-propargyl-2',3'-dideoxyguanosine, 3'-propargyl-2',3'-dideoxyuridine, 3'-propargyl-2',3'-dideoxycytidine, 2'-propargyl-2',3'-dideoxy-adenosine, 2'-propargyl-2',3'-dideoxyinosine, 2'-propargyl-2',3'-dideoxyguanosine, 2'-propargyl-2',3'-dideoxyuridine, and 2'-propargyl-2',3'-dideoxycytidine.

In some embodiments, a method for labeling an oligonucleotide for quantitative analysis may comprise incorporating a chemically reactive group at the 5' or 3' end of the oligonucleotide to form an oligonucleotide having a reactive end and contacting (e.g., reacting) the oligonucleotide having a reactive end with an isotopically labeled molecule (FIG. 25). For example, a chemically reactive group may be installed at the 5' end of an oligonucleotide by incubating the oligonucleotide with ATPγS and T4 PNK. Methods may comprise, for example, contacting an RNA substrate with an endoribonuclease and a PNK to produce oligoribonucleotides and incorporating a chemically reactive group in the oligoribonucleotides to form oligoribonucleotides having a 5' or 3' chemically reactive group, wherein the contacting and the incorporating may be performed as coupled reactions, for example, coupled reactions further including a phosphorylation reagent (e.g., ATPγS) in the reaction location. In some embodiments, it may be desirable to purify the RNA oligonucleotides prior to incubation with a PNK and the phosphorylation reagent (e.g., ATPγS) so that the chemically reactive group is installed at the 5' end of the oligonucleotide in a separate step. In some embodiments, phosphothiolated oligonucleotides may react with iodoacetamide- or maleimide-functionalized molecules (e.g., nucleotides) comprising isotope labels.

A chemically reactive group may be installed at the 3' end of an oligoribonucleotide, for example, by reaction with sodium (or potassium) periodate to generate a dialdehyde reactive group at the 3' end nucleotide 2',3'-diol position to produce a dialdehyde oligonucleotide. A dialdehyde oligonucleotide may react with hydrazine-, hydroxylamine-, or amine-functionalized molecules comprising isotope labels, including tandem mass tags. Similarly, a method may comprise installing a chemically reactive group to the 5' end of a capped oligoribonucleotide wherein the cap structure comprises a 2',3'-diol group. Converting a 5' cap comprising a 2',3'-diol to a dialdehyde may be concurrent (e.g., a coupled reaction) with the converting a 3' end nucleotide 2',3'-diol to a dialdehyde within the same oligonucleotide. Alternatively, the 3' end labeling may be blocked by incubating the oligonucleotide with a polymerase and a blocking 3'-deoxynucleotide (e.g., Cordycepin) or 2',3'-dideoxynucleotide prior the generation of the reactive dialdehyde to produce selectively labeled oligoribonucleotides having a 5' end cap comprising a 2',3'-diol. The methods may further comprise subsequent labeling by reaction with an appropriate molecular scaffold (e.g., amino acids, keto acids, fatty acids, diamines, amino alcohols, carbohydrates) comprising one or more combinations of heavy and light isotope atoms.

According to some embodiments, methods may include contacting an endoribonuclease with an RNase inhibitor in an amount sufficient to at least partially inhibit the activity of the endoribonuclease. RNase inhibitors may be useful to a number of biotechnological applications. For example, methods may include an RNase inhibitor to terminate (e.g., precisely terminate) an endoribonuclease reaction at a desired point (e.g., a desired time point, upon consumption of a desired amount of substrate, upon formation of a desired product, upon formation of products having desired size(s)). Methods may include an RNase inhibitor to achieve controlled partial digestion of an RNA substrate (for instance, to generate RNA oligonucleotides that are on average longer in length due to incomplete cleavage of every possible cutting site that is specific for a given endoribonuclease). Methods may include, for example, an RNase inhibitor to avoid or prevent overdigestion of an RNA substrate (i.e., cutting substrate at nonspecific or low-preferred sites) during additional sample processing steps in a multistep preparation workflow (such as, isotope labeling of the digested RNA). In some embodiments, methods may include an RNase inhibitor to avoid or prevent over-digestion of an RNA substrate immediately prior to sample analysis (for instance, during idle instrument times, such as column equilibration or instrument failure). Methods may include an RNase inhibitor to avoid or prevent over-digestion of an RNA substrate upon storage of a digested sample in the presence of the endoribonuclease. Methods may include an RNase inhibitor, for example, to study enzymatic activity (such as in kinetic studies in enzymology). Methods may include an RNase inhibitor, for example, to reduce cytotoxicity of an RNase during protein expression and/or purification.

Targeted Site-Specific Cleavage of RNA Substrates for Analysis of RNA Features.

Targeted cleavage of an RNA substrate may allow, according to some embodiments, one or more RNA oligonucleotide products of interest to be isolated. Isolation of one or more RNA oligonucleotide products may be coupled with analysis of certain RNA features, such as a 5' cap structure or nucleobase modification (e.g., 6-methyladenosine and 5-methylcytidine). Methods for assaying the identity and efficiency of cap incorporation in kilobase-long synthetic mRNA transcripts may be used in connection with quality control and/or characterization of mRNA therapeutics and vaccines. Cleavage of a pre-defined oligonucleotide segment (e.g., 5-30) from the 5' end of the mRNA substrate using a custom designed DNAzyme or ribozyme, or cleavage of a DNA-RNA hybrid duplex with RNase H (Beverly et al., Anal. Bioanal. Chem. 2016, 408:5021-30) may include analysis by denaturing gel electrophoresis or LC-MS.

RNase H (RNase H1) is a particular type of endonuclease that hydrolyzes phosphodiester bonds of RNA, when hybridized to DNA. RNase H is known to remove RNA primers from the Okazaki fragments of the replicating DNA. In vitro, RNase H cleaves one or more nucleotides away from the 5' and/or 3' of the target site (DNA-RNA hybrid duplex), giving rise to multiple cleavage products differing from each other by one or more nucleotides in length (with low or no particular nucleotide specificity). Formation of multiple cleavage products of a few nucleotides difference in length complicates the analysis by mobility-based or mass spectrometry-based methods. Application of RHase H methods may be limited by demands on DNA probe design. For example, applications of RNase H methods may be limited by the design of the DNA probe needed to form the duplex DNA-RNA substrate for RNase H binding and activity while also restricting its cutting region and avoiding spurious (or other unwanted) cleavage of the RNA substrate (e.g., through careful design of single-stranded probes comprising DNA-RNA or DNA-2'-O-methyl-RNA chimeras, wherein 4-6 DNA nucleotides are placed at 3' end of the probe). The present disclosure provides methods and compositions that, according to some embodiments, are free of such limitations. For example, methods and compositions including a nucleotide-specific endoribonuclease (such as a mono-, di-, or trinucleotide-specific endoribonuclease) that selectively hydrolyzes the phosphodiester bonds of single-stranded RNA obviate the need for carefully designed chimeric probes required for RNase H methods.

In some embodiments, a method may comprise contacting a DNA probe (e.g., 5 to 50 nucleotides long) and an RNA comprising sequence (e.g., a sequence having a 5' cap or a sequence having one or more nucleobase modifications) at least partially complementary to the DNA probe to form a DNA-RNA hybrid and contacting the DNA-RNA hybrid and a nucleotide-specific endoribonuclease. A method may comprise, according to some embodiments, (a) contacting an RNA substrate and one or more DNA probes, each optionally comprising an affinity domain (e.g., biotin), for example, wherein at least a portion of the RNA substrate and at least a portion of the DNA probe(s) are complementary, to form a DNA-RNA hybrid duplex comprising a double-stranded portion and a single-stranded portion;

(b) contacting the DNA-RNA hybrid duplex with an enzyme composition, the enzyme composition comprising a single-strand-specific nucleotide-specific endoribonuclease and, optionally, an RNA end-repair enzyme, to form a cleaved DNA-RNA hybrid duplex and one or more single-stranded RNA fragments of the RNA substrate by cleavage of the RNA substrate at one or more sites within the single-stranded portion by the single-strand-specific nucleotide-specific endoribonuclease;

(c) optionally, contacting the cleaved DNA-RNA hybrid duplex and a solid support comprising an affinity capture domain capable of binding the affinity domain (e.g., streptavidin) to form an affinity capture complex comprising the affinity domain bound to the affinity capture domain;

(d) optionally, washing the affinity capture complexes to remove unbound materials, if any; and (e) optionally, dissociating the cleaved DNA-RNA hybrid duplex to release the remaining portion of the RNA substrate from the one or more DNA probes.

A DNA probe may comprise a sequence complementary to a sequence of an RNA substrate. In some embodiments, a DNA probe may be shorter than an RNA substrate such that the duplex formed upon hybridization comprises RNA overhangs at the 5' and/or 3' ends. A DNA/RNA duplex, in some embodiments, may comprise a DNA probe and an RNA substrate longer than the DNA probe, wherein the RNA substrate has single-stranded overhangs at both the 5' and 3' ends. According to some embodiments, the portion of the RNA substrate hybridized to the DNA probe may be protected from endoribonucleases that cleave only single stranded RNA while the single-stranded overhangs at one or both of the 5' and 3' ends would be subject to cleavage.

In some embodiments, hybridization of a DNA probe to a complementary sequence of an RNA substrate may be directed or guided by an accessory protein, for example, a prokaryotic argonaute (e.g., a bacterial argonaute, such as *Thermus thermophilus* argonaute), whose endonucleolytic activity has been inactivated but retained its ability to search for their guide-defined substrate). Including an accessory protein may hasten hybridization (e.g., more rapid seeking of RNA substrate at a rate near the limit of diffusion). Including an accessory protein may improve (e.g., overcome limitations on) substrate accessibility; and/or facilitate hybridization by reducing the entropic barrier to duplex formation. In some embodiments, an accessory protein that selectively binds duplex substrates over single-stranded substrates (e.g., Carnation Italian Ringspot Virus p19 protein) may be used to stabilize or conceal the duplex segment. In some embodiments, one or more chemical additives may be included in methods or compositions of the disclosure to increase the stability and/or specificity of the DNA-RNA duplex, including salts (e.g, NaCl, $MgCl_2$), crowding agents (e.g., polyethylene glycol (PEG), Ficoll, Dextran, etc.), duplex strengtheners (e.g., betaine, proline, trehalose, proline, tetramethylammonium chloride, etc.), and ionic liquids (e.g., imidazolium, pyridinium, pyrrolidinium, and phosphonium cations; halides, tetrafluoroborate (BF4-), hexafluorophosphate (PF6-), and bis[(trifluoromethyl) sulfonyl]imide (NTf2-) anions).

A high-salt washing buffer may be used to wash away unbound RNA (e.g., the one or more single-stranded RNA fragments of the RNA substrate cleaved from the RNA substrate) while retaining solid support-bound DNA-RNA duplexes. To release (or elute) the RNA oligonucleotide strand (remaining portion of the RNA substrate) from captured DNA-RNA duplexes, a low-salt buffer (or water) or treatment with a DNase (e.g., DNase I) may be used. Alternatively, the RNA oligonucleotide strand (as part of the DNA-RNA duplexes) may be retained on the solid support for downstream applications.

According to some embodiments, a solid support may include any solid (flexible or rigid) material onto which a DNA-RNA hybrid duplex may be captured. For example, a solid support may include a matrix formed from an affinity capture domain or coated with the affinity capture domain. A solid support may be, for example, a bead including a magnetic bead, a column, a porous matrix, or a flat surface formed from for example, plastic or paper. In some embodiments, a solid support may be biological, non-biological, organic, inorganic or a combination thereof. A solid support, according to some embodiments, may have any desired form including, for example, particles, strands, precipitates, gels, sheets, tubings, spheres, containers, capillaries, cartridges, pads, slices, films, plates, slides, and/or have any desired shape, including, for example, a plane, a disc, a sphere, a ring, a torus, a cube, a cylinder, a cone, a vesica, a rod, and an ellipsoid. The surface of a solid support may comprise one or more materials including, for example, polymers, plastics, resins, polysaccharides, silica or silica-based materials, carbon, metals, inorganic glasses, and membranes. The surface of a solid support may comprise one or more functional groups. Example solid supports include glass surfaces (e.g., glass slides, microtiter plates) and suitable sensor elements. Sensor elements may include, for example, functionalized polymers (e.g., in the form of beads). Example solid supports also include chemically modified oxidic surfaces (e.g. silicon dioxide, tantalum pentoxide or titanium dioxide), chemically modified metal surfaces (e.g., noble metal surfaces such as gold or silver, copper or aluminium surfaces), magnetic surfaces (e.g., Fe, Mn, Ni, Co, and their oxides), quantum dots (e.g., III-V (GaN, GaP, GaAs, InP, or InAs) or II-VI (ZnO, ZnS, CdS, CdSe, or CdTe) semiconductors), Ln-doped fluoride nanocrystals, and rare earth-doped oxidic nanomaterials.

In some embodiments, a DNA probe may hybridize with and protect a portion of a single-strand RNA from cleavage by a single-strand specific endoribonuclease. Synthetic nucleic acids may hybridize a single-stranded RNA substrate and/or protect the single-stranded RNA substrate from endoribonuclease cleavage (e.g., like a DNA probe that hybridizes to such single-stranded RNA). Synthetic nucleic acids may include, for example, a peptide nucleic acid (PNA), a lock nucleic acid (LNA), an unlock nucleic acid (UNA), a bridge nucleic acid (BNA), a triazole nucleic acid, a morpholine nucleic acid, an amide-linked nucleic acid, a 1,5 anhydrohexitol nucleic acid (HNA), a cyclohexenyl nucleic acid (CeNA), an arabinose nucleic acid (ANA), a 2'-fluoro-arabinose nucleic acid (FANA), a α-L-threofuranosyl nucleic acid (TNA), a 4'-thioribose nucleic acid (4'S-RNA), a 2'-fluoro-4'-thioarabinose nucleic acid (4'S-FANA), a 4'-selenoribose nucleic acid (4' Se-RNA), an oxepane nucleic acid (ONA), or a combination thereof. Other synthetic nucleic acids that may be used include RNA probes comprising complete or partial 2'-OH nucleotides substitution with 2'-O-alkyl-nucleotides (e.g., 2'-O-methyl-nucleotides), 2'-O-methoxyethyl-nucleotides (MOE), 2'-fluoro-nucleotides, 2'-O-allyl-nucleotides, 2'-O-alkylamine-nucleotides (e.g., 2'-O-ethylamine-nucleotides), 2'-O-cyanoethyl-nucleotides, 2'-O-acetalester-nucleotides, and 2'-azido-nucleotides. Further synthetic nucleic acids that may be used include DNA or RNA probes comprising partial or complete backbone modifications such phosphorotrithioate (replacement of one non-bridging oxygen atom of the phosphate group with a sulfur atom), phosphorodithioate (both non-bridging oxygen atoms of the phosphate group are replaced with sulfur), alkylphosphonate (a non-bridging oxygen atom of the phosphate group has been replaced with alkyl group, e.g. methyl), arylphosphonate (a non-bridging oxygen atom of the phosphate group has been replaced with aryl group, e.g. phenyl), N-phosphoramidate (an oxygen atom is replaced with an amino group either at the 3'- or 5'-oxygen), boranophosphate (one non-bridging oxygen atom of the phosphate group is replaced with BH3), phosphonoacetate (PACE, one non-bridging oxygen atom of the phosphate group is replaced with an acetate group), and 2',5'-phosphodiester linkages.

In some embodiments, oligoribonucleotide products generated by cleavage of DNA-RNA hybrid duplexes may be quantified by mobility-based methods, such as gel- or capillary electrophoresis, or by mass spectrometric methods. In some embodiments, oligoribonucleotide products are quantified using calibration curves constructed employed authentic standards. In other embodiments, such oligoribonucleotides are labeled at their 5' or 3' end with stable isotopes for relative or absolute quantification as disclosed herein. Differential incorporation of stable isotopes may be used for multiplex quantitative analysis of oligonucleotide, enabling simultaneous analysis of multiple RNA features by means of isobaric tags.

Kits

The present disclosure further relates to kits including an endoribonuclease and/or an RNA end repair enzyme. For example, a kit may include an endoribonuclease having an amino acid sequence that (i) corresponds to an amino acid sequence of a first species (e.g., a vertebrate species (for example, *Homo sapiens, Sus scrofa*), a bacterial species (for example, *Escherichia coli*), a fungus species (for example, *Aspergillus oryzae*), a plant species (for example, *Momordica charantia, Cucumis sativus*), and an archaea species (for example, *Pyrococcus furiosus*)) or (ii) is a non-naturally occurring sequence. A kit may include, for example, an RNA end repair enzyme having an amino acid sequence that (i) corresponds to an amino acid sequence of a species other than the first species (e.g., a bacterial species or a bacteriophage species) or (ii) is a non-naturally occurring sequence. A kit may include one or more additional enzymes (e.g., an RNA polymerase, an RNA ligase), a denaturing agent (e.g., urea, formamide, dimethylformamide, guanidinium thiocyanate, sodium salicylate, dimethyl sulfoxide, propylene glycol, poly(ethylene glycol), and cetyltrimethylammonium bromide), a buffering agent, and any combination thereof. An enzyme may be included in a storage buffer (e.g., comprising glycerol and a buffering agent). In some embodiments, a kit may include a reaction buffer which may be in concentrated form, and the buffer may contain additives (e.g. glycerol), salt (e.g. KCl), reducing agent, EDTA or detergents, among others. A kit may include an endoribonuclease having specificity for one or more dinucleotide combinations (e.g., cleavage after a specific nucleotide followed by a purine, cleavage after a specific nucleotide followed by a pyrimidine, cleavage after a purine followed by a specific nucleotide, and cleavage after a pyrimidine followed by a specific nucleotide). For example, an endoribonuclease may have an average cleavage rate of once every 6-12 nucleotides. Examples of endoribonucleases for a kit may include hRNase 4, RNase T1, RNase U2, RNase A, Colicin E5, MC1, Cusativin, Csx1, MazF, ChpB, MqsR, and YafO. A kit may comprise an RNA end repair enzyme, for example, comprising phosphodiesterase and phosphomonoesterase activities. A kit may include, according to some embodiments, a divalent metal, for example, a divalent metal selected from magnesium(II), manganese(II), cobalt(II), and nickel(II). A kit may comprise one or more rNTPs including, for example, one, two, three of all four of rATP, rUTP, rGTP and rCTP. A kit may further comprise one or more modified nucleotides. In some embodiments, a kit may include an RNase inhibitor. In some embodiments, a kit may include an affinity-labeled DNA probe. One or more components of a kit may be included in one container for a single step or coupled reaction, or one or more components may be contained in one container (e.g., a box, case), but separated (e.g., in one or more tubes) from other components for sequential use or parallel use. The contents of a kit may be formulated for use in a desired method or process.

An enzyme, for example, an enzyme included in a kit, may have any desired form (e.g., fluid, freeze-dried, and lyophilized forms). An enzyme composition and/or kit may comprise non-ionic, ionic e.g. anionic or zwitterionic surfactants and crowding agents.

A kit may include instructions for using the components of the kit to practice a desired method (e.g., methods for analyzing an RNA substrate). Instructions may be recorded on a suitable recording medium. For example, instructions may be printed on a substrate, such as paper or plastic and/or displayed electronically. Instructions may be present in the kits as a package insert, in the labeling of the container of the kit or components thereof (i.e., associated with the packaging or sub-packaging). Instructions may be present as an electronic storage data file residing on a suitable computer readable storage medium (e.g. a CD-ROM, a flash drive). Instructions may be provided remotely using, for example, cloud or internet resources with a link or other access instructions provided in or with a kit.

EXAMPLES

Some specific example embodiments may be illustrated by one or more of the examples provided herein.

Example 1: Expression and Purification of Human RNase4 (hRNase 4)

Figure 1:
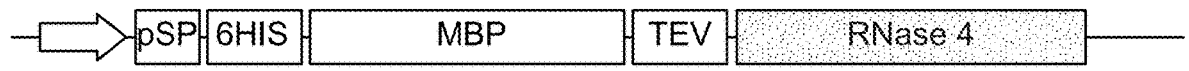
FIG. 1 shows a schematic of an example cassette used to produce recombinant hRNase 4 enzyme. pPS: periplasmic signal peptide; 6HIS:hexahistidine tag; MBP: maltose binding protein; TEV: TEV protease cleavage site.

Recombinant wild-type hRNase 4 enzyme was periplasmically expressed as a MBP fusion protein containing an N-terminal signal peptide (61.7 kDa) (see FIG. 1) and stored in an ammonium acetate buffer [100 mM NH$_4$OAC, pH 5.5, 0.5 mM DTT, 50% glycerol]. Expression of hRNase 4 was induced with 10 µM IPTG, and the protein was expressed from a periplasmic hRNase 4-containing plasmid in T7 Express lysY Competent *E. coli* [MiniF lysY (CamR)/fhuA2 lacZ:T7 gene1 [lon] ompT gal sulA11 R(mcr-73: miniTn10—TetS)2 [dcm] R(zgb-210:Tn10—TetS) endA1 Δ(mcrC-mrr)114:IS10] (NEB C3010) for 16 h at 16° C. The cells were lysed by sonication in lysis buffer (20 mM Tris/Cl pH 7.5, 200 mM NaCl, 1 mM DTT) and protease inhibitors (1 mM PMSF, 0.5 nM leupeptin, 2.75 mM benzamidine, 2 nM pepstatin), followed by the removal of cell debris by centrifugation at 21,000×g for 1 hour. The enzyme was purified from the crude extract using 10 mL BioRad Econo-Pac disposable chromatography columns packed with 1.5 mL Amylose Resin (NEB E8021). The flow rate during loading, washing, and elution was regulated to ~0.8 ml/min using a Discofix® 1-way stopcock. After elution in elution buffer (EB1; 20 mM Tris/Cl pH 7.5, 250 mM NaCl, 1 mM DTT, 10 mM maltose), the protein was loaded onto a GraviTrap His column, equilibrated with GTH column buffer (20 mM Na2HPO4 pH 7.5, 0.5 M NaCl, 1 mM DTT, 20% glycerol). hRNase 4 was eluted in two 3 ml fractions with GTH elution buffer (20 mM Na2HPO4 pH 7.5, 0.5 M NaCl, 1 mM DTT, 0.5 M imidazole, 20% glycerol). The enzyme-containing fraction was dialyzed into the hRNase 4 storage buffer (200 mM NH$_4$OAC, pH 5.5+1 mM DTT), and after dialysis supplemented with an equal volume of 100% glycerol.

Example 2: Characterization of Human hRNase 4 Activity and Cleavage Specificity

The activity and specificity of hRNase 4 cleavage was assessed utilizing a LC-MS/MS-based multiplexed cleavage assay. A defined pool of 13 synthetic oligonucleotides comprising all possible dinucleotide combinations (at least once) flanked by poly-adenosine sequences of varying lengths (Table 1) was prepared. To assess hRNase 4 activity and specificity, 5 µL of this oligonucleotide pool (comprising 25 pmol of each individual oligonucleotide) were digested with 2 µL of a 1:10, 1:20 or 1:40 dilution of hRNase 4 in 1× NEBuffer 1 (10 mM Bis-Tris-Propane-HCl, 10 mM MgCl2, 1 mM DTT, pH 7). The mixture was incubated at 37° C. for 1 h with shaking at 300 rpm. The resultant digestion products were filtered using a Millipore Ultrafree MC-GV spin column (0.22 um) at 13,400 rpm for 5 minutes.

TABLE 1

Synthetic oligonucleotides utilized to assess hRNase 4 cleavage activity and specificity. All possible dinucleotide motifs are shown.

| Dinucleotide(s) | Oligonucleotide Sequence | SEQ ID NO |
|---|---|---|
| AA | AAAAAAAAAAAA | 7 |
| AC/CA | AAAAAAAACAAAAAA | 11 |
| AG/GA | AAAAAAAAGAAAAAA | 13 |
| AU/UA | AAAAAAAAAAAAUAAAAAAAAAA | 2 |
| AC/CC/CA | AAAAAAAAAAACCAAAAAAAAA | 9 |
| AC/CG/GA | AAAAAACGAAAA | 6 |
| AC/CU/UA | AAAAAACUAAAA | 1 |
| AG/GC/CA | AAAAAAAAGCAAAAA | 10 |
| AG/GG/GA | AAAAAAGGAAAA | 8 |
| AG/GU/UA | AAAAAAAAAAGUAAAAAAAAA | 4 |
| AU/UC/CA | AAAAAAAAUCAAAAA | 12 |
| AU/UG/GA | AAAAAAAAAAAAUGAAAAAAAAAA | 5 |
| AU/UU/UA | AAAAAAAAAAAAUUAAAAAAAAAA | 3 |

Each sample was characterized by LC-MS/MS analysis. Liquid chromatographic separation of RNA oligonucleotides was performed on a Thermo Scientific Vanquish Horizon UHPLC equipped with a DNAPac RP Column (2.1×50 mm, 4 mm) at 70° C. using a 25-minute gradient of solvent A (1% hexafluoroisopropanol (HFIP), 0.1% N,N-diisopropylethylamine (DIEA), 1 µM EDTA) and increasing solvent B (5-35%) (80% Methanol, 0.075% HFIP, 0.0375% DIEA, 1 µM EDTA) at a 0.3 mL/min flow rate. MS/MS data were collected on a Thermo Scientific Q Exactive Plus Orbitrap Mass Spectrometer. Intact mass analysis was performed (scan range: 480-2500 m/z) at a resolution of 70,000. Raw intact MS data was deconvoluted utilizing ProMass (Novatia LLC) and Avalon peak detection and integration algorithm (Thermo Fisher Scientific). To determine the relative abundance of each input oligonucleotide and cleavage product following incubation with hRNase 4, deconvoluted mass data was compared with the theoretical masses of each input oligonucleotide and cleavage product using a 10-ppm mass difference cutoff.

A heatmap of the relative abundance of each input oligonucleotide within the oligonucleotide pool after incubation with hRNase 4 is shown in FIG. 2. Oligonucleotides comprising a uridine followed by a purine (abbreviated as "R") were cleaved by incubation with hRNase 4. The oligonucleotide comprising the 'UC' dinucleotide was not cleaved by hRNase 4 at any of the tested concentrations. Also, none of the oligonucleotides comprising 'CG', 'CC', 'CA' motifs were cleaved by hRNase 4. Cleavage analyses of oligonucleotides comprising the 'UU' dinucleotide motif and oligonucleotides comprising the "CU" dinucleotide motif were not conclusive because each of the oligonucleotides also included an 'UA' motif (which is cleaved by hRNase 4).

Figure 4:
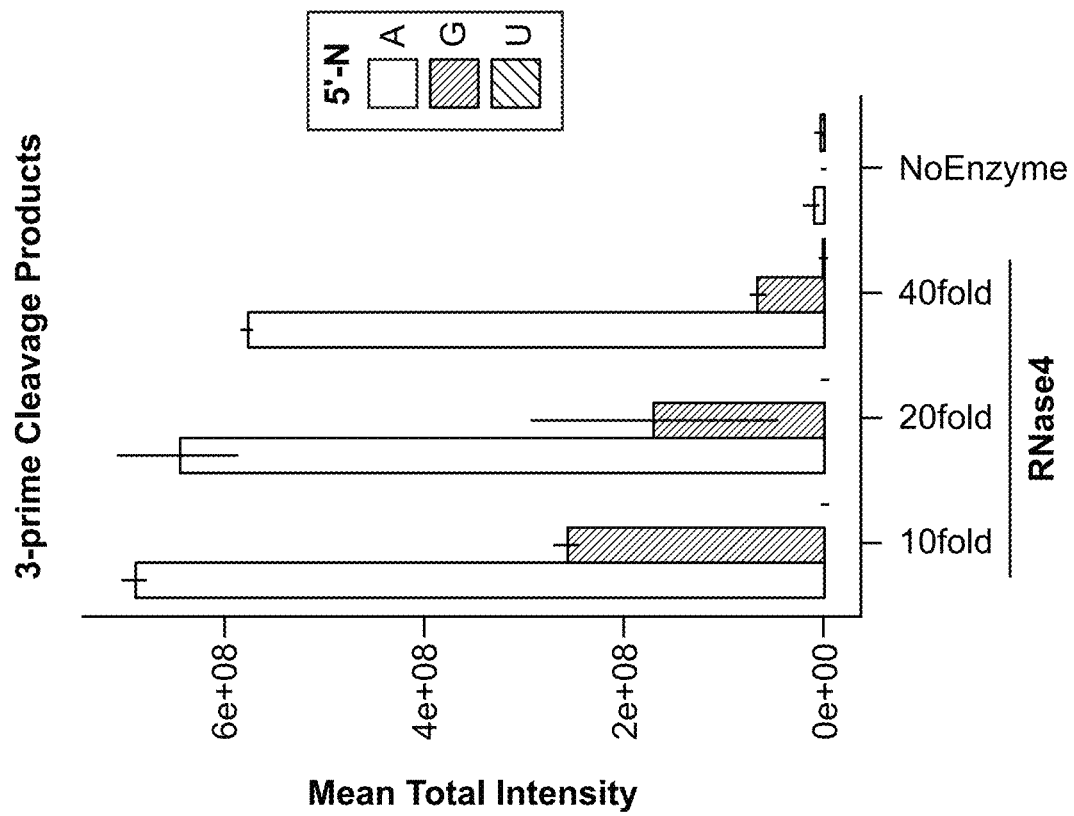
FIG. 4 shows an example bar chart of the mean total intensity of 3-prime cleavage products formed by digestion with hRNase 4. 3-Prime cleavage products are classified by their initial 5'-nucleotide residue. Error bars represent the standard deviation from two replicate digests. hRNase 4 primarily produced 3-prime cleavage products comprising a 5'-adenine or 5'-guanine.
Figure 3:
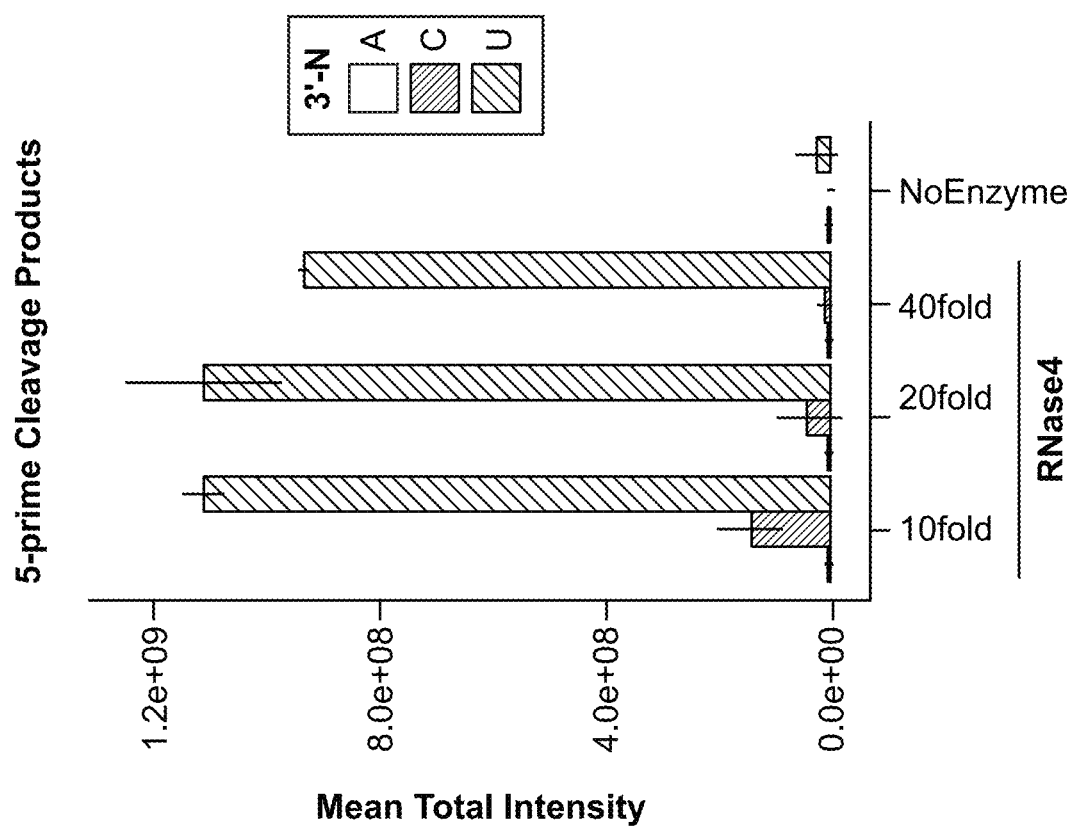
FIG. 3 shows an example bar chart of the mean total intensity of 5-prime cleavage products formed by digestion with hRNase 4. 5-Prime cleavage products are classified according to their terminal 3'-nucleotide residue. Error bars represent the standard deviation from two replicate digests. hRNase 4 primarily produced 5-prime cleavage products comprising a 3'-uridine nucleotide.

To better define the hRNase 4 cleavage specificity, the identities and quantities of each cleavage product were analyzed. First, the 5' cleavage products were analyzed with respect to the composition of their 3'-terminal nucleotide residue. For the purpose of this experiment, 5' cleavage products were grouped according to the composition of their 3'-terminal nucleotide residue, regardless of their phosphorylation status. As shown in FIG. 3, digestion with hRNase 4 resulted in an accumulation of 5' cleavage products comprising a uridine at the 3'-terminus. Digestion with hRNase 4 also produced, albeit to a much lesser extent and dependent upon the enzyme concentration, some very low levels of 5' cleavage products comprising a cytidine at the 3'-terminus. Next, the 3' cleavage products were analyzed with respect to the composition of their 5'-terminal nucleotide residue. For the purpose of this experiment, 3' cleavage products were grouped according to the composition of their 5'-terminal nucleotide residue, regardless of their phosphorylation status. As shown in FIG. 4, digestion with hRNase 4 resulted in an accumulation of 3' cleavage products comprising a 5'-adenosine or a 5'-guanosine (note that the higher total intensity of 5'-adenosine products at lower hRNase 4 dilutions is due to the fact that there were fourfold more 'UA' sites than 'UG' sites in the oligonucleotide pool; however, at higher hRNase 4 dilutions it is possible to observe a slight enrichment of 5'-adenosine products). Taken together, these data show that hRNase 4 cleaves after a uridine site followed by a guanine or adenine nucleotide. These data are consistent with reports suggesting that hRNase 4 may preferentially cleave RNA between 'UR' dinucleotides (i.e., on the 3' side of uridine and on the 5' side of adenosine or guanosine) (Shapiro et al., 1986; Zhou and Strydom, 1993; Teryzan et al., 1999).

Example 3: Prediction of hRNase 4 Cleavage Products in mRNA Transcripts

The utility of the 'UR' cleavage specificity of hRNase 4 for mRNA characterization by LC-MS/MS was assessed by computational comparison with the reported specificities of other endoribonucleases that have been previously used for analysis RNA by LC-MS/MS. A complete theoretical digestion of 1000 randomly selected human mRNA transcripts (less than 5000 bases in length) (RefSeq, https://www.ncbi.nlm.nih.gov/refseq/) (see FIG. 5A), of *E. coli* coding sequences (greater than 300 bases in length) (RefSeq) (see FIG. 5B) and of the BNT162b2, COVID-19 mRNA vaccine sequence (Vogel et al., 2021) (see FIG. 5C) was performed using the following endoribonuclease cleavage specificities (in the cases where discrepancies in the specificity of a given endoribonuclease have been reported, both reported specificities were used for calculation): Colicin E5 cleaves between 'GU'; Cusativin-2017 cleaves between 'CA', 'CG', and 'CU', but not between 'CC' (Addepalli et al., 2017); Cusativin-2021 cleaves between 'CG', 'CU', 'AU', and 'UU' (Grunberg et al., 2021); MC1-2015 cleaves at the 5' end of 'U' (Addepalli et al., 2015); MC1-2021 cleaves between 'AU', 'CU', and 'UU', but not between 'GU' (Grunberg et al., 2021); RNase A cleaves at the 3' end of 'C' and 'U'; and RNase T1 cleaves at the 3' end of 'G'.

Figure 5A:
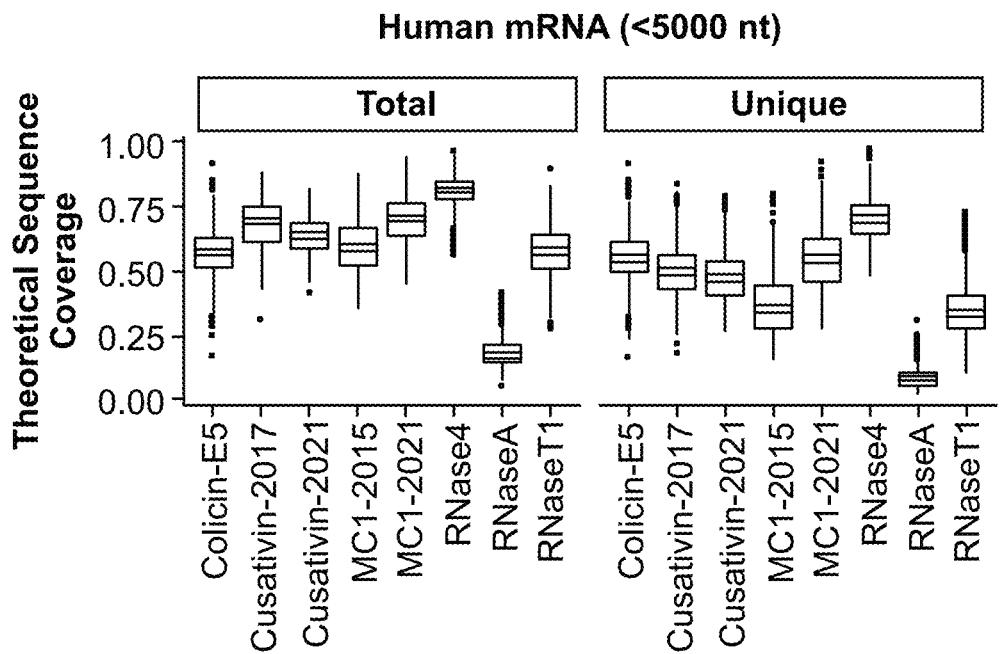
FIG. 5A shows the theoretical sequence coverage of hRNase 4 and various endoribonucleases for 1000 random human mRNA transcripts (RefSeq).
Figure 5B:
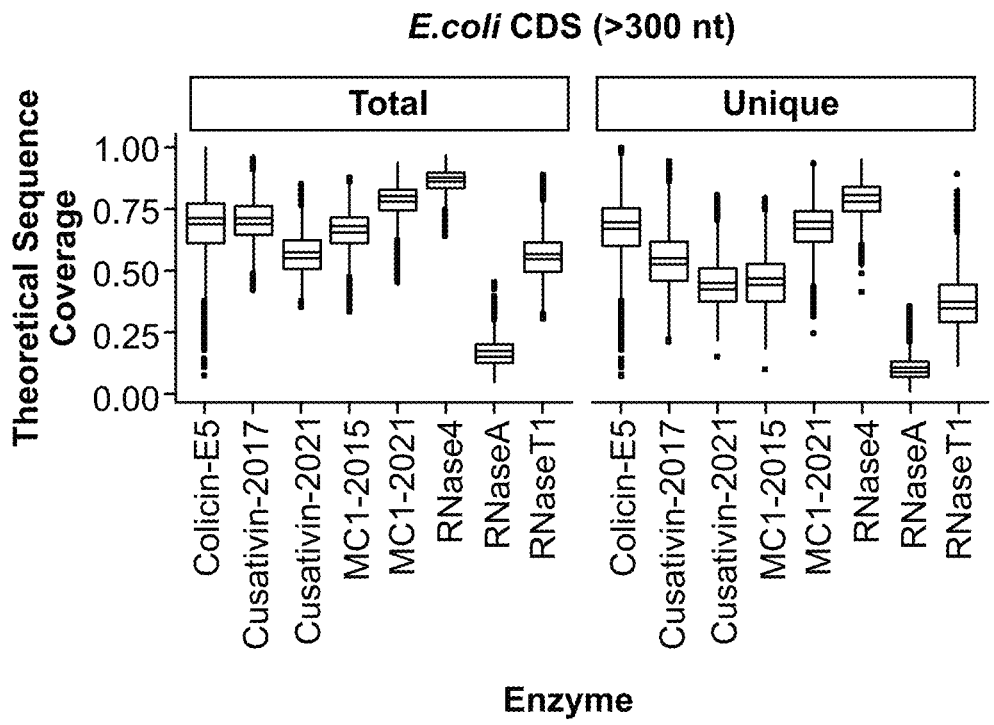
FIG. 5B shows the theoretical sequence coverage of hRNase 4 and various endoribonucleases for *E. coli* coding sequences (CDS).
Figure 5C:
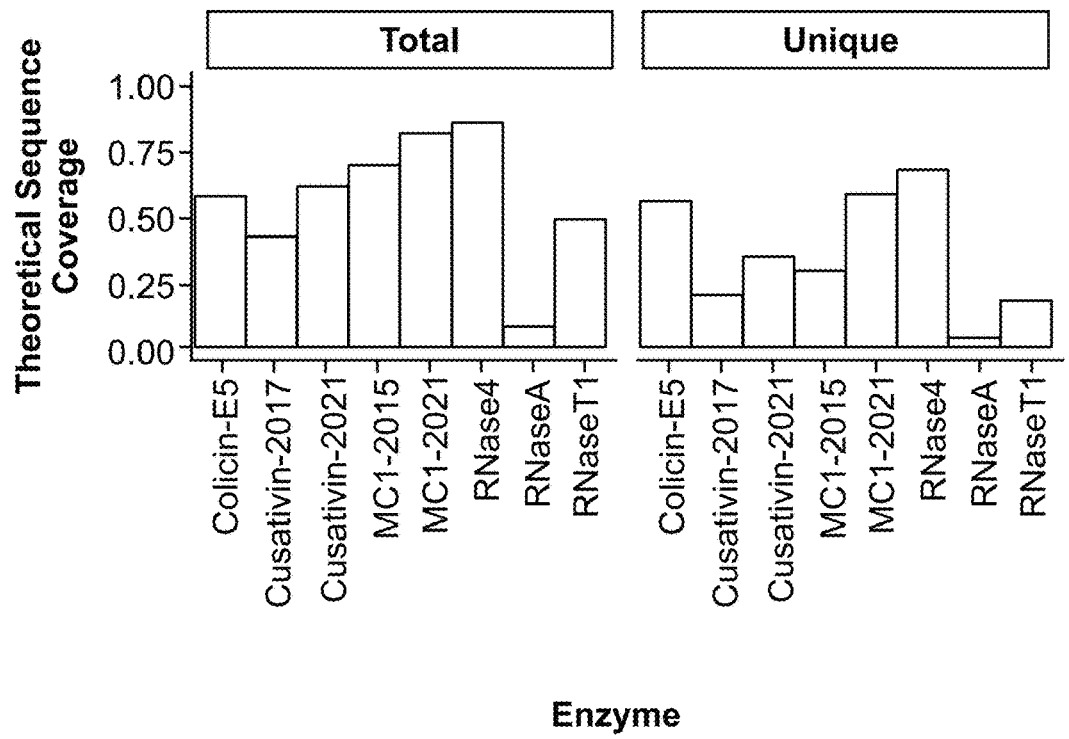
FIG. 5C shows the theoretical sequence coverage of hRNase 4 and various endoribonucleases for the BNT162b2 COVID-19 mRNA vaccine sequence.

The calculated sequence coverage for each mRNA transcript based on the predicted cleavage products formed by digestion with a given endoribonuclease is shown on FIG. 5. Only cleavage products between 4 and 40 nucleotides in length were utilized for the calculation of RNA sequence coverage, as they are the most useful for MS/MS sequencing purposes. Exact duplicate cleavage products were also excluded, as they are not uniquely mappable to a given RNA sequence. As shown in FIG. 5A-C (left panels), hRNase 4 produced the highest median total predicted sequence coverage among the tested endoribonuclease specificities across transcripts from species as diverse as human and *E. coli*. hRNase 4 also resulted in the highest median theoretical sequence coverage across all transcripts considering only cleavage products with a unique mass (i.e., excluding cleavage products with isomeric sequences) as shown in FIG. 5A-C (right panels).

Assuming an approximate equal and random distribution of 'G', 'C', 'A', and 'U' nucleotides within each of 1000 randomly selected human mRNA transcripts (RefSeq), one would expect that on average Colicin E5 would cleave once every 16 nucleotide residues, Cusativin (Grunberg et al., 2021) would cleave once every 4 nucleotide residues, MC1 (Grunberg et al., 2021) would cleave three times every 16 nucleotide residues, RNase A would cleave once every 2 nucleotide residues, RNase T1 would cleave once every 4 nucleotide residues, and hRNase 4 would cleave once every 8 nucleotide residues.

Figure 12:
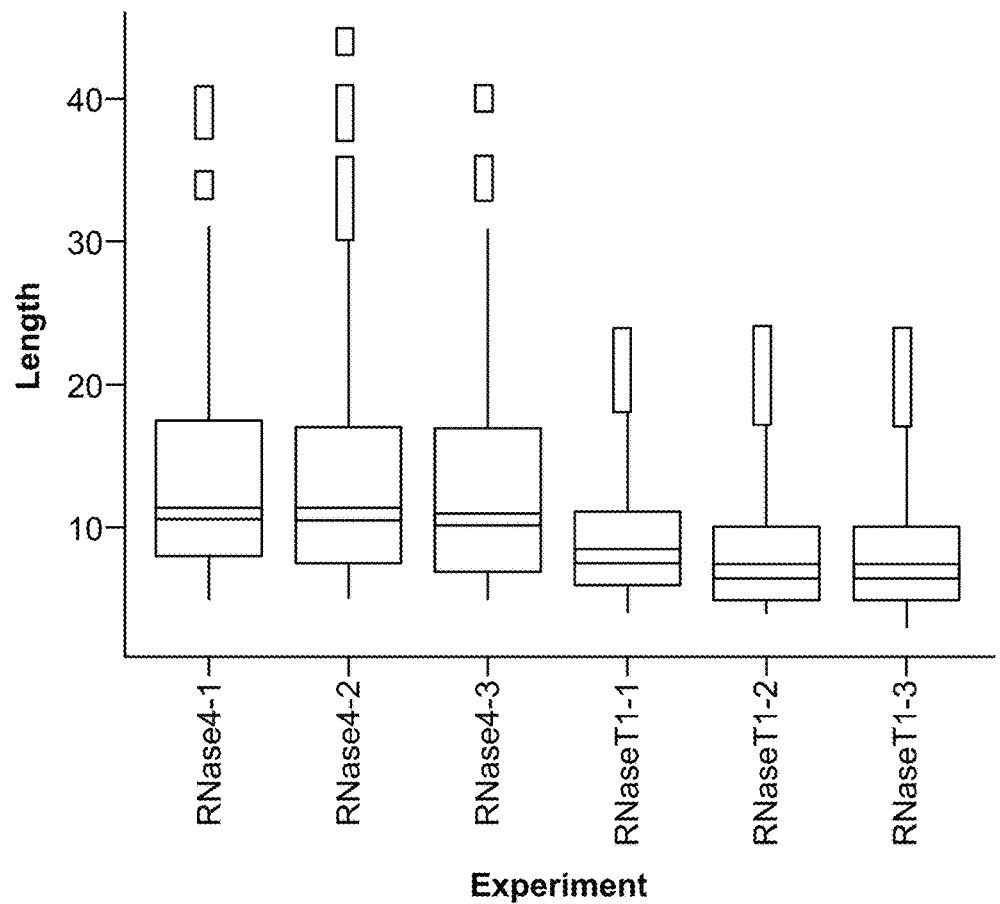
FIG. 12 shows the distribution of cleavage product lengths identified in each replicate from digestion of FLuc IVT mRNA with either hRNase 4/T4 PNK or RNaseT1. Increased median and maximum lengths were observed in the hRNase 4/T4 PNK condition in comparison with that of RNaseT1.

Identifying cleavage frequency as a results effective variable and/or optimizing cleavage frequency range for mass spectrometry-based RNA sequencing have been confounded, in part, because distance between consecutive endoribonuclease cleavage sites may vary in different RNA sequences and/or may result in oligonucleotides that are too short for sequencing purposes. Furthermore, the cleavage efficiency at any given endoribonuclease cleavage site may be affected by local RNA secondary structures and presence of RNA modifications. As shown in FIG. 12 for the experimental cleavage of FLuc IVT mRNA (1766 nt in length), most of the sequenced oligonucleotide products (25th-75th percentile) from hRNase 4 digestion were in the range of 9-18 nt (median length of 12 nt) with the longest products ranging from 41 to 45 nt in length. Comparatively, most of the sequenced oligonucleotide products from RNase T1 digestion were in the range of 7-12 nt (median length of 8 nt) with the longest product being 24 nt in length.

Discrepancies may exist between a predicted cleavage frequency and the corresponding actual or observed mean oligonucleotide product length (e.g., hRNase 4 has a predicted cleavage frequency of 1 out 8 nucleotides, but was observed experimentally to produce oligonucleotide products having median length of 12 nt; RNase T1 has a predicted cleavage frequency of 1 out 4 nucleotides, but was observed experimentally to produce oligonucleotide products having median length of 8 nt). The data shown in FIG. 5A-C may be used as a guide to select endoribonucleases that may improve sequencing and fingerprinting of mRNAs using LC-MS/MS techniques. For example, one may infer from FIG. 5A-C that cleavage frequencies within the range of once every 6-12 nucleotide residues provide the highest RNA sequence coverage as follows. Theoretical sequence coverage of endoribonucleases with cutting frequency lower than 6: Cusativin-2017 (3 out 16 nt or every ~5.3 nt), 68% mean coverage; MC1-2021 (3 out 16 nt or every ~5.3 nt), 69% mean coverage; MC1-2015 (1 out 4 nt), 59% mean coverage; Cusativin-2021 (1 out 4 nt), 63% mean coverage; RNase T1 (1 out 4 nt), 57% mean coverage; RNase A (1 out 2 nt), 18% mean coverage. Theoretical sequence coverage of endoribonucleases with cutting frequency higher than 12: Colicin E5 (1 out 16 nt), 56% mean coverage. Theoretical sequence coverage of hRNase 4 (1 out 8 nt cutting frequency), 81% mean coverage.

The impact of theoretical cleavage frequencies on the sequence coverage of human coding sequences (see FIG. 6A), E. coli coding sequences (see FIG. 6B), and BNT162b2 vaccine sequence (see FIG. 6C) was further assessed for three general classes of cleavage motifs. The classes of cleavage motifs were as follows: cleavage after a given single nucleotide ('N'); cleavage after a given single nucleotide followed a purine ('NR'); cleavage after a given single nucleotide followed a pyrimidine ('NY'); cleavage after a purine followed by a single nucleotide ('RN'); cleavage after a pyrimidine followed by a single nucleotide ('YN'); and cleavage between a single dinucleotide sequence ('NN'). For simplicity, the classes of cleavage motifs were represented as follows: cleavage after a given single nucleotide followed a purine ('NY') and cleavage after a given single nucleotide followed a pyrimidine ('RN') were represented as 'N(Y/R)'; cleavage after a purine followed by a single nucleotide ('RN') and cleavage after a pyrimidine followed by a single nucleotide ('YN') were represented as '(Y/R)N'.

On average, the expected cleavage frequency for endoribonucleases with 'N' specificity is 1 out of 4 nucleotide residues; the expected cleavage frequency for endoribonucleases with 'N(Y/R)' specificity is 1 out of 8 nucleotide residues; the expected cleavage frequency for endoribonucleases with 'NN' specificity is 1 out of 16 nucleotide residues. Examples of endoribonucleases with the 'N(Y/R)' specificity are those whose specificity comprise one of: a uridine followed by a pyrimidine; a cytidine followed by a pyrimidine; an adenosine followed by a pyrimidine; a guanosine followed by a pyrimidine; a uridine followed by a purine; a cytidine followed by a purine; an adenosine followed by a purine; or a guanosine followed by a purine. Similarly, endoribonucleases with '(Y/R)N' specificity also result in cleavage frequencies that are on average 1 out of 8 nucleotide residues. Examples of endoribonucleases with the '(Y/R)N' specificity are those whose specificity comprise one of: a pyrimidine followed by a uridine; a pyrimidine followed by a cytidine; a pyrimidine followed by an adenosine; a pyrimidine followed by a guanosine; a purine followed by a uridine; a purine followed by a cytidine; a purine followed by an adenosine; or a purine followed by a guanosine. Nucleotide combinations that result in cutting frequencies within the range of once every 6-12 nucleotide residues may include cleavage sites comprising two or more nucleotides. Examples of desirable cleavage specificities may include:

those having cutting frequencies of 6 out of 64 or every ~10.7 nucleotides (e.g., URH (wherein H=A or C or U), ARH, CRH, GRH, UYH, AYH, CYH, GYH, RUH, RAH, RCH, RGH, YUH, YAH, YCH, YGH, RHU, RHA, RHC, RHG, YHU, YHA, YHC, YHG, HRU, HRA, HRC, HRG, HYU, HYA, HYC, HYG, URD (wherein D=A or G or U), URB (wherein B=G or C or U), and URV (wherein V=A or C or G));

those having cutting frequencies of 8 out of 64 or every 8 nucleotides (e.g., RRR, YYY, RYR, YRR, RYY, YYR, RRK (wherein K=G or U), RRM (wherein M=A or C), RRS (wherein S=G or C), RRW (wherein W=A or U));

those having cutting frequencies of 2 out of 16 or every 8 nucleotides (e.g., UK, KU, UM, MU, US, SU, UW, WU); and those having cutting frequencies of 36 out of 256 or every ~7.1 nucleotides (e.g., RRHH, RHRH, HRHR, HHRR, YYHH, WWHH, KKHH, KMBD, RSHD); among other cleavage specificities.

Figure 6A:
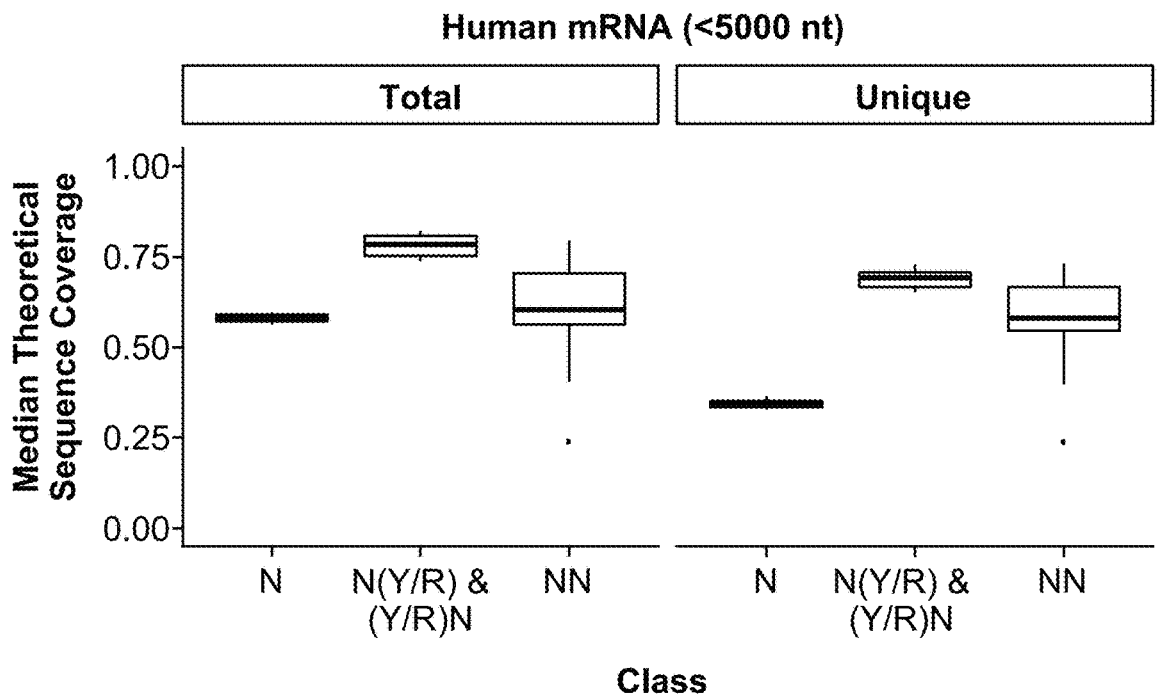
FIG. 6A shows the theoretical sequence coverage of the endoribonucleases for 1000 randomly selected human mRNA transcripts (RefSeq).
Figure 6B:
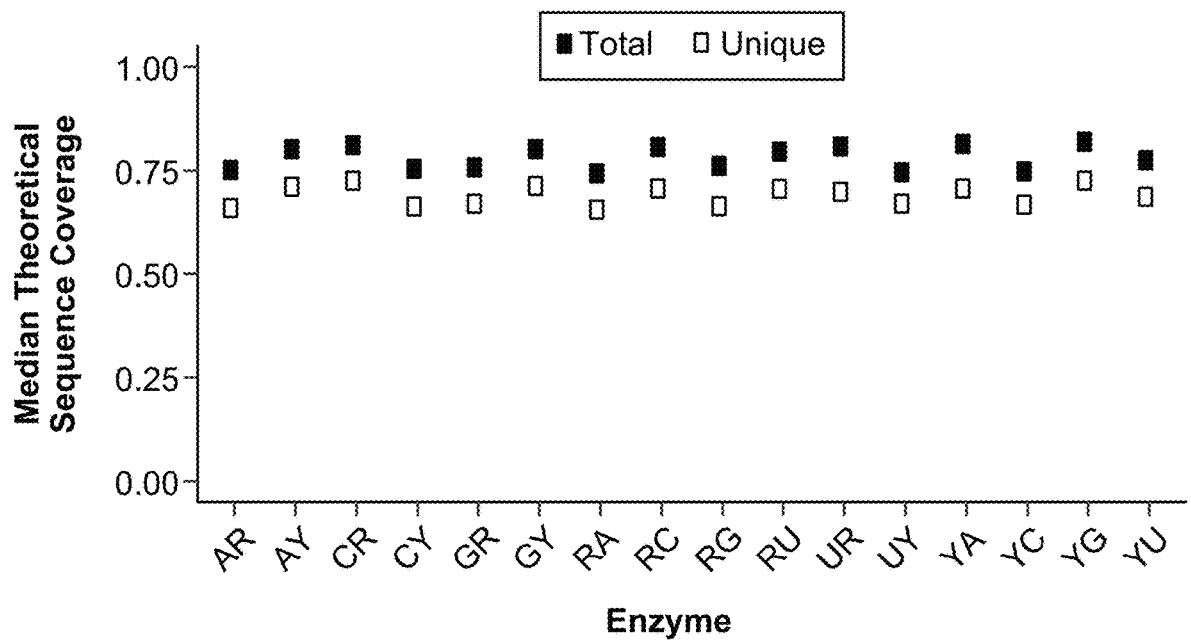
FIG. 6B shows the sequence coverages of individual hRNase 4-like ('N(Y/R) & (Y/R)N') cleavage specificities upon digestion of 1000 randomly selected human mRNA transcripts.
Figure 6C:
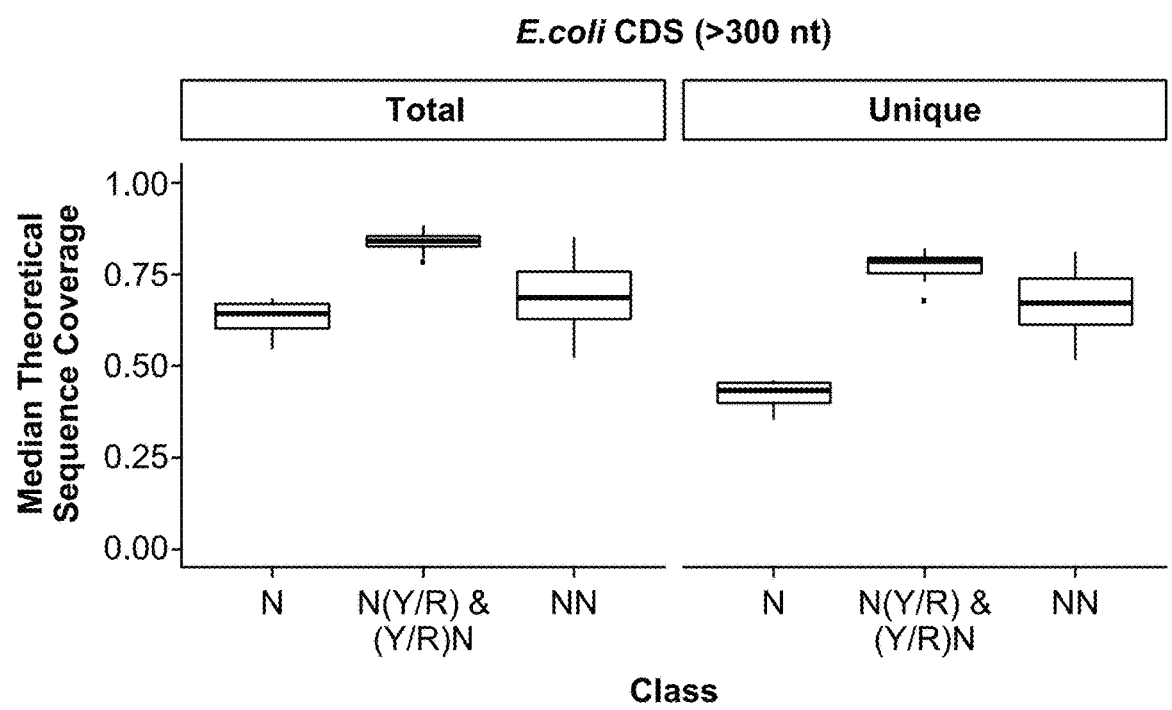
FIG. 6C shows the theoretical sequence coverage of the endoribonucleases for *E. coli* coding sequences (CDS).
Figure 6D:
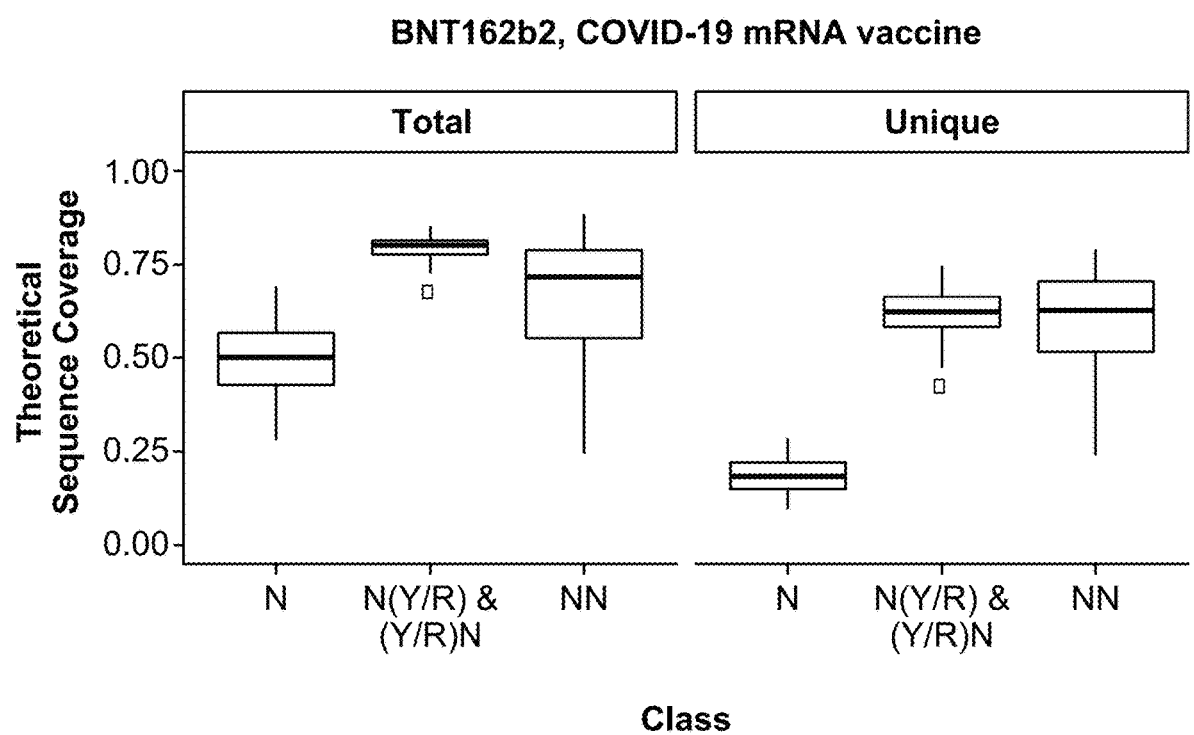
FIG. 6D shows the theoretical sequence coverage of the endoribonucleases for the BNT162b2 COVID-19 mRNA vaccine sequence. Endoribonucleases having hRNase 4-like cleavage specificities are predicted to produce superior mRNA coverage relative to endoribonucleases having a single dinucleotide sequence (NN) or single nucleotide (N) specificity.

As shown in FIG. 6A-C, cleavage specificities CN(Y/R) & (Y/R)N') that result in similar cleavage frequencies (1 out of 8) as to that of hRNase 4 produced consistently the highest theoretical sequence coverage (>75%) across a plurality of transcripts. In practice, the actual sequence coverage may vary, for example, where cleavage efficiency is a function of reaction conditions (e.g., buffer composition, pH, salt concentration, temperature, incubation time, etc.); enzyme specificity (e.g., some endonucleases show minor cleavage activities to other nucleotide combinations); enzyme quality (e.g., presence of contaminating nucleases or absence of essential/nonessential cofactors); and/or properties of the substrate RNA (e.g., the presence of secondary structure and/or RNA modifications). Endoribonucleases with cleavage specificity similar to the 'UR' of hRNase 4, such as 'N(Y/R)' or '(Y/R)N', may be suitable for applications such as mass spectrometry-based sequencing and fingerprinting of mRNA and other RNA substrates.

Example 4: Digestion of an RNA Oligonucleotide with T4 PNK and hRNase 4

Digestion of RNA with certain endonucleases may produce a mixture of cleavage products comprising 2',3'-cyclic-phosphate and 3'-phosphate at the 3' terminus. In many cases, this process depends on the enzyme concentration, the digestion buffer, and/or incubation time, in any combination. In some cases, the product mixture may also comprise 2',3'-hydroxylated species. In other cases, enzyme-independent hydrolytic opening of 2',3'-cyclic-phosphate may generate a mixture comprising 2',3'-cyclic-phosphate, 3'-phosphate, 2'-phosphate, 2',3'-hydroxy, 5'-phosphate, and/or 5'-hydroxy termini, in any combination. The occurrence of any of these mixtures convolutes analysis by mass spectrometry techniques. Therefore, it is highly desirable to resolve these mixtures prior to mass spectrometry analysis.

This example describes the digestion of a synthetic RNA oligonucleotide substrate by co-incubation with a mixture of T4 PNK (Phage T4 polynucleotide kinase) and hRNase 4. Briefly, 12.5 pmol of an RNA oligonucleotide substrate (Oligonucleotide #1: AAAAAAAAAAAAAUGAAAAAAAAAA)(SEQ ID NO:5) was incubated with a combination of 0.2 µL of T4 PNK and 1 µL of human hRNase 4 in 1×NEBuffer 1 (10 mM Bis-Tris-Propane-HCl, 10 mM MgCl$_2$, 1 mM DTT, pH 7) for 30 minutes at 37° C. A 9-minute gradient of solvent A (1% hexafluoroisopropanol (HFIP), 0.1% N,N-diisopropylethylamine (DIEA), 1 µM EDTA) and increasing solvent B (5-35%) (80% Methanol, 0.075% HFIP, 0.0375% DIEA, 1 µM EDTA) at a 0.3 mL/min flow rate was utilized for UHPLC analysis. A corresponding control hRNase 4 digestion in the absence of T4 PNK was utilized for comparison. The identity of all RNA cleavage products was confirmed by MS/MS analysis on a Thermo Scientific Q Exactive Plus Orbitrap Mass Spectrometer as described in Example 2.

FIG. 7 shows the overlaid UV chromatograms from hRNase 4 treatment of the Oligonucleotide #1 in the presence and absence of T4 PNK. A mixture of 5' cleavage products comprising 3'-phosphorylated and 2',3'-cyclic-phosphorylated ends was observed upon hRNase 4 digestion in the absence of T4 PNK (see FIG. 7, cleavage products #3 and #4). Whereas a single 5' cleavage product comprising a 2',3'-hydroxylated end was observed upon hRNase 4 digestion and addition of T4 PNK (see FIG. 7, cleavage product #2). A 3' cleavage product comprising a 5'-hydroxylated end was observed in both conditions in similar quantities (see FIG. 7, cleavage product #1). Taken together, these data demonstrate that the presence of an end-repair enzyme such as T4 PNK simplifies the analysis of hRNase 4 digests by deconvoluting mixtures of cleavage products comprising different phosphorylation statuses.

Example 5: Use of hRNase 4/T4 PNK for Sequencing and Mass Fingerprinting of an mRNA This example describes sequencing and fingerprinting of Firefly Luciferase messenger RNA (FLuc mRNA) by means of digestion with a combination of hRNase 4 and T4 PNK. For comparison purposes, digestion of FLuc mRNA was also performed with RNaseT1 alone.

A FLuc mRNA transcript was produced by in vitro transcription (IVT) utilizing the HiScribe™ T7 High Yield RNA Synthesis Kit (NEB, Catalog #E2040S). A linearized DNA template encoding the FLuc mRNA sequence (1 µg) under the control of T7 promoter was mixed with 10 mM rATP, 10 mM rGTP, 10 mM rCTP, 10 mM rUTP, and 2 µL of T7 RNA Polymerase in a 20 µL reaction volume. The resultant mixture was incubated at 37° C. for 2 h. The reaction mixture was diluted to 100 µL in 1× DNase 1 buffer (10 mM Tris-HCl, 2.5 mM MgCl2, 0.5 mM CaCl2, pH 7.6) and incubated with 2 µL of DNase 1 (NEB, Catalog #M0303S) for 15 minutes at 37° C. Subsequently, the in vitro transcribed FLuc mRNA (FLuc IVT mRNA) was purified utilizing an NEB Monarch RNA Cleanup Kit (500 µg) (NEB, Catalog #T2050L). The concentration of purified FLuc IVT mRNA was quantified utilizing a NanoDrop spectrophotometer (Thermo Fisher Scientific).

Figure 8:
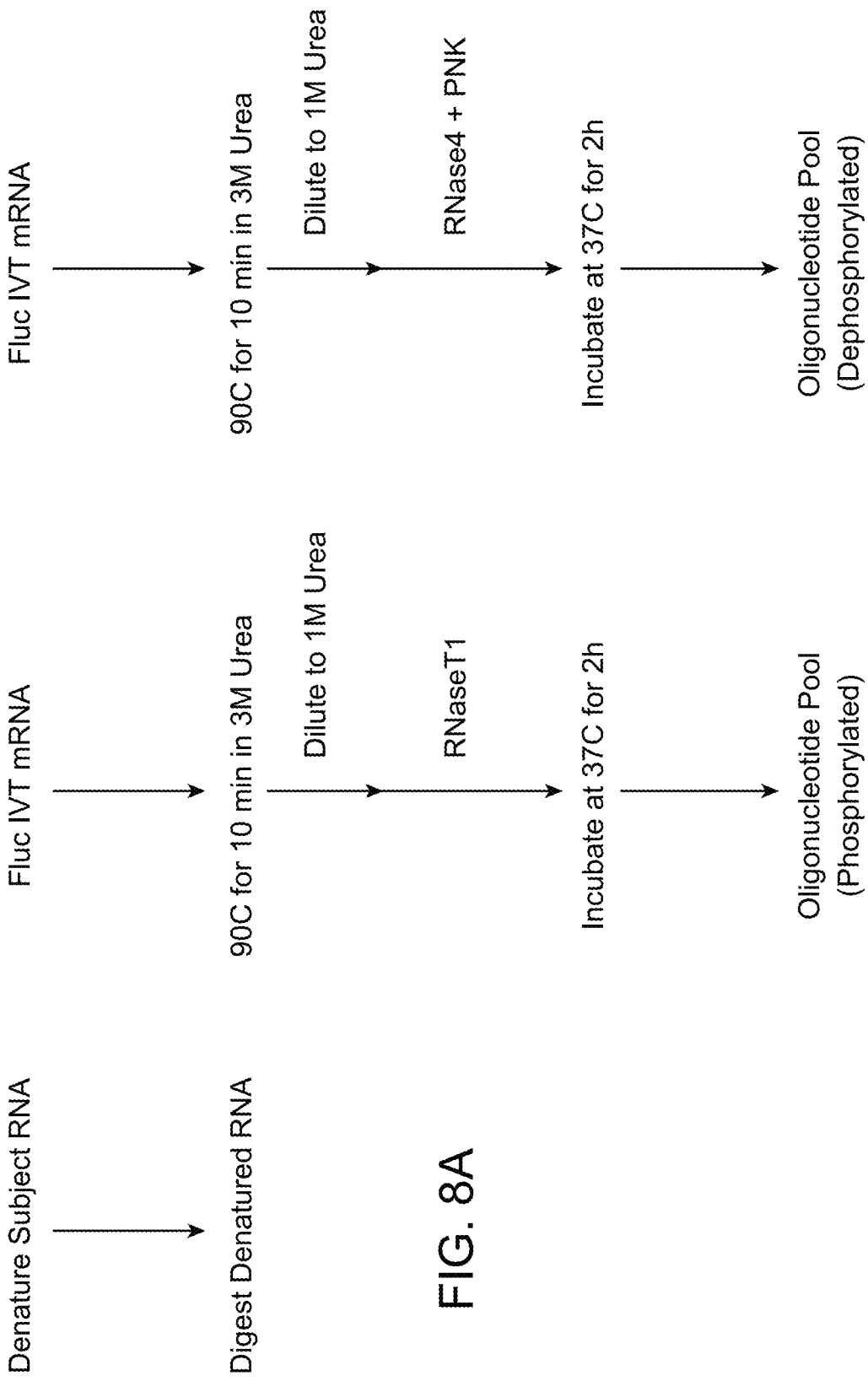
FIG. 8 shows example workflows used for digestion of an RNA.

Digestion using hRNase 4/T4 PNK was performed as illustrated in the example workflow in FIG. 8 (left panel) and example composition of Table 2. First, 10 µg of purified FLuc IVT mRNA was mixed with 3 M Urea in 1×NEBuffer 1 (10 mM Bis-Tris-Propane-HCl, 10 mM MgCl2, 1 mM DTT, pH 7). The mixture was heated to 90° C. for 10 minutes and cooled to room temperature. The mixture was diluted 3-fold in a 1×NEBuffer 1. Then 0.4 µL of T4 PNK (160 units) and 2 µL of purified recombinant human RNase4 was added to the reaction mixture (See Table 2). RNA digestion with hRNase 4/T4 PNK was performed for 2 h at 37° C. with shaking at 300 rpm. For comparison, a parallel digestion of FLuc IVT mRNA was performed using 1 µL of RNase T1 (FIG. 8, right panel). The resultant digestion products of either workflow were filtered using a Millipore Ultrafree MC-GV spin column (0.22 um) at 13,400 rpm for 5 minutes.

TABLE 2

Representative composition of an hRNase 4/T4 PNK digestion mixture

| Component | Volume | Final Concentration |
|---|---|---|
| NEBuffer 1 (10×) | 3 µL | 1 × NEBuffer 1 |
| human RNase4 | 2 µL | |
| T4 PNK (400,000 U/mL) | 0.4 µL | 160 Units |
| Urea (8M) | 3.75 µL | 1M |
| FLuc mRNA | x | 10 µg |
| Water | to 30 µL | |

Each sample was characterized by LC-MS/MS analysis as described in Example 2 with slight variations in the UHPLC gradient time and MS/MS parameters. A 25-minute UHPLC gradient was applied, and MS/MS data was collected with a Thermo Scientific Q Exactive Plus Orbitrap Mass Spectrometer in Top-5 ddMS2 acquisition mode at a resolution of 35,000 with a normalized collision energy of 20% in negative ionization mode. Theoretical prediction of the cleavage products generated by digestion of FLuc IVT mRNA with either hRNase 4 or RNase T1 is shown in FIG. 9. Complete digestion of FLuc IVT mRNA with hRNase 4 is predicted to produce a substantially higher sequence mapping (higher sequence coverage percentage) in comparison with RNaseT1. Notably, hRNase 4 is predicted to produce a high percentage of cleavage products with unique sequences, while RNase T1 is predicted to generate a high percentage of isomeric cleavage products.

Example 5A: hRNase 4/PNK-Based Mass Fingerprinting

The accurate determination of mass-to-charge (m/z) ratio of oligonucleotide cleavage products serves as a unique identifier of a particular RNA and allows identification of the unknown RNAs in a sample by matching the resulting oligonucleotide masses with the theoretical oligonucleotide masses of RNAs in a database (such as NCBI RefSeq).

Oligonucleotide mass fingerprinting was performed by deconvoluting raw intact MS data with ProMass software (Novatia LLC) and Avalon peak detection and integration algorithm (Thermo Fisher Scientific). Deconvoluted oligonucleotide masses detected in either the hRNase 4/T4 PNK condition or the RNaseT1 condition were compared to a database of human transcripts (RefSeq) in which the FLuc IVT mRNA sequence was spiked in. The product of the proportion of total spectral intensity explained by theoretical masses and the proportion of theoretical oligonucleotides identified in the spectra from each transcript was calculated, hereafter referred to as the score of each transcript.

Figures 10A, 10B:
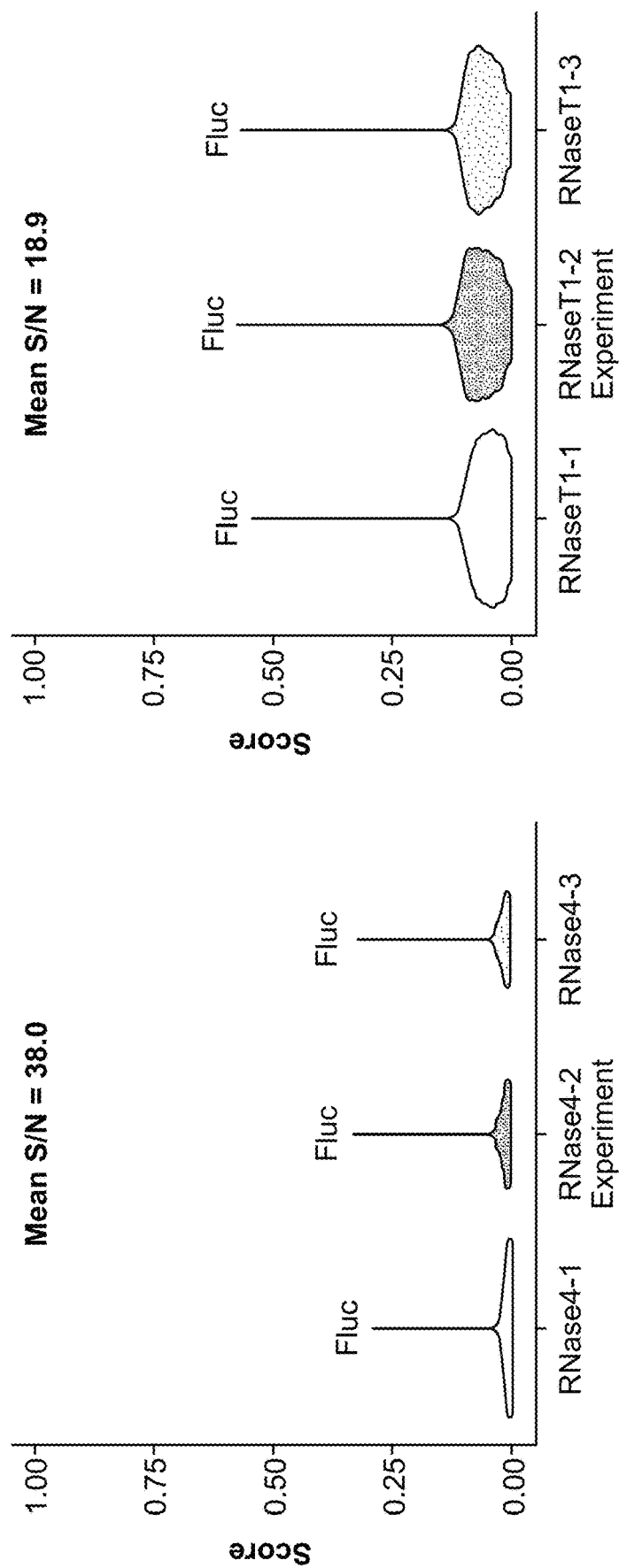
FIG. 10A shows the scoring distribution for digestion with hRNase 4/T4 PNK.
FIG. 10B shows the scoring distribution for digestion with RNase T1. A substantially higher background was observed using RNase T1 as a result of the high percentage of isomeric cleavage products.

As shown in FIG. 10 (upper panel), the value-based scoring analysis of the cleavage products generated by hRNase 4/T4 PNK permitted unambiguous identification of FLuc mRNA among all transcripts in the human transcriptome. These results indicate that mass fingerprint data produced upon digestion with hRNase 4/T4 PNK is sufficiently unique for identification of a particular transcript in the context of a human transcriptome database and have a lower identification background in comparison to mass fingerprints generated from digestion with RNaseT1 (FIG. 10, lower panel).

Example 5B: hRNase 4/T4 PNK-Based Sequencing

For hRNase 4/T4 PNK-based sequencing, the identities of sequenced cleavage products were inferred utilizing the Nucleic Acid Search Engine (NASE) (Wein et al., 2020) in OpenMS (version: 2.6.0). The search was conducted utilizing a theoretical digestion of the sequence of FLuc IVT mRNA with the cleavage specificity of either hRNase 4 or RNaseT1 and one missed cleavage at a 5% False Discovery Rate.

Figure 11:
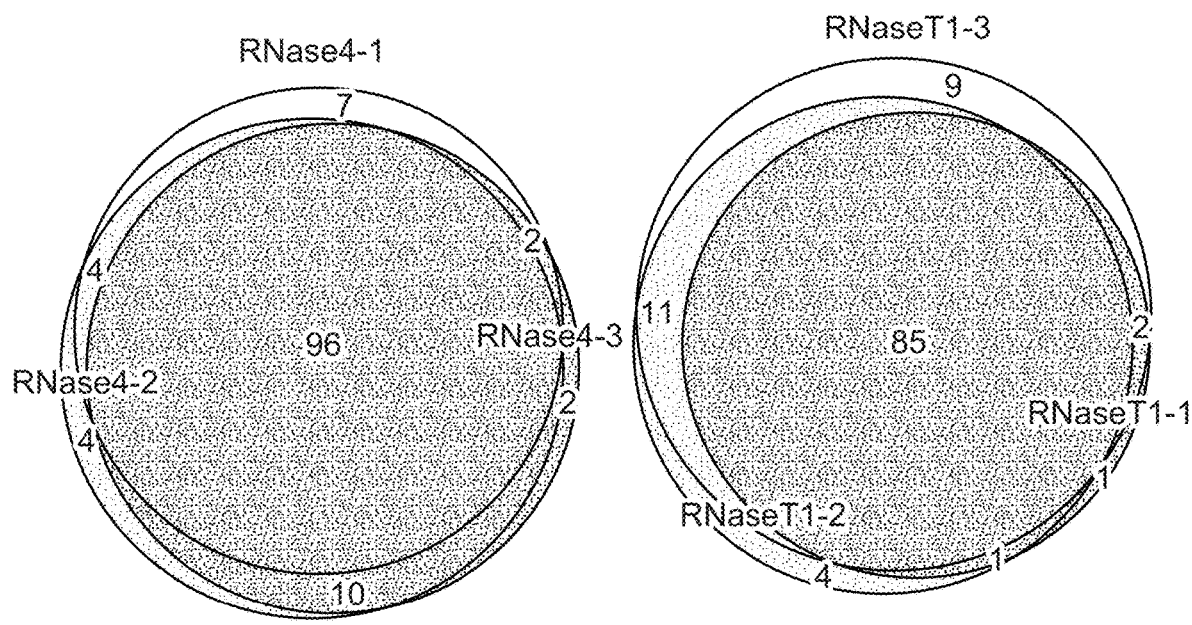
FIG. 11 shows the number of oligonucleotides identified in each pool of triplicate sequencing experiments of FLuc mRNA digests with the overlapping portion of each showing the oligonucleotides common to two or all three replicates. Most oligonucleotides were reproducibly identified in each pool with hRNase 4/T4 PNK (96) and RNase T1 (85). Each replicate had similar total number of spectral counts.

Digestion of FLuc IVT mRNA with either hRNase 4/T4 PNK or RNaseT1 resulted in reproducible sequencing profiles (results from 3 independent experiments are shown in FIG. 11, replicates 1-3). A total of 96 cleavage products were reproducibly observed in all hRNase 4/T4 PNK experiments and a total of 85 cleavage products were reproducibly observed in all RNase T1 experiments.

Figure 13:
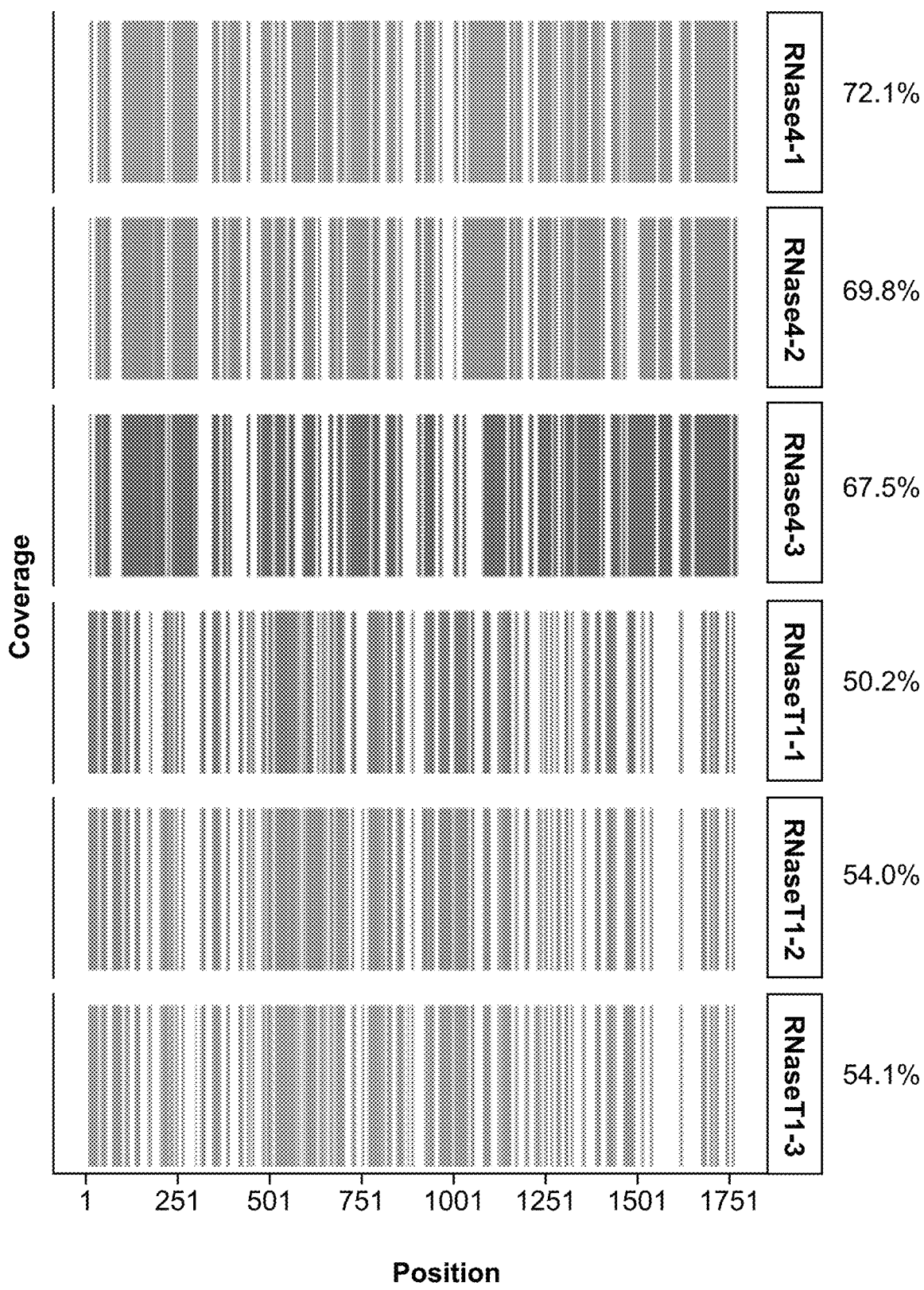
FIG. 13 shows the experimental coverage of FLuc mRNA observed in digests either with hRNase 4/PNK or with RNase T1. Improved sequence coverage of FLuc mRNA was observed in each hRNase 4/T4 PNK experiment (average 69.8%) relative to that of RNaseT1 (average 52.8%).
Figure 14:
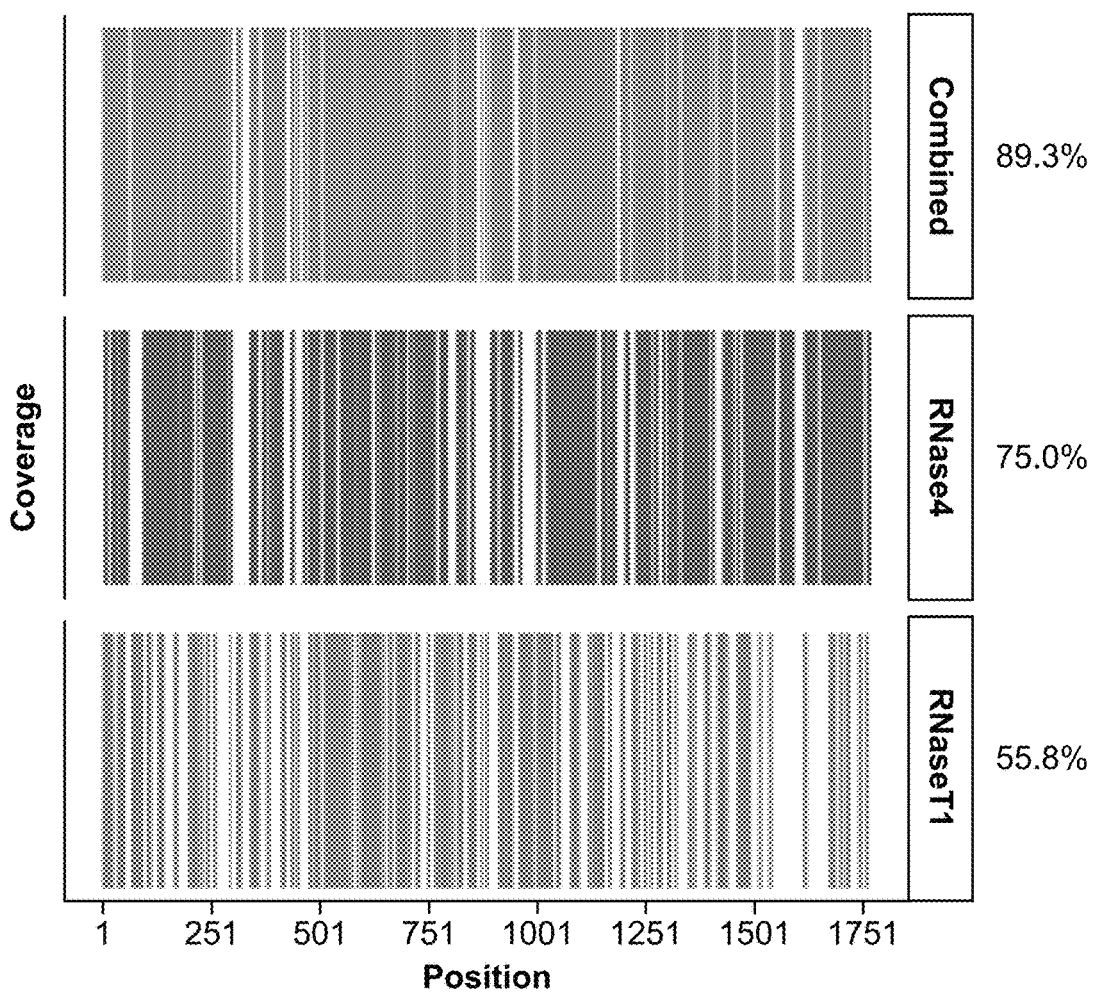
FIG. 14 shows the experimental coverage of FLuc mRNA observed in digests with RNaseT1 alone, hRNase 4 alone, or RNaseT1 and hRNase 4 in combination. Increased coverage may be obtained by combining oligonucleotide identifications across treatment with different endoribonucleases.

Specific differences in sequenced cleavage product length and total sequence coverage were observed in hRNase 4/T4 PNK digests in comparison to RNaseT1 digests. The median length and upper maximum length of cleavage products from hRNase 4/T4 PNK treatment were longer than those from RNase T1 treatment (see FIG. 12). In addition, total sequence coverages between 67.5% to 72.1% were obtained in hRNase 4/T4 PNK experiments, whereas coverages between 50.2% to 54.1% were obtained in RNase T1 experiments (see FIG. 13). FIG. 14 shows the FLuc mRNA sequence coverage after aggregating replicates of RNase T1 alone, hRNase 4/T4 PNK alone, or RNaseT1 and hRNase 4/T4 PNK combined. Aggregation of triplicate FLuc IVT mRNA digests resulted in 75% sequence coverage with hRNase 4/T4 PNK condition and 55.8% with RNaseT1 condition. Aggregation of FLuc IVT mRNA digests from combined hRNase 4/T4 PNK and RNaseT1 experiments resulted in an improvement in sequence coverage to 89.3%. Parallel digestion using hRNase 4/T4 PNK and RNase T1 may be beneficial due to the complementary cleavage specificities presented by these endoribonucleases.

Taken together, hRNase 4/T4 PNK resulted in a distribution of longer cleavage products with a higher overall coverage of the FLuc mRNA sequence in comparison to RNase T1. In addition, these data indicate that hRNase 4/T4 PNK offers a complementary alternative to conventional enzymatic tools such as RNase T1.

Example 6: MC1/T4 PNK-Based Sequencing an mRNA

This example shows that the composition embodying an RNA end-repair enzymes such as T4 PNK may be effectively extended to other endoribonucleases. The data presented here demonstrates the combination of T4 PNK with MC1, which is a uridine-specific endoribonuclease that produces a mixture of 2',3'-cyclic-phosphate and 3'-phosphate termini (Addepalli et al., 2015), for sequencing of FLuc IVT mRNA.

FLuc mRNA was prepared as described in Example 5. Digestion with MC1/T4 PNK was performed as follows: 5 µg of purified FLuc IVT mRNA was mixed with 3 M Urea in 1×NEBuffer 1 (10 mM Bis-Tris-Propane-HCl, 10 mM $MgCl_2$, 1 mM DTT, pH 7). The mixture was heated to 90° C. for 10 minutes and cooled to room temperature. The mixture was diluted 3-fold in a 1×NEBuffer 1. Then 0.2 µL of T4 PNK (20000 units) and 1 µL of ribonuclease MC1 were added to the reaction mixture. RNA digestion was performed for 1 h at 37° C. with shaking at 300 rpm. Digestions were performed in triplicate.

Figure 15:
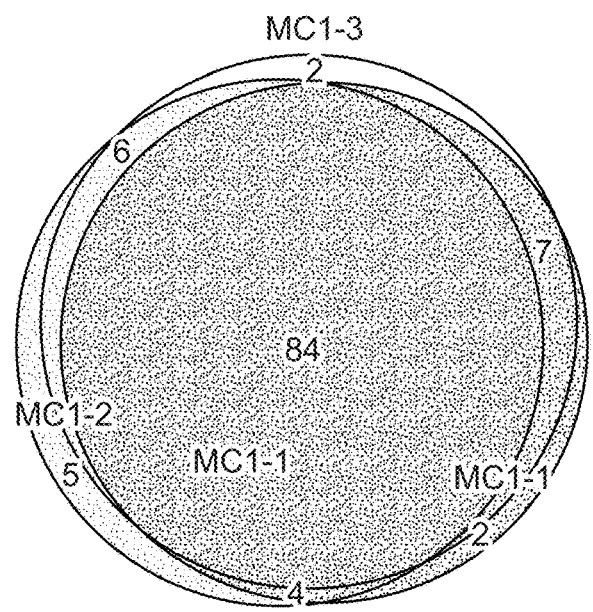
FIG. 15 shows the number of oligonucleotides identified in each pool of triplicate sequencing experiments of FLuc mRNA digests represented as a circle. The portions of circles that overlap represent oligonucleotides common to both (portions where two circles overlap) or all three (portions where all three circles overlap) replicates. Data is shown for MC1/T4 PNK-based digests and demonstrates that T4 PNK may be successfully co-incubated with diverse endoribonucleases to produce reproducible cleavage product identifications. MC1 belongs to the T2 RNase family and was isolated from seeds of the bitter gourd (*Momordica charantia*).
Figure 16:
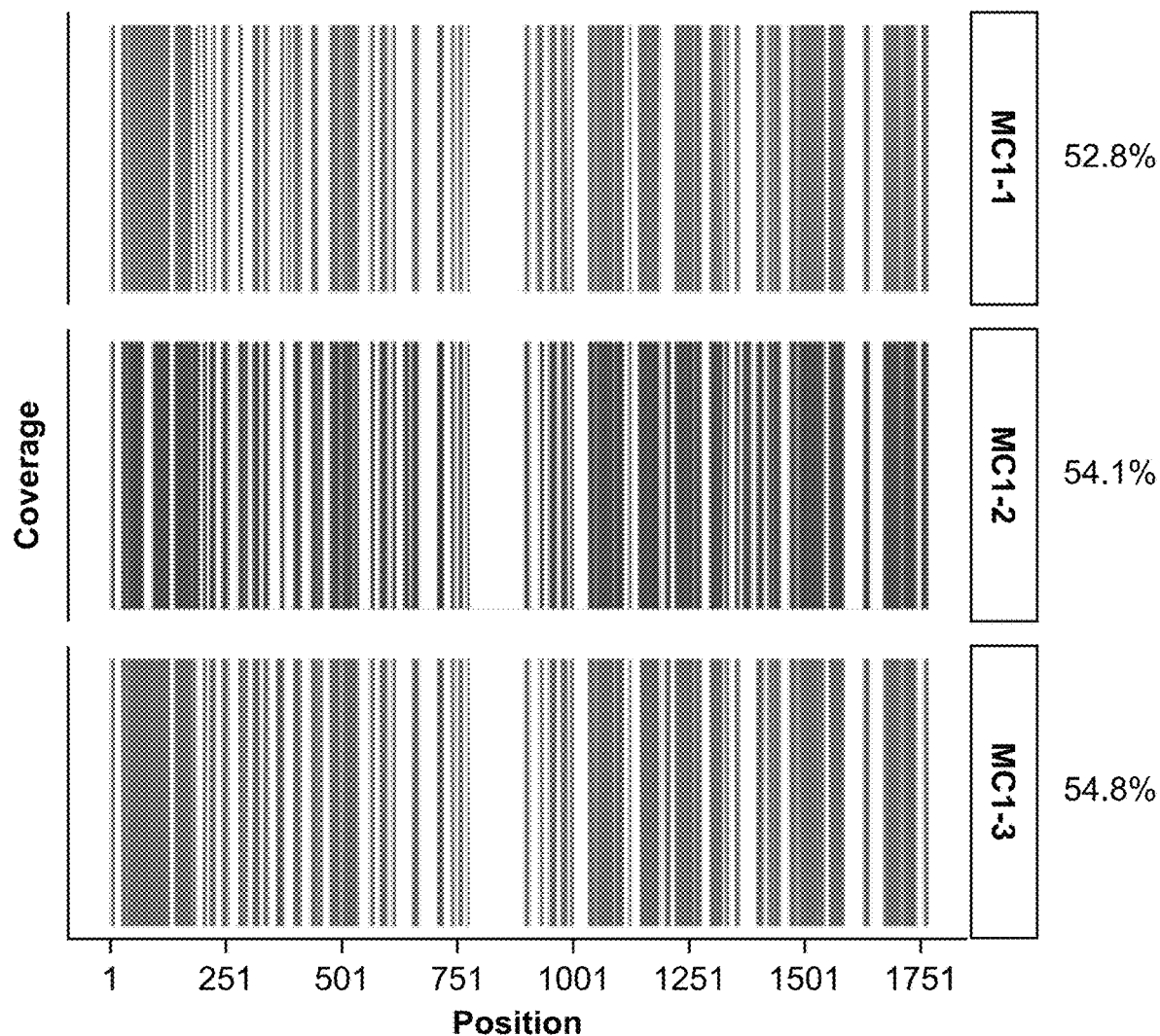
FIG. 16 shows the experimental coverage of FLuc mRNA observed in three digests with a composition of MC1/T4 PNK. Digestion with MC1/T4 PNK results in reproducible RNA sequence coverage.

Cleavage products from each digestion replicate were subjected to analysis by LC-MS/MS and the resultant data processed for sequencing analysis as described in Example 5, utilizing a theoretical digestion of FLuc IVT mRNA with the reported uridine specificity of MC1 (Grunberg et al., 2021). In total, 84 unique cleavage products were reproducibly sequenced across replicates (see FIG. 15) and an overall sequence coverage between 52-55% was obtained across FLuc IVT mRNA digestions with MC1/T4 PNK (see FIG. 16).

Taken together, the combination of MC1 and T4 PNK yielded a reproducible sequencing profile of FLuc mRNA, demonstrating that other endoribonucleases (beyond hRNase 4) may be combined with T4 PNK.

Example 7: hRNase 4/T4-PNK-Based Sequencing and Fingerprinting of a Human Erythropoietin (Epo) mRNA This example describes sequencing and fingerprinting of in vitro synthesized human erythropoietin (Epo) mRNA. Epo mRNA was in vitro transcribed either using canonical UTP, ATP, GTP, and CTP (herein referred as to U Epo mRNA or EpoU), or using mo5UTP replacing UTP to result in a Epo mRNA with full substitution of uridine with 5-methoxyuridine (herein referred as to mo5U Epo mRNA or EpomoU), or using m1YTP replacing UTP to result in a Epo mRNA with full substitution of uridine with 1-methyl-pseudouridine (herein referred as to m1Y Epo mRNA or Epom1Y). The incorporation of specific modified uridine nucleotides, including m1Y and mo5U has been shown to reduce immunogenicity and enhance translation/stability of exogenously delivered IVT mRNAs (Karikó et al., 2008; Anderson et al., 2010; Parr et al., 2020; Li et al., 2011; Svitkin et al., 2017). Furthermore, Epo mRNA has been utilized to demonstrate the therapeutic potential of IVT mRNAs in the treatment of anemia (Kariko et al., 2012, Thess et al., 2015). Hence, Epo mRNA fully modified with mo5U or m1Y was utilized as a model system to assess the use of hRNase 4 in combination with T4 PNK to characterize putative therapeutic mRNAs.

5 µg of purified mo5U/m1Y/U Epo mRNAs were prepared and digested with hRNase 4/T4 PNK or RNaseT1 essentially as described in Example 5. LC-MS/MS data was processed for mass fingerprinting and sequencing analysis as described in Example 5.

Figure 17:
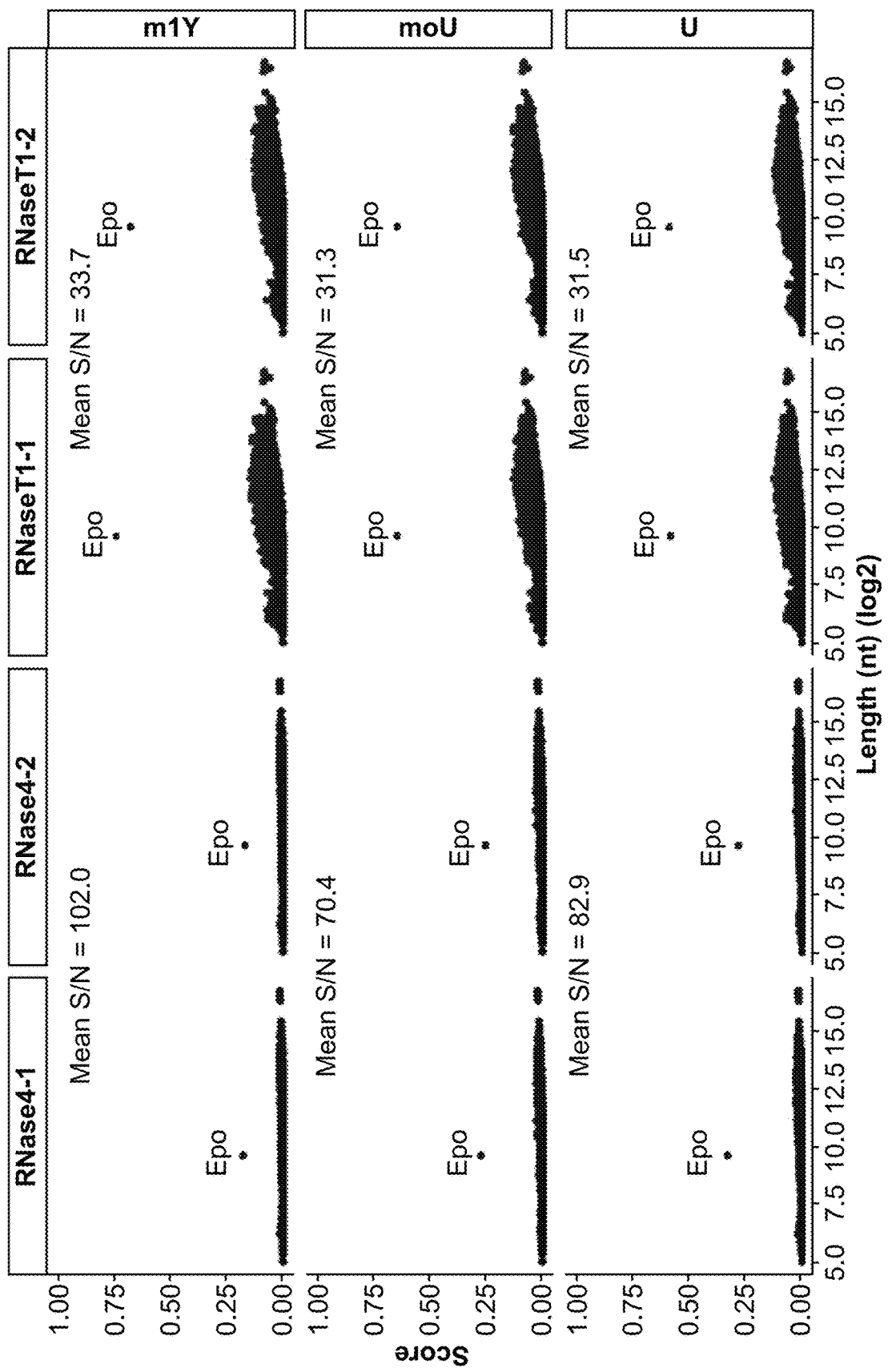
FIG. 17 shows the scoring distribution of an example search of the deconvoluted masses of Epo mRNA digests against a Epo mRNA-spiked in human transcriptome database. Epo mRNA cleavage products were generated by digestion EpoU, EpomoU, or Epom1Y mRNA either with hRNase 4/T4 PNK (replicate 1, column 1; replicate 2; column 2) or with RNase T1 (replicate replicate 1, column 3; replicate 2, column 4). The mean signal-to-noise ratio (S/N) of the score of each U-modified (lower row), $m^1Y$-modified (top row), or $mo^5U$-modified (middle row) EPO mRNA sequence relative to all other transcripts is reported at the top of each pair of graphs. Cleavage products produced by RNase T1 are generally shorter in length as exemplified in FIG. 11. Accordingly, there is a higher probability of mapping those oligonucleotides to unrelated transcript sequences thereby increasing the analysis background.

First, the specificity of each mass fingerprint in the context of a human transcriptome database supplemented with the synthetic Epo mRNA sequence was assessed. FIG. 17 shows the score (as defined in Example 5) of each transcript relative to RNA length. The synthetic Epo mRNA sequence could be uniquely identified relative to all other human transcripts in each of hRNase 4/T4 PNK or RNase T1 conditions. However, RNase T1 data exhibited a substantially higher identification background relative to that of hRNase 4/T4 PNK.

Figure 18A:
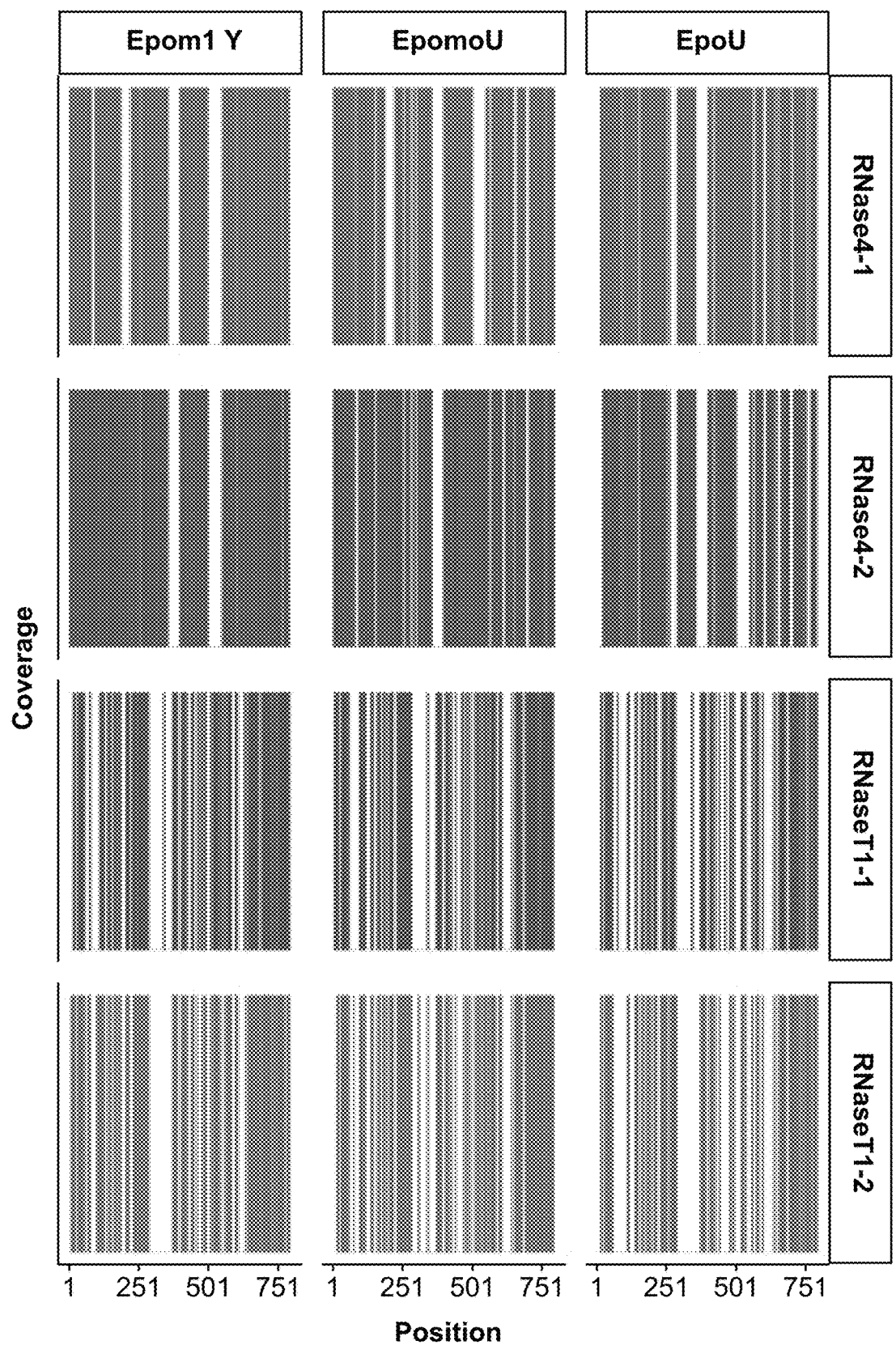
FIG. 18A shows the sequence coverage of fully modified EpoU (right column), EpomoU (middle column) or Epom1Y (left column) mRNAs upon analysis of cleavage products originated from digestion with either hRNase 4/T4 PNK (replicate 1, row 1; replicate 2, row 2) or with RNaseT1 (replicate 1, row 3; replicate 2, row 4).
Figure 18B:
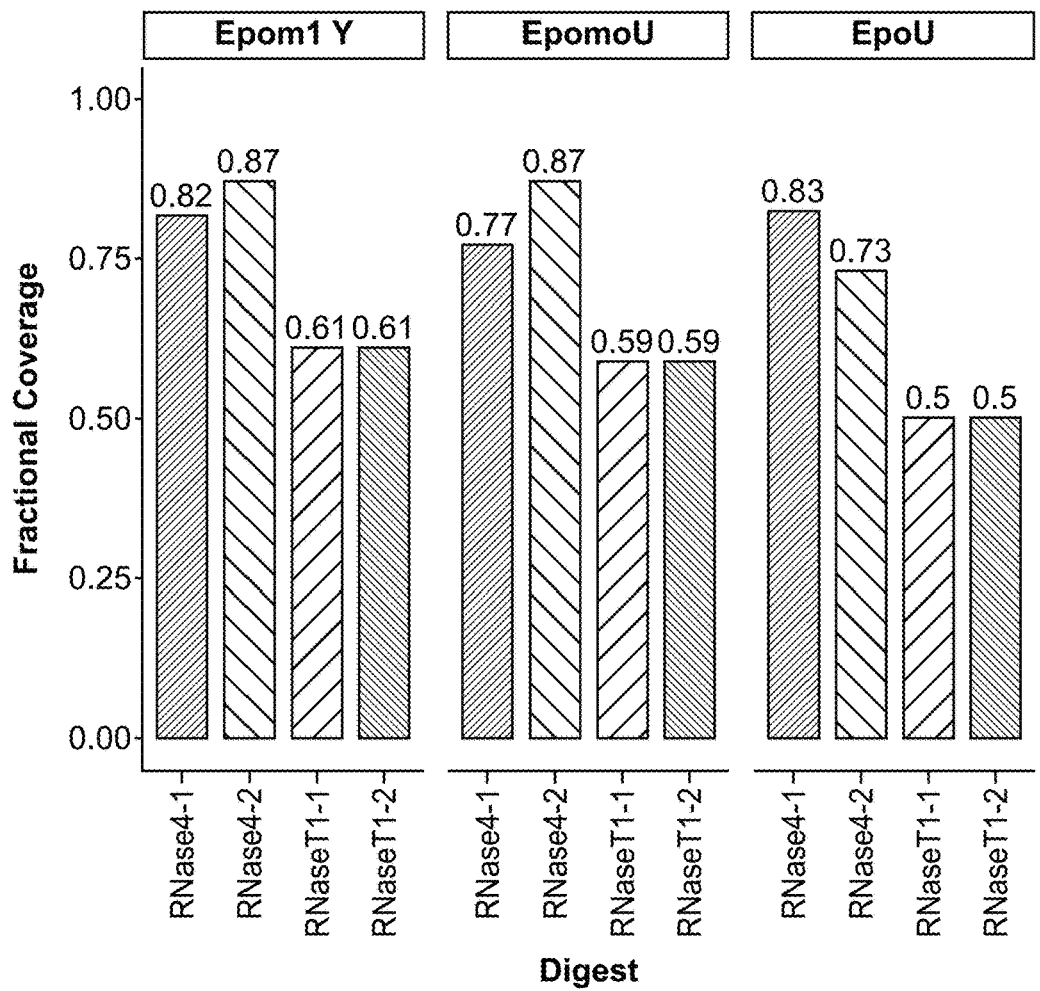
FIG. 18B shows the fractional coverage of fully modified EpoU, EpomoU or Epom1Y mRNAs upon analysis of cleavage products originated from digestion with either hRNase 4/T4 PNK or with RNaseT1. The hRNase 4/T4 PNK condition substantially increases coverage for canonical or base modified Epo mRNAs relative to the RNase T1 condition.

Second, the MS/MS-based sequencing data was examined from digestion of each of mo5U/m1Y/U Epo mRNAs with either hRNase 4/T4 PNK or RNaseT1. FIG. 18 shows the overall sequence coverage obtained in each digestion experiment. Digestion with hRNase 4/T4 PNK resulted in consistently higher sequence coverage (73-87%) relative to digestion with RNase T1 (50-61%) across all Epo mRNA substrates tested.

Taken together, these data support using a composition comprising hRNase 4 and T4 PNK for sequencing and fingerprinting therapeutic RNAs, including mRNAs comprising nucleotide modifications such as mo5U or m1Y. With its ability to cleave uridine-based RNA modifications (e.g., mo5U, Y, methylpseudouridine (m1Y) and 5-methoxyuridine (mo5U)), hRNase 4 may be useful for applications in the analysis of mRNA-based medicines (e.g., mRNA vaccines and therapeutics).

Example 8: hRNase 4/T4-PNK-Based Characterization of an Epo mRNA Comprising a 5-Prime m7GpppAm Cap and 3-Prime Poly-Adenosine (Poly-A) Tail This example describes the use of hRNase 4/T4 PNK for characterizing Epo mRNAs comprising a 5' terminal m7GpppAm cap and a 3' terminal 120-nt poly-adenosine (Poly-A). The presence of 5' cap and 3' poly-A tail structures may confer or improve the stability and/or translation of an IVT mRNA upon introduction into mammalian cells and organisms.

The synthesis of a 5' capped m7GpppAm Epo mRNA was performed utilizing Clean Cap AG® technology (Henderson et al., 2021). A 3' 120-nt poly-A tail was introduced by encoding the tail sequence in the DNA template that was utilized for in vitro transcription. 10 µg of purified U Epo mRNA comprising a 5' cap and 3' poly-A tail were prepared and digested with human hRNase 4/T4 PNK as described in Example 5. The purified U Epo mRNA from Example 7 (without both 5' cap and 3' poly-A tail) was used as a control.

First, the presumed oligonucleotides originating from the 5' end of both capped and uncapped Epo mRNAs were investigated. To this end, deconvoluted intact mass data were searched for the masses of all possible 5' cleavage products with three missed cleavages and variable addition of a monophosphate, diphosphate, triphosphate, "monomethyl" guanosine triphosphate or "dimethyl" guanosine triphosphate within a mass difference cutoff of 10 ppm. FIG. 19 shows a summary of the intensities of 5' cleavage products detected with and without a 5' m7GpppAm cap. Consistent with the presence of 5' cap m7GpppAm structure, oligonucleotides comprising deconvoluted masses equivalent to a triphosphorylated guanosine and two methyl groups were detected only in the capped Epo mRNA digests.

Figure 20:
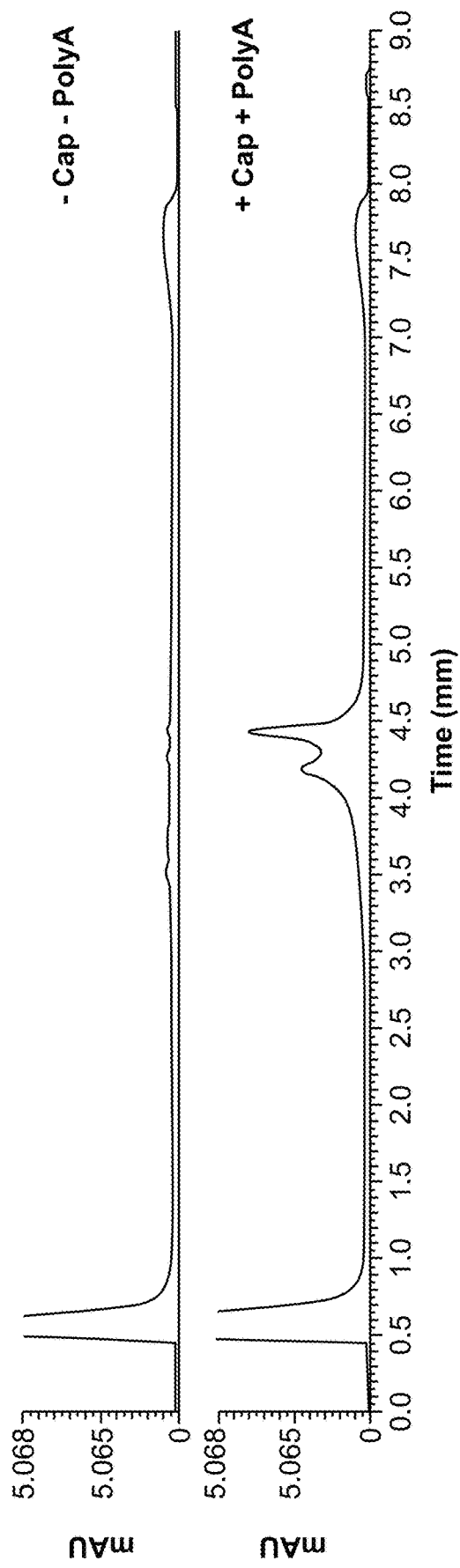
FIG. 20 shows example UV chromatograms of RNA cleavage products. The upper trace shows that no higher-retention cleavage products detected were detected in hRNase 4/T4 PNK treatment of Epo mRNA that lacked a poly-A tail whereas the lower trace shows that higher-retention cleavage products were detected in hRNase 4/T4 PNK treatment of Epo mRNA comprising a poly-A tail. These data show that polyA tails may be detected by cleavage with hRNase 4/T4 PNK.

Next, the presumed presence of a poly-A tails was examined in each Epo mRNA digest. To this end, cleavage products from each experiment were characterized by UHPLC analysis similar to the approach described in Example 2, which was modified with an increased 18-45% gradient of non-aqueous buffer. Notably, only the 3' poly-adenylated Epo mRNA samples exhibited a distinct chromatographic peak with higher retention, which was associated to the cleaved 3' poly-A tail sequence (see FIG. 20).

Taken together, these data indicate that a composition of hRNase 4/T4 PNK is useful for characterization of the 5' cap and 3' poly-A tail structures in mRNAs.

Example 9: hRNase 4/T4-PNK-Based Characterization of Uridine-Depleted Variants of CLuc mRNA This example describes the LC-MS/MS analysis of three highly similar uridine-depleted variants of CLuc (Cypridina luciferase) mRNA using a composition of hRNase 4/T4 PNK. Depletion of the number of uridines in an RNA template has been utilized as a strategy to reduce the immunogenicity of IVT mRNAs without the need for introduction of chemical modifications (Vaidyanathan, et al., 2018).

5 µg of each purified uridine-depleted variant of CLuc mRNA was prepared and digested with hRNase 4/T4 PNK and characterized by fingerprinting and sequencing as described in Example 5. A schematic representation of the depletion region in each of three uridine-depleted CLuc mRNAs (CLuc U1, CLuc U2, and CLuc U3) is shown FIG. 21.

Figure 21A:
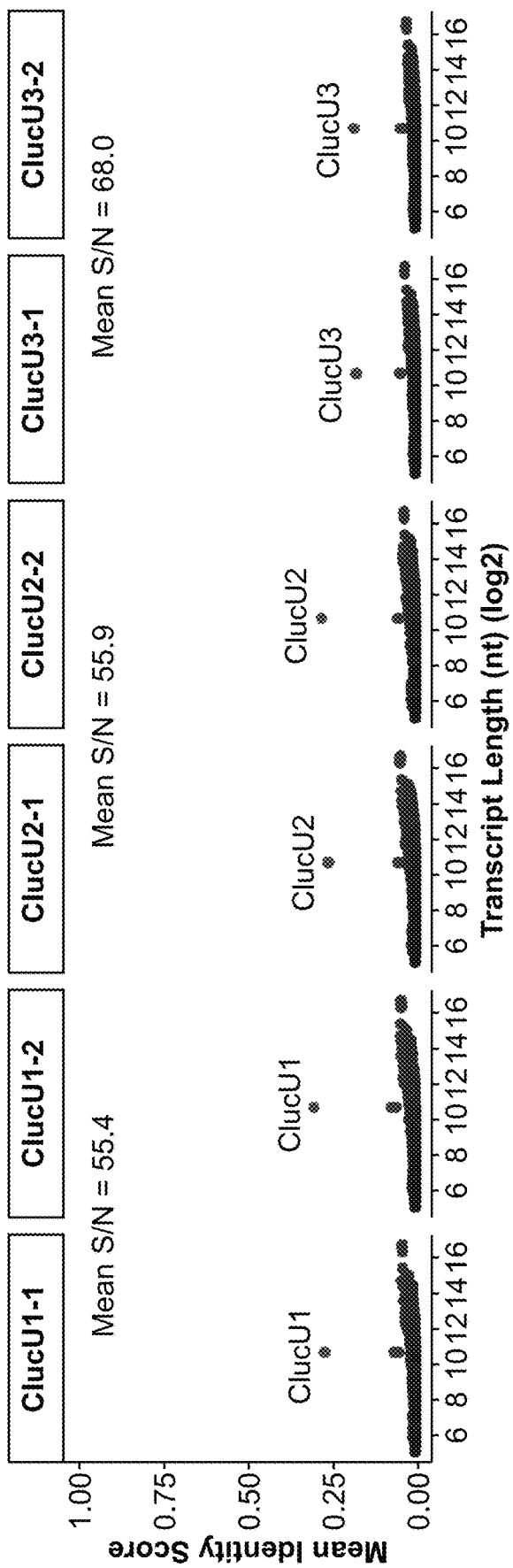
FIG. 21A shows the scoring distribution of an example search of the deconvoluted masses of uridine-depleted CLuc mRNA digests against a CLuc mRNA-spiked in human transcriptome database. Cleavage products derived from uridine-depleted CLuc mRNAs were generated by digestion with hRNase 4/T4 PNK (2 replicates per substrate). The mean signal-to-noise ratio (S/N) of the score of each uridine-depleted cLuc mRNA sequence relative to all other transcripts is reported at the top of each pair of graphs.
Figure 21B:
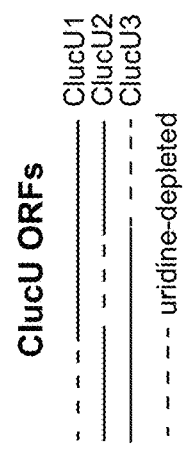
FIG. 21B shows a schematic representation of the relative location of depletion regions (broken lines) in each of three uridine-depleted CLuc mRNAs used in this experiment (CLuc U1, CLuc U2, and CLuc U3).

First, the specificity of each mass fingerprint in the context of a human transcriptome database supplemented with each uridine-depleted CLuc mRNA sequence was assessed (see FIG. 21). The correct uridine-depleted CLuc mRNA substrate was uniquely identified in each digestion experiment by LC-MS fingerprinting analysis.

Figure 22:
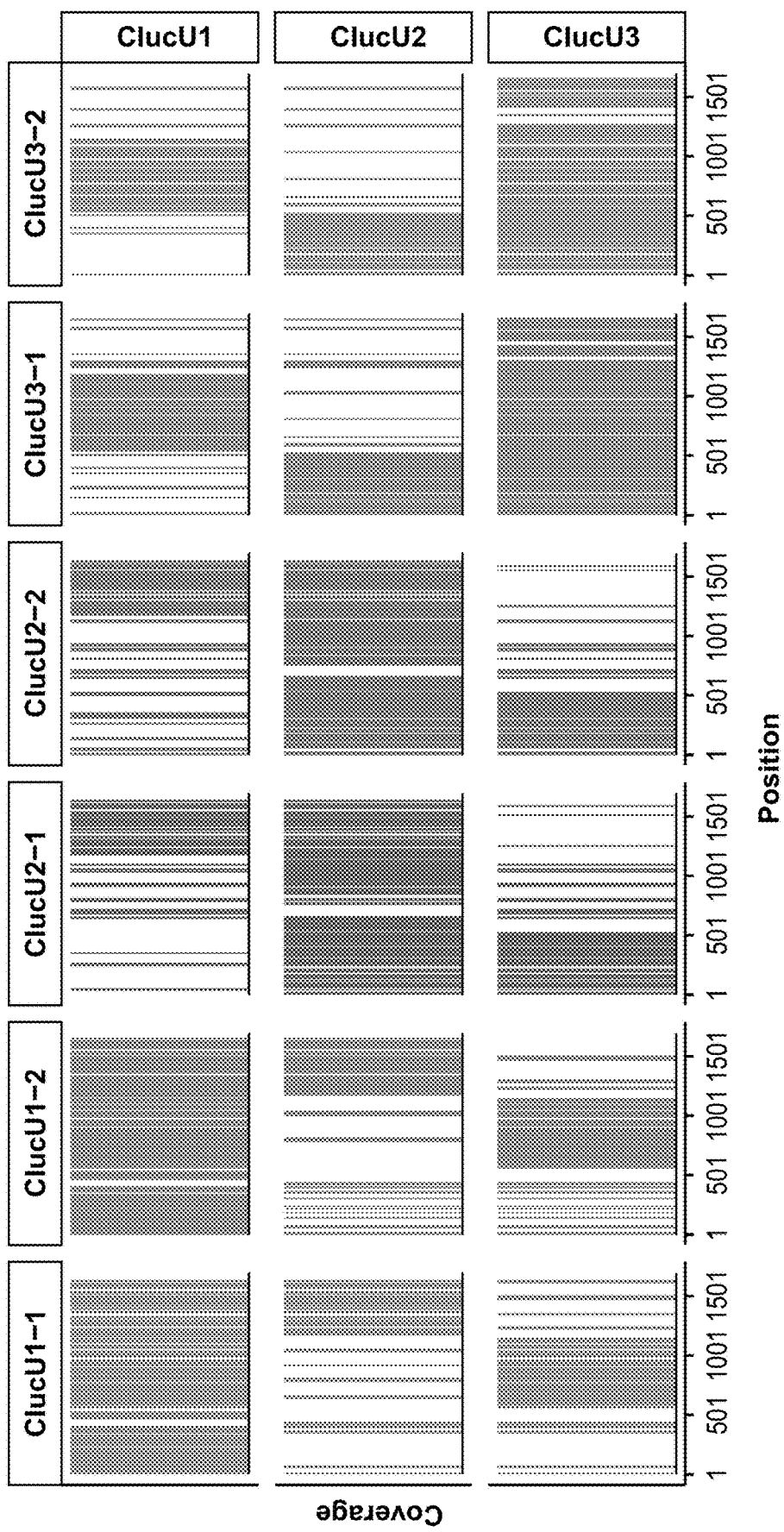
FIG. 22 shows a sequence coverage map of each uridine-depleted CLuc mRNA upon analysis of cleavage products originated from digestion with hRNase 4/T4 PNK, accounting for shared sequences between each sample. The detected coverages regions are represented for each of CLuc U1 (replicate 1 and 2, left columns), CLuc U2 (replicate 1 and 2, middle columns), CLuc U3 (replicate 1 and 2, right columns). Despite the similarity among these sequences, analysis of hRNase 4 digests enabled correct annotation of each mRNA comprising distinct uridine-depleted segments.
Figure 23:
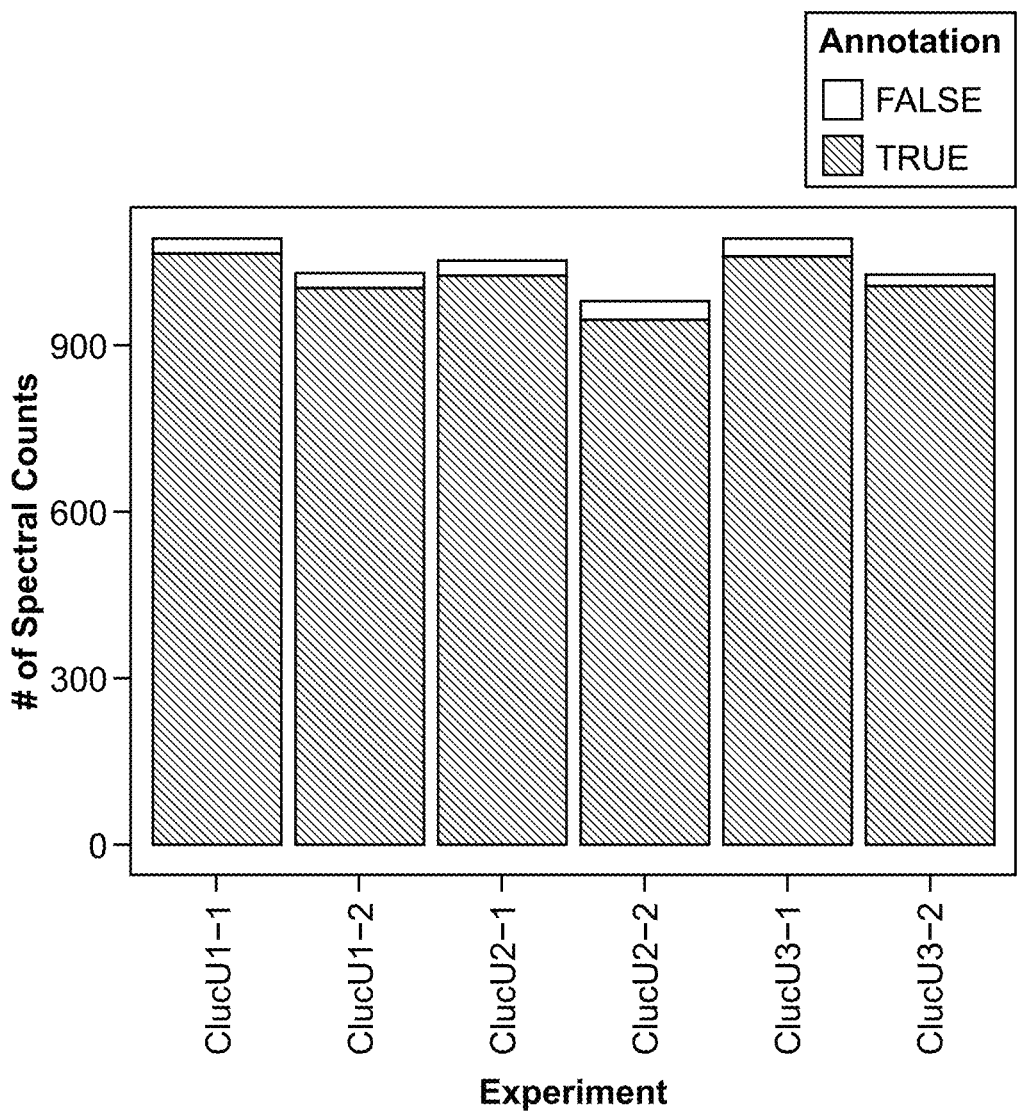
FIG. 23 shows the number of true positive and false positive oligonucleotide identifications of each uridine depleted CLuc mRNA upon digestion with hRNase 4/T4 PNK (2 replicates per sequence) in accordance with an example embodiment.

Next, the sequenced cleavage products detected in each hRNase 4/T4 PNK digest were assessed. FIG. 22 shows the sequence coverage of each uridine-depleted mRNA substrate in each hRNase 4/T4 PNK digest. In each experiment, the correct uridine-depleted CLuc mRNA sequence exhibited a substantially higher sequence coverage relative to the others. In addition, the vast majority of sequenced cleavage products detected could be confidently attributed to the correct uridine-depleted CLuc mRNA in each experiment (see FIG. 23).

Taken together, hRNase 4/T4 PNK may be utilized to discriminate between highly similar nucleotide-depleted substrates by both sequencing and fingerprinting techniques.

Example 10: Isotopically Labeling RNA Oligonucleotides for Quantification Analysis An example method to add one or more stable isotope mass labels to the 3'-end of dephosphorylated RNA oligonucleotides is described. RNA oligonucleotides are prepared by digestion of an RNA-of-interest using hRNase 4/T4 PNK or a related composition as described above. This labeling method may be useful for and/or combined with multiplexing and relative quantification of one or more RNA oligonucleotides.

Figure 24C:
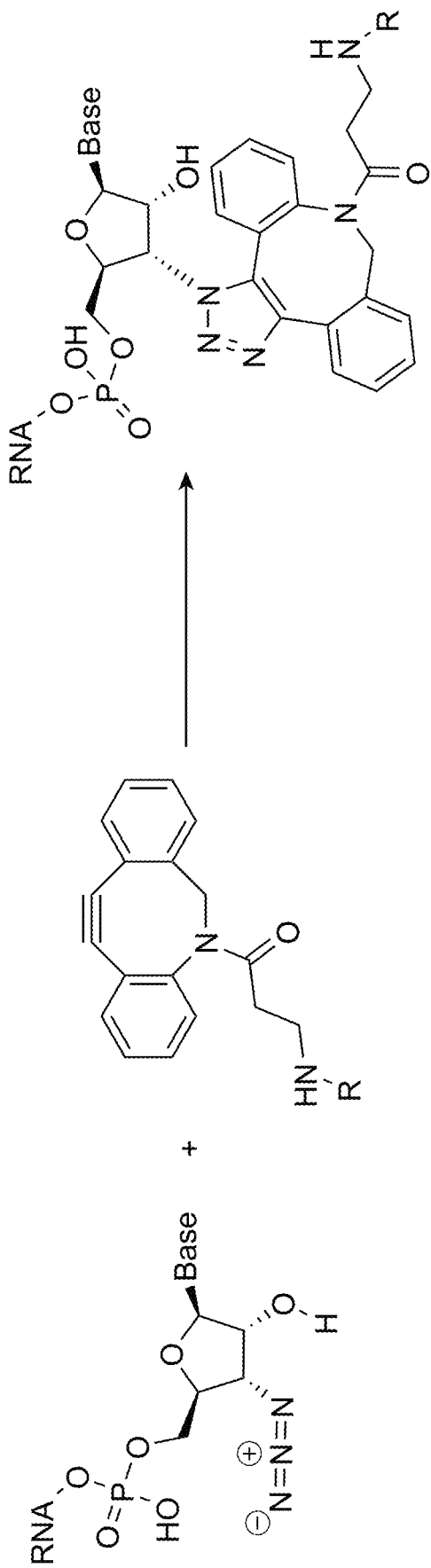

First, a non-template directed RNA polymerase is utilized to add a single 3'-azido-3'-deoxy-nucleotidetriphosphate (NTP) to the 3'-end of one or more RNA oligonucleotides (see FIG. 24A). Examples of a non-template directed RNA polymerase include, E. coli poly(A) polymerase, yeast poly (A) polymerase, DNA polymerase θ or any non-template directed RNA polymerase which accepts 3'-azido-3'-deoxy-NTPs as a substrate. Next, a Dibenzocyclooctyne (DBCO)-derived amino acid or peptide conjugate mass label is added to the 3'-terminal 3'-azido-3'-deoxy-nucleotide residue utilizing copper-free (also referred as to strain-promoted) click chemistry (Baskin et al., 2007) as shown in FIG. 24B and FIG. 24C. Examples of DBCO conjugate mass labels involving an amino acid and a dipeptide are shown in FIG. 24B.

Mass label conjugates may be utilized to produce "heavy" and "light" variants of differential isotopic composition for the comparison between two experimental conditions, for example for the analysis of 5'-capped and uncapped mRNAs. One sample (e.g., RNA oligonucleotides generated by digestion of an uncapped mRNA) is labeled with a "light" version of a mass tag as described above. The other sample (e.g., RNA oligonucleotides generated by digestion of a mRNA whose capping percentage is unknown) is labeled with a version of the same tag that comprises a "heavy" isotope. After labeling, the samples are combined and analyzed within the same experiment. Identical oligonucleotides from each sample co-elute as pairs of peaks and may be distinguished by the mass difference between the "heavy" and "light" isotope content. By establishing the ratio of signal intensities of oligonucleotides from the uncapped mRNA sample relative to the corresponding oligonucleotides from the sample whose capping percentage is unknown, it is possible to accurately determine the levels of capping in the unknown sample. Identification and quantitation of the relevant 5' end oligonucleotides are performed by a combination of intact MS and MS/MS fragment analyses. This approach may be extended to quantify other features of RNA substrates, such as RNA modification analysis. The mass tag concept is not restricted to isotopically labeled amino acids and could be extended as to other molecule classes (i.e., the group R in FIG. 24B could comprise a keto acid, a lipid, a carbohydrate, etc.).

DBCO dipeptide conjugates may be utilized to produce isobaric dipeptide (or polypeptide) mass tags. In this approach, each tag has the same molecular mass, but the positions of the "heavy" and "light" isotopes are distributed within the peptide. This is achieved, for instance, by placing combinations of 13C and 15N heavy isotopes at different positions for each tag, so that the total number of isotopes is constant for all tags, thus creating distinct reporter and balancing regions. Upon fragmentation, such as with a HCD (Higher-energy C-trap Dissociation; a collision-induced dissociation technique specific to the orbitrap mass spectrometer), reporter and balancing peptide fragments may be distinguished, and the identity and quantity of each mass tag determined. Samples labeled with distinct peptide conjugate mass labels may be multiplexed and compared by LC-MS/MS analysis as described in Example 2. This approach permits multiplexed analysis of several RNA features in the same experiment (for instance, the simultaneous analysis of multiple RNA modifications in a given mRNA).

In some embodiments, methods and workflows may include fragmentation of peptide-RNA nucleoside conjugates utilizing high energy collision dissociation (HCD). Labeling RNA oligonucleotides with isobaric tags with distinct stable isotopic distributions is an example of an approach that may be utilized to enable multiplexing and relative quantification of RNA oligonucleotides between different experimental samples. Various molecular scaffolds may be utilized as isobaric tags, such as amino acids, keto acids, fatty acids, diamines, amino alcohols, carbohydrates, and dipeptides among others. Dipeptides may be cleavable by fragmentation modalities such as HCD, at the amide bond between the N-terminal and C-terminal amino acids to produce an amino acid reporter anion. The amino acid reporter anion fragment may comprise a defined set of heavy and light isotopes in its composition so that differential isotopic composition between the isobaric tag and the reporter fragment distinguish and relatively quantitate labeled oligonucleotide from distinct samples and/or experimental conditions (e.g., capped and uncapped mRNAs), A 3'-azido-3'-deoxyadenosine nucleoside was independently conjugated to three amino acid/dipeptide labels by copper-free click chemistry reaction with DBCO-alanine, DBCO-alanine-phenylalanine or DBCO-alanine-Proline. FIGS. 24D-24F show the fragmentation pattern by HCD (with a normalized HCD of 30%) of the three 3'-azido-3'-deoxyadenosine derived peptide-nucleoside conjugates—including 3'-azido-3'-deoxyadenosine conjugated to DBCO-alanine (FIG. 24D), to DBCO-alanine-phenylalanine (FIG. 24E) and to DBCO-alanine-Proline (FIG. 24F). The single amino acid conjugate formed by the reaction of 3'-azido-3'-deoxyadenosine with DBCO-alanine was used as a model for the fragmentation studies. The main anions detected upon fragmentation of the nucleoside-alanine conjugate were derived from the adenosine nucleobase (denoted as A-base for simplicity), triazole-DBCO (denoted as DBCO for simplicity), and triazole-DBCO-alanine (denoted as DBCO-Ala for simplicity) fragments. The fragmentation of the dipeptide conjugates formed by the reaction of 3'-azido-3'-deoxyadenosine with DBCO-alanine-phenylalanine or with DBCO-alanine-Proline dipeptides is shown in FIG. 24E and FIG. 24F. Notably, fragmentation between the N-terminal and C-terminal amino acids for each of those dipeptide conjugates produced the intended amino acid reporter anion: phenylalanine (Phe) and proline (Pro) derived anions, respectively. These data suggest that this is a viable strategy to generate discrete reporter anions from nucleoside-peptides conjugates. By incorporating a defined set of heavy stable isotopes in a dipeptide such as those presented in this example, isobaric tags can be thus generated, and the corresponding reporter anions applied to oligonucleotide quantification.

Figure 26:
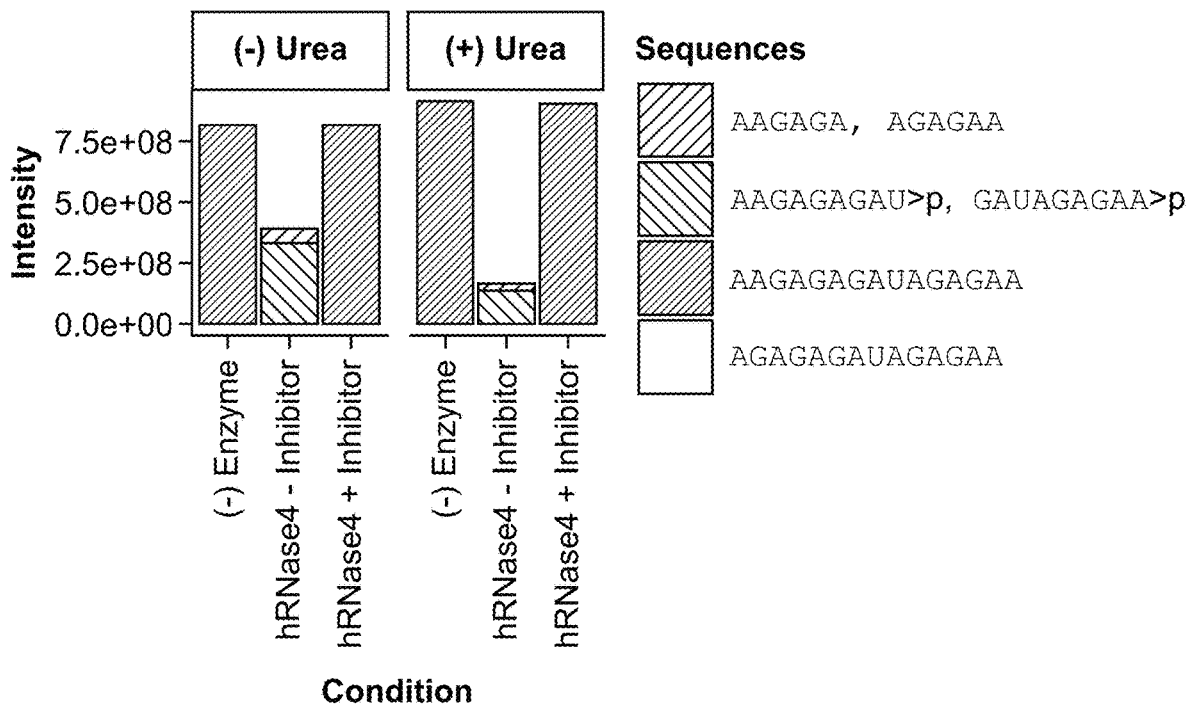
FIG. 26 shows the relative intensities of the oligonucleotides detected by LC-MS/MS analysis following hRNase 4 cleavage in the presence and absence of human placental RNase inhibitor. Data shown demonstrate that hRNase 4-mediated cleavage of an RNA oligonucleotide is inhibited by human placental RNase inhibitor. Sequences shown include SEQ ID NO: 23 and subsequences thereof (positions 1-6, positions 1-9, positions 2-15, positions 7-15, positions 10-15).

Example 11: Inhibition of hRNase 4 Activity with Human Placental RNase Inhibitor Shapiro et al., 1986 described the inhibition of human tumor cell secreted RNases by human placental RNase inhibitor. Herein the ability of human placental RNase inhibitor to inhibit the endoribonuclease activity of hRNase 4 was investigated. Briefly, 1 µL of a 1:10 dilution of hRNase 4 preincubated for 15 minutes at room temperature with 1 µL human placental RNase inhibitor (NEB, Cat #M0307S) in 1×NEBuffer 1. Next, a target RNA oligonucleotide (SEQ ID NO: 23; AAGAGAGAUAGAGAA) containing a single hRNase 4 cleavage site was added to the mixture and the reaction was incubated for 15 minutes at 37° C. Robust cleavage of the target oligonucleotide by hRNase 4 was observed in the absence of human placental RNase inhibitor (FIG. 26). However, cleavage of the target oligonucleotide was inhibited following preincubation of hRNase 4 with human placental RNase inhibitor. hRNase 4 activity was inhibited by human placental RNase inhibitor in the presence of 1 M urea, which helps unfold substrate RNA secondary structures.

Figure 27:
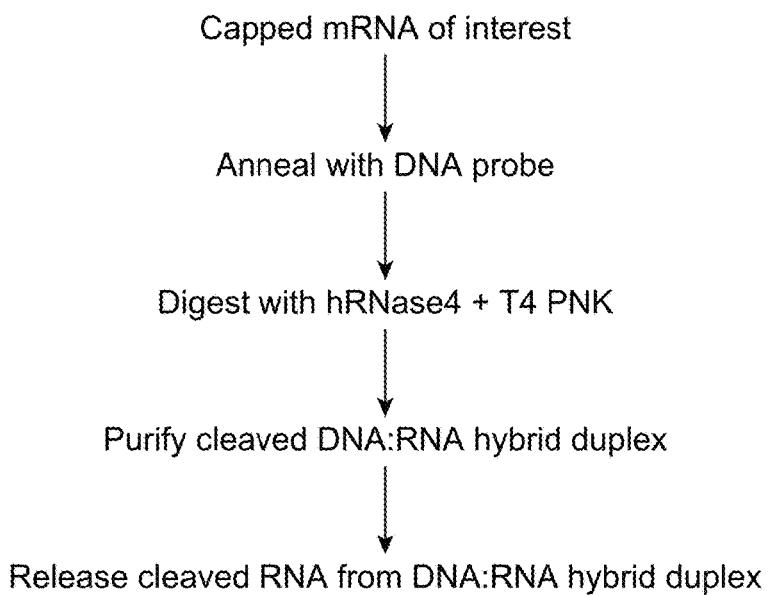
FIG. 27 shows an example of a workflow used for targeted site-specific cleavage and isolation of a 5'-capped RNA oligonucleotide for downstream capping analysis. In this example workflow the subject EPO mRNA is first annealed with a DNA probe (e.g., a biotinylated DNA probe) and then digested with a composition comprising hRNase 4 and T4 PNK. The DNA-RNA duplex formed after digestion is purified (e.g., by affinity capture using streptavidin beads) and the RNA oligonucleotide is released (e.g., by elution using DNase I).

Example 12: Targeted Substrate Protection and hRNase 4 Cleavage for mRNA Capping Analysis This example describes an example of methods for analysis of mRNA capping. FIG. 27 shows an example workflow illustrating this method. Briefly, a capped RNA substrate and a 5'-biotinylated DNA probe which is complementary to at least a portion of the capped RNA substrate (e.g., a segment of interest) are annealed to form an RNA/DNA duplex. The duplex and an enzyme composition (e.g., comprising hRNase 4 and optionally an RNA end repair enzyme) are combined to form a cleaved DNA-RNA hybrid duplex and one or more single-stranded RNA fragments of the RNA substrate. The cleaved DNA-RNA hybrid duplex may then be affinity purified (e.g., using streptavidin magnetic beads). The remaining portion of the RNA substrate included in the purified DNA-RNA hybrid duplex may be eluted, for example, by contacting the purified DNA-RNA hybrid duplex with a DNase I.

Figure 28A:
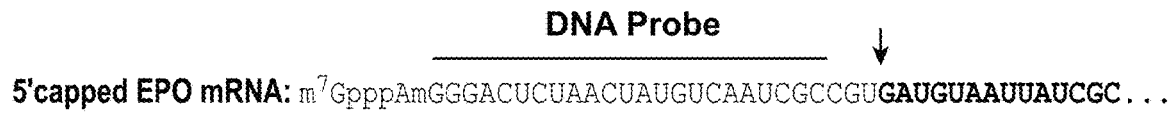
FIG. 28A shows a schematic representation of DNA-targeted hRNase 4 site-specific cleavage of an IVT Epo mRNA substrate. The arrow shows the closest 'UR' cleavage site near the DNA-RNA duplex region. The resulting RNA oligonucleotide product is shown in grey.

In this example, a 30-nt DNA probe sequence (SEQ ID NO: 24; /Biotin/GAGCTTCTGCAAAAAGAACAAG CAAGCCCT) was hybridized to the 5'-terminal sequence of a 5' m7GpppAm capped EPO mRNA (as illustrated in FIG. 28A) utilizing a touchdown hybridization approach (heating to 95° C. for 2 minutes, followed by slowly cooling to 22° C. at 0.1° C./s) in 1×NEBuffer 1 supplemented with 3 M urea. The hybridized mRNA solution was diluted to 1 M urea in NEBuffer 1 and a composition of hRNase 4/T4 PNK was added. The mixture was incubated at 37° C. for 1.5 hours. Digestion was stopped by addition of human placental RNase inhibitor. Next, the resulting duplex comprising the 5'-biotinylated DNA probe and the corresponding hybridized RNA oligonucleotide was purified utilizing streptavidin magnetic beads. The hybridized RNA was eluted by incubation with DNase I at 37° C. The isolated RNA oligonucleotide was characterized by LC-MS/MS. Comparative experiments were performed in the absence of either the DNA probe or hRNase 4/T4 PNK.

Figure 28B:
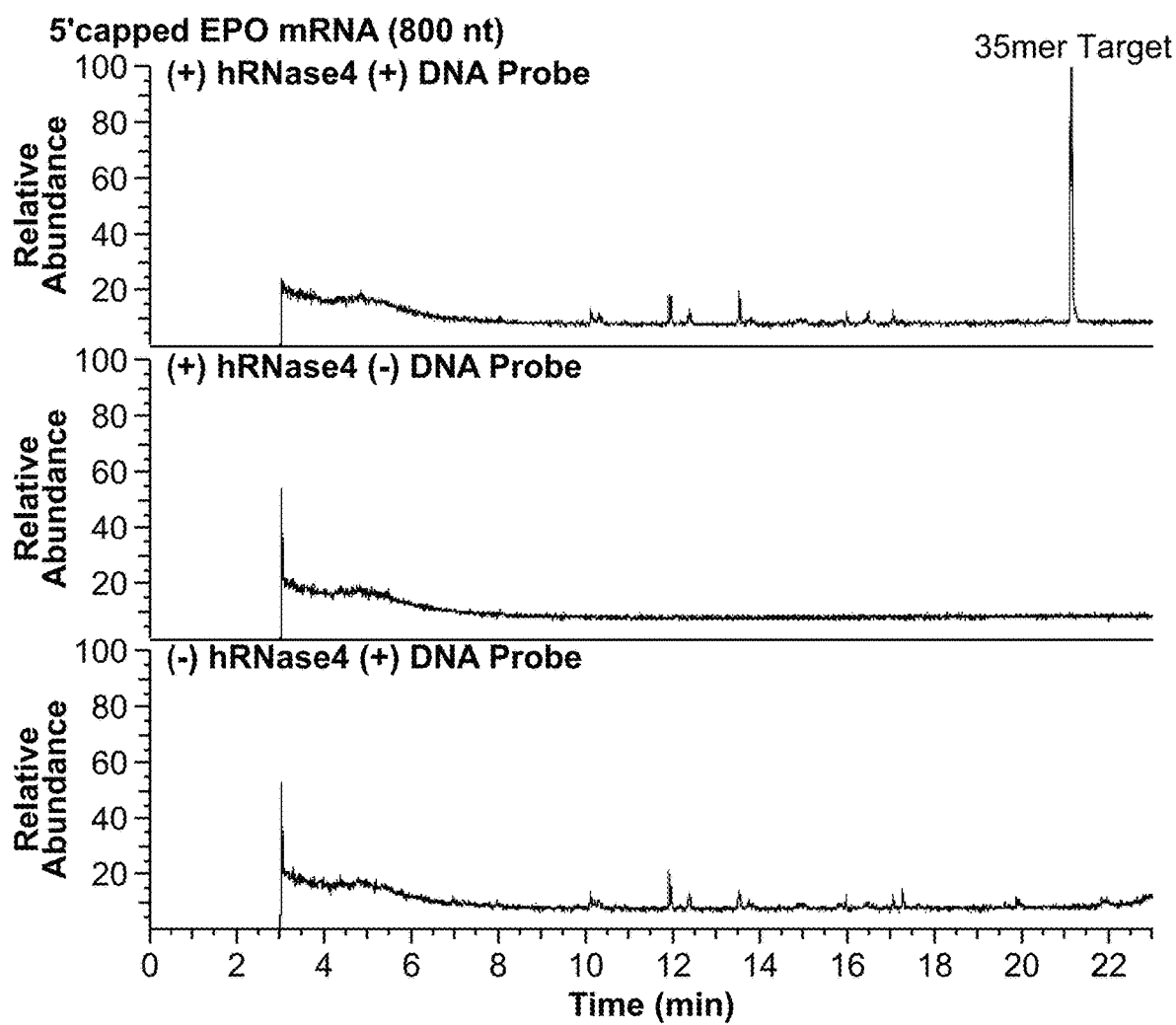
FIG. 28B shows a total ion chromatogram from LC-MS/MS characterization of the isolated RNA oligonucleotide (top panel) after its elution from bead-bound DNA-RNA duplex by treatment with DNase I. No oligonucleotide was isolated in absence of a DNA probe (middle panel) or in absence of hRNase 4 (lower panel).
Figure 28C:
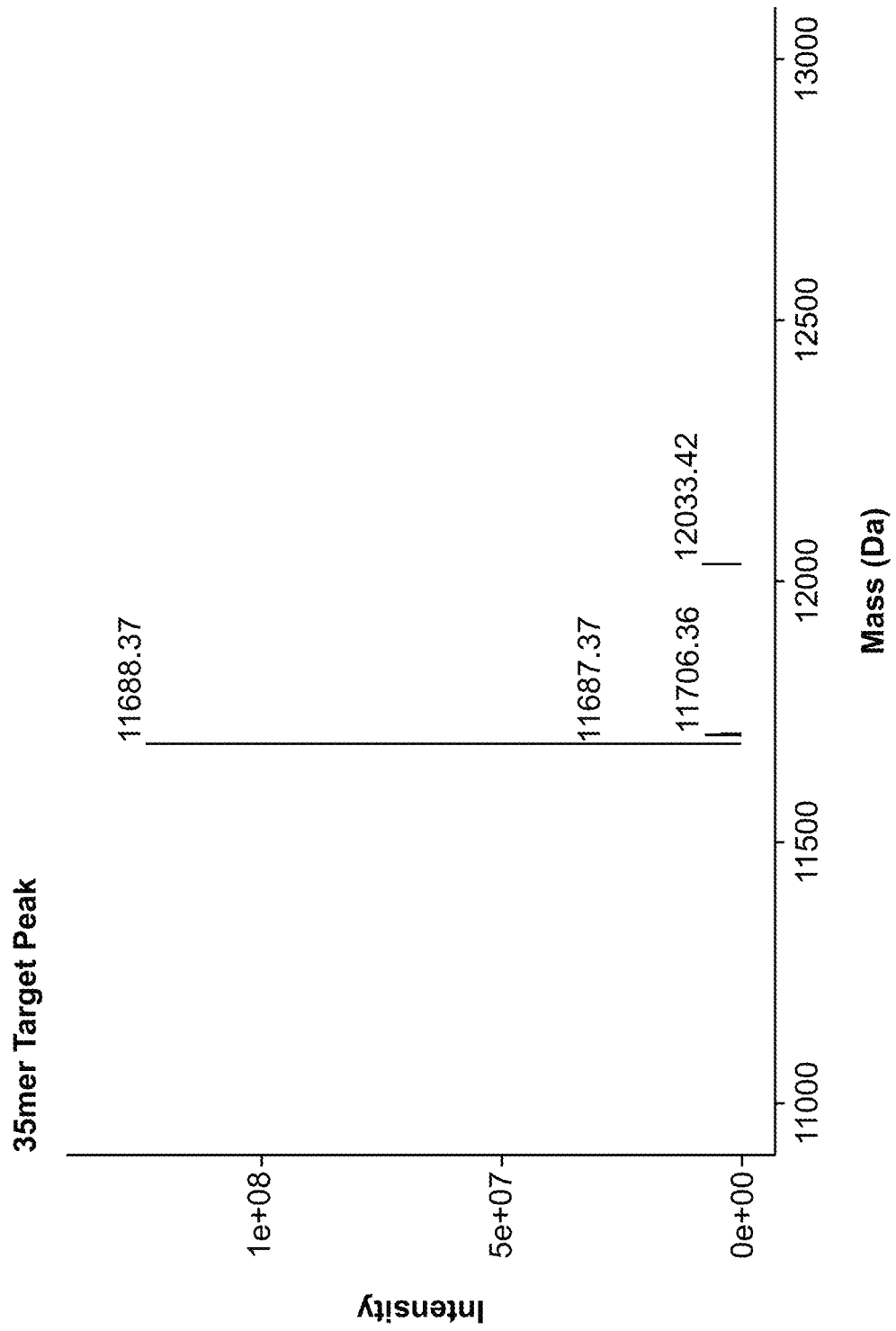
FIG. 28C shows a deconvoluted mass spectrum depicting the intact masses observed within the single chromatographic peak of FIG. 28B (35mer Target) in the sample treated with hRNase 4/T4 PNK in the presence of the biotinylated DNA-probe. Mass spectrometry analysis confirm the isolation of the desired 35mer RNA oligonucleotide comprising the mass of a m7GpppAm cap structure.

Analysis of the isolated RNA oligonucleotide by LC-MS indicated a single prominent chromatographic peak (FIG. 28B, top panel), whose identity was confirmed by mass spectrometry analysis (FIG. 28C). Notably, no corresponding chromatographic peak was detected in purifications performed in the absence of the DNA probe or in the absence of hRNase 4/T4 PNK (FIG. 28B, middle and lower panels).

FIG. 28C shows the deconvoluted mass of the RNA 35mer oligonucleotide corresponding to the 5'-terminal segment of EPO mRNA (SEQ ID NO: 25; AGGGCUUGCUUGUUC- UUUUUGCAGAAGCUCAGAAU) comprising 2 methyl groups and a guanine-triphosphate moiety, consistently with presence of a 5' m7GpppAm cap structure. This data suggests that hRNase 4 digestion is prevented in the region of a DNA-RNA hybrid duplex. Thus, the isolated RNA oligonucleotide product comprises the sequence that is "protected" by the DNA probe plus any subsequent ribonucleotides at the 3' end preceding an hRNase 4 'UR' cutting site (indicated by the arrow in FIG. 28A). A DNA/RNA duplex, in some embodiments, may comprise a DNA probe and an RNA substrate longer than the DNA probe, wherein the RNA substrate has single-stranded overhangs at both the 5' and 3' ends. Protecting an internal oligoribonucleotide segment of a given RNA substrate by hybridization with a DNA probe that leaves 5' and 3' overhangs may limit cleavage by hRNase 4 to the 5' and 3' UR sites that are nearest to the DNA probe-RNA substrate duplex.

Results shown in FIG. 28B and FIG. 28C demonstrate that protection of a portion of an RNA substrate from the action of a single-stranded nucleotide-specific endoribonuclease (e.g., hRNase 4) by hybridization with a complementary affinity tagged DNA probe (e.g., shorter than the RNA substrate) can be used to selectively isolate and analyze features of the protected portion, such as a cap structure and/or any modifications that are present. In some embodiments, the methods illustrated in this example may include contacting an RNA substrate with multiple biotinylated-DNA probes targeting different portions of the RNA substrate, permitting simultaneous analysis of such portions. Disclosed methods may be applied to RNA modification analysis, such as RNA identification, locating an RNA within a sequence, assessing RNA stoichiometry, detecting RNA presence, permanence, and/or dynamics (i.e., installation and removal), and detecting co-existence of RNA modifications.

TABLE 3

Sequences of IVT mRNAs used in this study.

| mRNA | Input | Sequence |
|---|---|---|
| FLuc (SEQ ID NO: 26) | 10 µg | GGGUCUAGAAAUAAUUUGUUUAACUUUAAGAAG GAGAUAUAACCAUGAAAAUCGAAGAAGGUAAAGG UCACCAUCACCAUCACCACGGAUCCAUGGAAGAC GCCAAAAACAUAAAGAAAGGCCCGGCGCCAUUCU AUCCUCUAGAGGAUGGAACCGCUGGAGAGCAACU GCAUAAGGCUAUGAAGAGAUACGCCCUGGUUCCU GGAACAAUUGCUUUUACAGAUGCACAUAUCGAGG UGAACAUCACGUACGCGGAAUACUUCGAAAUGUC CGUUCGGUUGGCAGAAGCUAUGAAACGAUAUGGG CUGAAUACAAAUCACAGAAUCGUCGUAUGCAGUG AAAACUCUCUUCAAUUCUUUAUGCCGGUGUUGGG CGCGUUAUUUAUCGGAGUUGCAGUUGCGCCCGCG AACGACAUUUAUAAUGAACGUGAAUUGCUCAACA GUAUGAACAUUUCGCAGCCUACCGUAGUGUUUGU UUCCAAAAGGGGUUGCAAAAAAUUUUGAACGUG CAAAAAAAAUUACCAAUAAUCCAGAAAAUUAUUA UCAUGGAUUCUAAAACGGAUUACCAGGGAUUUCA GUCGAUGUACACGUUCGUCACAUCUCAUCUACCU CCCGGUUUUAAUGAAUACGAUUUUGUACCAGAGU CCUUUGAUCGUGACAAAACAAUUGCACUGAUAAU GAAUUCCUCUGGAUCUACUGGGUUACCUAAGGGU GUGGCCCUUCCGCAUAGAACUGCCUGCGUCAGAU UCUCGCAUGCCAGAGAUCCUAUUUUUGGCAAUCA AAUCAUUCCGGAUACUGCGAUUUUAAGUGUUGUU CCAUUCCAUCACGGUUUUGGAAUGUUUACUACAC UCGGAUAUUUGAAUAUCUGAGUCGUCUU AAUGUAUAGAUUUGAAGAAGAGCUGUUUUUACGA UCCCUUCAGGAUUACAAAAUUCAAAGUGCUUGC UAGUACCAACCCUAUUUUCAUUCUUCGCCAAAAG CACUCUGAUUGACAAAUACGAUUUAUCUAAUUUA CACGAAAUUGCUUCUGGGGGCGCACCUCUUUCGA AAGAAGUCGGGGAAGCGGUUGCAAAACGCUUCCA UCUUCCAGGGAUACGACAAGGAUAUGGGCUCACU GAGACUACAUCAGCUAUUCUGAUUACACCCGAGG GGGAUGAUAAACCGGGCGCGGUCGGUAAAGUUGU UCCAUUUUUUGAAGCGAAGGUUGUGGAUCUGGAU ACCGGGAAAACGCUGGGCGUUAAUCAGAGAGGCG AAUUAUGUGUCAGAGGACCUAUGAUUAUGUCCGG UUAUGUAAACAAUCCGGAAGCGACCAACGCCUUG AUUGACAAGGAUGGAUGGCUACAUUCUGGAGACA UAGCUUACUGGGACGAAGACGAACACUUCUUCAU AGUUGACCGCUUGAAGUCUUUAAUUAAAAUACAAA GGAUAUCAGGUGGCCCCCGCUGAAUUGGAAUCGA UAUUGUUACAACACCCCAACAUCUUCGACGCGGG CGUGGCAGGUCUUCCCGACGAUGACGCCGGUGAA CUUCCCGCCGCCGUUGUUGUUUUGGAGCACGGAA AGACGAUGACGGAAAAAGAGAUCGUGGAUUACGU CGCCAGUCAAGUAACAACCGCGAAAAAGUUGCGC GGAGGAGUUGUGUUUGUGGACGAAGUACCGAAAG GUCUUACCGGAAAACUCGACGCAAGAAAAAUCAG AGAGAUCCUCAUAAAGGCCAAGAAGGGCGGAAAG UCCAAACUCGAGUAAGGUUAACCUGCAGGAGG |
| EPO (SEQ ID NO: 27) | 3 µg | GGGGCUUGCUUGUUCUUUUUGCAGAAGCUCAGAA UAAACGCUCAACUUUGGCACCAUGGGAGUGCACG AGUGUCCCGCGUGGUUGUGGUUGCUGCUGUCGCU CUUGAGCCUCCCACUGGGACUGCCUGUGCUGGGG GCACCACCCAGAUUGAUCUGCGACUCACGGGUAC UUGAGAGGUACCUUCUUGAAGCCAAAGAAGCCGA AAACAUCACAACCGGAUGCGCCGAGCACUGCUCC CUCAAUGAGAACAUUACUGUACCGGAUACAAAGG UCAAUUUCUAUGCAUGGAAGAGAAUGGAAGUAGG ACAGCAGGCCGUCGAAGUGUGGCAGGGGCUCGCG CUUUUGUCGGAGGCGGUGUUGCGGGGUCAGGCCC UCCUCGUCAACUCAUCACAGCCGUGGGAGCCCCU CCAACUUCAUGUCGAUAAAGCGGUGUCGGGGCUC CGCAGCUUGACGACGUUGCUUCGGGCUCUGGGCG CACAAAAGGAGGCUAUUUCGCCGCCUGACGCGGC CUCCGCGGCACCCCUCCGAACGAUCACCGCGGAC ACGUUUAGGAAGCUUUUAGAGUGUACAGCAAUU UCCUCCGCGGAAAGCUGAAAUUGUAUACUGGUGA AGCGUGUAGGACAGGGGAUCGCUAGGACUGACUA GGAUCUGGUUACCACUAAACCAGCCUCAAGAACA CCCGAAUGGAGUCUCUAAGCUACAUAAUACCAAC UUACACUUUACAAAAUGUUGUCCCCCAAAAUGUA GCCAUUCGUAUCUGCUCCUAAUAAAAAGAAAGUU UCUUCACAUUCUAGCUAGC |
| ClucU1 (SEQ ID NO: 28) | 5 µg | GGGAGACCCAAGCUUGGUACCGAGCUCGGAUCCG CCACCAUGAAGACCCUGAUCCUGGCCGUGGCCCU GGUGUACUGCGCCACCGUGCACUGCCAGGACUGC CCAUACGAACCAGACCCCCCGAACACCGUGCCAA CCAGCUGCGAGGCCAAGGAAGGCGAGUGCAUCGA CAGCAGCUGCGGCACCUGCACCAGAGACAUCCUG AGCGACGGCCUGUGCGAGAACAAGCCGGGAAAGA CAUGCUGCCGGAUGUGCCAGUACGUGAUCGAGUG CAGAGUGGAGGCCGCAGGAUGGUUCCGGACCUUC UACGGCAAGAGAUUCCAGUUCCAAGAGCCCGGCA CAUACGUGCUGGGCCAGGGAACCAAGGGCGGCGA CUGGAAAGUGAGCACUACCUGGAGAACCUCGAC GGCACCAAAGGCGCCGUGCUGACAAAGACAAGAC UGGAAGUCGCCGGCGACAUCAUCGACAUCGCGCA GGCCACCGAGAACCCCAUCACCGUGAACGGAGGC GCCGACCCCAUAAUCGCCAACCCCUACACAAUCG GCGAAGUGACAAUCGCCGUCUGGAAAUGCCAGG CUUCAACAUCACCGUCAUUGAGUUCUUCAAACUG AUCGUGAUCGACAUCCUCGGAGGAAGAUCUGUAA GAAUCGCCCCAGACACGACAAACAAAGGAAUGAU CUCUGGCCUCUGUGGAGAUCUUAAAAUGAUGGAA GAUACAGACUUCACUUCAGAUCCAGAACAACUCG CUAUUCAGCCUAAGAUCAACCAGGAGUUUGACGG UUGUCCACUCUAUGGAAAUCCUGAUGACGUUGCA UACUGCAAAGGUCUUCUCGGAGCCGUACAAGGACA GCUGCCGCAACCCCAUCAACUUCUACUACUACAC CAUCUCCUGCGCCUUCGCCCGCUGUAUGGGUGGA GACGAGCGAGCCUCACACGUGCUGCUUGACUACA GGGAGACGUGCGCUGCUCCCGAAACUAGAGGAAC |

TABLE 3-continued

Sequences of IVT mRNAs used in this study.

| mRNA | Input | Sequence |
|---|---|---|
| | | CUGCGUUUUGUCUGGACAUACUUUCUACGAUACA<br>UUUGACAAAGCAAGAUACCAAUUCCAGGGUCCCU<br>GCAAGGAGAUUCUUAUGGCCGCCGACUGUUUCUG<br>GAACACUUGGGAUGUGAAGGUUUCACACAGGAAU<br>GUUGACUCUUACACUGAAGUAGAGAAAGUACGAA<br>UCAGGAAACAAUCGACUGUAGUAGAACUCAUUGU<br>UGAUGGAAAACAGAUUCUGGUUGGAGGAGAAGCC<br>GUGUCCGUCCCGUACAGCUCUCAGAACACUUCCA<br>UCUACUGGCAAGAUGGUGACAUACUGACUACAGC<br>CAUCCUACCUGAAGCUCUGGUGGUCAAGUUCAAC<br>UUCAAGCAACUGCUCGUCGUACAUAUUAGAGAUC<br>CAUUCGAUGGUAAGACUUGCGGUAUUUGCGGUAA<br>CUACAACCAGGAUUUCAGUGAUGAUUCUUUUGAU<br>GCUGAAGGAGCCUGUGAUCUGACCCCCAACCCAC<br>CGGGAUGCACCGAAGAACAGAAACCUGAAGCUGA<br>ACGACUCUGCAAUAGUCUCUUCGCCGGUCAAAGU<br>GAUCUUGAUCAGAAAUGUAACGUGUGCCACAAGC<br>CUGACCGUGUCGAACGAUGCAUGUACGAGUAUUG<br>CCUGAGGGGACAACAGGGUUUCUGUGACCACGCA<br>UGGGAGUUCAAGAAAGAAUGCUACAUAAAGCAUG<br>GAGACACCCUAGAAGUACCAGAUGAAUGCAAAUA<br>GGC |
| ClucU2<br>(SEQ ID<br>NO: 29) | 5 µg | GGGAGACCCAAGCUUGGUACCGAGCUCGGAUCCG<br>CCACCAUGAAGACCUUAAUUCUUGCCGUUGCAUU<br>AGUCUACUGCGCCACUGUUCAUUGCCAGGACUGU<br>CCUUACGAACCUGAUCCACCAAACACAGUUCCAA<br>CUUCCUGUGAAGCUAAAGAAGGAGAAUGUAUUGA<br>UAGCAGCUGUGGCACCUGCACGAGAGACAUACUA<br>UCAGAUGGACUGUGUGAAAAUAAACCAGGAAAAA<br>CAUGUUGCCGAAUGUGUCAGUAUGUAAUUGAAUG<br>CAGAGUAGAGGCCGCAGGAUGGUUUAGAACAUUC<br>UAUGGAAAGAGAUUCCAGUUCCAGGAACCUGGUA<br>CAUACGUGUUGGGUCAAGGAACCAAGGGCGGCGA<br>CUGGAAGGUGUCCAUCACCCUGGAGAACCUGGAU<br>GGAACCAAGGGGGCUGUGCUGACCAAGACAAGAC<br>UGGAAGUGGCUGGAGACAUCAUUGACAUCGCUCA<br>AGCUACUGAGAAUCCCAUCACUGUAAACGGUGGA<br>GCUGACCCUAUCAUCGCCAACCCGUACACCAUCG<br>GCGAGGUCACCAUCGCUGUUGUUGAGAUGCCAGG<br>CUUCAACAUCACAGUGAUCGAAUUCUUCAAGCUG<br>AUCGUGAUCGACAUCCUCGGAGGAAGAUCUGUAA<br>GAAUCGCCCCAGACACAGCAAACAAAGGAAUGAU<br>CUCUGGCCUCUGUGGAGAUCUUAAAAUGAUGGAA<br>GCAUCGCCCCAGACACCGCGAACAAGGGCAUGAU<br>CAGCGGCCUGUGCGGAGACCUGAAGAUGAUGGAG<br>GACACCGACUUCACCAGCGACCCCGAGCAGCUGG<br>CCAUCCAGCCAAAAAUCAACCAGGAAUUCGACGG<br>CUGCCCCUGUACGGAAACCCCGACGACGUGGCC<br>UACUGCAAAGGCCUGCUCGAGCCGUACAAGGACA<br>GCUGCAGAAACCCCAUCAACUUCUACUACUACAC<br>CAUCAGCUGCGCUUCGCCAGGUGCAUGGGCGGC<br>GACGAAAGAGCCAGCCACGUCCUGCUGGACUACA<br>GAGAAACCUGCGCCGCCCCGGAGACACGGGGCAC<br>CUGCGUGCUGAGCGGCCACACCUUCUACGACACA<br>UUCGACAAGGCACGGUACCAGUUCCAGGGCCCAU<br>GCAAGGAGAUCCUGAUGGCCGCCGACUGCUUCUG<br>GAACACCUGGGACGUGAAGGUGAGCCACAGAAAC<br>GUCGACAGCUACACAGAGGUGGAGAAGGUGAGAA<br>UCAGAAAACAGAGCACAGUGGUGGAACUGAUCGU<br>GGACGGCAAGCAAAUUCUGGUUGGAGGAGAAGCC<br>GUGUCCGUCCCGUACAGCUCUCAGAACACUUCCA<br>UCUACUGGCAAGAUGGUGACAUACUGACUACAGC<br>CAUCCUACCUGAAGCUCUGGUGGUCAAGUUCAAC<br>UUCAAGCAACUGCUCGUCGUACAUAUUAGAGAUC<br>CAUUCGAUGGUAAGACUUGCGGUAUUUGCGGUAA<br>CUACAACCAGGAUUUCAGUGAUGAUUCUUUUGAU<br>GCUGAAGGAGCCUGUGAUCUGACCCCCAACCCAC<br>CGGGAUGCACCGAAGAACAGAAACCUGAAGCUGA<br>ACGACUCUGCAAUAGUCUCUUCGCCGGUCAAAGU<br>GAUCUUGAUCAGAAAUGUAACGUGUGCCACAAGC<br>CUGACCGUGUCGAACGAUGCAUGUACGAGUAUUG<br>CCUGAGGGGACAACAGGGUUUCUGUGACCACGCA<br>UGGGAGUUCAAGAAAGAAUGCUACAUAAAGCAUG<br>GAGACACCCUAGAAGUACCAGAUGAAUGCAAAUA<br>GGC |
| ClucU3<br>(SEQ ID<br>NO: 30) | 5 µg | GGGAGACCCAAGCUUGGUACCGAGCUCGGAUCCG<br>CCACCAUGAAGACCUUAAUUCUUGCCGUUGCAUU<br>AGUCUACUGCGCCACUGUUCAUUGCCAGGACUGU<br>CCUUACGAACCUGAUCCACCAAACACAGUUCCAA<br>CUUCCUGUGAAGCUAAAGAAGGAGAAUGUAUUGA<br>UAGCAGCUGUGGCACCUGCACGAGAGACAUACUA<br>UCAGAUGGACUGUGUGAAAAUAAACCAGGAAAAA<br>CAUGUUGCCGAAUGUGUCAGUAUGUAAUUGAAUG<br>CAGAGUAGAGGCCGCAGGAUGGUUUAGAACAUUC<br>UAUGGAAAGAGAUUCCAGUUCCAGGAACCUGGUA<br>CAUACGUGUUGGGUCAAGGAACCAAGGGCGGCGA<br>CUGGAAGGUGUCCAUCACCCUGGAGAACCUGGAU<br>GGAACCAAGGGGGCUGUGCUGACCAAGACAAGAC<br>UGGAAGUGGCUGGAGACAUCAUUGACAUCGCUCA<br>AGCUACUGAGAAUCCCAUCACUGUAAACGGUGGA<br>GCUGACCCUAUCAUCGCCAACCCGUACACCAUCG<br>GCGAGGUCACCAUCGCUGUUGUUGAGAUGCCAGG<br>CUUCAACAUCACCGUCAUUGAGUUCUUCAAACUG<br>AUCGUGAUCGACAUCCUCGGAGGAAGAUCUGUAA<br>GAAUCGCCCCAGACACAGCAAACAAAGGAAUGAU<br>CUCUGGCCUCUGUGGAGAUCUUAAAAUGAUGGAA<br>GAUACAGACUUCACUUCAGAUCCAGAACAACUCG<br>CUAUUCAGCCUAAGAUCAACCAGGAGUUUGACGG<br>UUGUCCACUCUAUGGAAAUCCUGAUGACGUUGCA<br>UACUGCAAAGGUCUUCUGGAGCCGUACAAGGACA<br>GCUGCCGCAACCCCAUCAACUUCUACUACUACAC<br>CAUCUCCUGCGCCUUCGCCCGCUGUAUGGGUGGA<br>GACGAGCGAGCCUCACACGUGCUGCUUGACUACA<br>GGGAGACGUGCGCUGCUCCCGAAACUAGAGGAAC<br>CUGCGUUUUGUCUGGACAUACUUUCUACGAUACA<br>UUUGACAAAGCAAGAUACCAAUUCCAGGGUCCCU<br>GCAAGGAGAUUCUUAUGGCCGCCGACUGUUUCUG<br>GAACACUUGGGAUGUGAAGGUUUCACACAGGAAU<br>GUUGACUCUUACACUGAAGUAGAGAAAGUACGAA<br>UCAGGAAACAAUCGACUGUAGUAGAACUCAUUGU<br>UGAUGGAAAACAGAUCCUGGUGGGCGGCAAGCC<br>GUGAGCGUGCCAUACAGCAGCCAAAACACCAGCA<br>UCUACUGGCAGGACGGCGACAUCCUGACAACCGC<br>CAUCCUGCCCGAGGCACUGGUGGUGAAGUUCAAC<br>UUCAAACAGCUGCUGGUGGUCCACAUCAGAGACC<br>CCUUCGACGGCAAGACAUGCGGAAUCUGCGGCAA<br>CUACAACCAGGACUUUCAGCGACGACAGCUUCGAC<br>GCCGAGGGCGCCUGCGACCUGACCCCCAACCCGC<br>CCGGCUGCACCGAGGAACAGAAGCCAGAGGCCGA<br>AAGACUGUGCAACAGCCUCUUCGCCGGACAGAGC<br>GACCUGGACCAGAAGUGCAACGUGUGCCACAAAC<br>CGGACAGAGUGGAACGGUGCAUGUACGAAUACUG<br>CCUGCGGGGCCAGCAGGGAUUCUGCGACCACGCC<br>UGGGAGUUCAAGAAGGAGUGCUACAUCAAGCACG<br>GCGACACCCUGGAGGUGCCAGACGAGUGCAAGUA<br>GGC |

Example 13: DNA Probe-Directed RNA Cleavage with Site-Specific Ribonucleases

Targeted cleavage of an RNA substrate with site-specific ribonucleases may be directed by hybridization of the RNA substrate with complementary DNA probe(s). For example, an RNA substrate may be annealed to one or more DNA probes, each complementary to one or more sequences of interest within the RNA substrate sequence, forming one or more DNA/RNA duplex segments. Segments comprising DNA/RNA duplexes may be cleaved upstream and/or downstream of the double-stranded region, for example, using a ribonuclease capable of cleaving single-stranded RNA, optionally in the presence of a repair enzyme. In some instances, the RNA cleavage may occur at nucleotide positions within the internal edges of the double-stranded region (presumably due to local conformation fluctuations, also referred as to breathing or fraying, that may form transient single-stranded regions; or by the action the ribonuclease itself). Resultant products of ribonuclease digestion, whether cleaved DNA/RNA duplex segments or cleaved single-stranded segments, or both, may be assessed by LC-MS/MS analysis. Optional steps of isolation of the cleaved DNA/RNA duplex segments may be employed prior to LC-MS/MS analysis, such as capturing the cleaved DNA/RNA duplex segments by means of affinity enrichment followed by selective elution of the corresponding RNA strand.

FIG. 29 shows example results of an assay to assess the cleavage of an RNA substrate (SEQ ID NO: 31; GGGA-CUCUAACUAUGUCAAUCGCCGUGAU-GUAAUUAUCGC) hybridized to a DNA probe (SEQ ID NO: 32; ATTGACATAGTTAGAGTCCC). In this example, the first 20 nucleotides of a 40mer RNA sequence were hybridized with a complementary 20mer DNA probe to form at least partially duplex DNA/RNA polynucleotides, which were then cleaved using one of several ribonucleases. Hybridization of the RNA substrate and DNA probe was conducted by heating to 80° C. for 2 minutes, followed by slowly cooling at 0.1° C./s to 22° C. to form a DNA/RNA duplex solution. Next, the hybridized DNA/RNA duplex solution was diluted in a reaction buffer appropriate for each ribonuclease. TABLE 4 shows the ribonucleases and reaction buffers used in this example. The ribonucleases included three site-specific RNases (hRNase 4, MC1 and RNase T1) and two ribonucleases with poor specificity (RNase A and RNase I$_f$). A composition of 1 µL of a 5-fold dilution series of each RNase was added to the reaction mixture. T4 PNK (1:75 dilution) (400,000U/mL) was added to the hRNase 4, MC1 and RNase T1 reaction mixtures. Each mixture was heated for 30 minutes at 37° C. The resultant mixture was characterized by LC-MS/MS. Comparative experiments were performed in the absence of either the DNA probe or ribonuclease.

TABLE 4

RNases assayed for DNA probe-directed RNA cleavage activity

| RNase | Reaction Buffer |
|---|---|
| hRNase 4 | 1 × NEB buffer r1.1 |
| MC1 | 1 × NEB buffer r1.1 |
| RNase T1 | 1 × NEB buffer r1.1 |
| RNase A | 1 × NEB buffer r1.1, 300 mM NaCl |
| RNase If | 1 × NEB buffer 3 |

RNA cleavage products were classified as "protected products" if they were associated with limited cleavage of the hybridized DNA/RNA duplex, including products with overhangs, 3'-overhangs in combination with 5'-recessed ends (less than 4 nt internal to the hybrid duplex), blunt ends and 3'-recessed ends (less than 4 nt internal to the hybrid duplex) with respect to the hybridized DNA/RNA duplex. Products classified as "internal products" refer to those RNA cleavage products resulting from one or more cleavage events within the DNA/RNA duplex (greater than 4 nt internally from either end of the hybrid duplex). Products classified as "external products" refer to those cleavage products resulting from cleavage events only in the unhybridized (single stranded) regions of the RNA substrate.

The tested RNases produced different levels of protected products following DNA/RNA hybridization and cleavage. The plurality of protected products in digests with site-specific RNases (hRNase 4, MC1 and RNase T1) exhibited well-defined 3'-overhangs terminating at the respective recognition site immediately following the hybridized DNA/RNA duplex (FIG. 29). In contrast, the less-specific RNases (RNase A and RNase If) yielded a mixture of products with variable 3'-recessed ends and 3'-overhangs relative to the DNA hybridized region. The sequences of the most abundant protected products and their positions are shown in the right panel (light gray).

As such, RNA cleavage with site-specific RNases can be directed to predictable and well-defined sites by DNA probe hybridization. Data shown demonstrate that the 5' and 3' heterogenicity in the resulting cleavage products is a function of ribonuclease utilized in the protection assay. At higher ribonuclease concentrations, the product heterogenicity may increase at different levels for different ribonucleases.

Figure 30A:
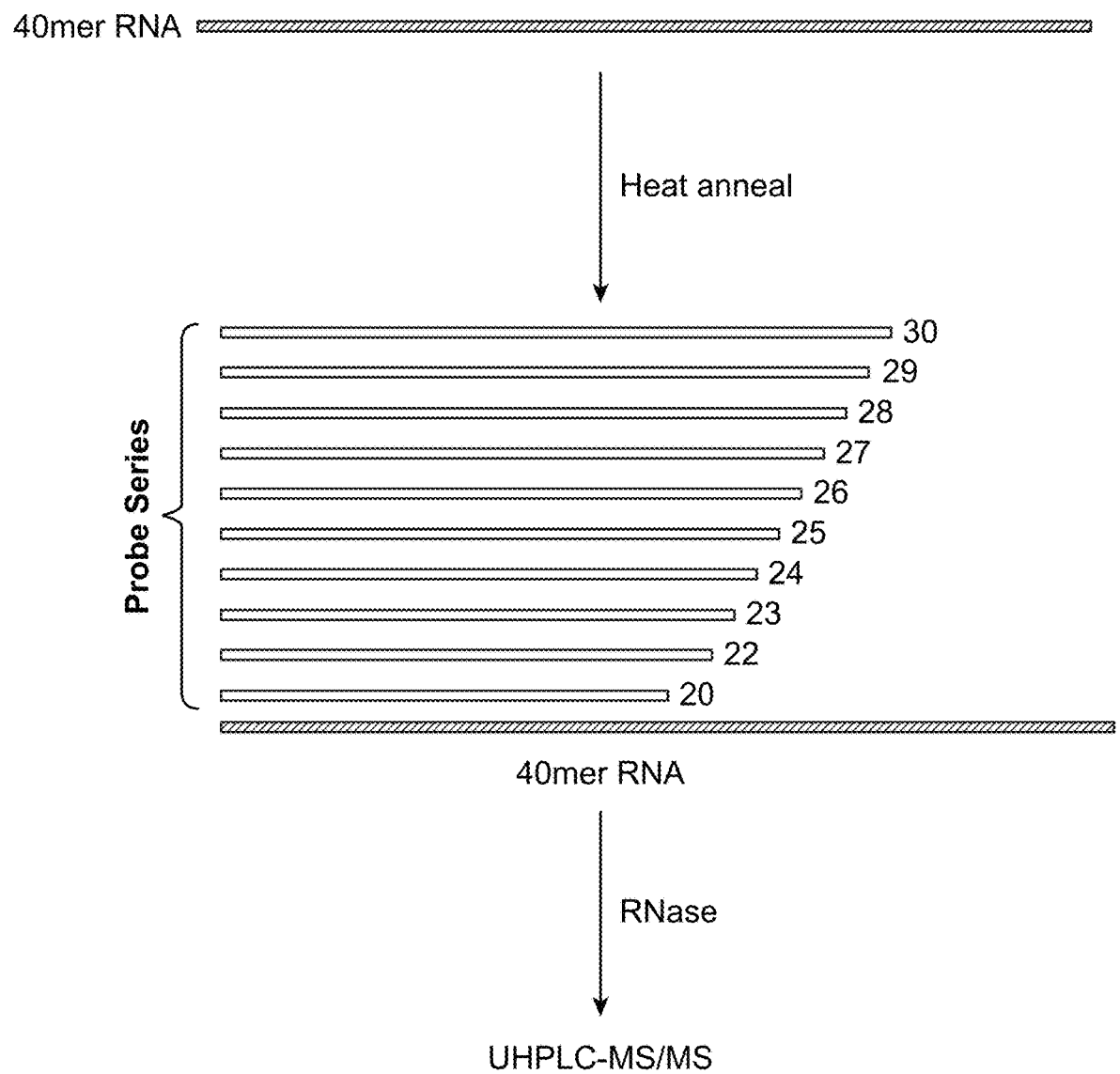
FIG. 30A illustrates a series of example ribonuclease protection assays with a 40mer RNA and complementary DNA probes ranging from 20 to 30 nucleotides in length.

Example 14: Varying DNA Probe Lengths in DNA Probe-Directed RNA Cleavage with Site Specific RNases FIG. 30A shows an example experiment to examine how cleavage of a DNA probe-hybridized RNA substrate changes with varying DNA probes. In this example, the 40mer RNA of Example 13 was hybridized with one of a sequential series of DNA probes ranging from 22 to 30 nucleotides in length. The sequences of the DNA probes were designed to be complementary to the 5' end of the RNA substrate sequence (TABLE 5). Hybridization and RNase digestion with a composition of 1 µL of hRNase 4 (1:75 dilution), RNase T1 (1:100 dilution) or MC1 (1:25 dilution), each in combination with T4 PNK (1:75 dilution) (400,000U/mL), were performed as described in Example 13.

TABLE 5

DNA probe sequences used to assess DNA probe-directed RNA cleavage with site specific RNases

| Probe Sequence | SEQ ID NO |
|---|---|
| ATTGACATAGTTAGAGTCCC | 33 |
| CGATTGACATAGTTAGAGTCCC | 34 |
| GCGATTGACATAGTTAGAGTCCC | 35 |
| GGCGATTGACATAGTTAGAGTCCC | 36 |
| CGGCGATTGACATAGTTAGAGTCCC | 37 |
| ACGGCGATTGACATAGTTAGAGTCCC | 38 |
| CACGGCGATTGACATAGTTAGAGTCCC | 39 |
| TCACGGCGATTGACATAGTTAGAGTCCC | 40 |
| ATCACGGCGATTGACATAGTTAGAGTCCC | 41 |
| CATCACGGCGATTGACATAGTTAGAGTCCC | 42 |

Figure 30B:
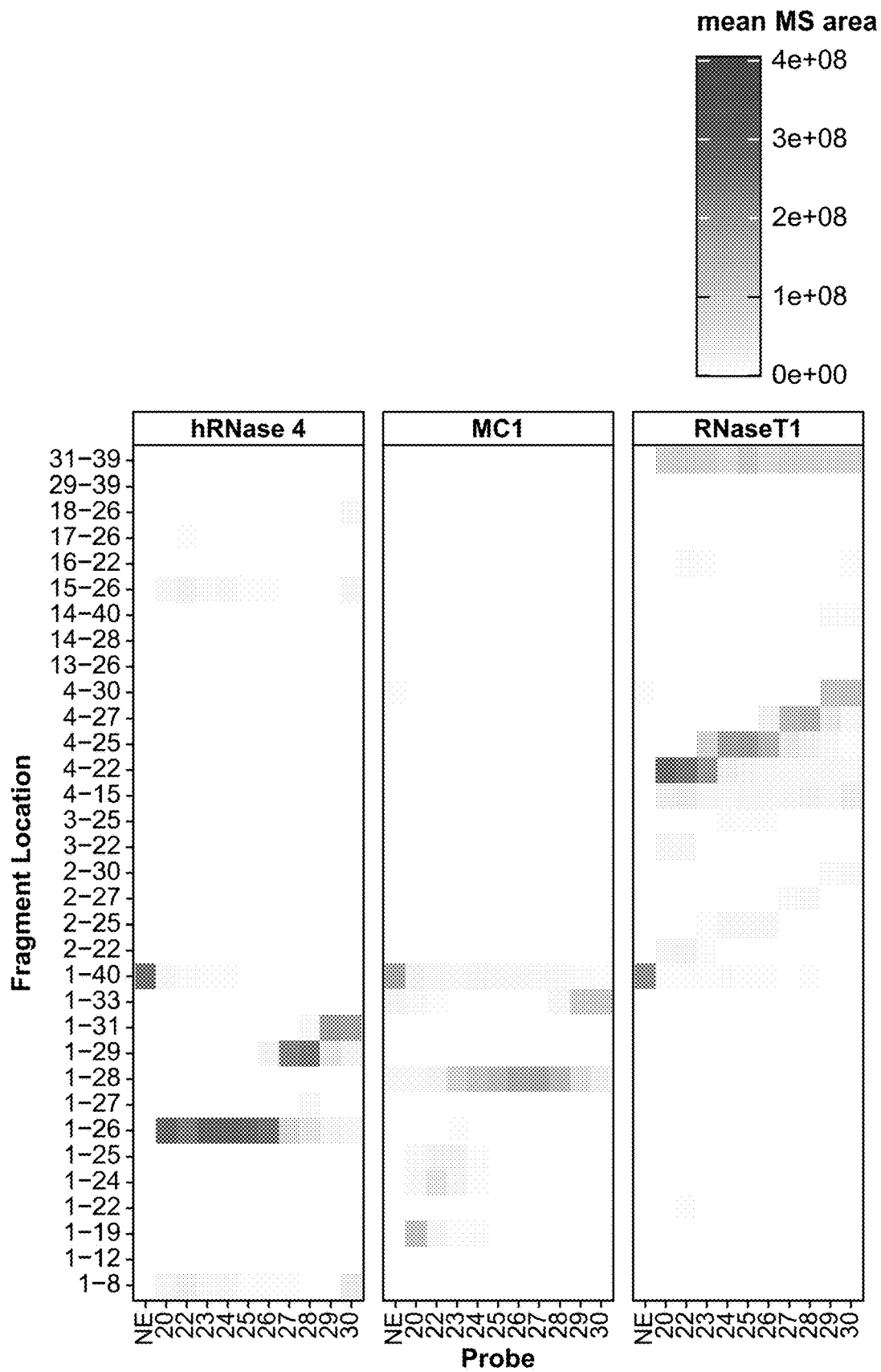
FIG. 30B illustrates a heatmap of oligonucleotide products identified in ribonuclease protection assays using hRNase 4, MC1 or RNase T1 with various DNA probes (NE: no enzyme). Tile shade relates to the mean signal area of each identified oligonucleotide in each experiment.

FIG. 30B shows the cleavage pattern of each site-specific ribonuclease at and around the varying DNA/RNA duplex regions. All site-specific RNases produced cleavage products primarily with 3'-overhangs or blunt ends terminating at the first respective recognition site immediately downstream of the DNA probe hybridized region (FIG. 30B, bottom panel). With the increase in probe length, a noticeably transition to the formation of longer protected products was observed, which were a result of cleavage at subsequent recognition sites downstream of the DNA probe hybridized region. Upon DNA probe hybridization overlapping a given recognition site a mixture of cleavage products from cleavage at successive downstream and upstream recognition sites was observed.

Taken together, these data indicate that site-specific RNases can be utilized to generate predictable and well-defined cleavage products by DNA hybridization. Well-defined cleavage products may be correlated with the protection of regions of interest within the RNA substrate through hybridization with a DNA probe. Notably, hRNase 4 appears to show less cleavage product heterogenicity for a wider range of DNA probes.

Example 15: Comparing the Use of hRNase 4 and RNase H in Ribonuclease Protection Assays RNase H may be used for analysis of synthetic mRNA 5' cap incorporation and cleaves RNA substrate at adjacent phosphodiester bonds 5' and 3' to the RNA hybridized to the 5' deoxynucleotide of an DNA-RNA chimera probe. However, RNase H may also cleave one or more nucleotides away from 5' and 3' of the target site, giving rise to multiple cleavage products that differ by one or more nucleotides, thereby complicating product analysis by electrophoresis or LC-MS/MS. As such, extensive optimization of the DNA-RNA chimera probe is usually required to achieve uniform cleavage of an RNA substrate at predetermined sites. This example shows a comparison between the specificities of hRNase 4 and RNase H to cleave an RNA substrate in vitro at a pre-defined site at or near a double-stranded segment generated by hybridizing a complementary probe to the 5' end of the target RNA substrate.

In this example, 10 µg of a synthetic FLuc mRNA transcript (Seq ID NO:26) were first capped with a Faustovirus Capping Enzyme (FCE; NEB Cat #M2081S) and then methylated at the 2'-O position of the first nucleotide adjacent to the cap structure with a mRNA Cap 2'-O-Methyltransferase (NEB Cat #M0366S), according to manufacturer's instructions, to produce a capped FLuc mRNA that comprise a 5'-terminal m7GpppGm (Cap 1) structure and a series of intermediate products, including a 5'-terminal diphosphate (pp or 2p), a 5'-terminal triphosphate (ppp or 3p), a 5'-terminal guanosine triphosphate (Gppp), and 5'-terminal m7GpppG (Cap 0).

This 5'-end m7GpppGm modified FLuc mRNA was hybridized either with a 25-nt biotinylated DNA probe (SEQ ID NO: 51) for cleavage conditions with hRNase 4, or with a 25-nt desthiobiotinylated DNA-RNA chimeric probe (DNA/RNA probe; SEQ ID NO: 55), wherein the first 6 positions at the 5' end are deoxyribonucleotides and the remaining 19 positions are ribonucleotides; deoxyribonucleotides are denoted by a preceding 'd') for cleavage conditions with RNase H. Hybridization was performed utilizing a touchdown approach (by heating to 80° C. followed by a ramp-down at 0.1° C./s to 22° C.) in absence of a denaturant (e.g., such as urea). The DNA/FLuc mRNA hybrid was cleaved utilizing a composition of 1 µL of hRNase 4 (10-fold dilution) and 0.4 µL of T4 PNK (400,000U/mL) in NEB buffer r1.1 at 37° C. for 1 hour. Each digestion was stopped by addition of 1 µL of human placental RNase inhibitor. The cleaved DNA/RNA duplex segment was affinity purified utilizing streptavidin magnetic beads and eluted by heating to 80° C. in water. For comparison, the DNA-RNA chimera/FLuc mRNA hybrid was cleaved utilizing 1 µL of Thermostable RNase H (NEB Cat #M0523 S), then affinity purified utilizing streptavidin magnetic beads and eluted by heating to 80° C. in water as above.

Figure 31B:
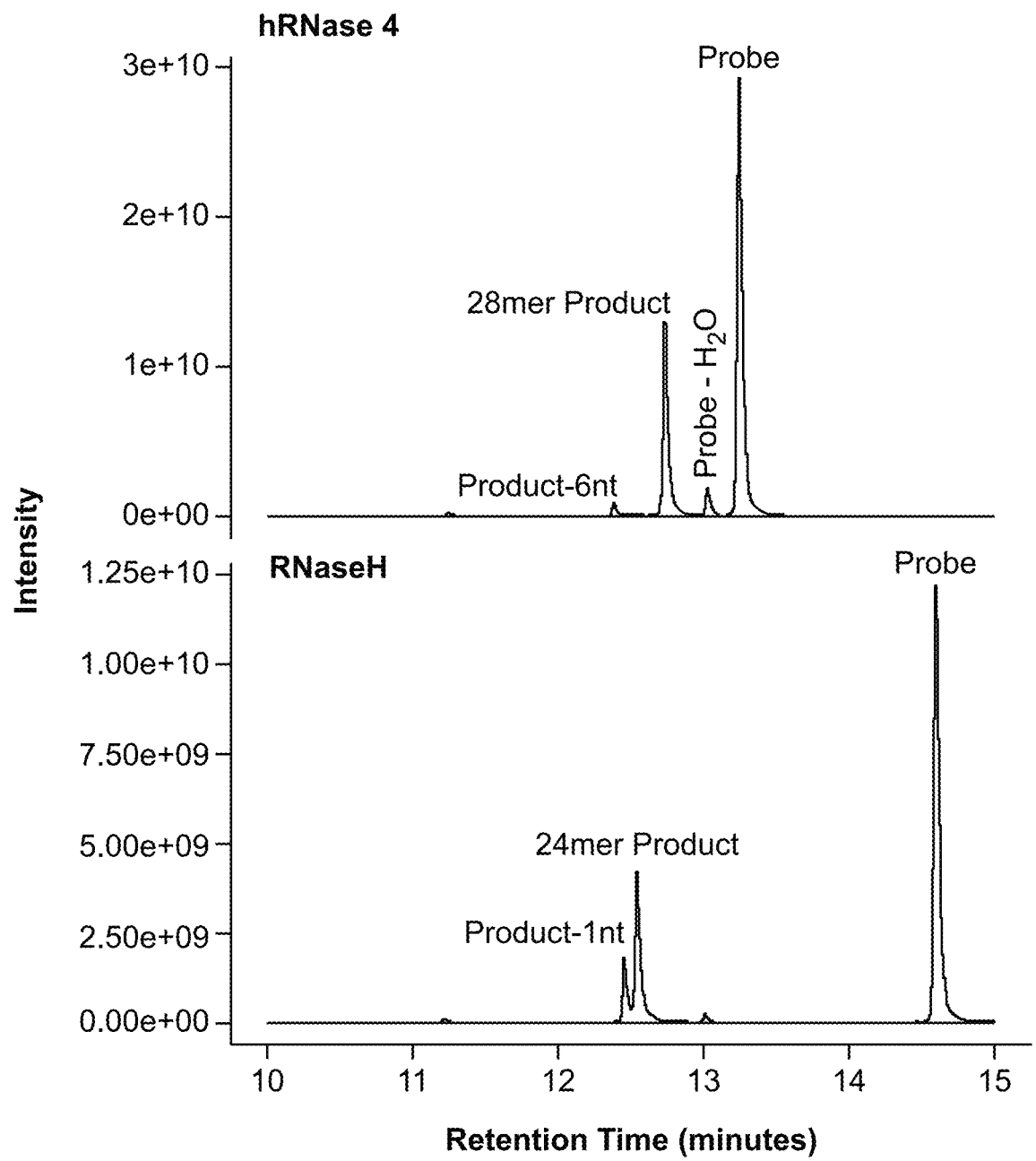
FIG. 31B illustrates products from an example FLuc mRNA 5'-end sequence cleavage with either hRNase 4 (top) or RNase H (bottom) following a biotin enrichment step. RNase H produces a significant amount of an additional cleavage sequence that is one nucleotide shorter ('Product-1 nt') than that of the main cleavage sequence (24mer).

Digestion of the FLuc mRNA substrate hybridized to the DNA probe is expected to produce a 28mer RNA cleavage product terminating at the first hRNase 4 recognition site following (i.e., at a more 3' position on the mRNA substrate than) the DNA/RNA hybridized region of the FLuc mRNA. Digestion of the same FLuc mRNA substrate/DNA probe duplex with RNase H is expected to yield a 24mer RNA cleavage product (FIG. 31A). Two main chromatographic peaks were observed in the hRNase 4/T4 PNK reaction after cleavage and DNA/RNA duplex enrichment (FIG. 31B, top panel). These peaks correspond to the 28mer RNA cleavage product and the biotinylated DNA probe. In contrast, the RNase H reaction yielded three main chromatographic peaks, corresponding to the 23mer ('Product-1 nt') and 24mer RNA products and the biotinylated DNA probe (FIG. 31B, bottom panel). These data accord with observations that probe-directed RNase H cleavage of an RNA substrate may not be uniform and may result in multiple cleavage products around a pre-defined site. On the other hand, probe-directed hRNase 4 cleavage resulted in a substantially more specific formation of the expected cleavage product, indicating that protecting a sequence segment of interest with a complementary probe and contacting the RNA substrate with a site-specific ribonuclease that preferentially cuts single-stranded RNA is a superior strategy to generate predetermined oligonucleotides for LC-MS/MS analysis.

Figure 31C:
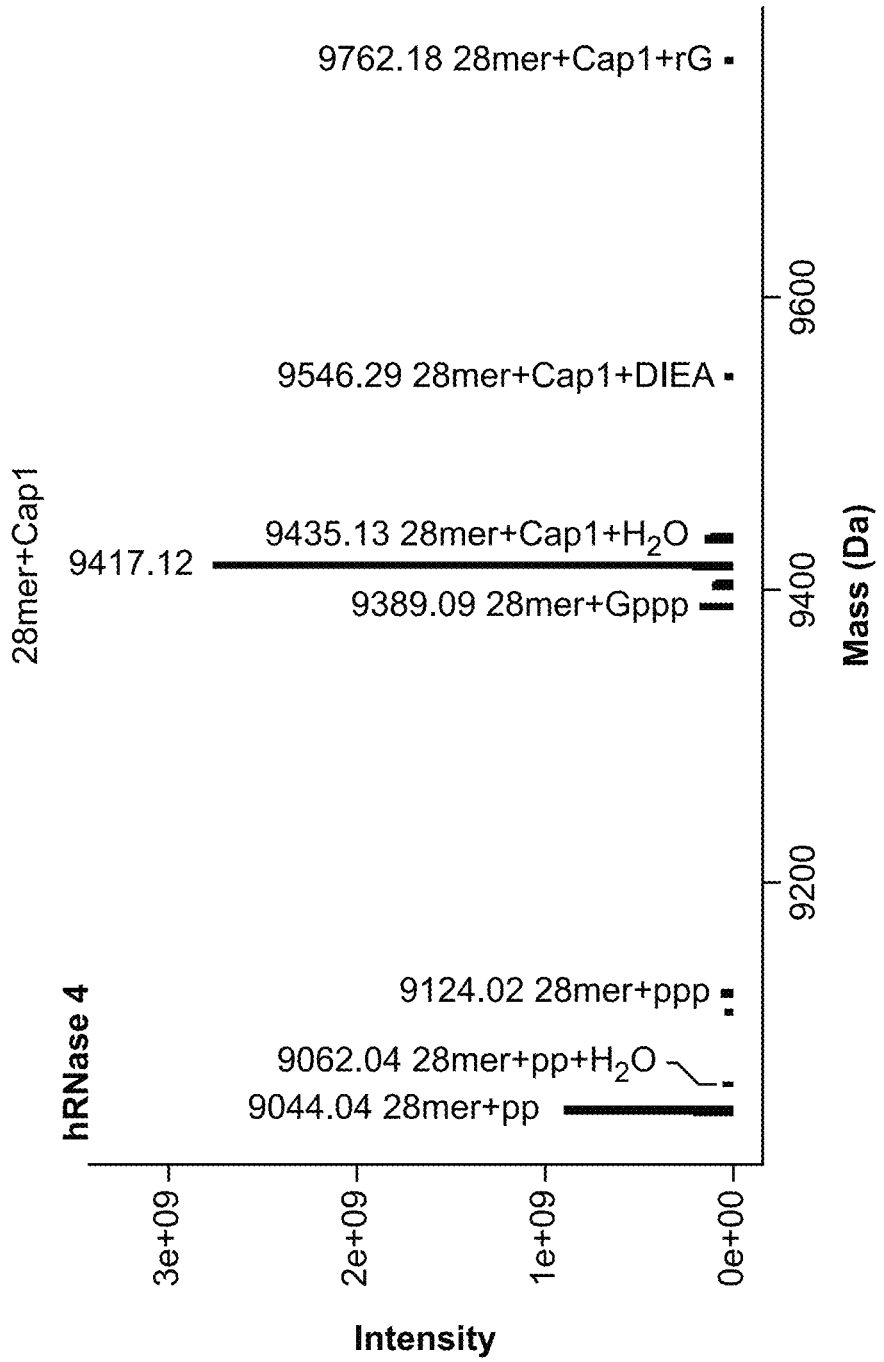
FIG. 31C illustrates deconvoluted mass spectra of the main cleavage product peak of hRNase 4 digest (the 28mer) from FIG. 31B.
Figure 31D:
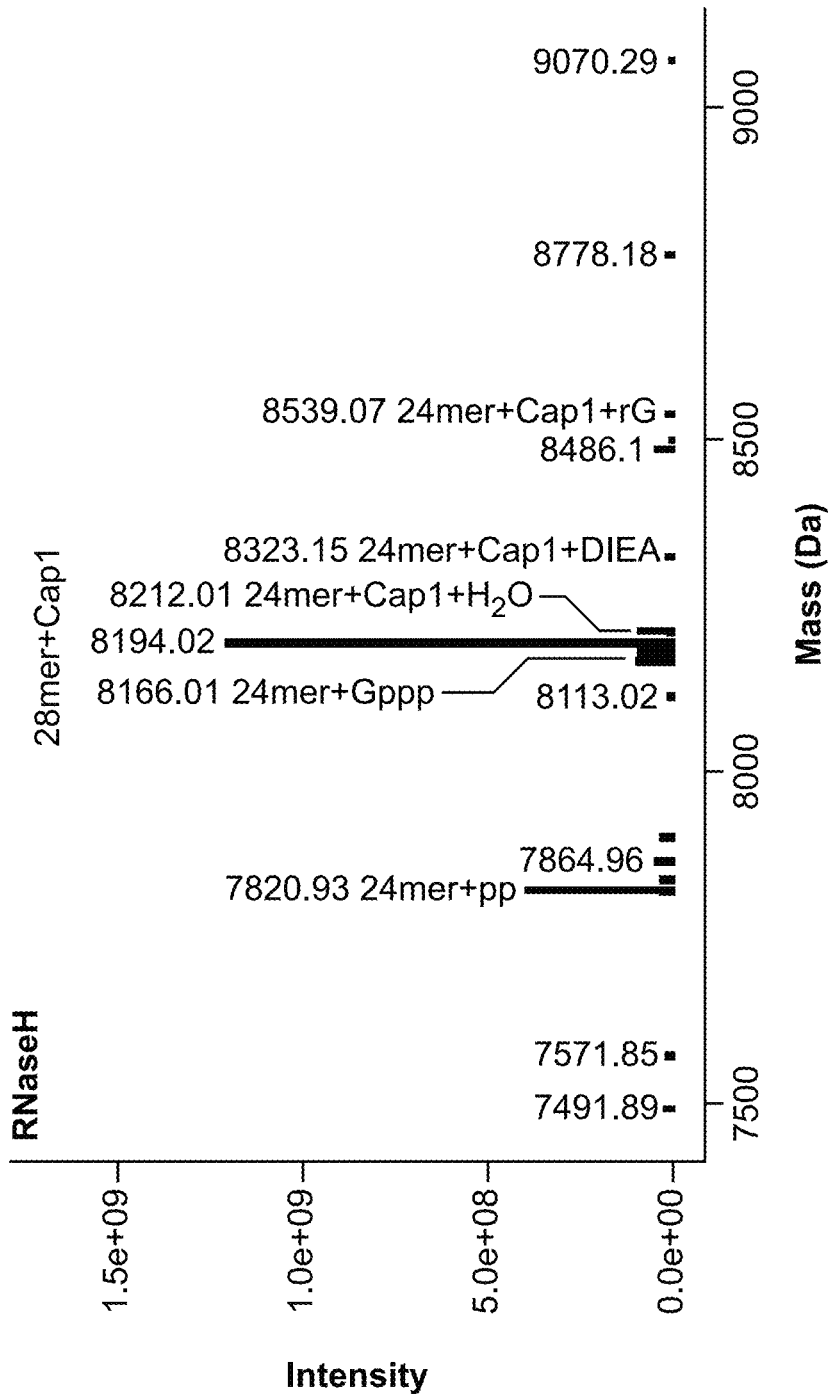
FIG. 31D illustrates deconvoluted mass spectra of the main cleavage product peak of RNaseH digest (the 24mer) from FIG. 31B. Both cleavage products of FIG. 31C (28mer) and FIG. 31D (24mer) comprise a mixture of the individual sequences with different 5' ends, which may include 5'-pp (diphosphate or 2p), 5'-ppp (triphosphate or 3p), 5'-Gppp, Cap 0 (5'-m$^7$GpppG) and Cap 1 (5'-m$^7$GpppGm).

FIG. 31C shows the deconvoluted mass spectrum of the 28mer cleavage product peak of FIG. 31B (hRNase 4 condition). FIG. 31D shows the deconvoluted mass spectrum of the 24mer cleavage product peak of FIG. 31B (RNase H condition). Both mass spectra are consistent with the formation of a series of intermediary modifications of the RNA 5' end resulting from incomplete enzymatic capping and/or methylation of the FLuc mRNA (described above). These include 5'-pp (diphosphate or 2p or pp), 5'-ppp (triphosphate or 3p or ppp), 5'-Gppp, and Cap 1 (5'-m7GpppGm).

Figure 31F:
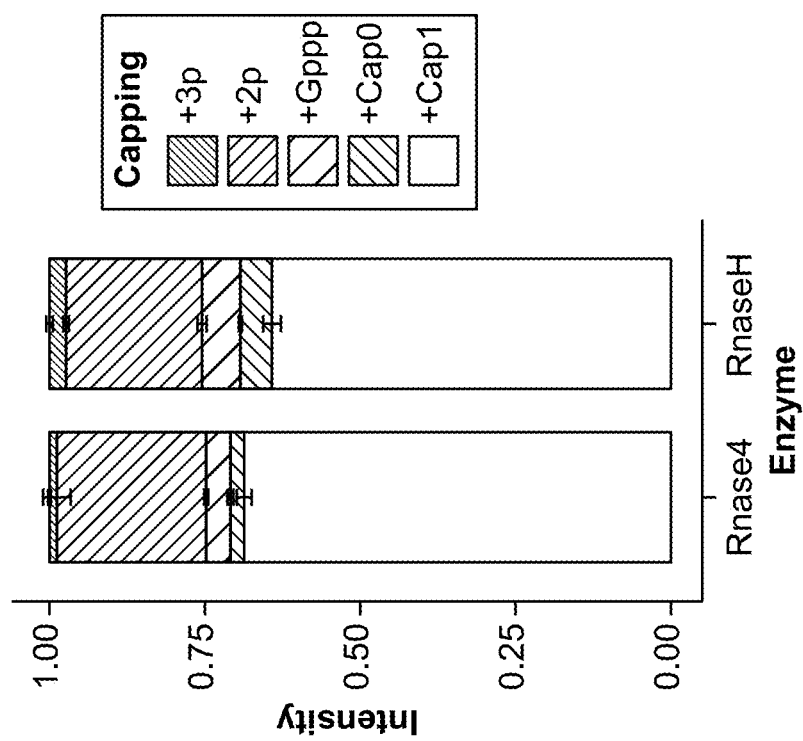
FIG. 31F illustrates distribution of the different 5' ends in all identified sequences for each of hRNase 4 or RNase H digests averaged from two replicates. Data shown demonstrate that the relative quantification of capped products and their intermediates in the hRNase 4 condition is comparable to that of RNase H enzyme, indicating that hRNase 4 can be effectively used for analysis of mRNA capping efficiency. The presence of a 3' end repair enzyme, such as T4 PNK, in combination with hRNase 4 may produce molecules with consistent, dephosphorylated 3' termini and, thereby, reduce ambiguity in the attribution of mRNA 5' modification.
Figure 31E:
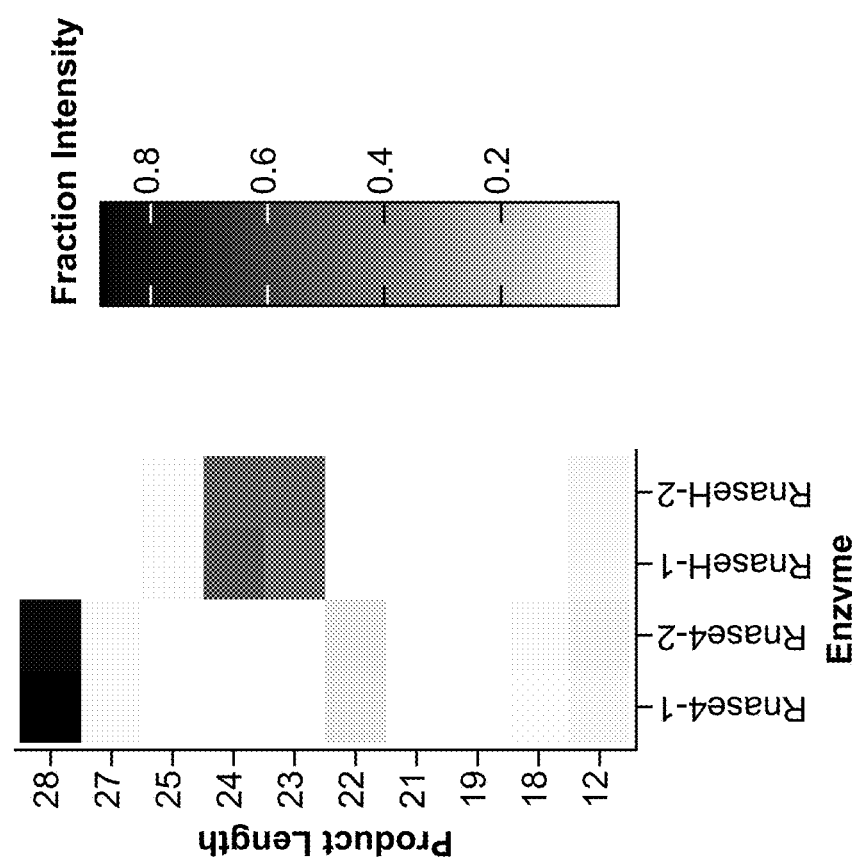
FIG. 31E illustrates an example heatmap of the intensity of the Cap 1 modified oligonucleotides detected in two independent experiments using hRNase 4 or RNase H. RNase H produces two abundant Cap 1 oligonucleotide product sequences (23mer and 24mer), whereas hRNase 4 produces predominantly one (28mer).

A search of all annotated 5'-end products with a Cap 1 structure in the hRNase 4 condition revealed that the vast majority came from the 28mer product (87.5±1.4%), whereas in the RNase H condition, the 5'-end products with a Cap 1 structure are distributed between of the 23mer (45.7±2.3%) and 24mer (51.5±2.5%) product sequences (FIG. 31E). Hence, a framework for increasing the precision of RNA cleavage (e.g., by optimizing the identity and sequence of the protection probe for each RNA substrate of interest) while may be required in applications involving RNase H, may not be at all necessary in applications involving hRNase 4.

A relative quantitation of the products with different 5'-end modifications, and by extension, a relative measure of FLuc mRNA capping efficiency is shown in FIG. 31F. The aggregate results of hRNase 4 and RNaseH largely agree with each other. In both the hRNase 4 and RNaseH reactions, the Cap 1 product represented the majority of species identified (66.7±1.2% and 64.2±1.4%, respectively). The relative abundance of intermediary products also exhibited good concordance between the hRNase 4 and RNaseH conditions, with the diphosphorylated product (24.0±2.2% and 21.9±0.4%, respectively) exhibiting the highest relative abundance among all intermediary products.

Taken together, these data demonstrate that ribonucleases, such as hRNase 4, that feature a high degree of specificity for cleaving a single-stranded RNA substrate at defined sites (e.g., specificity for cleaving an RNA at one or more dinucleotide, trinucleotide or tetranucleotide combinations) may be useful to characterize the extent of mRNA 5' end capping. RNase 4 results are comparable to RNase H results but with differences. For example, RNase H requires a double-stranded RNA target such that the DNA probe must be chimeric requiring both a DNA and an RNA portion and even with such a probe, RNaseH cleavage products vary in size by −2 to +2 nucleotides around the recognition site, complicating fragment analysis.

Disclosed methods, in some embodiments, may be used to analyze aspects of the protected RNA segment, including modifications present in the segment, such as a cap structure. For example, disclosed methods may include contacting an RNA substrate with (a) a probe targeting an internal segment of the RNA substrate of interest, (b) a probe targeting a 3' end segment of the RNA substrate of interest or (c) multiple probes (e.g., multiple biotinylated-DNA probes) targeting different portions of the RNA substrate, permitting simultaneous analysis of such portions. Disclosed methods may be applied to RNA modification analysis, such as RNA identification, locating an RNA within a sequence, assessing RNA stoichiometry, detecting RNA presence, permanence, and/or dynamics (i.e., installation and removal), and detecting co-existence of RNA modifications.

In some embodiments, RNA 5' end cap analysis methods, including methods of analyzing cap structures present in mRNAs (e.g., 7-methylguanosine triphosphate cap), small nuclear RNAs (e.g., 2,2,7-trimethylguanosine triphosphate cap or γ-monomethyl phosphate cap) and mitochondrial RNA (e.g., NAD cap), may include contacting a sample and a 5'→3' exoribonuclease that is capable of hydrolyzing 5'-monophosphate RNA in the 5' to 3' direction and that does not hydrolyze 5'-capped RNA. Examples of such 5'-phosphate-dependent exonucleases include XRN-1 (NEB, Cat #M0338S) and Terminator (LGC, Biosearch Technologies, Cat #TER51020). Treatment of an RNA sample with XRN-1 or Terminator, prior or after contacting the RNA substrate (or fragments thereof) with a site-specific endoribonuclease such as hRNase 4, may reduce the complexity of the sample and facilitate data analysis of RNA 5'-capped ends.

By selecting appropriate probe sequences, disclosed methods may be applied for detecting RNA segments originated from abortive transcription initiation events; or RNA segments originated from premature transcription termination events (e.g., resulting in truncated RNAs); or RNA segments originated from cis-primed transcription extension and/or self-primed transcription extension that result in a transcript pool comprising longer than encoded RNA products, often forming regions of double-stranded RNA that may trigger innate immune response and affect the action of RNA vaccines and therapeutics.

Disclosed methods may be used in absence of a protection probe so that it permits that RNA segments comprising double-stranded regions or other structural regions (e.g., hairpins, stem loops, pseudoknots, etc.) that may form within an RNA substrate of interest (intramolecular structures) or may form among multiple RNAs or DNA/RNA hybrids (intermolecular structures), including triple or quadruple helices, to be either directly analyzed by LC-MS/MS or undergo a process of purification to isolate the double-stranded and/or other structural regions prior to LC-MS/MS analysis. In these embodiments, the structured region(s) will (in analogy to a region protected by an exogenous probe) direct the ribonuclease to cleave the RNA only at accessible sites (e.g., ribonuclease specific sites located at unstructured or poorly structured regions), thus enabling analyses of such structured region(s). Disclosed methods may be used to determine RNA structured regions implicated in certain biological functions, such as translation modulators, splicing regulatory elements, microRNA processing sites, riboswitches, IRES, and others.

In some embodiments, a cap analysis method may be performed in the absence of a protection probe, for example, where site-specific ribonuclease access to the subject RNA segment is limited by a protein (e.g., an RNA binding protein or an antibody), by an RNA ligand (e.g., cellular metabolites such as adenosylcobalamin, lysine, glycine, flavin mononucleotide, etc. as well as synthetic small molecule binders such as fluorescent dyes and drugs like branaplam and risdiplam), by a divalent ion (e.g., a salt of magnesium, calcium, zinc, manganese, etc.) or by a multi-component biological structure (e.g., a ribosome, a lipid-based membrane, etc.). For example, RNA cleavage by a site-specific ribonuclease in the surrounding region(s) of the bound element (for instance an RNA binding protein, an RNA ligand, or a ribosome) may be used to determine the identity of the sequence to which this element is bound, the relative occupancy, and/or binding dissociation properties.

In some embodiments, chemical crosslinking may be performed prior to contacting the RNA with a site-specific ribonuclease (e.g., hRNase 4). The RNA may be crosslinked intramolecularly and/or intramolecularly (e.g., to complementary probe, to an RNA binding protein, to a ribosome, to an aptamer, to another DNA or RNA strand). The RNA may be cleaved by a site-specific ribonuclease in the surrounding region(s) of the crosslinked region for isolation and analyses.

Example 16: The Effect of Varying the RNA 5'-End Sequence in Probe-Directed RNA Cleavage with hRNase 4 or RNase H In some embodiments, disclosed methods may be applied to analysis of mRNA capping in transcripts with distinct 5'-UTR sequences and with sequences comprising full replacement of uridine sites (U) with 1-methyl pseudouridine sites ($m^1\Psi$ or $m^1Y$) as illustrated in this example. Synthetic mRNA transcripts were constructed by replacing the FLuc mRNA 5'-UTR coding sequence with the coding sequence of the 5'-UTR of interest. TABLE 6 lists the mRNA 5'-UTR sequences used in this example. Transcripts were produced by in vitro transcription (IVT) utilizing the HiScribe™ T7 High Yield RNA Synthesis Kit (NEB, Catalog #E2040S) utilizing either canonical UTP or $m^1\Psi$TP replacing UTP to result in full substitution of uridine with 1-methyl-pseudouridine as described in Examples 5 and 7. Each mRNA was capped with FCE and methylated with a 2'-O-methyltransferase to produce a 5' terminal $m^7$GpppGm (Cap 1) containing product and a series of intermediary 5' end capped and uncapped products as described in Example 15.

TABLE 6 mRNA 5'-UTR coding sequences used in this study

| Name | 5'-UTR Coding Sequence | SEQ ID NO |
|---|---|---|
| FLuc | GGGTCTAGAAATAATTTTGTTTAACTTTA AGAAGGAGATATAACC | 47 |
| Comirnaty | GGGAATAAACTAGTATTCTTCTGGTCCCC ACAGACTCAGAGAGAACCCGCCACC | 48 |

TABLE 6-continued mRNA 5'-UTR coding sequences used in this study

| Name | 5'-UTR Coding Sequence | SEQ ID NO |
|---|---|---|
| HBB | GGGACATTTGCTTCTGACACAACTGTGTT CACTAGCAACCTCAAACAGACACCACC | 49 |
| pRNA21 | GGGAAATAAGAGAGAAAAGAAGAGTAAGA AGAAATATAAGAGCCACC | 50 |

Each mRNA was hybridized to a corresponding biotinylated DNA probe (TABLE 7) utilizing the touchdown hybridization approach as described in Example 15. Each hybridized DNA/RNA duplex was digested with either hRNase 4/T4 PNK or RNase H, affinity purified and characterized by LC-MS/MS as described in Example 15.

TABLE 7

Probe sequences used to assess probe-directed RNA cleavage of mRNAs comprising distinct 5'-UTRs

| Name | Probe Sequence | SEQ ID NO |
|---|---|---|
| FLuc R4 | /5BiosG/GTTAAACAAAATTATTTCTAG ACCC | 51 |
| Comirnaty R4 | /5BiosG/AAGAATACTAGTTTATTCCC | 52 |
| HBB R4 | /5BiosG/TGTGTCAGAAGCAAATGTCC | 53 |
| pRNA21 R4 | /5BiosG/TTCTTACTCTTCTTTTCTCTC TTATTTCCC | 54 |
| FLuc RH | dGdTdTdAdAdACAAAAUUAUUUCUAGAC CC/3dtb/ | 55 |
| Comirnaty RH | dAdCdCdAdGdAAGAAUACUAGUUUAUUC CC/3dtb/ | 56 |
| HBB RH | dAdGdTdTdGdTGUCAGAAGCAAAUGUCC C/3dtb/ | 57 |
| pRNA21 RH | dGdGdGdAdAdAUAAGAGAGAAAAGAAGA GU/3dtb/ | 58 |

Probes used for hRNase 4 protection cleavage are denoted by 'R4'. Probes used for RNase H protection cleavage are marked with 'RH'. Deoxyribonucleotides in the DNA-RNA chimera probes are preceded by 'd'.

Figure 32A:
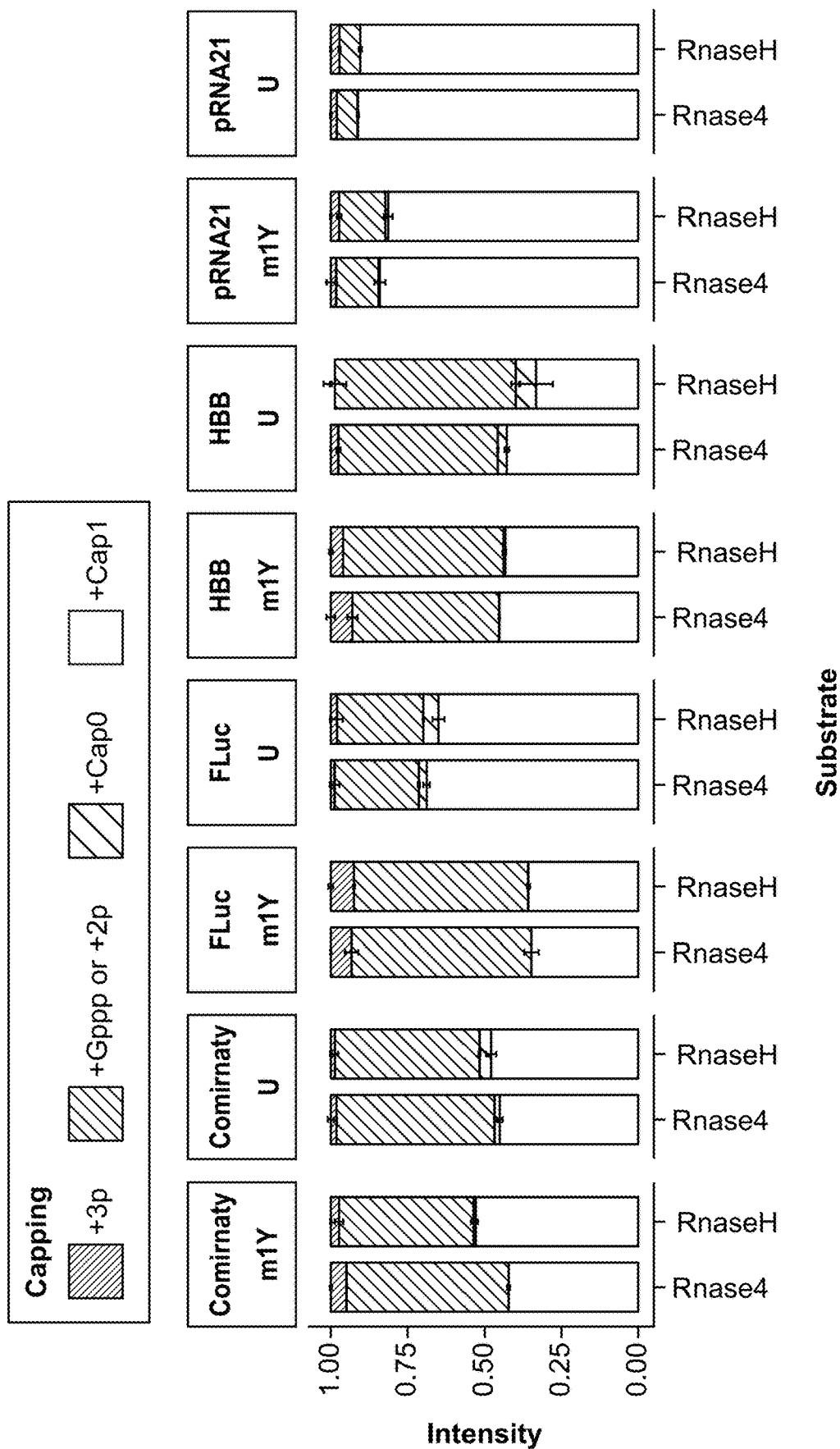
FIG. 32A compares hRNase 4 and RNase H for the analysis of the enzymatic capping efficiency of unmodified (U) and fully modified (m1Y) mRNA. Data shown illustrate the distribution of 5' ends in a population of capped mRNAs revealed by analyses with hRNase 4 or RNase T1. Comparable distributions of capped products and intermediates were obtained in both the hRNase 4 analysis and the RNase T1 analysis.

FIG. 32A shows the extent of capping observed for each mRNA substrate. A relative quantitation of the cleavage products with different 5' end modifications was determined for each of the hRNase 4 and RNaseH conditions as described in Example 15. A range of capping efficiencies (30-90%) was detected across U or $m^1\Psi$-modified mRNAs with distinct 5'-UTRs. However, the mean relative abundance of each mRNA 5' end product (comprising a 5'-pp, or a 5'-ppp, or a 5'-Gppp, or a Cap 0, or a Cap 1) was consistent in both the hRNase 4 and RNaseH conditions.

Figure 32B:
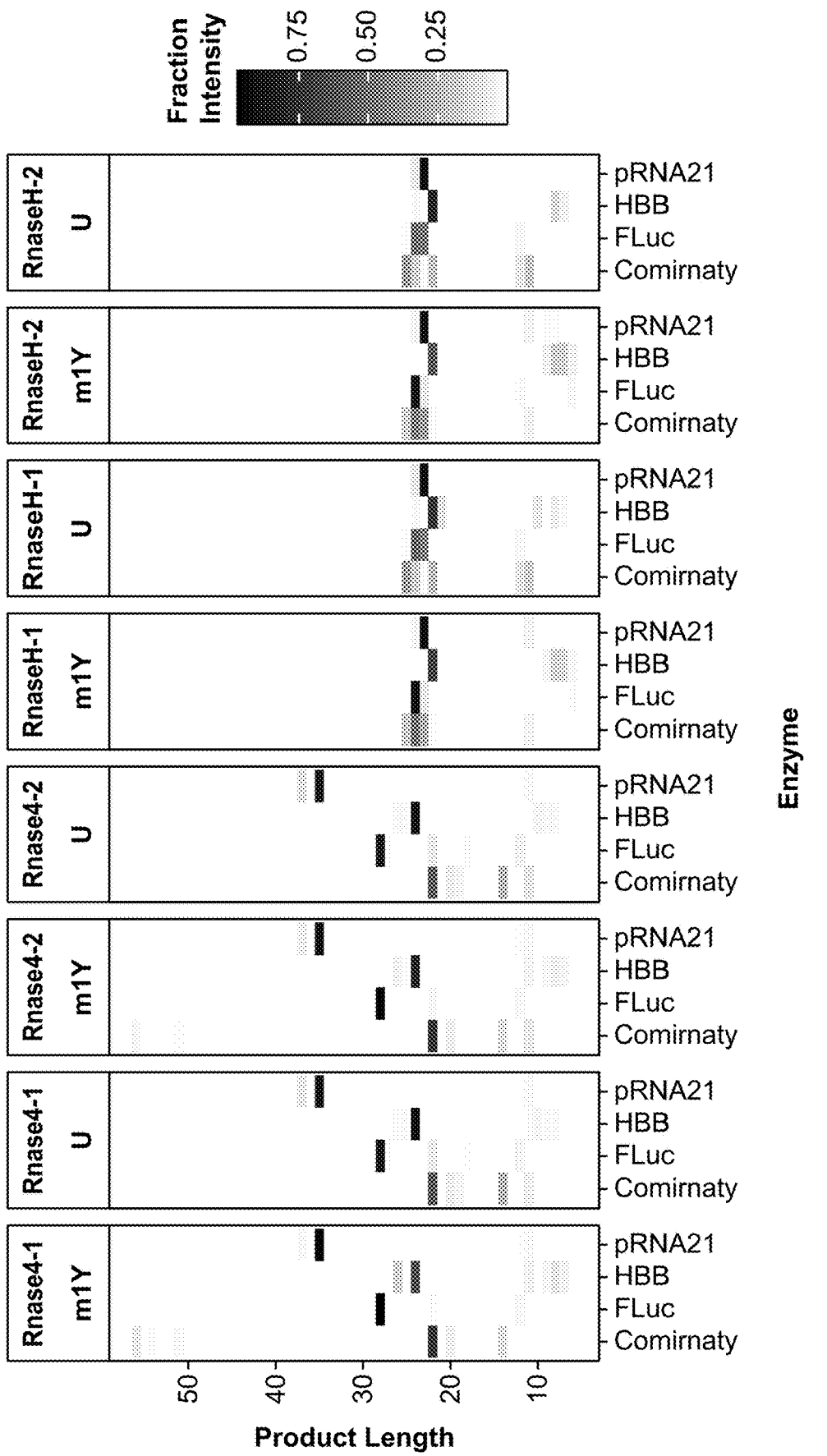
FIG. 32B illustrates an example heatmap of the intensity of Cap-1 modified oligonucleotides of various lengths detected for each mRNA variant. In contrast to hRNase 4, RNase H displayed a higher propensity to spuriously cleave one or more nucleotides upstream or downstream from the target site resulting in a mixture of cleaved products differing from each other by one or more nucleotides in length, even after extensive probe optimization.

FIG. 32B shows the length distribution of $m^7$GpppGm (Cap 1) capped cleavage products observed in each of the hRNase 4 and RNaseH conditions. Cap 1 products of identical length were detected for both U and mid'-modified variants of a particular mRNA 5'-UTR. Notably, the hRNase 4 condition yielded predominantly Cap 1 products of a discrete length, resulting from cleavage of each mRNA substrate at an hRNase 4 recognition site downstream of the DNA probe hybridized region in each target mRNA. In contrast, a higher heterogeneity regarding the length distribution of the Cap 1 products for each individual mRNA substrate was observed in the RNase H condition. While for certain mRNA substrates (for instance, mRNA comprising HBB and pRNA21 5'-UTRs) cleavage with RNase H resulted in primarily one product, for other mRNAs (for instance, mRNA comprising Comirnaty and FLuc 5'-UTRs) cleavage with RNase H resulted in mixtures of products varying by one or more nucleotides in length.

Collectively, these data demonstrate that ribonucleases such as hRNase 4 are useful to assess mRNA 5' end capping across mRNAs with a diversity of 5' end sequences. The ability of hRNase 4 to produce specific cleavage at defined sites surrounding a protected portion of an RNA substrate may yield a more defined set of RNA cleavage products, which may advantageously simplify data analysis and facilitate the assessment of aspects of interest, such as the presence of a cap, a tail and/or modifications (e.g., endogenous modifications, synthetically incorporated modifications, or RNA modifications resulting from damage caused by irradiation, exposure to hazardous chemicals, temperature or pH fluctuation, among others).

Example 17: DNA Probe-Directed Selective Purification of RNA Poly(A) Tails with hRNase 4

According to some embodiments, disclosed workflows may be applied to selectively cleaving and purifying an mRNA 3' end poly(A) tail utilizing a site-specific ribonuclease. For such embodiments, care may be taken to select a site-specific ribonuclease (e.g., hRNase 4) that is not adenosine specific (i.e., does not cleave a 3',5'-phosphodiester bond with specificity for adenosine at the main anchoring site B1). A workflow may include, for example, contacting an mRNA 3' end poly(A) tail with a DNA probe to form a duplex product in which the DNA probe is annealed to at least a portion of the poly(A) tail and one or more additional nucleotides immediately upstream of poly(A) tail sequence.

FIG. 33 shows a representative example of a deconvoluted LC-MS/MS spectrum of oligonucleotide cleavage products comprising regions of the mRNA poly(A) tail that were isolated from the capped and polyadenylated synthetic EPO mRNA of EXAMPLE 8. The in vitro synthesize EPO mRNA, whose coding sequence encoded a 120-nt poly(A) tail, was annealed to a biotinylated DNA probe an (SEQ ID NO: 59/5BiosG/TTTTT/iBiodT/TTTTT/iBiodT/TTTTTTTTTTTVN), contacted with hRNase 4 and T4 PNK, and then purified with the use of magnetic streptavidin beads. After elution from the beads, a 126-nt product cleavage product comprising a distribution of poly(A) tail-related oligonucleotides sequences differing in mass from each other by a single adenosine residue (FIG. 33) was identified.

Collectively, these data demonstrate the use of a ribonuclease such as hRNase 4 for isolation of mRNA poly(A) tail sequence regions for analysis by LC-MS/MS.

Figure 34:
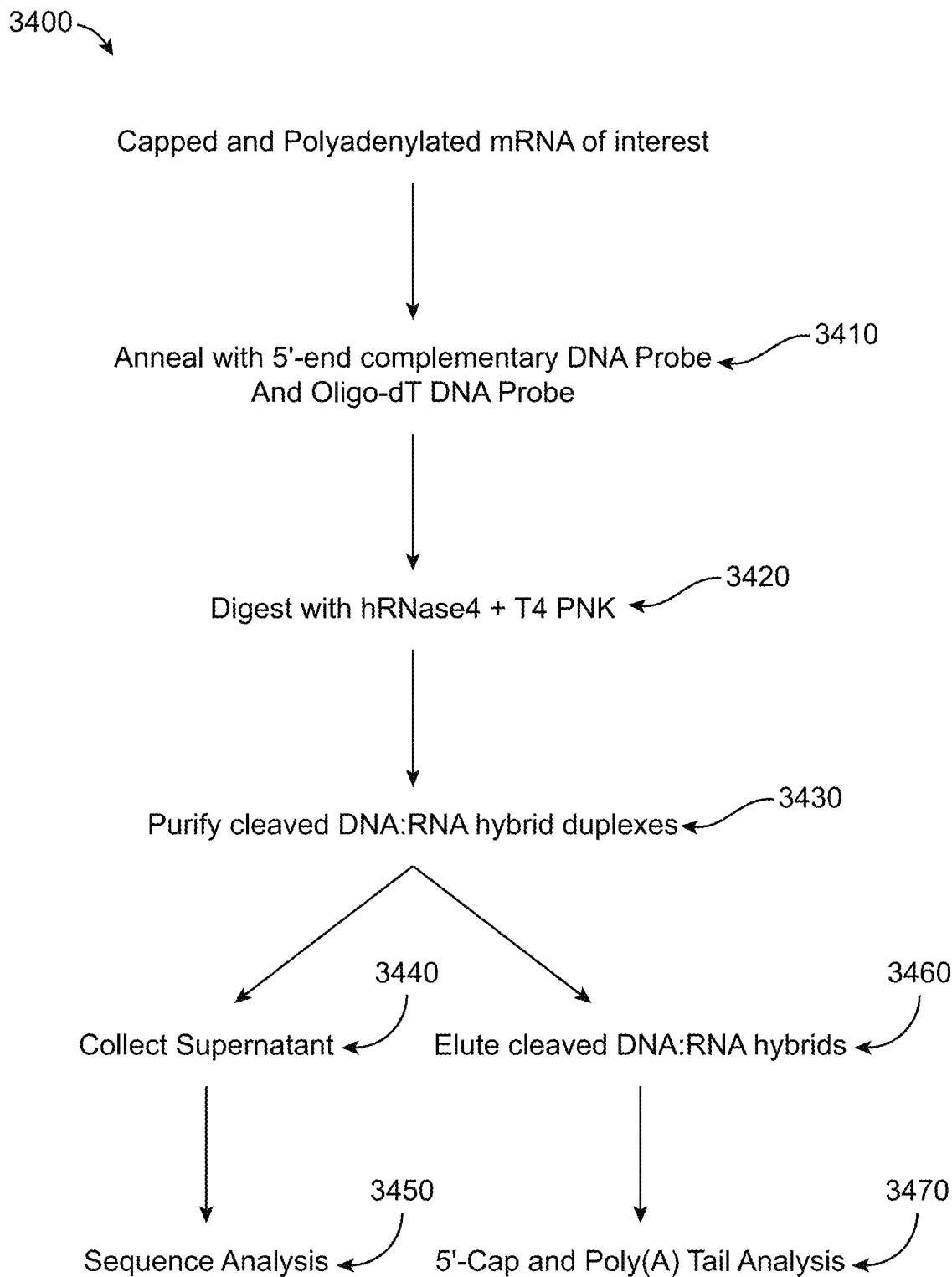
FIG. 34 illustrates an example workflow 3400 used for integrative analysis of 5' cap, poly(A) tail, and an mRNA internal sequence (also referred as to mRNA body sequence) using hRNase 4. In this example workflow, subject RNA is annealed 3410 with DNA probes targeted to the RNA 5' and 3' ends, wherein each DNA probe independently of each other may comprise an affinity group. Hybridized RNA is digested 3420 with hRNase 4, optionally in a composition with T4 PNK. Cleaved DNA-RNA duplexes are purified 3430 (e.g., by affinity capture) and the cleaved single-stranded RNA oligonucleotides are collected 3440 (supernatant). The supernatant fraction containing the cleaved single-stranded RNA oligonucleotides may be used for analysis 3450 of the mRNA internal sequence. DNA-RNA duplexes may be eluted 3460 and used for 5' cap and poly(A) tail analysis 3470 (e.g., directly or after releasing the RNA strands by DNase I treatment).

Example 18: Integrated Analysis of an mRNA Sequence, 5'-Cap and Poly(A) Tailing Using hRNase 4/T4 PNK Examples workflows are provided to characterize in a single experimental preparation the three primary parts of a eukaryotic mRNA: a 5' end cap, an internal (or body) sequence, and a 3' end poly(A) tail. Available methods for analysis of mRNA by LC-MS/MS frequently require independent analytical workflows to characterize each of these modules. FIG. 34 shows an example of an analytical workflow for integrated mRNA analysis enabled by the use of a site-specific ribonuclease such as hRNase 4, optionally in combination with a repair enzyme such as T4 PNK.

In FIG. 34 workflows, an mRNA comprising a 5' end cap, an internal RNA sequence, and a 3' end poly(A) tail, contacts a 5' targeting DNA probe complementary to the 5' end of the mRNA and a 3' DNA targeting probe complementary to the 5' end of the mRNA to form annealed polynucleotide products comprising in a 5' to 3' direction relative to the mRNA, a double-stranded first DNA probe/5' mRNA segment, an internal single-stranded sequence, and a double-stranded second DNA probe/3' mRNA segment. Annealed polynucleotides may be contacted with hRNase 4, optionally in combination with T4 PNK, to selectively generate cleavage products (oligonucleotides). Cleavage products may be isolated and analyzed by LC-MS/MS. For example, a capped and poly-adenylated mRNA may be annealed to two complementary DNA probes, each optionally comprising one or more affinity tags. One DNA probe may be complementary to the 5' end sequence of the mRNA and the other DNA probe may be an oligo-dT probe complementary to the poly(A) tail, forming DNA/mRNA hybrids at the mRNA 5' end and 3' end poly(A) tail, respectively, so that these regions are protected from cleavage by the ribonuclease. A digestion reaction may comprise contacting annealed polynucleotides with a composition including a site-specific ribonuclease (e.g., hRNase 4) and a repair enzyme (e.g., T4 PNK) to form products site-specifically cleaved at accessible regions of the mRNA substrate (e.g., the internal single-stranded sequence) to form cleavage products comprising single-stranded fragments of the mRNA, the double-stranded first DNA probe/5' mRNA segment, and the double-stranded second DNA probe/3' mRNA segment. Next, single-stranded fragments and cleaved DNA/mRNA duplex segments may be separated from each other (e.g., by affinity purification) wherein one fraction comprises single-stranded fragments and another comprises duplex segments. One or more fractions may be subject to LC-MS/MS analysis. For example, single-stranded fragments (e.g., in a supernatant fraction of an affinity purification) may be subjected to LC-MS/MS and to characterize the internal mRNA sequence and/or cleaved DNA/mRNA hybrid duplexes (e.g., in an eluted fraction of an affinity purification) may be subjected to LC-MS/MS to characterize the 5' cap and 3' poly(A) tail. The combined analysis of cleavage products, resulting from the internal mRNA sequence fraction and from the cap and poly(A) tail fraction, can be used for an integrated characterization of an mRNA substrate of interest (e.g., characterization of the RNA sequence and any modifications) from a single experimental preparation within the same workflow.

In some embodiments, a mRNA comprising a 5' end cap, an internal RNA sequence, and a 3' end poly(A) tail may be annealed to one or more DNA probes, each complementary to at least a portion of the mRNA (e.g., each independently designed to be complementary to 5' and/or 3' end regions of the mRNA substrate). In some embodiments, a workflow may additionally comprise one or more DNA probes targeting selected regions of the internal mRNA sequence. In some embodiments, a DNA probe targeting the mRNA 3' end may comprise an oligo-dT DNA probe. In some embodiments, a DNA probe targeting an mRNA 3' end may comprise one or more additional nucleotides complementary to the mRNA sequence immediately upstream of the oligo-dT DNA probe binding site. Each of the DNA probes targeting the 5' or 3' end regions of the mRNA may independently of each other comprise an affinity group (e.g., a biotin) so that the DNA-RNA duplex can be isolated by affinity purification at any stage of the workflow. The affinity group may be attached to the 5' end of the DNA probe, to the 3' end of the DNA probe, or internally to the 5' end of the DNA probe (e.g., the affinity group may be covalently linked to the base an internal nucleotide, for instance to the 5-position of thymine). In some embodiments, multiple affinity groups (e.g., multiples of the same affinity group or affinity groups of different chemical composition) may be used to increase purification efficiency and/or allow purification using multiple affinity matrices. In other embodiments, the DNA does not comprise an affinity group and the isolation of the DNA-RNA duplex may be performed by size exclusion chromatography (SEC), gel filtration chromatography, anion-exchange chromatography (AEX), hydrophilic interaction liquid chromatography (HILIC), reversed-phase liquid chromatography (RP-LC), ion-paring reversed-phase liquid chromatography (IP-RP-LC), solid-phase reversible immobilization (e.g., SPRI paramagnetic beads), or any combination thereof (also referred as multimodal or mixed-mode chromatography). In some embodiments, a DNA-RNA duplex may be analyzed directly without isolation or purification.

In some embodiments, an mRNA comprising a 5' end cap, an internal RNA sequence, and a 3' end poly(A) tail, and annealed to one or more targeting DNA probes, may be contacted with hRNase 4, optionally in combination with T4 PNK, to selectively generate cleavage products (oligonucleotides) by cutting in regions of the mRNA sequence that comprise accessible ribonuclease cleavage sites (e.g., sites not protected by the targeting DNA probe). Oligonucleotide cleavage products comprising a mixture of DNA-RNA duplex (DNA-RNA hybrids) region(s) and single-stranded RNA regions may be either directly analyzed by LC-MS/MS or undergo a process of purification to isolate the cleaved DNA-RNA duplex region(s) prior to LC-MS/MS analysis. Cleaved DNA-RNA duplex region(s) may be isolated by affinity purification; by purification using of one or more of the chromatographic or immobilization modes described above; or both. After isolation of the cleaved DNA-RNA duplex regions(s), the remaining supernatant enriched in single-stranded internal mRNA regions may be either directly analyzed by LC-MS/MS or undergo purification using of one or more of the chromatographic or immobilization modes described above, and then be analyzed by LC-MS/MS. The isolated DNA-RNA duplex region(s) may be eluted as appropriated according to the method of purification chosen and then analyzed by LC-MS/MS.

What is claimed is:

1. A composition comprising:
   (a) a human RNase 4 in an amount having catalytic activity equivalent to 100 to 10,000 units of RNase T1, wherein one unit of RNase T1 causes an increase in absorbance of 1.0 at 260 nm in 15 minutes when yeast RNA is hydrolyzed at 37° C. and pH 7.5 in a reaction comprising 50 mM Tris-HCl, 2 mM EDTA, and 3 mg/mL of the yeast RNA;
   (b) a bacterial RNA end repair enzyme or a bacteriophage RNA end repair enzyme; and
   (c) an RNA comprising at least 1,000 nucleotides in an amount of 0.01 μg to 100 μg, wherein the human RNase 4 specificity is selected from (1) cleavage after a specific nucleotide followed by a purine, (2) cleavage after a specific nucleotide followed by a pyrimidine, (3) cleavage after a purine followed by a specific nucleotide, and (4) cleavage after a pyrimidine followed by a specific nucleotide; and
   wherein the RNA end repair enzyme comprises phosphodiesterase and phosphomonoesterase activities.

2. A composition according to claim 1, wherein the human RNase 4 cleaves on average once every 6-12 nucleotides.

3. A composition according to claim 1, wherein the RNA end repair enzyme is present in an amount of 10 units to 100,000 units.

4. The composition according to claim 1, wherein the RNA end repair enzyme is a T4 polynucleotide kinase-phosphatase or a Cth polynucleotide kinase-phosphatase.

5. The composition according to claim 1 further comprising one or more of a denaturing agent, a buffering agent, and an RNA substrate.

6. A composition according to claim 1, wherein the RNA comprises messenger RNA (mRNA), ribosomal RNA (rRNA), transfer RNA (tRNA), small RNA (sRNA), microRNA (miRNA), long non-coding RNA (lncRNA), circular RNA (circRNA), aptamer RNA, antisense RNA, silencing RNA (siRNA), guide RNA (gRNA), or any combination thereof.

* * * * *

SEQUENCE LISTING

```
Sequence total quantity: 58
SEQ ID NO: 1          moltype = RNA  length = 12
FEATURE               Location/Qualifiers
source                1..12
```

```
                              mol_type = other RNA
                              organism = synthetic construct
SEQUENCE: 1
aaaaaactaa aa                                                              12

SEQ ID NO: 2                  moltype = RNA   length = 25
FEATURE                       Location/Qualifiers
source                        1..25
                              mol_type = other RNA
                              organism = synthetic construct
SEQUENCE: 2
aaaaaaaaaa aaataaaaaa aaaaa                                                25

SEQ ID NO: 3                  moltype = RNA   length = 25
FEATURE                       Location/Qualifiers
source                        1..25
                              mol_type = other RNA
                              organism = synthetic construct
SEQUENCE: 3
aaaaaaaaaa aaattaaaaa aaaaa                                                25

SEQ ID NO: 4                  moltype = RNA   length = 22
FEATURE                       Location/Qualifiers
source                        1..22
                              mol_type = other RNA
                              organism = synthetic construct
SEQUENCE: 4
aaaaaaaaaa agtaaaaaaa aa                                                   22

SEQ ID NO: 5                  moltype = RNA   length = 25
FEATURE                       Location/Qualifiers
source                        1..25
                              mol_type = other RNA
                              organism = synthetic construct
SEQUENCE: 5
aaaaaaaaaa aaatgaaaaa aaaaa                                                25

SEQ ID NO: 6                  moltype = RNA   length = 12
FEATURE                       Location/Qualifiers
source                        1..12
                              mol_type = other RNA
                              organism = synthetic construct
SEQUENCE: 6
aaaaaacgaa aa                                                              12

SEQ ID NO: 7                  moltype = RNA   length = 12
FEATURE                       Location/Qualifiers
source                        1..12
                              mol_type = other RNA
                              organism = synthetic construct
SEQUENCE: 7
aaaaaaaaaa aa                                                              12

SEQ ID NO: 8                  moltype = RNA   length = 12
FEATURE                       Location/Qualifiers
source                        1..12
                              mol_type = other RNA
                              organism = synthetic construct
SEQUENCE: 8
aaaaaaggaa aa                                                              12

SEQ ID NO: 9                  moltype = RNA   length = 22
FEATURE                       Location/Qualifiers
source                        1..22
                              mol_type = other RNA
                              organism = synthetic construct
SEQUENCE: 9
aaaaaaaaaa accaaaaaaa aa                                                   22

SEQ ID NO: 10                 moltype = RNA   length = 15
FEATURE                       Location/Qualifiers
source                        1..15
                              mol_type = other RNA
                              organism = synthetic construct
SEQUENCE: 10
aaaaaaaagc aaaaa                                                           15

SEQ ID NO: 11                 moltype = RNA   length = 15
FEATURE                       Location/Qualifiers
```

```
source             1..15
                   mol_type = other RNA
                   organism = synthetic construct
SEQUENCE: 11
aaaaaaaaca aaaaa                                                           15

SEQ ID NO: 12      moltype = RNA   length = 15
FEATURE            Location/Qualifiers
source             1..15
                   mol_type = other RNA
                   organism = synthetic construct
SEQUENCE: 12
aaaaaaaatc aaaaa                                                           15

SEQ ID NO: 13      moltype = RNA   length = 15
FEATURE            Location/Qualifiers
source             1..15
                   mol_type = other RNA
                   organism = synthetic construct
SEQUENCE: 13
aaaaaaaaga aaaaa                                                           15

SEQ ID NO: 14      moltype = RNA   length = 11
FEATURE            Location/Qualifiers
source             1..11
                   mol_type = other RNA
                   organism = synthetic construct
SEQUENCE: 14
gaaaaaaaaa a                                                               11

SEQ ID NO: 15      moltype = RNA   length = 14
FEATURE            Location/Qualifiers
source             1..14
                   mol_type = other RNA
                   organism = synthetic construct
SEQUENCE: 15
aaaaaaaaaa aaat                                                            14

SEQ ID NO: 16      moltype = RNA   length = 14
FEATURE            Location/Qualifiers
source             1..14
                   mol_type = other RNA
                   organism = synthetic construct
misc_feature       14
                   note = 2'3'-cP
SEQUENCE: 16
aaaaaaaaaa aaat                                                            14

SEQ ID NO: 17      moltype = RNA   length = 14
FEATURE            Location/Qualifiers
source             1..14
                   mol_type = other RNA
                   organism = synthetic construct
misc_feature       14
                   note = 3'P
SEQUENCE: 17
aaaaaaaaaa aaat                                                            14

SEQ ID NO: 18      moltype = RNA   length = 20
FEATURE            Location/Qualifiers
source             1..20
                   mol_type = other RNA
                   organism = synthetic construct
misc_feature       20
                   note = +pp
SEQUENCE: 18
ggggcttgct tgttctttttt                                                     20

SEQ ID NO: 19      moltype = RNA   length = 11
FEATURE            Location/Qualifiers
source             1..11
                   mol_type = other RNA
                   organism = synthetic construct
misc_feature       11
                   note = +pp
SEQUENCE: 19
ggggcttgct t                                                               11

SEQ ID NO: 20      moltype =    length =
```

```
SEQUENCE: 20
000

SEQ ID NO: 21           moltype = RNA   length = 12
FEATURE                 Location/Qualifiers
source                  1..12
                        mol_type = other RNA
                        organism = synthetic construct
misc_feature            12
                        note = +2Me+Gppp
SEQUENCE: 21
agggcttgct tg                                                            12

SEQ ID NO: 22           moltype =    length =
SEQUENCE: 22
000

SEQ ID NO: 23           moltype = RNA   length = 15
FEATURE                 Location/Qualifiers
source                  1..15
                        mol_type = other RNA
                        organism = synthetic construct
SEQUENCE: 23
aagagagata gagaa                                                         15

SEQ ID NO: 24           moltype = DNA   length = 30
FEATURE                 Location/Qualifiers
source                  1..30
                        mol_type = other DNA
                        organism = synthetic construct
SEQUENCE: 24
gagcttctgc aaaaagaaca agcaagccct                                         30

SEQ ID NO: 25           moltype = RNA   length = 35
FEATURE                 Location/Qualifiers
source                  1..35
                        mol_type = other RNA
                        organism = synthetic construct
SEQUENCE: 25
agggcttgct tgttcttttt gcagaagctc agaat                                   35

SEQ ID NO: 26           moltype = RNA   length = 1766
FEATURE                 Location/Qualifiers
source                  1..1766
                        mol_type = other RNA
                        organism = synthetic construct
SEQUENCE: 26
gggtctagaa ataattttgt ttaactttaa gaaggagata taaccatgaa aatcgaagaa         60
ggtaaaggtc accatcacca tcaccacgga tccatggaag acgccaaaaa cataaagaaa        120
ggcccggcgc cattctatcc tctagaggat ggaaccgctg gagagcaact gcataaggct        180
atgaagagat acgccctggt tcctggaaca attgctttta cagatgcaca tatcgaggtg        240
aacatcacgt acgcggaata cttcgaaatg tccgttcggt tggcagaagc tatgaaacga        300
tatgggctga atacaaatca cagaatcgtc gtatgcagtg aaaactctct tcaattcttt        360
atgccggtgt gggcgcgtt atttatcgga gttgcagttg cgcccgcgaa cgacatttat        420
aatgaacgtg aattgctcaa cagtatgaac atttcgcagc ctaccgtagt gtttgttcc        480
aaaaagggggt tgcaaaaaat tttgaacgtg caaaaaaaat taccaataat ccagaaaatt        540
attatcatgg attctaaaac ggattaccag ggatttcagt cgatgtacac gttcgtcaca        600
tctcatctac ctcccggttt taatgaatac gattttgtac cagagtcctt tgatcgtgac        660
aaaacaattg cactgataat gaattcctct ggatctactg ggttacctaa gggtgtggcc        720
cttccgcata gaactgcctg cgtcagattc tcgcatgcca gagatcctat ttttggcaat        780
caaatcattc cggatactgc gattttaagt gttgttccat tccatcacgg ttttggaatg        840
tttactacac tcggatattt gatatgtgga tttcgagtcg tcttaatgta tagatttgaa        900
gaagagctgt ttttacgatc ccttcaggat tacaaaattc aaagtgcgtt gctagtacca        960
accctatttt cattcttcgc caaaagcact ctgattgaca atacgattt atctaattta       1020
cacgaaattg cttctggggg cgcacctctc tcgaaagaag tcgggaagc ggttgcaaaa       1080
cgcttccatc ttccagggat acgacaagga tatgggctca ctgagactac atcagctatt       1140
ctgattacac ccgagggga tgataaaccg ggcgcggtcg gtaaagttgt tccatttttt       1200
gaagcgaagg ttgtggatct ggataccggg aaaacgctgg gcgttaatca gagaggcgaa       1260
ttatgtgtca gaggacctat gattatgtcc ggttatgtaa acaatccgga agcgaccaac       1320
gccttgattg acaaggatgg atggctacat tctggagaca tagcttactg ggacgaagac       1380
gaacacttct tcatagttga ccgcttgaag tctttaatta aatacaaagg atatcaggtg       1440
gcccccgctg aattggaatc gatattgtta caaccccca acatcttcga cgcgggcgtg       1500
gcaggtcttc ccgacgatga cgccggtgaa cttcccgccg ccgttgttgt tttgagcac       1560
ggaaagacga tgacggaaaa agagatcgtg gattacgtcg ccagtcaagt aacaaccgcg       1620
aaaaagttgc gcggaggagt tgtgtttgtg gacgaagtac cgaaaggtct taccggaaaa       1680
ctcgacgcaa gaaaaatcag agagatcctc ataaaggcca agaagggcgg aaagtccaaa       1740
ctcgagtaag gttaacctgc aggagg                                           1766

SEQ ID NO: 27           moltype = RNA   length = 801
```

```
FEATURE              Location/Qualifiers
source               1..801
                     mol_type = other RNA
                     organism = synthetic construct
misc_feature         801
                     note = C or C followed by a polyA tail
SEQUENCE: 27
ggggcttgct tgttctttt  gcagaagctc agaataaacg ctcaactttg gcaccatggg   60
agtgcacgag tgtcccgcgt ggttgtggtt gctgctgtcg ctcttgagcc tcccactgtg  120
actgcctgtg ctgggggcac caccccagatt gatctgcgac tcacgggtac ttgagaggta 180
ccttcttgaa gccaaagaag ccgaaaacat cacaaccgga tgcgccgagc actgctccct  240
caatgagaac attactgtac cggatacaaa ggtcaatttc tatgcatgga agagaatgga  300
agtaggacag caggccgtcg aagtgtggca ggggctcgcg cttttgtcgg aggcggtgtt  360
gcggggtcag gccctcctcg tcaactcatc acagccgttg gagcccctcc aacttcatgt  420
cgataaagcg gtgtcggggc tccgcagctt gacgacgttg cttcgggctc tgggcgcaca  480
aaaggaggct atttcgccgc ctgacgcggc ctccgcggca ccctccgaa cgatcaccgc   540
ggacacgttt aggaagcttt ttagagtgta cagcaatttc ctccgcggaa agctgaaatt  600
gtatactggt gaagcgtgta ggacagggga tcgctaggac tgactaggat ctggttacca  660
ctaaaccagc ctcaagaaca cccgaatgga gtctctaagc tacataatac caacttacac  720
tttacaaaat gttgtcccc aaaatgtagc cattcgtatc tgctcctaat aaaaagaaag   780
tttcttcaca ttctagctag c                                            801

SEQ ID NO: 28        moltype = RNA  length = 1703
FEATURE              Location/Qualifiers
source               1..1703
                     mol_type = other RNA
                     organism = synthetic construct
SEQUENCE: 28
gggagaccca agcttggtac cgagctcgga tccgccacca tgaagaccct gatcctggcc   60
gtggcctgg tgtactgcgc caccgtgcac tgccaggact gcccatacga accagacccc  120
ccgaacaccg tgccaaccag ctgcgaggcc aaggaaggcg agtgcatcga cagcagctgc  180
ggcacctgca ccagagacat cctgagcgac ggcctgtgcg agaacaagcc gggaaagaca  240
tgctgccgga tgtgccagta cgtgatcgag tgcagagtgg aggccgcagg atggttccgg  300
accttctacg gcaagagatt ccagttccaa gagcccggca catcgtgct gggccaggga  360
accaagggcg gcgactggaa agtgagcatc accctggaga acctcgacgg caccaaaggc  420
gccgtgctga caaagacaag actggaagtc gccggcgaca tcatcgacat cgcgcaggcc  480
accgagaacc ccatcaccgt gaacggaggc gccgaccca taatcgccaa ccctacaca   540
atcggcgaag tgacaatcgc cgtcgtggaa atgccaggct tcaacatcac cgtcattgag  600
ttcttcaaac tgatcgtgat cgacatcctc ggaggaagat cgtaagaat cgccccagac  660
acagcaaaca aaggaatgat ctctggcctc tgtggagatc ttaaaatgat ggaagataca  720
gacttcactt cagatccaga acaactgctc attcagccta agatcaacca ggagtttgac  780
ggttgtccca tctatggaaa tcctgatgac gttgcatact gcaaaggtct tctggagccg  840
tacaaggaca gctgccgcaa cccatcaac ttctactact acaccatctc ctgcgccctc   900
gcccgctgta tgggtggaga cgagcgagcc tcacacgtgc tgcttgacta cagggagacg  960
tgcgctgctc ccgaaactag aggaacctgc gttttgtctg gacatacttt ctacgataca 1020
tttgacaaag caagataccc attccagggt ccctgcaagg agattcttat ggccgccgac 1080
tgtttctgga acacttggga tgtgaaggtt tcacacagga atgttgactc ttacactgaa 1140
gtagagaaag tacgaatcag gaaacaatcg actgtagtag aactcattgt tgatggaaaa 1200
cagattctgg ttggaggaga agccgtgtcc gtcccgtaca gctctcagaa cacttccatc 1260
tactggcaag atggtgacat actgactaca gccatcctac ctgaagctct ggtggtcaag 1320
ttcaacttca agcaactgct cgtcgtacat attagagatc cattcgatgg taagacttgc 1380
ggtatttgcg gtaactacaa ccaggatttc agtgatgatt cttttgatgc tgaaggagcc 1440
tgtgatctga ccccccaacc accgggatgc accgaagaac agaaacctga agctgaacga 1500
ctctgcaata gtctcttcgc cggtcaaagt gatcttgatc agaaatgtaa cgtgtgccac 1560
aagcctgacc gtgtcgaacg atgcatgtac gagtattgcc tgaggggaca cagggtttc  1620
tgtgaccacg catgggagtt caagaaagaa tgctacataa agcatggaga cacctagaa  1680
gtaccagatg aatgcaaata ggc                                         1703

SEQ ID NO: 29        moltype = RNA  length = 1703
FEATURE              Location/Qualifiers
source               1..1703
                     mol_type = other RNA
                     organism = synthetic construct
SEQUENCE: 29
gggagaccca agcttggtac cgagctcgga tccgccacca tgaagacctt aattcttgcc   60
gttgcattag tctactgcgc cactgttcat tgccaggact gtccttacga acctgatcca  120
ccaaacacag ttccaacttc ctgtgaagct aaagaaggag aatgtattga tagcagctgt  180
ggcacctgca cagagacat actatcagat ggactgtgtg aaaataaacc aggaaaaaca  240
tgttgccgaa tgtgtcagta tgtaattgaa tgcagagtga aggccgcagg atggtttaga  300
acattctatg gaaagagatt ccagttccag gaacctggta catacgtgtt gggtcaagga  360
accaagggcg gcgactggaa ggtgtccatc accctggaga acctggatgg aaccaagggg  420
gctgtgctga ccaagacaag actggaagtg gctggagaca tcattgacat cgctcaagct  480
actgagaatc ccatcactgt aaacggtgga gctgacccta tcatcgccaa cccgtacacc  540
atcgggaagg tcaccatcgc tgttgttgag atgccaggct tcaacatcac agtcattgag  600
ttcttcaagc tgatcgtgat cgacatactg gcggacggga gcgtgcgcat cgccccagac  660
accgcgaaca aggcatgat cagcggcctg tgcggagacc tgaagatgat ggaggacacc  720
gacttccca gcgaccccga gcagctggcc atccagccaa aaatcaacca ggaattcgac  780
ggctgccccc tgtacggaaa ccccgacgac gtggcctact gcaaggcct gctcgagccg  840
tacaaggaca gctgcagaaa ccccatcaac ttctactact acaccatcag ctgcgccttc  900
```

```
gccaggtgca tgggcggcga cgaaagagcc agccacgtcc tgctggacta cagagaaacc    960
tgcgccgccc cggagacacg gggcacctgc gtgctgagcg ccacaccctt ctacgcacac   1020
ttcgacaagg cacggtacca gttccagggc ccatgcaagg agatcctgat ggccgccgac   1080
tgcttctgga acacctggga cgtgaaggtg agccacagaa cgtcgacag ctacacagag    1140
gtggagaagg tgagaatcag aaaacagagc acagtgtgg aactgatcgt ggacggcaag    1200
caaattctgg ttggaggaga agccgtgtcc gtcccgtaca gctctcagaa cacttccatc   1260
tactggcaag atggtgacat actgactaca gccatcctac ctgaagctct ggtggtcaag   1320
ttcaacttca gcaactgct cgtcgtacat attagagatc cattcgatgg taagacttgc    1380
ggtattgcg gtaactacaa ccaggatttc agtgatgatt cttttgatgc tgaaggagcc    1440
tgtgatctga cccccaaccc accgggatgc accgaagaac agaaacctga agctgaacga   1500
ctctgcaata gtctcttcgc cggtcaaagt gatcttgatc agaaatgtaa cgtgtgccac   1560
aagcctgacc gtgtcgaacg atgcatgtac gagtattgcc tgaggggaca caggggtttc   1620
tgtgaccacg catgggagtt caagaaagaa tgctacataa agcatggaga caccctagaa   1680
gtaccagatg aatgcaaata ggc                                            1703

SEQ ID NO: 30            moltype = RNA  length = 1703
FEATURE                  Location/Qualifiers
source                   1..1703
                         mol_type = other RNA
                         organism = synthetic construct
SEQUENCE: 30
gggagaccca agcttggtac cgagctcgga tccgccacca tgaagacctt aattcttgcc     60
gttgcattag tctactgcgc cactgttcat tgccaggact gtccttacga acctgatcca    120
ccaaacacag ttccaacttc ctgtgaagct aaagaaggag aatgtattga tagcagctgt    180
ggcacctgca cgagagacat actatcagat ggactgtgtg aaaataaacc aggaaaaaca    240
tgttgccgaa tgtgtcagta tgtaattgaa tgcagagtaa ggccgcgcagg atggtttaga   300
acattctatg gaaagagatt ccagttccag gaacctggta catacgtgtt gggtcaagga    360
accaagggcg gcgactggaa ggtgtccatc acccctggaga acctggatgg aaccaagggg   420
gctgtgctga ccaagacaag actggaagtg gctggagaca tcattgacat cgctcaagct   480
actgagaatc ccatcactgt aaacggtgga gctgacccta tcatcgccaa cccgtcacc    540
atcggcgagg tcaccatcgc tgttgttgag atgccaggct tcaacatcac cgtcattgag    600
ttcttcaaac tgatcgtgat cgacatcctc ggaggaagat ctgtaagaat cgccccagac    660
acagcaaaca aaggaatgat ctctggcctc tgtggagatc ttaaaatgat ggaagataca    720
gacttcactt cagatccaga caactgctgc attcagccta agatcaacca ggagttgaa    780
ggttgtccac tctatggaaa tcctgatgac gttgcatact gcaaggtct tctggagccg    840
tacaaggaca gctgccgcaa ccccatcaac ttctactact acaccatctc ctgcgccttc    900
gcccgctgta tgggtggaga cgagcgagcc tcacacgtgc tgcttgacta cagggagacg    960
tgcgctgctc ccgaaactag aggaacctgc gttttgtctg gacatacttt ctacgataca   1020
tttgacaaag caagatacca attccagggt ccctgcaagg agattcttat ggccgccgac   1080
tgtttctgga acacttggga tgtgaaggtt tcacacagga atgttgactc ttacactgaa   1140
gtagagaaag tacgaatcag gaaacaatcg actgtagtag aactcattgt tgatggaaaa   1200
cagatcctgg tgggcggcga agccgtgagc gtgccataca gcagccaaaa caccagcatc   1260
tactggcaga acggcgacat cctgacaacc gccatcctgc ccgaggcact ggtggtcaag   1320
ttcaacttca acagctgct ggtggtccac atcagagacc ccttcgacgg caagacatgc   1380
ggaatctgcg gcaactacaa ccaggacttc agcgacgaca cttcgacgc cgagggcgcc   1440
tgcgacctga ccccccaaccc gcccggctgc accgaggaac agaagccaga ggccgaaaga   1500
ctgtgcaaca gcctcttcgc cggacagagc gacctgaaca agaagtgcaa cgtgtgccac   1560
aaaccggaca gagtggaacg tgcatgtac gaatactgcc tgcggggcca cagggattc    1620
tgcgaccacg cctgggagtt caagaaggag tgctacatca gcacggcga caccctggag   1680
gtgccagacg agtgcaagta ggc                                            1703

SEQ ID NO: 31            moltype = RNA  length = 40
FEATURE                  Location/Qualifiers
source                   1..40
                         mol_type = other RNA
                         organism = synthetic construct
SEQUENCE: 31
gggactctaa ctatgtcaat cgccgtgatg taattatcgc                             40

SEQ ID NO: 32            moltype = DNA  length = 20
FEATURE                  Location/Qualifiers
source                   1..20
                         mol_type = other DNA
                         organism = synthetic construct
SEQUENCE: 32
attgacatag ttagagtccc                                                   20

SEQ ID NO: 33            moltype = DNA  length = 20
FEATURE                  Location/Qualifiers
source                   1..20
                         mol_type = other DNA
                         organism = synthetic construct
SEQUENCE: 33
attgacatag ttagagtccc                                                   20

SEQ ID NO: 34            moltype = DNA  length = 22
FEATURE                  Location/Qualifiers
source                   1..22
                         mol_type = other DNA
```

```
                              organism = synthetic construct
SEQUENCE: 34
cgattgacat agttagagtc cc                                             22

SEQ ID NO: 35            moltype = DNA   length = 23
FEATURE                  Location/Qualifiers
source                   1..23
                         mol_type = other DNA
                         organism = synthetic construct
SEQUENCE: 35
gcgattgaca tagttagagt ccc                                            23

SEQ ID NO: 36            moltype = DNA   length = 24
FEATURE                  Location/Qualifiers
source                   1..24
                         mol_type = other DNA
                         organism = synthetic construct
SEQUENCE: 36
ggcgattgac atagttagag tccc                                           24

SEQ ID NO: 37            moltype = DNA   length = 25
FEATURE                  Location/Qualifiers
source                   1..25
                         mol_type = other DNA
                         organism = synthetic construct
SEQUENCE: 37
cggcgattga catagttaga gtccc                                          25

SEQ ID NO: 38            moltype = DNA   length = 26
FEATURE                  Location/Qualifiers
source                   1..26
                         mol_type = other DNA
                         organism = synthetic construct
SEQUENCE: 38
acggcgattg acatagttag agtccc                                         26

SEQ ID NO: 39            moltype = DNA   length = 27
FEATURE                  Location/Qualifiers
source                   1..27
                         mol_type = other DNA
                         organism = synthetic construct
SEQUENCE: 39
cacggcgatt gacatagtta gagtccc                                        27

SEQ ID NO: 40            moltype = DNA   length = 28
FEATURE                  Location/Qualifiers
source                   1..28
                         mol_type = other DNA
                         organism = synthetic construct
SEQUENCE: 40
tcacggcgat tgacatagtt agagtccc                                       28

SEQ ID NO: 41            moltype = DNA   length = 29
FEATURE                  Location/Qualifiers
source                   1..29
                         mol_type = other DNA
                         organism = synthetic construct
SEQUENCE: 41
atcacggcga ttgacatagt tagagtccc                                      29

SEQ ID NO: 42            moltype = DNA   length = 30
FEATURE                  Location/Qualifiers
source                   1..30
                         mol_type = other DNA
                         organism = synthetic construct
SEQUENCE: 42
catcacggcg attgacatag ttagagtccc                                     30

SEQ ID NO: 43            moltype = AA   length = 530
FEATURE                  Location/Qualifiers
source                   1..530
                         mol_type = protein
                         organism = synthetic construct
SEQUENCE: 43
MKIKTGARIL ALSALTTMMF SASALAKIHH HHHHEEGKLV IWINGDKGYN GLAEVGKKFE      60
KDTGIKVTVE HPDKLEEKFP QVAATGDGPD IIFWAHDRFG GYAQSGLLAE ITPDKAFQDK     120
LYPFTWDAVR YNGKLIAYPI AVEALSLIYN KDLLPNPPKT WEEIPALDKE LKAKGKSALM    180
FNLQEPYFTW PLIAADGGYA FKYENGKYDI KDVGVDNAGA KAGLTFLVDL IKNKHMNADT    240
DYSIAEAAFN KGETAMTING PWAWSNIDTS KVNYGVTVLP TFKGQPSKPF VGVLSAGINA    300
```

```
ASPNKELAKE FLENYLLTDE GLEAVNKDKP LGAVALKSYE EELVKDPRIA ATMENAQKGE    360
IMPNIPQMSA FWYAVRTAVI NAASGRQTVD EALKDAQTGS GSGSENLYFQ GQDGMYQRFL    420
RQHVHPEETG GSDRYCNLMM QRRKMTLYHC KRFNTFIHED IWNIRSICST TNIQCKNGKM    480
NCHEGVVKVT DCRDTGSSRA PNCRYRAIAS TRRVVIACEG NPQVPVHFDG              530

SEQ ID NO: 44            moltype = AA  length = 504
FEATURE                  Location/Qualifiers
source                   1..504
                         mol_type = protein
                         organism = synthetic construct
SEQUENCE: 44
KIHHHHHHEE GKLVIWINGD KGYNGLAEVG KKFEKDTGIK VTVEHPDKLE EKFPQVAATG     60
DGPDIIFWAH DRFGGYAQSG LLAEITPDKA FQDKLYPFTW DAVRYNGKLI AYPIAVEALS    120
LIYNKDLLPN PPKTWEEIPA LDKELKAKGK SALMFNLQEP YFTWPLIAAD GGYAFKYENG    180
KYDIKDVGVD NAGAKAGLTF LVDLIKNKHM NADTDYSIAE AAFNKGETAM TINGPWAWSN    240
IDTSKVNYGV TVLPTFKGQP SKPFVGVLSA GINAASPNKE LAKEFLENYL LTDEGLEAVN    300
KDKPLGAVAL KSYEEELVKD PRIAATMENA QKGEIMPNIP QMSAFWYAVR TAVINAASGR    360
QTVDEALKDA QTGSGSGSEN LYFQGQDGMY QRFLRQHVHP EETGGSDRYC NLMMQRRKMT    420
LYHCKRFNTF IHEDIWNIRS ICSTTNIQCK NGKMNCHEGV VKVTDCRDTG SSRAPNCRYR    480
AIASTRRVVI ACEGNPQVPV HFDG                                          504

SEQ ID NO: 45            moltype = AA  length = 119
FEATURE                  Location/Qualifiers
source                   1..119
                         mol_type = protein
                         organism = synthetic construct
SEQUENCE: 45
QDGMYQRFLR QHVHPEETGG SDRYCNLMMQ RRKMTLYHCK RFNTFIHEDI WNIRSICSTT     60
NIQCKNGKMN CHEGVVKVTD CRDTGSSRAP NCRYRAIAST RRVVIACEGN PQVPVHFDG     119

SEQ ID NO: 46            moltype = AA  length = 301
FEATURE                  Location/Qualifiers
source                   1..301
                         mol_type = protein
                         organism = synthetic construct
SEQUENCE: 46
MKKIILTIGC PGSGKSTWAR EFIAKNPGFY NINRDDYRQS IMAHEERDEY KYTKKKEGIV     60
TGMQFDTAKS ILYGGDSVKG VIISDTNLNP ERRLAWETFA KEYGWKVEHK VFDVPWTELV    120
KRNSKRGTKA VPIDVLRSMY KSMREYLGLP VYNGTPGKPK AVIFDVDGTL AKMNGRGPYD    180
LEKCDTDVIN PMVVELSKMY ALMGYQIVVV SGRESGTKED PTKYYRMTRK WVEDIAGVPL    240
VMQCQREQGD TRKDDVVKEE IFWKHIAPHF DVKLAIDDRT QVVEMWRRIG VECWQVASGD    300
F                                                                   301

SEQ ID NO: 47            moltype = DNA  length = 45
FEATURE                  Location/Qualifiers
source                   1..45
                         mol_type = other DNA
                         organism = synthetic construct
SEQUENCE: 47
gggtctagaa ataattttgt ttaactttaa gaaggagata taacc                    45

SEQ ID NO: 48            moltype = DNA  length = 54
FEATURE                  Location/Qualifiers
source                   1..54
                         mol_type = other DNA
                         organism = synthetic construct
SEQUENCE: 48
gggaataaac tagtattctt ctggtcccca cagactcaga gagaacccgc cacc           54

SEQ ID NO: 49            moltype = DNA  length = 56
FEATURE                  Location/Qualifiers
source                   1..56
                         mol_type = other DNA
                         organism = synthetic construct
SEQUENCE: 49
gggacatttg cttctgacac aactgtgttc actagcaacc tcaaacagac accacc         56

SEQ ID NO: 50            moltype = DNA  length = 47
FEATURE                  Location/Qualifiers
source                   1..47
                         mol_type = other DNA
                         organism = synthetic construct
SEQUENCE: 50
gggaaataag agagaaaaga agagtaagaa gaaatataag agccacc                   47

SEQ ID NO: 51            moltype = DNA  length = 26
FEATURE                  Location/Qualifiers
source                   1..26
                         mol_type = other DNA
```

```
                    organism = synthetic construct
misc_feature
                    note = 5' Bios
SEQUENCE: 51
ggttaaacaa aattatttct agaccc                                      26

SEQ ID NO: 52       moltype = DNA  length = 21
FEATURE             Location/Qualifiers
source              1..21
                    mol_type = other DNA
                    organism = synthetic construct
misc_feature
                    note = 5' Bios
SEQUENCE: 52
gaagaatact agtttattcc c                                           21

SEQ ID NO: 53       moltype = DNA  length = 21
FEATURE             Location/Qualifiers
source              1..21
                    mol_type = other DNA
                    organism = synthetic construct
misc_feature
                    note = 5' Bios
SEQUENCE: 53
gtgtgtcaga agcaaatgtc c                                           21

SEQ ID NO: 54       moltype = DNA  length = 31
FEATURE             Location/Qualifiers
source              1..31
                    mol_type = other DNA
                    organism = synthetic construct
misc_feature
                    note = 5' Bios
SEQUENCE: 54
gttcttactc ttcttttctc tcttatttcc c                                31

SEQ ID NO: 55       moltype = DNA  length = 25
FEATURE             Location/Qualifiers
misc_feature        1..6
                    note = DNA
misc_feature        7..25
                    note = RNA
source              1..25
                    mol_type = other DNA
                    organism = synthetic construct
misc_feature        25
                    note = 3' desthiobiotin
SEQUENCE: 55
gttaaacaaa attatttcta gaccc                                       25

SEQ ID NO: 56       moltype = DNA  length = 25
FEATURE             Location/Qualifiers
misc_feature        1..6
                    note = DNA
misc_feature        7..25
                    note = RNA
source              1..25
                    mol_type = other DNA
                    organism = synthetic construct
misc_feature        25
                    note = 3' desthiobiotin
SEQUENCE: 56
accagaagaa tactagttta ttccc                                       25

SEQ ID NO: 57       moltype = DNA  length = 24
FEATURE             Location/Qualifiers
misc_feature        1..6
                    note = DNA
misc_feature        7..24
                    note = RNA
source              1..24
                    mol_type = other DNA
                    organism = synthetic construct
misc_feature        24
                    note = 3' desthiobiotin
SEQUENCE: 57
agttgtgtca gaagcaaatg tccc                                        24

SEQ ID NO: 58       moltype = DNA  length = 25
```

```
FEATURE                 Location/Qualifiers
misc_feature            1..6
                        note = DNA
misc_feature            7..25
                        note = RNA
source                  1..25
                        mol_type = other DNA
                        organism = synthetic construct
misc_feature            25
                        note = 3' desthiobiotin
SEQUENCE: 58
gggaaataag agagaaaaga agagt                                              25
```